US011993770B2

(12) United States Patent
Baltes

(10) Patent No.: US 11,993,770 B2
(45) Date of Patent: *May 28, 2024

(54) METHODS FOR TARGETED INSERTION OF DNA IN GENES

(71) Applicant: BLUEALLELE CORPORATION, Oakdale, MN (US)

(72) Inventor: Nicholas J. Baltes, Oakdale, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,745

(22) Filed: Dec. 1, 2023

(65) Prior Publication Data

US 2024/0141318 A1    May 2, 2024

Related U.S. Application Data

(63) Continuation of application No. 17/830,011, filed on Jun. 1, 2022, which is a continuation of application No. 17/590,613, filed on Feb. 1, 2022, now Pat. No. 11,365,407, which is a continuation of application No. 17/366,290, filed on Jul. 2, 2021, now Pat. No. 11,254,930, which is a continuation of application No. 16/800,444, filed on Feb. 25, 2020, now Pat. No. 11,091,756, which is a continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
  *C12N 15/10* (2006.01)
  *C12N 15/90* (2006.01)

(52) U.S. Cl.
  CPC ......... *C12N 15/102* (2013.01); *C12N 15/907* (2013.01); *C12N 2310/20* (2017.05); *C12N 2800/80* (2013.01)

(58) Field of Classification Search
  None
  See application file for complete search history.

(56) References Cited

U.S. PATENT DOCUMENTS

| | | | |
|---|---|---|---|
| 6,228,639 B1 | 5/2001 | Gaitanaris | |
| 6,740,503 B1 | 5/2004 | Harrington et al. | |
| 7,005,299 B1 | 2/2006 | Smith et al. | |
| 9,255,250 B2 | 2/2016 | Gregory et al. | |
| 9,677,070 B2 | 6/2017 | Allison et al. | |
| 9,765,404 B2 | 9/2017 | Sastry-Dent et al. | |
| 10,240,115 B2 | 3/2019 | Tang | |
| 2004/0106566 A1 | 6/2004 | Lin et al. | |
| 2005/0064474 A1 | 3/2005 | Umov | |
| 2005/0208489 A1 | 9/2005 | Carroll | |
| 2012/0046349 A1* | 2/2012 | Bell | A61P 11/06 435/320.1 |
| 2013/0280222 A1 | 10/2013 | Kay et al. | |
| 2014/0130205 A1 | 5/2014 | Bhyri | |
| 2016/0040155 A1 | 2/2016 | Maizels et al. | |
| 2016/0102322 A1 | 4/2016 | Ravinder et al. | |
| 2016/0281111 A1 | 9/2016 | Cotta-Ramusino et al. | |
| 2017/0073664 A1 | 3/2017 | Mccafferty et al. | |
| 2018/0023075 A1 | 1/2018 | Liang et al. | |
| 2018/0110877 A1 | 4/2018 | Wilson et al. | |
| 2018/0112213 A1 | 4/2018 | Welstead et al. | |
| 2018/0119123 A1 | 5/2018 | Gori et al. | |
| 2018/0273932 A1 | 9/2018 | Bothmer et al. | |
| 2018/0296603 A1 | 10/2018 | Gori et al. | |
| 2018/0362590 A1 | 12/2018 | Monds et al. | |
| 2019/0032089 A1 | 1/2019 | Townes et al. | |
| 2019/0032092 A1 | 1/2019 | Gong et al. | |
| 2019/0032156 A1 | 1/2019 | Gong et al. | |
| 2019/0093114 A1 | 3/2019 | Bower et al. | |
| 2019/0134221 A1 | 5/2019 | Bumcrot et al. | |
| 2019/0136210 A1 | 5/2019 | Cotta-Ramusino et al. | |
| 2019/0276850 A1 | 9/2019 | Brinkmann et al. | |
| 2019/0330603 A1 | 10/2019 | Ahlfors et al. | |
| 2019/0390189 A1 | 12/2019 | Lee et al. | |
| 2020/0040362 A1* | 2/2020 | Carlo | C12N 15/111 |
| 2020/0231974 A1 | 7/2020 | Jarvis et al. | |
| 2020/0270617 A1* | 8/2020 | Finn | A61K 48/005 |

FOREIGN PATENT DOCUMENTS

| | | |
|---|---|---|
| BR | 102014027 448 A2 | 9/2015 |
| CA | 2906747 A1 | 9/2014 |
| EP | 2893025 B1 | 7/2015 |
| EP | 3114227 A1 | 1/2017 |
| EP | 3122880 A2 | 2/2017 |
| EP | 3344771 A1 | 7/2018 |
| EP | 3375877 A1 | 9/2018 |
| EP | 3426784 A1 | 1/2019 |
| EP | 3556858 A2 | 10/2019 |
| EP | 3592140 A1 | 1/2020 |
| ES | 2653212 T3 | 2/2018 |
| ES | 2699848 T3 | 2/2019 |
| ES | 2730378 T3 | 11/2019 |
| JP | 2020530769 A | 10/2020 |
| WO | 2010097437 A1 | 9/2010 |

(Continued)

OTHER PUBLICATIONS

Blueallele, LLC in connection with PCT/US2019/058857 filed Oct. 30, 2019, "The International Search Report and the Written Opinion of the International Searching Authority, or the Declaration", 19 pages, mailed Jun. 23, 2020.

(Continued)

*Primary Examiner* — Anoop K Singh
(74) *Attorney, Agent, or Firm* — Arrigo, Lee, Guttman & Mouta-Bellum, LLP; Carla Mouta-Bellum

(57) ABSTRACT

Methods and compositions for modifying the coding sequence of endogenous genes using rare-cutting endonucleases and transposases. The methods and compositions described herein can be used to modify the coding sequence of endogenous genes.

6 Claims, 8 Drawing Sheets

Specification includes a Sequence Listing.

(56) References Cited

FOREIGN PATENT DOCUMENTS

| | | | | |
|---|---|---|---|---|
| WO | 2013075008 | A1 | 5/2013 | |
| WO | 2013169802 | A1 | 11/2013 | |
| WO | 2015017866 | A1 | 2/2015 | |
| WO | 2015089351 | A1 | 6/2015 | |
| WO | 2015153780 | A1 | 10/2015 | |
| WO | 2015173436 | A1 | 11/2015 | |
| WO | 2016073990 | A2 | 5/2016 | |
| WO | 2016109840 | A2 | 7/2016 | |
| WO | 2016161380 | A1 | 10/2016 | |
| WO | 2016172727 | A1 | 10/2016 | |
| WO | 2016182959 | A8 | 11/2016 | |
| WO | 2017048995 | A1 | 3/2017 | |
| WO | 2017155408 | A1 | 9/2017 | |
| WO | 2018009534 | A1 | 1/2018 | |
| WO | 2018009562 | A1 | 1/2018 | |
| WO | WO-2018009534 | A1 * | 1/2018 | ............ A61K 38/46 |
| WO | 2018195555 | A1 | 10/2018 | |
| WO | 2018197020 | A1 | 11/2018 | |
| WO | 2019005851 | A1 | 1/2019 | |
| WO | 2019092505 | A1 | 5/2019 | |
| WO | 2019113149 | A1 | 6/2019 | |
| WO | 2019118875 | A1 | 6/2019 | |
| WO | 2019157326 | A1 | 8/2019 | |
| WO | 2019157326 | A2 | 9/2019 | |
| WO | 2019183123 | A1 | 9/2019 | |
| WO | WO-2019178500 | A1 * | 9/2019 | ........... A61K 31/711 |
| WO | 2019210216 | A2 | 10/2019 | |
| WO | 020082042 | A2 | 4/2020 | |
| WO | 2020082041 | A1 | 4/2020 | |
| WO | 2020082046 | A2 | 4/2020 | |
| WO | 2020082047 | A1 | 4/2020 | |

OTHER PUBLICATIONS

Robert, Francois, "Bidirectional terminators: an underestimated aspect of gene regulation", Curr Genet, vol. 64, pp. 389-391, 2018.
Ouyang et al., "CRISPR/Cas9-Targeted Deletion of Polyglutamine in Spinocerebellar Ataxia Type 3-Derived Induced Pluripotent Stem Cells", vol. 27, No. 11, pp. 756-770, 2018.
Blueallele, LLC in connection with PCTUS2019/056083 filed Oct. 14, 2019, "The International Search Report and the Written Opinion of the International Searching Authority, or the Declaration", 21 pages, mailed Dec. 19, 2019.
Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.
Gilles et al., "Efficient CRISPR-mediated gene targeting and transgene replacement in the beetle Tribolium castaneum", The Company of Biologists, vol. 142, pp. 2832-2839, Jun. 29, 2015.
Hahm et al., "Construction of retroviral vectors with enhanced efficiency of transgene expression", Journal of Virological Methods, vol. 121, pp. 127-136, May 27, 2004.
Hildinger et al., "Design of 5' Untranslated Sequences in Retroviral Vectors Developed for Medical Use", Journal of Virology, vol. 73, No. 5, pp. 4083-4089, May 1999.
Intellia Therapeutics, "Q3 2018 Earnings and Corporate Development", Powerpoint, 23 pages, presented Oct. 31, 2018.
Ruan et al., "Highly efficient CRISPR/Cas9-mediated transgene knockin at the H11 locus in pigs", Scientific Reports, 10 p. Sep. 18, 2015.
Suzuki et al., "In vivo genome editing via CRISPR/Cas9 mediated homology-independent targeted integration", Nature, vol. 540, 24 pages, Dec. 1, 2016.
Uno et al., "CRISPR/Cas9-induced transgene insertion and telomere-associated truncation of a single human chromosome for chromosome engineering in CHO and A9 cells", Scientific Reports, 10 pages, Oct. 6, 2017.
Yao et al., "Homology-mediated end joining-based targeted integration using CRISPR/Cas9", Cell Research, vol. 27, pp. 801-814, Apr. 6, 2017.
Sheng et al Canadian Journal of Microbiology, 445-454 (Year: 2014).
Ryu et al Plant Molecular Biology 54: 489-502 (Year: 2004).
Senis et al Nucleic acid Res. , 45(1), e3 (Year: 2016).
Kaiser Science, 317, 580 (Year: 2007).
Frank et al N. Engl. J Med. Jul 9;361 (2): 161-9 (Year: 2009).
Edelstein Journal Gene Med., 597-602 (Year: 2004).
High Nature, 435, 577-579 (Year: 2005).
Ramirez Nature Methods, 5(5): 374-375 (Year: 2008).
Li Nature, Jul. 14,, 475, 7355, 217-221 (Year: 2011).
Christian Genetics, 757-761 (Year: 2010).
Hauschild PNAS, 108( 29), 12013-12017 (Year: 2011).
Hsu et al Nat Biotechnology. Sep. 31 (9):827-32 (Year: 2013).
Lee et al., (Drug Discovery Today: Disease Models, vol. 20, 13-20 (Year: 2016).
Kosicki et al Nature Biotechnology, 36, 765-771 (Year: 2018).
Robert et al Curr Genetics, 64(2):389-391 (Year: 2018).
Cox et al., Nature Medicine 21 (2), 121-13 (Year: 2015).
Kuscu et al Nature biotechnology, 32(7), 677 (Year: 2014).
Kleinstiver Nature, 523, 481-485 (Year: 2015).
Pluta et al. (Acta Biochimica Polonica. Nov. 23, 2009. 54(4): 531-595) (Year: 2009).
Kurosaki et al. (Journal of Human Genetics (2011) 56, 727-733). (Year: 2011).
Great Britain Search Report, issued Feb. 8, 2023, in connection with Great Britain Application No. GB2300487.2, 1 page.
Ohmori et al. "CRISPR/Cas9-mediated genome editing via postnatal administration of AAV vector cures haemophilia B mice", Sci Rep, Jun. 23, 2017, vol. 7, No. 1, article No. 4159 (11 pages).
Finn, Jonathan Ph.D. "Supra-therapeutic levels of transgene expression achieved in vivo by CRISPR/Cas9 mediated targeted gene insertion", 26thAnnual Congress of the European Society of Cell Therapy, Oct. 18, 2018, (14 pages).
Yew et al. Human Gene Therapy 8:575-584 (Year 1997).

* cited by examiner

METHODS FOR TARGETED INSERTION OF DNA IN GENES

CROSS-REFERENCE TO RELATED APPLICATIONS

This application is a continuation of previously filed and co-pending application U.S. Ser. No. 17/830,011, filed Jun. 1, 2022, which is a continuation of U.S. Ser. No. 17/590,613, filed Feb. 1, 2022, now U.S. Pat. No. 11,365,407, issued Jun. 1, 2022, which is a continuation of U.S. Ser. No. 17/366,290 filed Jul. 2, 2021, now U.S. Pat. No. 11,254,930, issued Feb. 2, 2022, which is a continuation of U.S. Ser. No. 16/800,444 filed Feb. 25, 2020, now U.S. Pat. No. 11,091,756, issued Jul. 28, 2021, which is a continuation of U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

REFERENCE TO SEQUENCE LISTING SUBMITTED ELECTRONICALLY

This application contains a Sequence Listing which has been submitted electronically in XML format. The Sequence Listing XML is incorporated herein by reference. Said XML file, created on Jan. 10, 2024, is named 1026_004-US7.xml and is 418,594 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
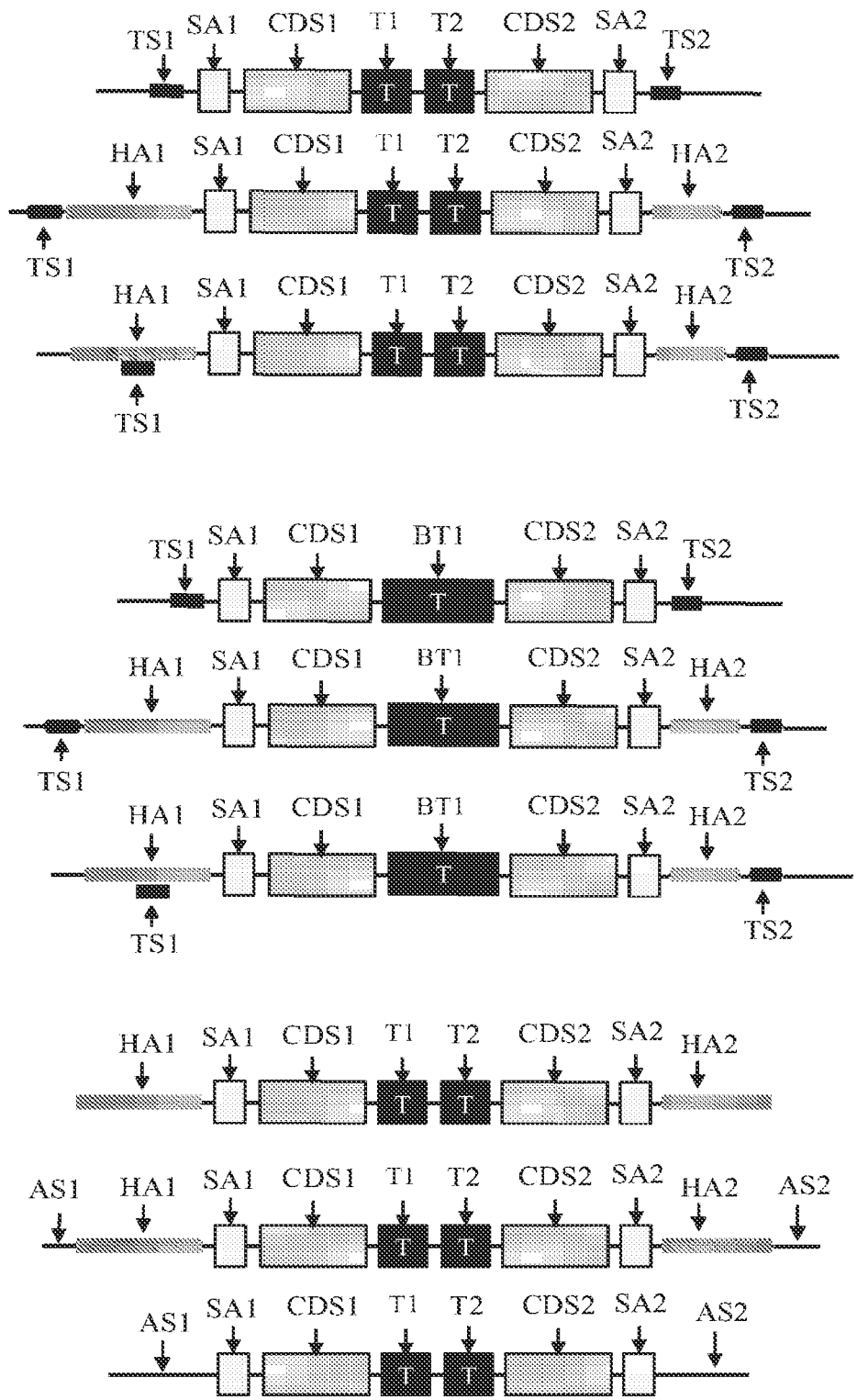
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HA1 homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence, but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence, but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence, but encode the same amino acids. The transgene can be harbored on a vector, wherein the vector format is selected from double-stranded linear DNA, double-stranded circular DNA, or a viral vector. The viral vector is can include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence, but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO:41, and the right end can comprise the sequence shown in SEQ ID NO:13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

As used herein, the terms "nucleic acid" and "polynucleotide," can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" can be used interchangeably to refer to amino acid residues covalently linked together. The term also applies to proteins in which one or more amino acids are chemical analogues or modified derivatives of corresponding naturally-occurring amino acids.

The terms "operatively linked" or "operably linked" are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron's 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally-occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequence. For example, the product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "head-to-head" refers to an orientation of two units in opposite and reverse directions. The two units can be two sequences on a single nucleic acid molecule, where the 5' end of each sequence are placed adjacent to each other. For example, a first nucleic acid having the elements, in a 5' to 3' direction, [promoter 1]-[partial coding sequence 1]-[splice donor 1] and a second nucleic acid having the elements [promoter 2]-[partial coding sequence 2]-[splice donor 2] can be placed in head-to-head orientation resulting in [splice donor 1 RC]-[partial coding sequence 1 RC]-[promoter 1 RC]-[promoter 2]-[partial coding sequence 2]-[splice donor 2] where RC refers to reverse complement.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]-[partial coding sequence 1]-[terminator 1] and a second nucleic acid having the elements [splice acceptor 2]-[partial coding sequence 2]-[terminator 2] can be placed in tail-to-tail orientation resulting in [splice acceptor 1]-[partial coding sequence 1]-[terminator 1]-[terminator 2 RC]-[partial coding sequence 2 RC]-[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC1, GAL1, GAL7, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG_008198.2 and corresponding SEQ ID NO:42. The exon and intron boundaries can be defined with the sequence provided in SEQ ID NO:42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alpha1A protein. A representative sequence of the CACNA1A gene can be found with NCBI Reference Sequence: NG_011569.1 and corresponding SEQ ID NO:43. The exon and intron boundaries can be defined with the sequence provided in SEQ ID NO:43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm nih.gov. Instructions explaining how to use the l2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\outputtxt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output-txt-q-1-r2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\outputtxt); and all other options are left at their default setting. For example, the following command can be used to generate an output file containing a comparison between two amino acid sequences: C:\B12seq -i c:\seq1.txt -j c:\seq2.txt-p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
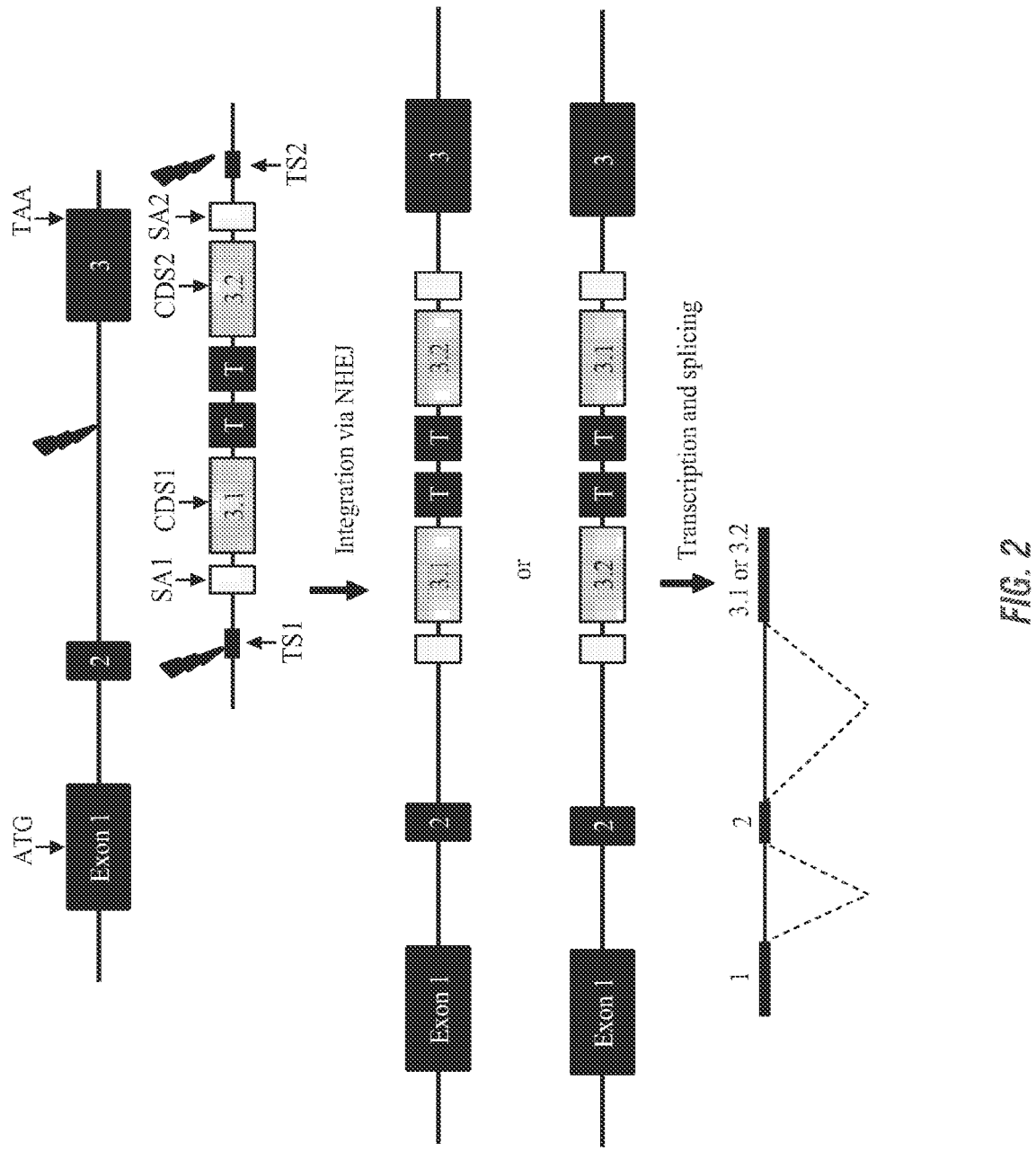
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
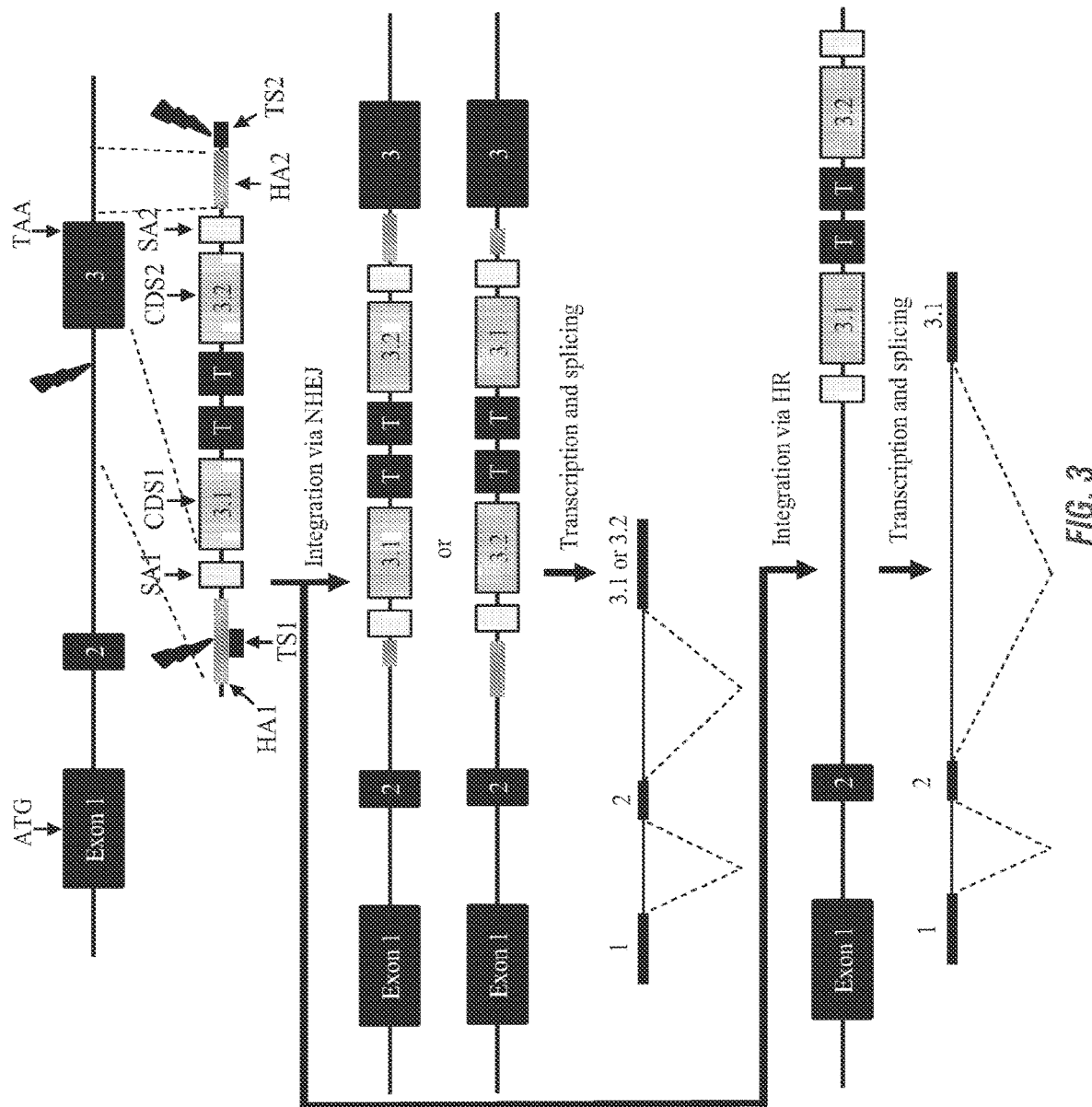
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., *Science* 10.1126/science.aax9181, 2019; Klompe et al., *Nature*, 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO:30) or *Anabaena cylindrica* (SEQ ID NO:31). In one embodiment, the transgenes described herein comprising a left (SEQ ID NO:32) and right transposon end (SEQ ID NO:33) can be delivered to cells along with ShCas12k, tnsB, tnsC, TniQ and a gRNA (SEQ ID NO:14). Alternatively, the CRISPR transposase can include the Cas6 protein, along with helper proteins including Cas7, Cas8 and TniQ. In one embodiment, the transgenes described herein comprising a left (SEQ ID NO:41) and right transposon end (SEQ ID NO:13) can be delivered to eukaryotic cells along with Cas6 (SEQ ID NO:37), Cas7 (SEQ ID NO:37), Cas8 (SEQ ID NO:37), TniQ (SEQ ID NO:37), TnsA (SEQ ID NO:37), TnsB (SEQ ID NO:37), TnsC (SEQ ID NO:37) and a gRNA (SEQ ID NO:12). The proteins can be administered to cells directly as purified protein, or encoded on RNA or DNA. If encoded on RNA or DNA, the sequence can be codon optimized for expression in eukaryotic cells. The gRNA (SEQ ID NO:12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]-[partial coding sequence 1]-[terminator 1]-[terminator 2 RC]-[partial coding sequence 2 RC]-[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[rare-cutting endonuclease cleavage site 1]. In another embodiment, the combination can be, from 5' to 3', [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]-[splice acceptor 1]-[partial coding sequence 1]-[terminator 1]-[terminator 2 RC]-[partial coding sequence 2 RC]-[splice acceptor 2 RC]-[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]-[homology arm 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]-[splice acceptor 1]-[partial coding sequence 1]-[terminator 1]-[terminator 2 RC]-[partial coding sequence 2 RC]-[splice acceptor 2 RC]-[homology arm 2]-[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators, and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7 kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), herpes simplex, pox virus, hybrid adenoviral vector, epstein-bar virus, lentivirus, or herpes simplex virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, algae, animals, fungi and protists. The eukaryotic organisms can also include plant cells, algae cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, tomato, alfalfa), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc), flowering plants (e.g., petunia, rose, chrysanthemum), conifers and pine trees (e.g., pine fir, spruce); poplar trees (e.g. *P. tremula×P. alba*); fiber crops (cotton, jute, flax, bamboo) plants used in phytoremediation (e.g., heavy metal accumulating plants); oil crops (e.g., sunflower, rape seed) and plants used for experimental purposes (e.g., *Arabidopsis*). The methods disclosed herein can be used within the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.* The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary algae species include microalgae, diatoms, *Botryococcus braunii, Chlorella, Dunaliella tertiolecta, Gracileria, Pleurochrysis carterae, Sorgassum* and *Ulva.*

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpf1). The CRISPR system can include variants which display broad PAM capability (Hu et al., Nature 556, 57-63, 2018; Nishimasu et al., Science DOI: 10.1126, 2018) or higher on-target binding or cleavage activity (Kleinstiver et al., Nature 529:490-495, 2016). The gene editing reagent can be in the format of a nuclease (Mali et al., Science 339:823-826, 2013; Christian et al., Genetics 186:757-761, 2010), nickase (Cong et al., Science 339:819-823, 2013; Wu et al., Biochemical and Biophysical Research Communications 1:261-266, 2014), CRISPR-FokI dimers (Tsai et al., Nature Biotechnology 32:569-576, 2014), or paired CRISPR nickases (Ran et al., Cell 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1: Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO:17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO:18. The individual elements within pBA1135 are shown in SEQ ID NOS:44-51. SEQ ID NO:44 comprises the left homology arm, nuclease target site, and splice acceptor. SEQ ID NO:45 comprises the partial coding sequence (exon 10 and 11) of a non-pathogenic ATXN3 gene. SEQ ID NO:46 comprises the SV40 p(A) terminator sequence. SEQ ID NO:47 comprises the BGH terminator in reverse complement. SEQ ID NO:48 comprises the reverse complement, codon adjusted partial coding sequence (exon 10 and 11) of a non-pathogenic ATXN3 gene. SEQ ID NO:49 comprises the sequence for the splice acceptor. SEQ ID NO:50 comprises the sequence for the right homology arm. SEQ ID NO:51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO:19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO:20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
|---|---|---|
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |

TABLE 1-continued

Primers for detecting integration of transgenes in ATXN3.

| Primer Name | Sequence (5' to 3') | SEQ ID NO: |
|---|---|---|
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
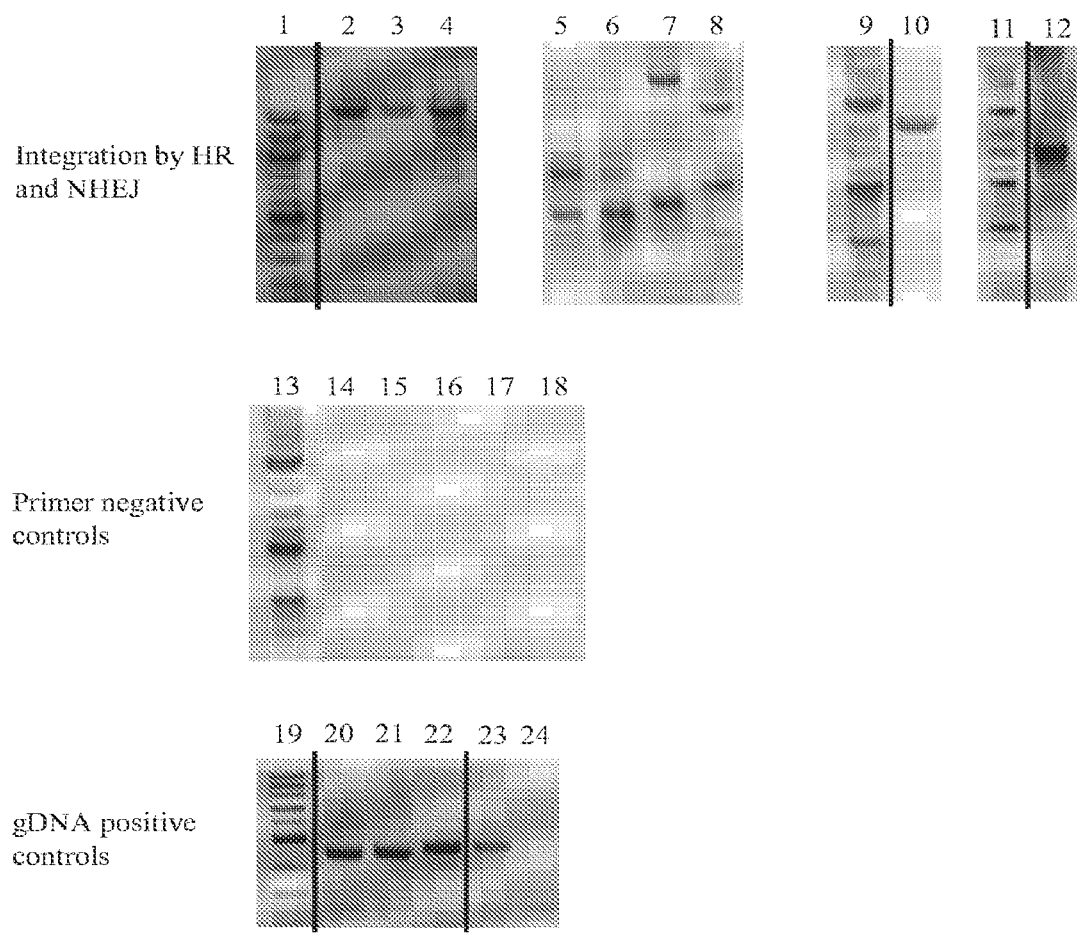
FIG. 8 are images of gels detecting integration of transgenes into the ATXN3 gene. 1, 100 bp ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1kb ladder with darker bands running at 500 bp, 1,000 bp and 3,000 bp; 9, 1kb ladder with darker bands running at 500 bp, 1,000 bp and 3,000 bp; 10, pBA1135 inverted 5' junction; 11, 1kb ladder with darker bands running at 500 bp, 1,000 bp and 3,000 bp; 12, pBA1136 inverted 5' junction; 13, 1kb ladder with darker bands running at 500 bp, 1,000 bp and 3,000 bp; 14, primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate size bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2: Targeted Integration of DNA in the CACNA1A Gene

Figure 4:
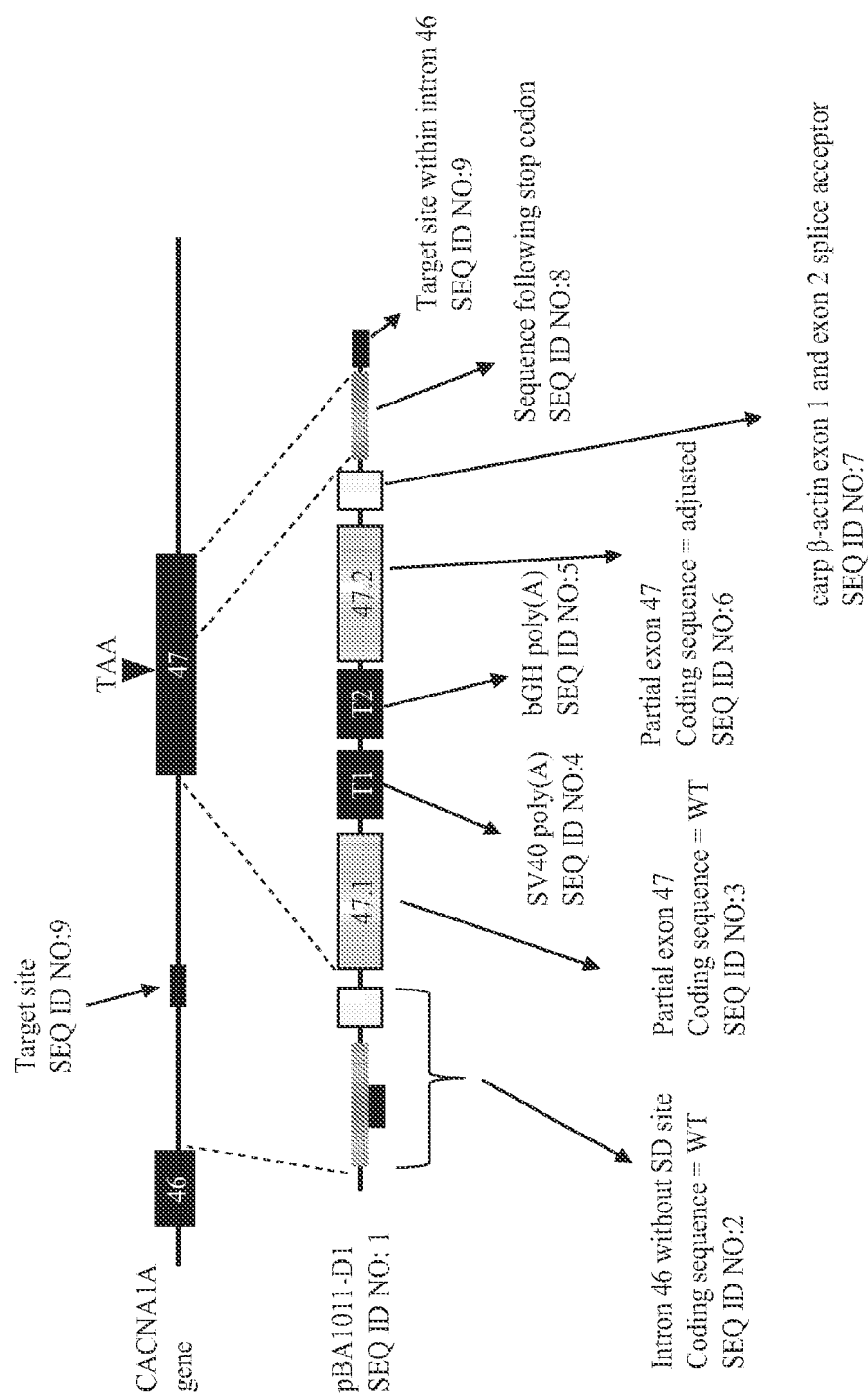
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO:9) and a splice acceptor sequence. The first homology arm is followed by a first coding sequence comprising the CACNA1A exon 47 and a non-expanded CAG repeat sequence (SEQ ID NO:3). Following the first coding sequence is a SV40 poly(A) termination sequence (SEQ ID NO:4). In a tail-to-tail orientation, a second set of functional elements is present. The beginning of the second set of elements comprises a target site for the nuclease (SEQ ID NO:9) followed by a second homology arm. The second homology arm harbors 446 bp which is homologous to sequence immediately following the stop coding (SEQ ID NO:8). This sequence was determined to be free of consensus branch or splice acceptor sequences via in silico analysis. Following the second homology arm is a second splice acceptor from carp beta-actin intron 1 (SEQ ID NO:7). Following the splice acceptor is a codon optimized version of the CACNA1A exon 47 (SEQ ID NO:6) and a bGH poly(A) terminator (SEQ ID NO:5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO:9.

Figure 5:
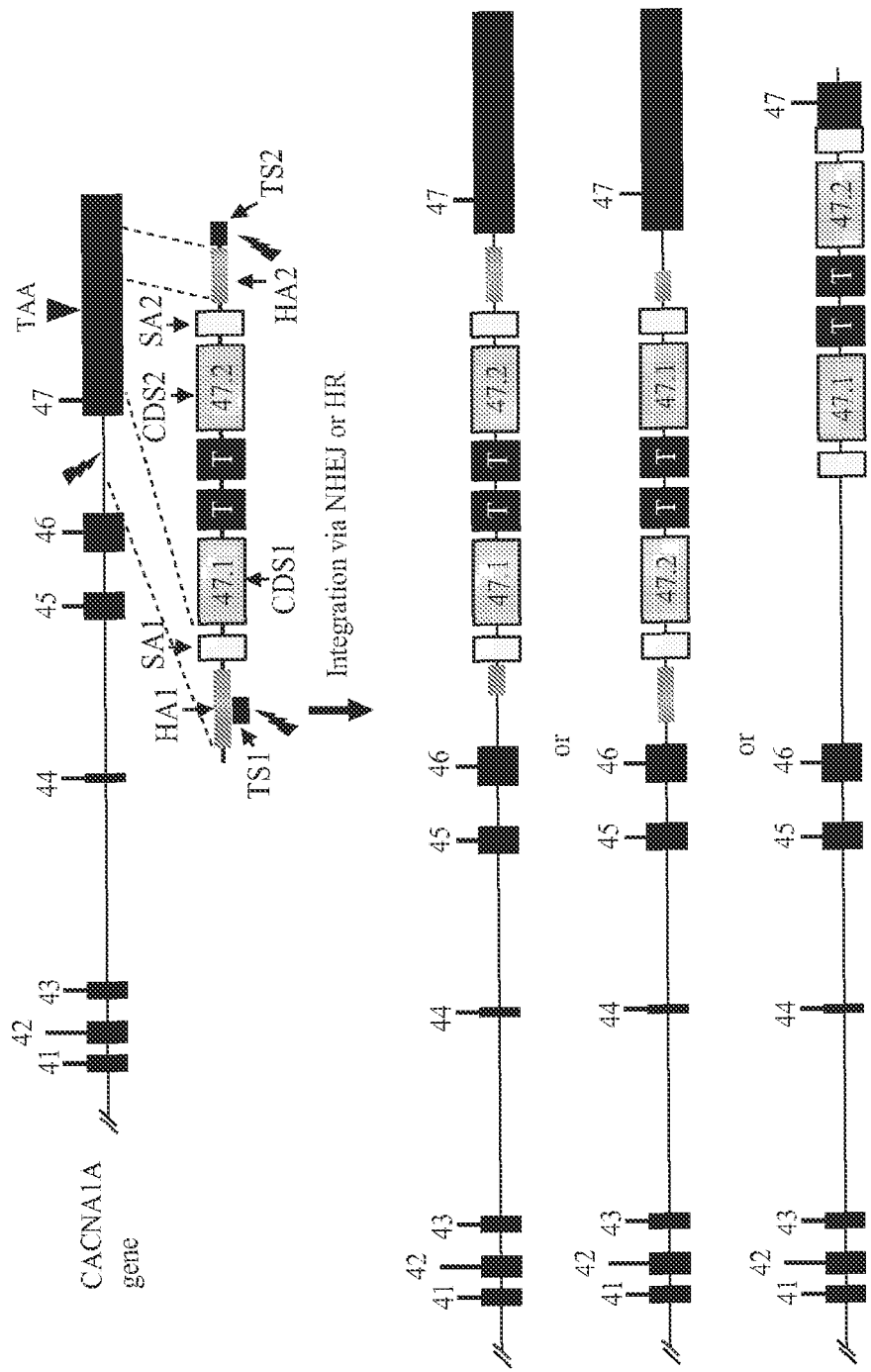
FIG. 5 is an illustration of the integration outcomes for the pB1011-D1 transgene within the CACNA1A gene.
Figure 6:
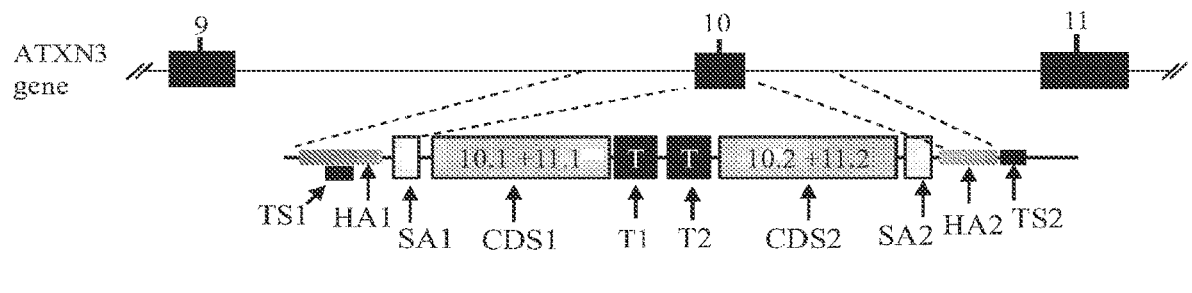
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3: Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO:10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO:11.

Figure 7:
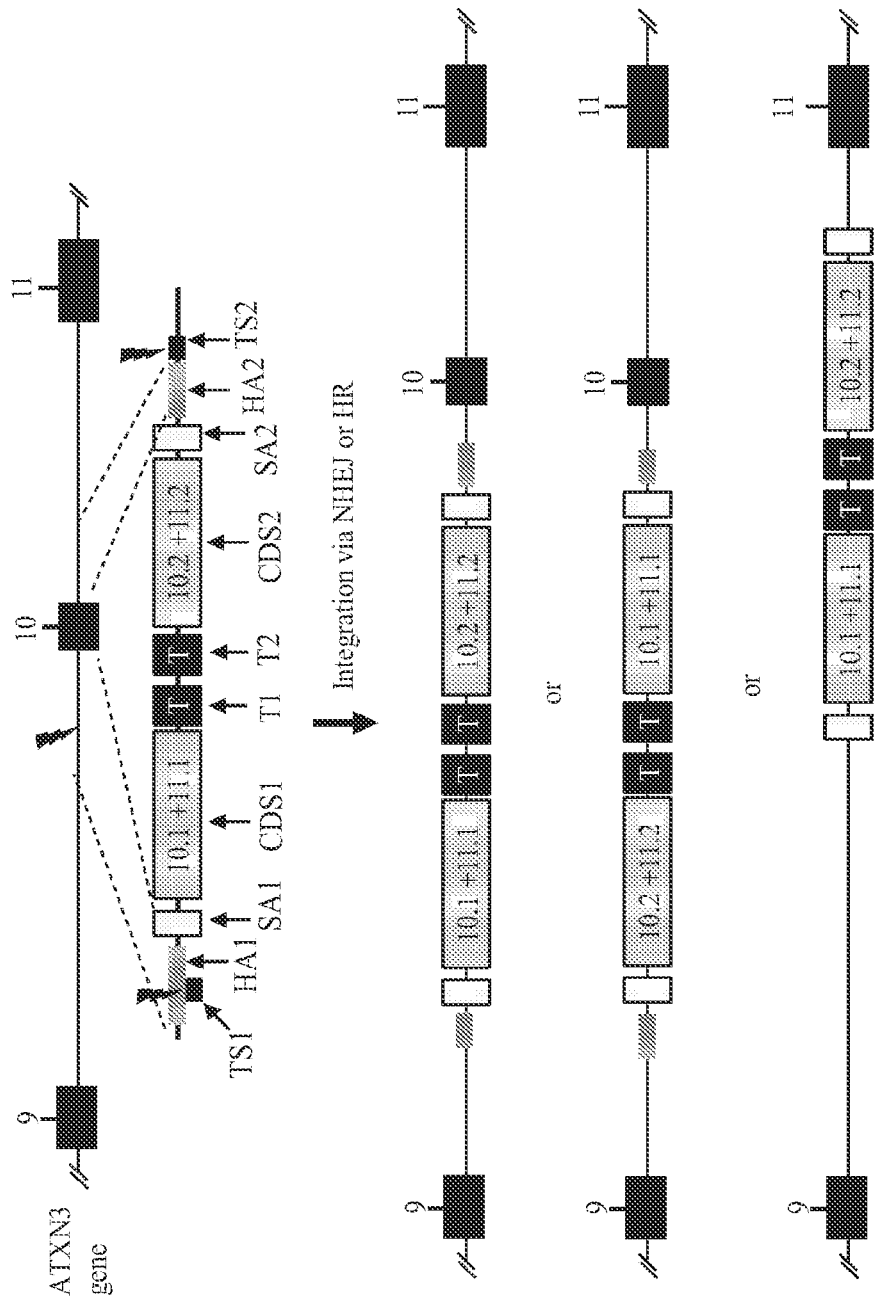
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4: Targeted Integration of DNA in the ATXN3 Gene Using Cas12k Transposases An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA targeted sequence CCGCCCGACCTTTCACTTTC (SEQ ID NO:15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5: Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA is designed to target sequence CCCGGATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant nucleic acid comprising,
(i) a transgene, the transgene comprising from 5' to 3' orientation:
a first splice acceptor, a first coding sequence, a first terminator, a second terminator reverse complement, a second coding sequence reverse complement, and a second splice acceptor reverse complement, wherein the first coding sequence is operably linked to the first splice acceptor and first terminator, and the second coding sequence is operably linked to the second splice acceptor and second terminator,
wherein the first and second coding sequences differ in nucleic acid sequence but encode the same amino acids, wherein said amino acids encoded by the first and second coding sequences correspond to amino acids encoded by an endogenous gene, and
wherein the transgene is equal to or less than 4.7 kb, and
(ii) adeno-associated virus inverted terminal repeats flanking the transgene, and wherein the recombinant nucleic acid is in a circular conformation.

2. The recombinant nucleic acid of claim 1, wherein the first terminator is selected from the group consisting of an SV40 poly(A) and a BGH poly(A).

3. The recombinant nucleic acid of claim 2, wherein the second terminator is selected from the group consisting of an SV40 poly(A) and a BGH poly(A).

4. The recombinant nucleic acid of claim 1, wherein the transgene does not comprise homology arms.

5. The recombinant nucleic acid of claim 1, wherein the endogenous gene is selected from the group consisting of Factor VIII, Factor IX, GBA, GLA, IDS, IDUA, ATXN3, USH2A, and G6PT.

6. The recombinant nucleic acid of claim 1, wherein the endogenous gene encodes alpha-1 antitrypsin.

* * * * *

SEQUENCE LISTING

```
Sequence total quantity: 51
SEQ ID NO: 1            moltype = DNA  length = 3527
FEATURE                 Location/Qualifiers
source                  1..3527
                        mol_type = other DNA
                        organism = synthetic construct
SEQUENCE: 1
gtgcggctgc aagtgacccc aggctgggct cggccgggag gcggggagga gagaagggga   60
tacccatcc  aacagccact ctaggcaaag gtccccggat cccggctgtg accacctccc   120
atcctgcccc caagccaccg gggtgcccgg cggccggagc ggacacggat ccccaccaca   180
ccagctgcct atgctgtccc cccagccccc ttgcccaccc gccgcccct ccccgccgcc    240
cgcagctgct tgctcctcgg ttgtggatca tatttgagtt ctgggccgtg ccgcccgacc   300
tttcactttc ctttaacccg gcttctgttt ttgtttcaat tatgatttct gtcctctgga   360
cgcctgtgag taatttttga aacttctgct attttttaacc ccgaaactta caaaactcca   420
tttctcattt ctcttttcac tttgttgtgt tggttttcga ctcctcccct ccctgtctca   480
ctcccctcc  tcccctccct cctccctgtg gctgttgctt ttttccattc aatgtcctgt    540
gtcccccctc tcctcctcct cctcctcctc ccctccccc tcctccctct cctcccggcc    600
cctctcccctt cgctcccctc tcttcctccc aatcccgtgt ctcctttgat tttgttgtat   660
cttttttttt gatttccttt gtttcaatttt tcgtgtaggg cagtagttcc gtaagtggaa   720
gccagcccc  ctcaacatct ggtaccagca ctccgcggcg gggccgccgc cagctccccc    780
agaccccctc caccccccgg ccacacgtgt cctattcccc tgtgatccgt aaggccggcg   840
gctcggggcc cccgcagcag cagcagcagc agcagcagca gcagcagcag caggcggtgg   900
ccaggccggg ccgggcggcc accagcggcc ctcgaggta cccaggcccc acggccgagc    960
ctctggccgg agatcggccg cccacggggg gccacagcag cggccgctcg cccaggatgg  1020
agaggcgggt cccaggcccg gcccggagcg agtcccccag ggcctgtcga cacggcgggg  1080
cccggtgccc ggcatctggc ccgcacgtgt ccgaggggcc cccgggtccc cggcaccatg  1140
gctactaccg gggctccgac tacgacgagg ccgatgcccc gggcagcggg ggcggcgagg  1200
aggccatggc cggggcctac gacgcgccac cccccgtacg acacgcgtcc tcgggcgcca  1260
ccgggcgctc gcccaggact ccccgggcct cgggccggc ctgcgcctcg ccttctcggc   1320
acggccggcg actccccaac ggctactacc cggcgcagg actggccagg cccgcgggc    1380
cgggctccag gaagggcctg cacgaaccct acagcgagag tgacgatgat tggtgctaaa  1440
acttgtttat tgcagcttat aatggttaca aataaagcaa tagcatcaca aatttcacaa  1500
ataaagcatt tttttcactg cattctagtt gtggtttgtc caaactcatc aatgtatctt  1560
atcatgtctg gatctcccca gcatgcctgc tattctcttc ccaatcctcc cccttgctgt  1620
cctgccccac cccacccccc agaatagaat gacacctact cagacaatgc gatgcaattt  1680
cctcattta  ttaggaaagg acagtgggag tggcaccttc cagggtcaag gaaggcacgg  1740
ggagggggca aacaacagat ggctggcaac tagaaggcac agtcagcacc agtcgtcgtc  1800
ggattcgctg tagggttcat ggagacccctt ccgagaccca ggtcctcttg gccgggccaa  1860
gccgtgtgca gggtaatatc cattggggag cctccggcca tgccgagaag gtgaagcgca  1920
cgctggtcct gacgcccggg gggtgcgagg agacctccct gtcgccccgg aagacgcatg  1980
cctaacggga ggcggagcat cataagcacc agccatcgct tcctcgccac caccactgcc  2040
gggcccgtca gcttcgtcat agtcagaacc ccgataatat ccgtgatggc gaggccctgg  2100
aggtccttcg ctaacgtgtg gcccagaagc aggccaccgc gcacctccat ggcgacatgc  2160
tctaggactc tcgcttcttg caggtccagg aacccgccgc tccattcgcg ggcttcgccc  2220
actactgtgt ccacctgtcg gagggcggtc tccggcaagg ggttcagcgg ttgggcctgg  2280
atagcgccgc ggaccggagg tagcagcccg accgggtcgt gctaccgctt gctgttgctg  2340
ttgttgctgt tgctgctgtt gttgttgggg tggcccgcta cctcccgctt ttctaataac  2400
tggtgaataa ctcacatgtg ggcgcggagt ggatggtgtc tgagggagtt gccttctccc  2460
tcggcggggt gtagacgtac cagatgttga aggcgccggg ctcccgctta ctgaactact  2520
gtaaatgaat gagaaaaccg gtttagaaag tgcacagctg tcagggaagt caacacttca  2580
gtgagcatgt gaccatgtgg agtcagcttc ctgtttcgtg ctgcaatcgc ccgggcgagg  2640
tggcgcccgc ccggccccc  acgcacccca cgcacacacc ccaccgagg agccgcgcag   2700
aggccgcggg ggcccagcac agagggcccg ggagagggcc agccgggaga ccccagactc  2760
tggagaggcc agggctgggc cacaaggggtg tcccgcagag accctcggcc aaaagagacc  2820
ctcctgggca gccacgcgc ccccaacca  gccccgatcc cccacccac  gacaggggct   2880
ctcgggtggg aggcagggag cagacaaacc acacagccga gggatttgaa ttaactcagc  2940
cattttttgga gaactttggg gaacatgaaa aaaaaaaaaa aaaaaaaaaa aaaaaacatt  3000
tttaaaagaa aaaacggga  gaaaaaaata gcttctattg atgagtttta tcatctcaat   3060
tgaatctttc ctttccctga tgaagacagc tggtggccga gtgcggcaaa gaagccagaa  3120
ggaaccagaa tcccagtgcc ctacacccac caccagacac actcacaccc acacacgttc  3180
tcagacacac acaagagtgc ttgccggtta taccaaaccc tactattact gcctgcagaa  3240
atcaatttaa aaaaataata ataacaataa acaatttaaa aaaggacaaa aaaattaatg  3300
```

```
attgagaaaa gaggcatttt tttctgacat ttggtcctgc ttgaaacaac aaaagaagaa    3360
gaaaaaccca ccatcaccac cgattccttt gcttcttttt tccttttttc ctaccttgtt    3420
tgaaaaccgt gggcttggga ctgtgaatta ttgcatgaca ttcaaaaaga aaaaaaaaat    3480
aaaaaaaagt tgaatcaaat ttctgtcctc tggacgcctg tgagtaa                  3527

SEQ ID NO: 2             moltype = DNA   length = 703
FEATURE                  Location/Qualifiers
source                   1..703
                         mol_type = other DNA
                         organism = synthetic construct
SEQUENCE: 2
gtgcggctgc aagtgacccc aggctgggct cggccgggag gcggggagga gagaagggga    60
taccccatcc aacagccact ctaggcaaag gtccccggat cccggctgtg accacctccc   120
atcctgcccc caagccaccg gggtgccggg cggccggacg ggacacggat ccccaccaca   180
ccagctgcct atgctgtccc cccagccccc ttgcccaccc gccgcccctt ccccgccgcc   240
cgcagctgct tgctcctcgg ttgtggatca tatttgagtt ctgggccgtg ccgcccgacc   300
tttcactttc ctttaacccg gcttctgttt ttgtttcaat tatgatttct gtcctctgga   360
cgcctgtgag taattttttga aacttctgct attttaacc ccgaaactta caaaactcca   420
tttctcattt ctcttttcac tttgttgtgt tggttttcga ctcctccct ccctgtctca    480
ctcccccctcc tccctcccct cctccctgtg gctgttgctt ttttccattc aatgtcctgt   540
gtccccccctc tcctcctcct cctcctctc cccctcccc tcctccctct cctccgggcc    600
cctctccctt cgctcccctc tcttcctccc aatcccgtgt ctcctttgat tttgttgtat   660
ctttttttt gattccttt gtttcaattt tcgtgtaggg cag                       703

SEQ ID NO: 3             moltype = DNA   length = 736
FEATURE                  Location/Qualifiers
source                   1..736
                         mol_type = other DNA
                         organism = synthetic construct
SEQUENCE: 3
tagttccgta agtggaagcc cagcccctc aacatctggt accagcactc cgcggcgggg     60
ccgccgccag ctcccccaga cccctccac ccccggcca cacgtgtcct attcccctgt    120
gatccgtaag gccggcggct cggggccccc gcagcagcag cagcagcagc agcagcagca   180
gcagcagcag gcggtggcca ggccgggccg ggcggccacc agcggggctc ggaggtaccc   240
aggccccacg gccgagcctc tggccggaga tcggccgacc acgggggcc acagcagcgg   300
ccgctcgccc aggatggaga ggcgggtccc aggcccggcc cggagcgagt cccccagggc   360
ctgtcgacac ggcggggccc ggtggccggc atctggcccg cacgtgtccg aggggccccc   420
gggtccccgg caccatggct actaccgggg ctccgactac gacgaggccg atgggcccgg   480
cagcgggggc ggcgaggagg ccatggccgg ggcctacgac gcgccaccc ccgtacgacc    540
cgcgtcctcg ggcgccaccg ggcgctcgcc caggactccc cgggcctcgg gccggctg     600
cgcctcgcct tctcggcacg gccggcgact ccccaacggc tactaccgg cgcacggact    660
ggccaggccc cgcgggccgg gctccaggaa gggcctgcac gaaccctaca gcgagagtga   720
cgatgattgg tgctaa                                                   736

SEQ ID NO: 4             moltype = DNA   length = 135
FEATURE                  Location/Qualifiers
source                   1..135
                         mol_type = other DNA
                         organism = synthetic construct
SEQUENCE: 4
aacttgttta ttgcagctta taatggttac aaataaagca atagcatcac aaatttcaca    60
aataaagcat ttttttcact gcattctagt tgtggtttgt ccaaactcat caatgtatct   120
tatcatgtct ggatc                                                    135

SEQ ID NO: 5             moltype = DNA   length = 208
FEATURE                  Location/Qualifiers
source                   1..208
                         mol_type = other DNA
                         organism = synthetic construct
SEQUENCE: 5
tccccagcat gcctgctatt ctcttcccaa tcctccccct tgctgtcctg ccccacccca    60
cccccagaa tagaatgaca cctactcaga caatgcgatg caatttcctc attttattag    120
gaaaggacag tgggagtggc accttccagg gtcaaggaag gcacggggga ggggcaaaca   180
acagatggct ggcaactaga aggcacag                                      208

SEQ ID NO: 6             moltype = DNA   length = 736
FEATURE                  Location/Qualifiers
source                   1..736
                         mol_type = other DNA
                         organism = synthetic construct
SEQUENCE: 6
tcagcaccag tcgtcgtcgg attcgctgta gggttcatgg agacccttcc gagacccagg    60
tcctcttggc cgggccaagc cgtgtgcagg gtaatatcca ttggggagcc tccggccatg   120
ccgagaaggt gaagcgaacg ctggtcctga gccccgggg gtgcgaggag acctccctgg   180
cgccccggaa gacgcatgcc taacgggagg cggagcatca taagcaccag ccatcgcttc   240
ctcgccacca ccactgccgg gccgtcagc ttcgtcatag tcagaacccc gataatatcc    300
gtgatggcga ggcctggag gtccttcgct aacgtgtggc ccagaagcag gccaccgcgc   360
acctccatgc cgacatgctc taggactctc gcttcttgca ggtccaggaa cccgccgctc   420
cattcgcggg cttcgcccac tactgtgtcc acctgtcgga gggcggtctc cggcaagggg   480
```

```
ttcagcggtt gggcctggat agcgccgcgg accggaggta gcagcccgac cgggtcgtgc    540
taccgcttgc tgttgctgtt gttgctgttg ctgctgttgt tgttggggtg gcccgctacc    600
tcccgctttt ctaataactg gtgaataact cacatgtggg cgcggagtgg atggtgtctg    660
agggagttgc cttctccctc ggcggggtgt agacgtacca gatgttgaag gcgccgggct    720
cccgcttact gaacta                                                    736

SEQ ID NO: 7            moltype = DNA   length = 110
FEATURE                 Location/Qualifiers
source                  1..110
                        mol_type = other DNA
                        organism = synthetic construct
SEQUENCE: 7
ctgtaaatga atgagaaaac cggtttagaa agtgcacagc tgtcagggaa gtcaacactt    60
cagtgagcat gtgaccatgt ggagtcagct tcctgtttcg tgctgcaatc                110

SEQ ID NO: 8            moltype = DNA   length = 446
FEATURE                 Location/Qualifiers
source                  1..446
                        mol_type = other DNA
                        organism = synthetic construct
SEQUENCE: 8
gcccgggcga ggtggcgccc gcccggcccc ccacgcaccc cacgcacaca ccccacccga    60
ggagccgcgc agaggccgcg ggggcccagc acagagggcc cgggagaggg ccagccggga    120
gaccccagac tctggagagg ccagggctgg gccacaaggg tgtcccgcag agaccctcgg    180
ccaaaagaga ccctcctggg cagccacggc gcccccaac cagcccgat ccccccaccc     240
acgacaggag ctctcgggtg ggaggcaggg agcagacaag ccacacagcc aagggatttg    300
aattaactca gccattttg gagaactttg gggaacatga aaaaaaaaa aaaaaaaaa       360
aaaaaaaaca tttttaaaag aaaaaacggg gagaaaaaa tagcttctat tgatgagttt    420
tatcatctca attgaatctt tcctttt                                        446

SEQ ID NO: 9            moltype = DNA   length = 24
FEATURE                 Location/Qualifiers
source                  1..24
                        mol_type = other DNA
                        organism = synthetic construct
                        note = Target site
SEQUENCE: 9
tttctgtcct ctggacgcct gtga                                           24

SEQ ID NO: 10           moltype = DNA   length = 2288
FEATURE                 Location/Qualifiers
source                  1..2288
                        mol_type = other DNA
                        organism = synthetic construct
SEQUENCE: 10
atttcattta tcaggtgttc agtgaatgct tactatgtaa cagcacagtt atcagcactg    60
gggaaataga tgagtaagat aagatttgca cttttcattg cttacatgcc ataaagaggg    120
aaataaagag aacaccagat gatgataagt ttatgctgag aattaaaatg aagtgatgaa    180
ataatgggaa tgtcaggtgg ctactttgg tgggatggtc aggaaaggca tctctgggga    240
gataaatttt aagctcagac ctgagtgaaa agaatgagcc agccatggaa acattatgtt    300
aactcacatg gtagtttgaa atgctttatc tgatcaaagg tacttatttt tggtgacttt    360
caacaatatt aagggtctat aaaccaacac tcatttgcat aagaataact accagtgaat    420
cttttttgtat gataggtttt ttgtttgttg ttttttttgag acagagtctc gctctgtcgc    480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtatttt agtagagatg gggtttcacc gtgttgtcca ggctcgtgtc    660
aaacttctga cctcaagcca tccacccgcc tcggcctccc aaagtgctgg gattacaggt    720
gtgagccacc actcctggcc atgataggtt attttgtgat gaaaatacct acctcttaat    780
ttgtctgata aatttaaatt ttatgtctag atttcctaag atcagcactt ccatatttta    840
aagtaatctg tatcgagcta actgctcttg cattcttta ataccagtga ctactttgat    900
tcgtgaaaca atgtatttc cttatgaata gttttttctca tggtgtattt attctttaa    960
gttttgtttt taaatatac ttcacttttg aatgtttcag acagcagcaa aagcagcaac    1020
agcagcagca gcagcagcag caggggggacc tatcaggaca gagttcacat ccatgtgaaa    1080
ggccacccac cagttcagga gcacttggga gtgatctatg tgatgctatg agtgaagaag    1140
acatgcttca ggcagctgtg accatgtctt tagaaactgt cagaaatgat ttgaaaacag    1200
aaggaaaaaa ataaaacttg tttattgcag cttataatgg ttacaaataa agcaatagca    1260
tcacaaattt cacaaataaa gcattttttt cactgcattc tagttgtggt ttgtccaaac    1320
tcatcaatgt atcttatcat gtctggatct ccccagcatg cctgctatc tcttcccaat    1380
cctccccctt gctgtcctgc cccaccccac cccccagaat agaatgacac ctactcagac    1440
aatgcgatgc aatttcctca ttttattagg aaaggacagt gggagtggca ccttccaggg    1500
tcaaggaagg cacggggag gggcaaacaa cagatggctg gcaactagaa ggcacagcta    1560
cttcttgccc tcggtcttca ggtcgttgcg cacggtctcc aggctcatgg tcacggcggc    1620
ctgcagcatg tcctcctcgc tcatggcgtc gcccaggtcg ctgcccaggg cgccgctgct    1680
ggtggcgggg cgctgcgcag ggtggcgct ctggccgctc aggtcgcct gctgctgctg    1740
ctgctgctgc tgctgctgct tctgctgctg tctgtaaatg aatgagaaaa ccggtttaga    1800
aagtgcacag ctgtcaggga agtcaacact tcagtgagca tgtgaccatg tggagtcagc    1860
ttcctgtttc gtgctgcaat cgtaaggcct gctaccatt catcatgttc gctaccttca    1920
cactttatct gacatacgag ctccatgtga ttttgctttt acattattct tcattccctc    1980
tttaatcata ttaagaatct taagtaaatt tgtaatctac taaatttccc tggattaagg    2040
```

```
agcagttacc aaaagaaaaa aaaaaaaaaa agctagatgt ggtggctcac atctgtaatc   2100
ccagcacttt gggaaaccaa ggcaggagag gattgctaga acatttaatg aatactttaa   2160
cataataatt taaacttcac agtaatttgt acagtctcca aaaattcctt agacatcatg   2220
gatatttttc ttttttttgag atggagtctt gctctgtcac tttgagacag agtctcgctc   2280
tgtcgccc                                                            2288

SEQ ID NO: 11          moltype = DNA   length = 24
FEATURE                Location/Qualifiers
source                 1..24
                       mol_type = other DNA
                       organism = synthetic construct
                       note = Target site
SEQUENCE: 11
tttgagacag agtctcgctc tgtc                                          24

SEQ ID NO: 12          moltype = RNA   length = 60
FEATURE                Location/Qualifiers
misc_difference        9..40
                       note = a, c, g, or u
source                 1..60
                       mol_type = other RNA
                       organism = synthetic construct
                       note = gRNA
SEQUENCE: 12
ctgataacnn nnnnnnnnnn nnnnnnnnnn nnnnnnnnnn gtgaactgcc gagtaggtag   60

SEQ ID NO: 13          moltype = DNA   length = 47
FEATURE                Location/Qualifiers
source                 1..47
                       mol_type = genomic DNA
                       organism = Vibrio cholerae
SEQUENCE: 13
aattatcaat tttatgggtgt aattatcatt ttatggttgt atcaaca                47

SEQ ID NO: 14          moltype = RNA   length = 258
FEATURE                Location/Qualifiers
misc_difference        236..258
                       note = a, c, g, or t
source                 1..258
                       mol_type = other RNA
                       organism = synthetic construct
                       note = gRNA
SEQUENCE: 14
tattaatagc gccgcaattc atgctgcttg cagcctctga attttgttaa atgagggtta   60
gtttgactgt ataaatacag tcttgctttc tgaccctggt agctgctcac cctgatgctg   120
ctgtcaatag acaggatagg tgcgctccca gcaataaggg cgcggatgta ctgctgtagt   180
ggctactgaa tcaccccccga tcaaggggga accctccaaa aggtgggttg aaagtnnnnn   240
nnnnnnnnnn nnnnnnnn                                                 258

SEQ ID NO: 15          moltype = DNA   length = 20
FEATURE                Location/Qualifiers
source                 1..20
                       mol_type = other DNA
                       organism = synthetic construct
                       note = Target site
SEQUENCE: 15
ccgcccgacc tttcactttc                                               20

SEQ ID NO: 16          moltype = DNA   length = 20
FEATURE                Location/Qualifiers
source                 1..20
                       mol_type = other DNA
                       organism = synthetic construct
                       note = Target site
SEQUENCE: 16
cccggatccc ggctgtgacc                                               20

SEQ ID NO: 17          moltype = DNA   length = 2391
FEATURE                Location/Qualifiers
source                 1..2391
                       mol_type = other DNA
                       organism = synthetic construct
SEQUENCE: 17
atttcattta tcaggtgttc agtgaatgct tactatgtaa cagcacagtt atcagcactg   60
gggaaataga tgagtaagat aagatttgca ctttcattag cttacatgcc ataaagaggg   120
aaataaagag aacaccagat gatgataagt ttatgctgag aattaaaatg aagtgatgaa   180
ataatgggaa tgtcaggtgg ctactttttgg tgggatggtc aggaaaggca tctctgggaa   240
gataaatttt aagctcagac ctgagtgaaa agaatgagcc agccatggaa acattatgtt   300
aactcacatg gtagtttgaa atgctttatc tgatcaaagg tacttatttt tggtgacttt   360
```

-continued

```
caacaatatt aagggtctat aaaccaacac tcatttgcat aagaataact accagtgaat    420
cttttttgtat gataggtttt ttgtttgttg ttttttttgag acagagtctc gctctgtcgc  480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tccaccgcc tcggcctccc aaagtgctgg gattacaggt     720
gtgagccacc actcctggcc atgataggtt attttgtgat gaaaatacct acctcttaat    780
ttgtctgata aatttaaatt ttatgtctag atttcctaag atcagcactt ccatattta     840
aagtaatctg tatcagacta actgctcttg cattcttta ataccagtga ctactttgat     900
tcgtgaaaca atgtattttc cttatgaata gttttttctca tggtgtattt attctttta    960
gttttgtttt taaatatac ttcactttg aatgtttcag acagcagcaa aagcagcaac      1020
agcagcagca gcagcagcag caggggacc tatcaggaca gagttcacat ccatgtgaaa     1080
ggccagccac cagttcagga gcacttggga gtgatctagg tgatgctatg agtgaagaag    1140
acatgcttca ggcagctgtg accatgtctt tagaaactgt cagaaatgat ttgaaaacag    1200
aaggaaaaaa ataaaacttg tttattgcag cttataatgg ttacaaataa agcaatagca    1260
tcacaaattt cacaaataaa gcattttttt cactgcattc tagttgtggt ttgtccaaac    1320
tcatcaatgt atcttatcat gtctggatct ccccagcatg cctgctattc tcttcccaat    1380
cctccccctt gctgtcctgc cccacccac ccccagaat agaatgacac ctactcagac     1440
aatgcgatgc aatttcctca ttttattagg aaaggacagt gggagtggca ccttccaggg   1500
tcaaggaagg cacgggggag gggcaaacaa cagatggctg gcaactagaa ggcacagcta    1560
cttcttgccc tcggtcttca ggtcgttgcg cacggtctcc aggctcatgg tcacggcggc    1620
ctgcagcatg tcctcctcgc tcatgcagtc gcccaggtcg ctgcccaggg cgccgctgct    1680
ggtggcgggg cgctcgcagg ggtggctgct ctggccgctc aggtcgccct gctgctgctg    1740
ctgctgctgc tgctgctgct tctgctgctg tctgtaaatg aatgagaaaa ccggtttaga    1800
aagtgcacag ctgtcaggga gtcaacact tcagtgagca tgtgaccatg tggagtcagc     1860
ttcctgttc gtgctgcaat cgtaaggcct gctcaccatt catcatgttc gctaccttca     1920
cactttatct gacatacgag ctccatgtga ttttttgcttt acattattct tcattccctc   1980
tttaatcata ttaagaatct taagtaaatt tgtaatctac taaatttccc tggattaagg    2040
agcagttacc aaaagaaaaa aaaaaaaaaa agctagatgt ggtggctcac atctgtaatc    2100
ccagcacttt gggaaaccaa ggcaggagag gattgctaga acatttaatg aatactttaa    2160
cataataatt taaacttcac agtaatttgt acagtctcca aaaattcctt agacatcatg    2220
gatattttc ttttttttgag atggagtctt gctctttta gctcagacct gagtgaaaag    2280
aatttgagac agagtctcgc tctgtcgcct ttcctaagat cagcacttcc atatttggtg    2340
actttcaaca atattaaggg tctataaacc aacactcatt gcataagaa t             2391
```

SEQ ID NO: 18  moltype = DNA  length = 20
FEATURE        Location/Qualifiers
source         1..20
               mol_type = other DNA
               organism = synthetic construct
               note = Target site
SEQUENCE: 18
aatatggaag tgctgatctt                                                20

SEQ ID NO: 19  moltype = DNA  length = 1205
FEATURE        Location/Qualifiers
source         1..1205
               mol_type = other DNA
               organism = synthetic construct
SEQUENCE: 19
```
tttaagctca gacctgagtg aaaagaattt gagacagagt ctcgctctgt cgcctttcct    60
aagatcagca cttccatatt ttaaagtaat ctgtatcaga ctaactgtc ttgcattctt     120
ttaataccag tgactacttt gattcgtgaa acaatgtatt ttccttatga atagtttttc    180
tcatggtgta tttattcttt taagttttgt ttttaaata tacttcactt ttgaatgttt    240
cagacagcag caaaagcagc aacagcagca gcagcagcag cagcaggggg acctatcagg   300
acagagttca catccatgtg aaaggccagc caccagttca ggagcacttg ggagtgatct   360
aggtgatgct atgagtgaag aagacatgct tcaggcagct gtgaccatgt ctttagaaac   420
tgtcagaaat gatttgaaaa cagaaggaaa aaataaaac ttgtttattg cagcttataa    480
tggttacaaa taaagcaata gcatcacaaa tttcacaaat aaagcatttt tttcactgca   540
ttctagttgt ggtttgtcca aactcatcaa tgtatcttat catgtctgga tctccccagc   600
atgcctgcta ttctcttccc aatcctcccc cttgctgtcc tgcccaccc cacccccag    660
aatagaatga cacctactca gacaatgcga tgcaatttcc tcatttattt aggaaaggac   720
agtgggagtg gcaccttcca gggtcaagga aggcacgggg gaggggcaaa caacagatgg   780
ctggcaacta gaaggcacag ctacttcttg ccctcggtct tcaggtcgtt gcgcacggtc   840
tccaggctca tggtcacggc ggcctgcagc atgtcctcct cgctcatggc gtcgcccagg   900
tcgctgccca gggcgccgct gctggtggcg gggcgctcgc aggggtggct gctctggccg   960
ctcaggtcgc cctgctgctg ctgctgctgc tgctgctgct gcttctgctg ctgtctgtaa   1020
atgaatgaga aaaccggttt agaaagtgca cagctgtcag ggagtcaac acttcagtga    1080
gcatgtgacc atgtggagtc agcttcctgt ttcgtgctgc aatcgtaagg cctgctcacc   1140
attcatcatg ttcgctacct tcacactttat ctgacatacg agctccatgt gattttgcttt 1200
tattt                                                                1205

SEQ ID NO: 20  moltype = DNA  length = 1723
FEATURE        Location/Qualifiers
source         1..1723
               mol_type = other DNA
               organism = synthetic construct
SEQUENCE: 20
atttcattta tcaggtgttc agtgaatgct tactatgtaa cagcacagtt atcagcactg    60

```
gggaaataga tgagtaagat aagatttgca ctttcattag cttacatgcc ataaagaggg    120
aaataaagag aacaccagat gatgataagt ttatgctgag aattaaaatg aagtgatgaa    180
ataatgggaa tgtcaggtgg ctactttgg tgggatggtc aggaaaggca tctctgggga    240
gataaatttt aagctcagac ctgagtgaaa agaatgagcc agccatgaaa acattatgtt    300
aactcacatg gtagtttgaa atgctttatc tgatcaaagt tacttatttt tggtgacttt    360
caacaatatt aagggtctat aaaccaaac tcatttgcat aagaataact accagtgaat    420
cttttttgtat gataggtttt ttgtttgttg ttttttttgag acagagtctc gctctgtcgc    480
ccaggctgga gtgcagtggc gcgatcttgg ctcactgcaa cctctacctc cccggttcaa    540
gtgattctcc tgcctcagcc tcccaaagta gctgggatta caggtgcctg ccaccacgcc    600
tggctaattt ttgtattttt agtagagatg gggtttcacc gtgttgtcca ggctcgtgtc    660
aaacttctga cctcaagcca tcccccgcc tcggcctccc aaagtgctgg gattacaggt    720
gtgagccacc actcctggcc atgataggtt attttgtgat gaaatacct acctcttaat    780
ttgtctgata aatttaaatt ttatgtctag aaatcctaag atcagcactt ccatatttta    840
aagtaatctg tatcagacta actgctcttg cattctttta ataccagtga ctactttgat    900
tcgtgaaaca atgtatttc cttatgaata gttttctca tggtgtattt attctttaa    960
gttttgtttt ttaaatatac ttcacttttg aatgtttcag acagcagcaa agcagcaac   1020
agcagcagca gcagcagcag caggggggacc tatcaggaca gagttcacat ccatgtgaaa   1080
ggccagccac cagttcagga gcacttggga gtgatctagg tgatgctagg agtgaagaag   1140
acatgcttca ggcagctgtg accatgtctt tagaaactgt cagaaatgat ttgaaaacag   1200
aaggaaaaa ataaaacttg tttattgcag cttataatgg ttacaaataa agcaatagca   1260
tcacaaattt cacaaataaa gcattttttt cactgcattc tagttgtggt ttgtccaaac   1320
tcatcaatgt atcttatcat gtctggatcg taaggcctgc tcaccattca tcatgttcgc   1380
taccttcaca ctttatctga catacgagct ccatgtgatt tttgctttac attattcttc   1440
attccctctt taatcatatt aagaatctta agtaaatttg taatctacta aatttccctg   1500
gattaaggag cagttaccaa aagaaaaaaa aaaaaaaag ctagatgtgg tggctcacat   1560
ctgtaatccc agcactttgg gaaaccaagg caggagagga ttgctagaac atttaatgaa   1620
tactttaaca taataattta aacttcacag taatttgtac agtctccaaa aattccttag   1680
acatcatgga tatttttctt tttttgagat ggagtcttgc tct                    1723

SEQ ID NO: 21          moltype = DNA   length = 19
FEATURE                Location/Qualifiers
source                 1..19
                       mol_type = other DNA
                       organism = synthetic construct
                       note = Primer
SEQUENCE: 21
caaaggtgcc cttgaggtt                                                19

SEQ ID NO: 22          moltype = DNA   length = 20
FEATURE                Location/Qualifiers
source                 1..20
                       mol_type = other DNA
                       organism = synthetic construct
                       note = Primer
SEQUENCE: 22
aggagaagtc tgccgttact                                               20

SEQ ID NO: 23          moltype = DNA   length = 22
FEATURE                Location/Qualifiers
source                 1..22
                       mol_type = other DNA
                       organism = synthetic construct
                       note = Primer
SEQUENCE: 23
ggacaaacca caactagaat gc                                            22

SEQ ID NO: 24          moltype = DNA   length = 20
FEATURE                Location/Qualifiers
source                 1..20
                       mol_type = other DNA
                       organism = synthetic construct
                       note = Primer
SEQUENCE: 24
taggaaagga cagtgggagt                                               20

SEQ ID NO: 25          moltype = DNA   length = 24
FEATURE                Location/Qualifiers
source                 1..24
                       mol_type = other DNA
                       organism = synthetic construct
                       note = Primer
SEQUENCE: 25
ccattatgtc tcagttgttc agtg                                          24

SEQ ID NO: 26          moltype = DNA   length = 19
FEATURE                Location/Qualifiers
source                 1..19
                       mol_type = other DNA
                       organism = synthetic construct
```

```
                        note = Primer
SEQUENCE: 26
ccagaccatc tcagacacc                                              19

SEQ ID NO: 27           moltype = DNA  length = 18
FEATURE                 Location/Qualifiers
source                  1..18
                        mol_type = other DNA
                        organism = synthetic construct
                        note = Primer
SEQUENCE: 27
ggctgggctt ccacttac                                               18

SEQ ID NO: 28           moltype = DNA  length = 22
FEATURE                 Location/Qualifiers
source                  1..22
                        mol_type = other DNA
                        organism = synthetic construct
                        note = Primer
SEQUENCE: 28
gtggtttgtc caaactcatc aa                                          22

SEQ ID NO: 29           moltype = DNA  length = 22
FEATURE                 Location/Qualifiers
source                  1..22
                        mol_type = other DNA
                        organism = synthetic construct
                        note = Primer
SEQUENCE: 29
agtaactctg cacttcccat tg                                          22

SEQ ID NO: 30           moltype = AA  length = 639
FEATURE                 Location/Qualifiers
source                  1..639
                        mol_type = protein
                        organism = Scytonema hofmanni
SEQUENCE: 30
MSQITIQARL ISFESNRQQL WKLMADLNTP LINELLCQLG QHPDFEKWQQ KGKLPSTVVS   60
QLCQPLKTDP RFAGQPSRLY MSAIHIVDYI YKSWLAIQKR LQQQLDGKTR WLEMLNSDAE  120
LVELSGDTLE AIRVKAAEIL AIAMPASESD SASPKGKKGK KEKKPSSSSP KRSLSKTLFD  180
AYQETEDIKS RSAISYLLKN GCKLTDKEED SEKFAKRRRQ VEIQIQRLTE KLISRMPKGR  240
DLTNAKWLET LLTATTTVAE DNAQAKRWQD ILLTRSSSLP FPLVFETNED MVWSKNQKGR  300
LCVHFNGLSD LIFEVYCGNR QLHWFQRFLE DQQTKRKSKN QHSSGLFTLR NGHLVWLEGE  360
GKGEPWNLHH LTLYCCVDNR LWTEEGTEIV RQEKADEITK FITNMKKKSD LSDTQQALIQ  420
RKQSTLTRIN NSFERPSQPL YQGQSHILVG VSLGLEKPAT VAVVDAIANK VLAYRSIKQL  480
LGDNYELLNR QRRQQQYLSH ERHKAQKNFS PNQFGASELG QHIDRLLAKA IVALARTYKA  540
GSIVLPKLGD MREVVQSEIQ AIAEQKFPGY IEGQQKYAKQ YRVNVHRWSY GRLIQSIQSK  600
AAQTGIVIEE GKQPIRGSPH DKAKELALSA YNLRLTRRS                        639

SEQ ID NO: 31           moltype = AA  length = 642
FEATURE                 Location/Qualifiers
source                  1..642
                        mol_type = protein
                        organism = Anabaena cylindrica
SEQUENCE: 31
MSVITIQCRL VAEEDSLRQL WELMSEKNTP FINEILLQIG KHPEFETWLE KGRIPAELLK   60
TLGNSLKTQE PFTGQPGRFY TSAITLVDYL YKSWFALQKR RKQQIEGKQR WLKMLKSDQE  120
LEQESQSSLE VIRNKATELF SKFTPQSDSE ALRRNQNDKQ KKVKKTKKST KPKTSSIFKI  180
FLSTYEEAEE PLTRCALAYL LKNNCQISEL DENPEEFTRN KRRKEIEIER LKDQLQSRIP  240
KGRDLTGEEW LETLEIATFN VPQNENEAKA WQAALLRKTA NVPFPVAYES NEDMTWLKND  300
KNRLFVRFNG LGKLTFEIYC DKRHLHYFQR FLEDQEILRN SKRQHSSSLF TLRSGRIAWL  360
PGEEKGEHWK VNQLNFYCSL DTRMLTTEGT QQVVEEKVTA ITEILNKTKQ KDDLNDKQQA  420
FITRQQSTLA RINNPFPRPS KPNYQGKSSI LIGVSFGLEK PVTVAVVDVV KNKVIAYRSV  480
KQLLGENYNL LNRQRQQQQR LSHERHKAQK QNAPNSFGES ELGQYVDRLL ADAIIAIAKK  540
YQAGSIVLPK LRDMREQISS EIQSRAENQC PGYKEGQQKY AKEYRINVHR WSYGRLIESI  600
KSQAAQAGIA IETGKQSIRG SPQEKARDLA VFTYQERQAA LI                    642

SEQ ID NO: 32           moltype = DNA  length = 208
FEATURE                 Location/Qualifiers
source                  1..208
                        mol_type = other DNA
                        organism = synthetic construct
                        note = Transposon left end
SEQUENCE: 32
tacagtgaca aattatctgt cgtcggtgac agattaatgt cattgtgact atttaattgt   60
cgtcgtgacc catcagcgtt gcttaattaa ttgatgacaa attaaatgtc atcaatataa  120
tatgctctgc aattattata caaagcaatt aaaacaagcg ataaaagga cttgctttca  180
acccaccct aagtttaata gttactga                                     208
```

```
SEQ ID NO: 33            moltype = DNA  length = 219
FEATURE                  Location/Qualifiers
source                   1..219
                         mol_type = other DNA
                         organism = synthetic construct
                         note = Transposon right end
SEQUENCE: 33
cgacagtcaa tttgtcatta tgaaaataca caaaagcttt ttcctatctt gcaaagcgac    60
agctaatttg tcacaatcac ggacaacgac atctattttg tcactgcaaa gaggttatgc   120
taaaactgcc aaagcgctat aatctatact gtataaggat tttactgatg acaataattt   180
gtcacaacga catataatta gtcactgtac acgtagaga                          219

SEQ ID NO: 34            moltype = AA  length = 394
FEATURE                  Location/Qualifiers
source                   1..394
                         mol_type = protein
                         organism = Vibrio cholerae
SEQUENCE: 34
MFLQRPKPYS DESLESFFIR VANKNGYGDV HRFLEATKRF LQDIDHNGYQ TFPTDITRIN    60
PYSAKNSSSA RTASFLKLAQ LTFNEPPELL GLAINRTNMK YSPSTSAVVR GAEVFPRSLL   120
RTHSIPCCPL CLRENGYASY LWHFQGYEYC HSHNVPLITT CSCGKEFDYR VSGLKGICCK   180
CKEPITLTSR ENGHEAACTV SNWLAGHESK PLPNLPKSYR WGLVHWWMGI KDSEFDHFSF   240
VQFFSNWPRS FHSIIEDEVE FNLEHAVVST SELRLKDLLG RLFFGSIRLP ERNLQHNIIL   300
GELLCYLENR LWQDKGLIAN LKMNALEATV MLNCSLDQIA SMVEQRILKP NRKSKPNSPL   360
DVTDYLFHFG DIFCLWLAEF QSDEFNRSFY VSRW                               394

SEQ ID NO: 35            moltype = AA  length = 640
FEATURE                  Location/Qualifiers
source                   1..640
                         mol_type = protein
                         organism = Vibrio cholerae
SEQUENCE: 35
MQTLKELIAS NPDDLTTELK RAFRPLTPHI AIDGNELDAL TILVNLTDKT DDQKDLLDRA    60
KCKQKLRDEK WWASCINCVN YRQSHNPKFP DIRSEGVIRT QALGELPSFL LSSSKIPPYH   120
WSYSHDSKYV NKSAFLTNEF CWDGEISCLG ELLKDADHPL WNTLKKLGCS QKTCKAMAKQ   180
LADITLTTIN VTLAPNYLTQ ISLPDSDTSY ISLSPVASLS MQSHFHQRLQ DENRHSAITR   240
FSRTTNMGVT AMTCGGAFRM LKSGAKFSSP PHHRLNSKRS WLTSEHVQSL KQYQRLNKSL   300
IPENSRIALR RKYKIELQNM VRSWFAMQDH TLDSNILIQH LNHDLSYLGA TKRFAYDPAM   360
TKLFTELLKR ELSNSINNGE QHTNGSFLVL PNIRVCGATA LSSPVTVGIP SLTAFFGFVH   420
AFERNINRTT SSFRVESFAI CVHQLHVEKR GLTAEFVEKG DGTISAPATR DDWQCDVVFS   480
LILNTNFAQH IDQDTLVTSL PKRLARGSAK IAIDDFKHIN SFSTLETAIE SLPIEAGRWL   540
SLYAQSNNNL SDLLAAMTED HQLMASCVGY HLLEEPKDKP NSLRGYKHAI AECIIGLINS   600
ITFSSETDPN TIFWSLKNYQ NYLVVQPRSI NDETTDKSSL                         640

SEQ ID NO: 36            moltype = AA  length = 352
FEATURE                  Location/Qualifiers
source                   1..352
                         mol_type = protein
                         organism = Vibrio cholerae
SEQUENCE: 36
MKLPTNLAYE RSIDPSDVCF FVVWPDDRKT PLTYNSRTLL GQMEAASLAY DVSGQPIKSA    60
TAEALAQGNP HQVDFCHVPY GASHIECSFS VSFSSELRQP YKCNSSKVKQ TLVQLVELYE   120
TKIGWTELAT RYLMNICNGK WLWKNTRKAY CWNIVLTPWP WNGEKVGFED IRTNYTSRQD   180
FKNNKNWSAI VEMIKTAFSS TDGLAIFEVR ATLHLPTNAM VRPSQVFTEK ESGSKSKSKT   240
QNSRVFQSTT IDGERSPILG AFKTGAAIAT IDDWYPEATE PLRVGRFGVH REDVTCYRHP   300
STGKDFFSIL QQAEHYIEVL SANKTPAQET INDMHFLMAN LIKGGMFQHK GD           352

SEQ ID NO: 37            moltype = AA  length = 199
FEATURE                  Location/Qualifiers
source                   1..199
                         mol_type = protein
                         organism = Vibrio cholerae
SEQUENCE: 37
MKWYYKTITF LPELCNNESL AAKCLRVLHG FNYQYETRNI GVSFPLWCDA TVGKKISFVS    60
KNKIELDLLL KQHYFVQMEQ LQYFPHISNTV LVPEDCTYVS FRRCQSIDKL TAAGLARKIR   120
RLEKRALSRG EQFDPSSFAQ KEHTAIAHYH SLGESSKQTN RNFRLNIRML SEQPREGNSI   180
FSSYGLSNSE NSFQPVPLI                                                199

SEQ ID NO: 38            moltype = AA  length = 230
FEATURE                  Location/Qualifiers
source                   1..230
                         mol_type = protein
                         organism = Vibrio cholerae
SEQUENCE: 38
MATSLPTPSA ITTSALEYAF HTPARNLTKS RGKNIHRYVS VKMSKRITVE STLECDACYH    60
FDFEPSIVRF CAQPIRFLYY LNGQSHSYVP DFLVQFDTNE FVLYEVKSAY AKNKPDFDVE   120
WEAKVKAATE LGLELELVEE SDIRDTVVLN NLKRMHRYAS KDELNNVHNS LLKIIKYNGA   180
QSARCLGEQL GLKGRTVLPI LCDLLSRCLL DTRLDKPLSL ESRFELASYG              230
```

```
SEQ ID NO: 39              moltype = AA  length = 603
FEATURE                    Location/Qualifiers
source                     1..603
                           mol_type = protein
                           organism = Vibrio cholerae
SEQUENCE: 39
MAKKGFSSFH RKAVSSQDTL ESIELVSSAN CLESVTYQDI SAFPETIAVE INFRLSILRF    60
LARKCETIVA KSIEPHRVEL QQNYSRKIPS AITIYRWWLA FRKSDYNPIS LAPNIKDRGN   120
RETKVSTVVD SIMEQAVERV ISGRKVNVSS AYKRVRRKVR QYNLTHGTKY TYPKYESVRK   180
RVKKKTPFEL LAAGKGERVA KREFRRMGKK ILTSSVLERV EIDHTVVDLF AVHEEYRIPL   240
GRPWLTQLVD CYSKAVIGFY LGFEPPSYVS VSLALKNAIQ RKDDLISSYE SIENEWLCYG   300
IPDLLVTDNG KEFLSKAFDQ ACESLLINVH QNKVETPDNK PHVERNYGTI NTSLLDDLPG   360
KSFSQYLQRE GYDSVGEATL TLNEIREIYL IWLVDIYHKK PNQRGTNCPN VAWKKGCQEW   420
EPEEFSGSKD ELDFKFAIVD YKQLTKVGIT VYKELSYSND RLAEYRGKKG NHKVQFKYNP   480
ECMAVIWVLD EDMNEYFTVN AIDYEYASRV SLWQHKYNMK YQAELNSAEY DEDKEIDAEI   540
KIEEIADRSI VKTNKIRARR RGARHQENSA RAKSISNANP ASIQKHEDEI VSADNDDWDI   600
DYV                                                                603

SEQ ID NO: 40              moltype = AA  length = 330
FEATURE                    Location/Qualifiers
source                     1..330
                           mol_type = protein
                           organism = Vibrio cholerae
SEQUENCE: 40
MSETREARIS RAKRAFVSTP SVRKILSYMD RCRDLSDLES EPTCMMVYGA SGVGKTTVIK    60
KYLNQNRRES EAGGDIIPVL HIELPDNAKP VDAARELLVK MGDPLALYET DLARLTKRLT   120
ELIPAVGVKL IIIDEFQHLV EERSNRVLTQ VGNWLKMILN KTKCPIVIFG MPYSKVVLQA   180
NSQLHGRFSI QVELRPFSYQ GGRGVFKTFL EYLDKALPFE KQAGLANESL QKKLYAFSQG   240
NMRSLRNLIY QASIEAIDNQ HETITEEDFV FASKLTSGDK PNSWKNPFEE GVEVTEDMLR   300
PPPKDIGWED YLRHSTPRVS KPGRNKNFFE                                   330

SEQ ID NO: 41              moltype = DNA  length = 105
FEATURE                    Location/Qualifiers
source                     1..105
                           mol_type = genomic DNA
                           organism = Vibrio cholerae
SEQUENCE: 41
tgttgatgca accataaagt gatatttaat aattatttat aatcagcaac ttaaccacaa    60
aacaaccata tattgatatc tcacaaaaca accataagt gatat                   105

SEQ ID NO: 42              moltype = DNA  length = 48031
FEATURE                    Location/Qualifiers
source                     1..48031
                           mol_type = genomic DNA
                           organism = Homo sapiens
SEQUENCE: 42
gtgggggccg ttggctccag acaaataaac atgagtcca tcttccacga gaaagtgagt     60
gtccgcgttc ggtggggagc tgtctgccgc gcgtggcgg gcgtggagcg cggcatcacc    120
gcctctcgga gggctgggtg gggcccgagt cgccccatg ccgatctcgc ccggcgaggg    180
gcgacgccgc agcctcccgc ctcctcggct cgaggagggg agcatcacct acgccccta    240
ttcccgcg gccccgccc tgggagccgg gaggagtat gggcggggcc gggggcgtct        300
cgggacacgg gagtggggtg gcgcccagtg ggtttgcttc tgcctttctc cgtcactttc   360
catcgctttt cggaggattc cttcaccct cccaatcct tccctctccc tagggtctag     420
ctagagtcat ctctgggaca cctccctcaa cccctcctac cctaatcctg gcagaattaa   480
cttttcctcc tccggactgc tcaattctat atggagtctt tccctacacg tagatctttg   540
gggtcttgtt cgtgtctttc ccctgcacta ggtccgcgag cctcccgagg gaggagacct   600
tggctcgccc actgtagggc ctgacattta ggaagtgaag taggaaaccc ggcgtgcccc   660
taaacaggga agtcgtcaca agagttttta ttacgggatg tttgggtttg gtttcttttg   720
gtactcccat ctttccggag caggcggcca gctttgtttt taggtattag gagtggactg   780
ggatgatttt gttgtagtct gcctagcctg ctgtcccttt aactcttccg tgaccatgca   840
cttgaagata ctgtttgtga tatgtaaaga aactcctcgt ttctctcata ctattatcca   900
gccatttgtg tgtgagtgaa gccttcccca ggacagcttt ggcacatggt atcatgtttc   960
ataatagttt cgtgttttgga aagagttgct ggtaaggctg ttatttaata ggaggagcaa  1020
agggttttg ttttattaaa tacttataaa tgatcattta tcccagacat ttaaaattca    1080
cacacacaca acaaataaag caaagacaaa agaatacatt taccaaatgt aaatctgtag  1140
cataaatttt ttttaatttt tatttttaaag atggggtctc attctgtcac ccaggcaggt  1200
gtgcaatgga gagatcatgg ctcactgcag ccttgatctc ctaggcacaa gcgatcctcc   1260
cgcctctgcc tccagagtag ctgggactac aggtgcatat cgccagggcc aggtaatgct   1320
tttgggagag acggggtctc gctgttgc ccaggctggt ctcgaactcc tggactcagg     1380
tgattctccc acctcggcct ctcgaagtgc tgtgattaca ggcgtgagcc actgtgcctg   1440
gaacaaattg ttaagtacaa tgcttttcat tgtagaaaac atctcggaaa cttttgaaat   1500
aggctgatgt tcagtgggg aggaaggact cagtcgtata gttgtcacta attttttgac    1560
ttgattgaca tgactcgtaa atcatagaca atagagattt ggttgcttgg ctgagtagag   1620
tgcgtgaaaa atacacactg acttttttt ttttttttttt aaaggtaagt ttggctcttg   1680
tcacccaggc tggagtgcaa tggcgccatc atggctcact gcaacctccg cctcccgtt    1740
caagcgattc tcctgcctca gtctcccag tagctgagat tacaggcgcc cgccaccacg    1800
cccagctaat ttttgtattt ttagtagaga cagggtttca ccatgttggc caggctggtc   1860
tccaactcct gacaggtggt ccgccgcct cggcctccca aagtgctggg attacaggcg    1920
tgagccaccg caccggcca tatttttgtt attaattttc aaaggctttg gtgtgggacc   1980
```

```
acatttcaac atggaaggcc ttaaacatgt tccacactac ttcctgagaa ttagacaaga   2040
tttttaacaa tattgttacc tagttgggac acatttgtac tgacccatgg gatgaaaaaa   2100
agctgagtgc tagcctagtg aaaatctact tacccgaaag aaatccctct tagtctgggt   2160
gcagtggctc acaccagtgc tttgggaggc ccagacgggc ggatcatgag gtcagtagtt   2220
tgagaccagc ctggccaaca tggtgaaacc ccgtctctac taaaaataca aaaaattagc   2280
caggtgtggt ggcaggcgcc tgtaatccca ggtactctgg aggctgaggc aggagaattg   2340
cttgaacccg agaggcagag gttgcagtga gccgagaccg tgccactgca cttcagcctg   2400
ggcaacagag cgagactccg tctcaaaaaa aagaaaagga aaaagagtc cctcttaatt   2460
atcagcatgt gtataggcct acagatactt caggaatacc tttaccatta tcatcaactt   2520
gtatctacat agcatgtgaa gattcaacaa tttagttttt tgggcgtcct caagagtacg   2580
cacctataac catatggccc aattgttaat ctcctataca gtccattctg ggaatgtttg   2640
ggcttactgt gccatttttc cgttcactgc cttcccctct gcaatatacc tttaacccctt   2700
gctaggtcct gggtttggag agccagagaa ccaactttgg ccctaaagaa gctgtgtagg   2760
tagcaatatc tgcctacgaa gggccttgca accatttcct cttggaacct tggtttcctc   2820
tttctgagta gtcactttga gtacccttta ttaagttaga atgtaaaaac agttctcac   2880
tgatatatct gcagtgcctg agagagggcc tggcacagag taagtactca ataaatattt   2940
gaatggggcc gggcgtggtg agacctgtct ctacaagaat gaacaaaatt agctgggcgt   3000
gttagcacat gcctgtagac ttgggaggct gaggtgggag gattgcatga gtctgggagg   3060
tcgaggctgt agtgagccat gatcgcacca ctgcactcca gcctagggga cagagcaaga   3120
tcctgtctca aaagaaaaaa atgtatatat ttgaatggat aaagagatgg ctttgagttt   3180
ctgagatata tatggtgctg tttatctaaa gtaaacaagt tttctgtaaa tattttaagg   3240
ctttgcaggc cagctgtagt ctctgtcaca cattcttatt tgtgcatgtt tttcccaacc   3300
atgtaaaaat gtaaagtgca ttcttagcta ctggggcagg ttgaatttgg cccatgggct   3360
agagtttgcc aaccctaac ttaaaccttt gtactaactt tatgaccact actgggatttt   3420
tgttgttgtt tgttttagtt ctggtgcctg ctttgtttt ttttttttttt ttaatcctct   3480
tgctgatgtt tcttggtgca gttactgtgc catttgtatt ggtgcttttta atgtaatgca   3540
aactggtaat aatatctaaa cttgctgggg ttgtacataa aattattgaa aagattgaaa   3600
agatgctgag cattgactct gtggcattca ttatgccctt ttgtgattgc tggattttag   3660
ccatctttag gacatttgag ctttaggaga agccaaattc tgtataaatg acttgaagtg   3720
ctaatagcac aggttttgaa acctctgcct gggtttgagt ctcagctctg ccttttacta   3780
cctgtgtgat cctgagcaag ttacttagta tccctgtcct ctagtttcct cctctgtagt   3840
gtggggataa taacatagac ataacctgag agttagagtg tagagaaggc tccctggcag   3900
atagtgctgt agaagtactg gccattgcca ttactcaggt gcttgtgttt gctgaacctc   3960
atagtaaggg ctcggagagc actaagagga ggtgagaaat gctgctagat tgacagctg   4020
tccccagata gcccattccc gagagcaccct taggtttata cctgatttgt gttgtagtta   4080
gtagtgtctc tggtaatttg aactagtttc aggttggtct tgaaaacctg ggggaggttgg   4140
gggtaaatga tttggtagca gttctctttt gtgatttat acattatctt tgtagaactg   4200
cagtttgcta attctctgag cccaacacaa tgaagtctgg gcctaaaatc atagaatttc   4260
ttttattttt ttttttgttt ttaatttatt tattcccctcc ctccctcctt tcttcctttc   4320
ttccttttct ttctttcttt ccttccttcc ttccttcttt cttttcttttc tttcttttct   4380
ttctttggag tctcactctg tcaccaggct ggagtgcagt ggcacgaact ttcttcagag   4440
tctcactttg tcaccaggct ggagtgcagt ggcgcgaact cagctcactg caacctccgt   4500
ctcctgagtt caagagattc tcctgcctca gcctcccgag tagctgggac tataggcatg   4560
tgccaccatg cccagctaat tttcttattt ttagtagaga cgaggtttca ccatgttggc   4620
caggatggtc ttgatctctt gacctcgtga tccacctgcc tcagcctccc aaagtgcggg   4680
gattacaggc gtgagctacc acgcccagcc tattttttat tttttgaggc agagtctcac   4740
tctgtcaccc aggctggagt gcagtggtgc aatctcagct cactgcaacc tccgcctcct   4800
gggttcaggt gattctcctg ccttagcctc ctgagcacct gggactacag gcgcctgcca   4860
ccacacctgg ctaattctta tattttagt agaggcgggg tttcaccatg ttggccaggc   4920
tggtctcgaa ctcctgatct caagtgatca acctgccttg gcctcccaaa gtgctggaat   4980
tacaccatg agccaccatg cccagccaaa tcatgagatt tcaataccgc tgaacttgga   5040
ttatggcaaa gtgaacttct gctttgatta aagcttgatg agagaggtgg ctggggatag   5100
tttgagataa gggcaaggca ggaaaatgca taatcttacg tgggctcatt gtcattgtac   5160
aattcttttg gtccatgtgg aatttgatcc gtcctatgac ttaagttatg tttattttttg   5220
ttttatttt tatttatttt gtgtcttttt gagagacatg atgttgctct gtcacctggg   5280
ccagaataca gtggcacaat cttagctccg tgtagccttg aactcctggg ctcaagtgat   5340
cctcccacct cagcccctca aacagttgag attatagtat gaaccactgt gcctagcctt   5400
aagtgatttt taaatttgta ctgaacagtt tgtccttttcc ttccattaaa tcatattaga   5460
agtacagaac ttgatatttc ctgtagcaat acagttttc ttttgatgaa tttgatttca   5520
agtacttatt tttcataatt taaagctatt ttttatagag agaatttttaa tcaaatattt   5580
ggatgtcact attgctatat atggtattaa gtatggtgac catagtttgt aaactccaaa   5640
ctgacagcaa gacaggaaat ttgtgttagc aaaggctttt tcttactgt ttgaattttt   5700
taaaaattag atacaataca gagaggagca cacaaatcat taagagtaca gctcagcgaa   5760
ttttcacaca gtgaactgt gtaaacagca agtaacaaaa gatttacctg catcctataa   5820
cctcccatta ttccccttttc taggtactgt ctctccactg cattcccacc aaatataacc   5880
actatgctga attctgacat cataaatgag ttttgcctga ttttgagctt ttgtgactgg   5940
aagtgtacag tgtatatacc ctttcgattc tgtcctcttt agtttaccat tgtttgagaa   6000
atttatccat actgttccag aattaactac tgttaattaat tgttaattaa ctactgttgt   6060
agttaattca tcctccattg tatctagtat ttttttgtga gtaaacacaa tttccattct   6120
actgtgatcc cagctatcca tttgggtcgt ttccagtttg gggtccatta caaatagtaa   6180
tgctatctgt aatgctattt tgtattacta caaatagtaa tgcatttgt ggcacaaaaa   6240
tactgctttt gtgaacattc ttatacatgt cttttgatga atgtatgttt gcattgctgt   6300
tgtttacatt atgtacctag taatggaatt gctagatcat aggagatgta tatattaagc   6360
tttagtggat gcattacata attattagtt attaccaattt ataccetcat   6420
cagtagtata caacagtttc tgtatctcta atctccaaca ttttagccat tttagagttt   6480
gtgtactaac acattgtggt tttaatttac atttccctga tgactaataa agttgagtac   6540
ctcttttgtg ttctttatag ccatttgact gtcttgtgaa gtgcttgttt gtcttgccta   6600
ttttttcttttt ctttctttct ttttcttcct tccttccttt ctttcttttct tcttttcttc   6660
cttccttctt ttctttctttt ctgtcttttct ttcttgtctt tcttgtctttt ctgtcttttct   6720
```

```
tggtcttgcc ctgtcaccca tgctggagtg cagtggtgca gtctcagctt actgtagcct    6780
cgacctttt  ggggctcaag ttatcctcct ttctcagcct cccaagaagc tggactacaa    6840
gcacgcacca ccatgctcag ttaattttt  attttttgta gaaatgggt  ttcaccatgt    6900
tgtccaggct ggtctcaaac ttctgggctc aagtaatcct cctgccttgg cctcccaaaa    6960
tgctgggatt acaggcatga gccaccgcag ccagccttgg ctatttttca aaaggatata    7020
agtagaacat ctgtatatcc cttcaatttg catattattc agtaagagtt gcactctggt    7080
agtagaaata tataaggagg agaaagaagt ggaaacaaaa agtctattct catgagaaga    7140
cttggggat  agtgttctct ctagctccaa gctacttatt ccttacgaaa agttgaagat    7200
aaacttatct cagactgagg ctgtctcaat gttgtcttcc tattccatta tacacatata    7260
acccatattt ttttcaccag ctgaattttg ctcctagaaa attgattcat caggaaaaat    7320
atccgtcttg caaggtggtt ctcttagag  tctgctgtgt gacatagctc aggacaaatt    7380
gtgtgatgtc agataggttg ggttaaggaa tagaccttat tggggaaaga gagaacttgg    7440
agggccaagg ttagcaggag aaggaaatgt tctctcatct gccgtcaatt cagggagggg    7500
caaacctggt gtctgtgttc acagggaggg atccatccat ctgtgattct cccttcttat    7560
caggtagcat gggaaagcta cactgttgcg ggggaggaggg tcacacgcag gctacttagt    7620
accaggcacc ctggacttgg attcaggttg ccagttgtgt gagaaactgc ccagcacctg    7680
aaggccctga acccatgaga agttgtacct acctcccatg aggaggaatc ctgtcatccc    7740
atgggagctg agcttgggtg cagtccctct tgctggcttg tccaggagtg agctccaggg    7800
ttgtttggga cagttctgct cattgcttta cactgtgtat acattatctg tagagttcca    7860
tgaagagaac ttcagcactg taactgcaag ttttaacatg gaacagaatt tttctcacct    7920
gtattaattc ttaagatttg aagttctatc aacaagcatt tagattgtgt ggagattttt    7980
ttattttat  ttttggagac agagtcttgc tctgttaccc agactggagt ggcagtggca    8040
tggtcttggc tcactgcagg ctctacttcc tgggttcaag cgattctcat gcctcagtgt    8100
cctgattagc taggactaca ggtacacacc accatgctgg ctaatttttg tattttagt     8160
agagacgagg tttcaccgta ttggtcaggc tggtctcgaa ctcccagcct caagcagtcc    8220
acccacctcg gcctcccaaa ctgctgggat tacaggtgcg agccaccatg cttgactgac    8280
atcatcatgt taaagaata  aatgttctag ggagctgggc acagtgtcat gtttctgtag    8340
ttctagctgc tcgggaggct gaggcaggaa gatcccttga gccctggagt tcaagtccag    8400
cctgggcaac atagtgagat ctcttttttt aaataaataa ataactgttc tagggactaa    8460
aatttccttt caccattagt aatttactgt agaatctcca agaatgaact tatttttaggt   8520
actgaaaatg agggagacta aatgttttat acagtagttt ttagtaaaat atgagatttg    8580
atgcatttga tagatgatgt ttgttttaaaa taattcttaa attttttgatc atgtaattat   8640
agtttcatta atggtagatt tgtaaaataa atgttaccaa atgaaaatgc atgtacctat    8700
gttaattatc cttatctaaa gctgaaagtt cagttcaact atgttaaaac atagtagggg    8760
cctggcaggg tggctcttgc ctgtaatccc agaacttagg gaggccaagg tgggcagatc    8820
acgaggtcag gagatcgaga ccatcctggc taacattgtg aaaccgtatc gctactaaaa    8880
atacaaaaaa ttagccgggc atggcggtgg gcacctgtag tcgcagctac ttggtaggct    8940
gaggcaggag aatggcgtga actcaggagg cagagcttac agtgagccga gatcatgcca    9000
ctgcactcca ggctgggtga cagagcaaga ctccatctca aaaaaaaaaa aaagttggc     9060
caggtgtggc ggctcacacc tgtaatccca gcacttttgg aggccgaggc aggcggatca    9120
caagatcagg agtttgagac cagcctggct aacagagtga aaccctgtat atactaaaaa    9180
tacaaaaatt agccaggcat ggtggtgcat gcctgtagtc ccagctactt gagaggctga    9240
ggcaggagaa tcacttgaac ccgggaggcg gaggttgtgg taagctgaga ttgctccact    9300
gcactccagc ctggacaaca gagcaagact ctgtctcaaa aaaaaaaaaa attaatgatt    9360
aaattattta ggggagccgg gcgcagtggc tcacgcctgt aatcccagca ctttgggagg    9420
ccaaggcggg cggatcacga ggtcaggaga tcaagaccat cctggctaac acaggatgaa    9480
accccgtctc tactaaaaat acaaaaattt agccgggcgt ggtggcgggt gcctgtagta    9540
ccagctactc gggaggctga ggcaggagaa tggcatgaac ccgggtggcg gagcttgcag    9600
tgagccaaga tagcgccact gcactccggc tgggtgaaa  gagtgagact ccgtctcaaa    9660
aaaaaaaaaa aattatttag gggaagatac tatacaattc tgtttaacaa gtcacatttt    9720
aattttttct tttggaaata ttagcaagaa ggctcacttt gtgctcaaca ttgcctgaat    9780
aacttattgc aaggagaata ttttagcccct gtggaattat cctcaattgc acatcagctg    9840
gatgaggagg agaggatgag aatgcagaag ggaggagtta ctagtgaaga ttatcgcacg    9900
tttttacagg tactgatttt aaactcacta agtcacattt ctttttttt  ttttttttg    9960
agacggagtc tcgccctgtt gcccatgctg gagtgcaata gcgcgatctc ggctcactgc   10020
aacctctgcc tcccgggttc aagcgattct cctgcctcag cctcccaagt agctgggatt   10080
acaggcacac ggcactatgc ccggctaatt ttttgtatct ttgttagaga tgggtttca    10140
ccatgttggt caggttggtc tcaaactcct gaccttatga tccacctgtc ttggcctccc   10200
aaagtgctgg gattataggt gtgagccacc acacccggct tacatttttct ttaaaaatgt   10260
ggataccatt tagaaaagga tgggccattc ttcctataggg gatctgactg gtgaattata   10320
actgtgctgt taactttgga aatgggaatg cacaagatat tgttttaaat atgcacgcta   10380
atgcagtttt gtatccttct ttccccaccc ccaccccttgc ttcaactacc tgtcaaaatt   10440
aacagcagcc ttctggaaat atggatgaca gtggtttttt ctctattcag gtaagtagtc   10500
acaagcatgt actatgtgtt gcttacatcc caggcaccgt ttcacagcct ttcaatgctc   10560
actgtaacaa ggcgaccttc ggaagttctt ctgtctacag agtatagatt atactctaga   10620
gtactagatt ttttttttct tgagacagag tctcgttctg tcacctaggc tggagtgcag   10680
tggcgtgatc ttggctcact gtagcctctg cctcccgggt tcaagcgatc ctcctgcctc   10740
agcctcccaa gtagctggga ttacaggcac ccgccaccac accagttaat atttgtattt   10800
ttagtagaga tagtgggtt  tcaccgtgtt ggccagtctg gtctccaact cctgacctca   10860
gcctcccaaa gtgctgggat tacaggtgtg agccactgca cctggccaac tagagtacta   10920
gatttttata tagataaaca tgaaggatt  gtagaatctt catattagag tgggcatttt   10980
aaaaattcct tcttgagaaa gattaatttg catctggatg ctaataataa ccttaattct   11040
ggccgggcgc ggtggctcac acctgtaatc ccagcacttt ggggaggccg aggtgggcgg   11100
atcacgaggt caggagattg agaccatcct ggctaacatg gtgaaacccc gtctctacta   11160
aaaatacaaa aattagctgg acgtggtgac acgtgcctgt aatcccagct actcgggagg   11220
ctgaggcagg agaatcgctt gaaccaggga gtcgtaggtt gcagtgagcc aagatcgcgc   11280
cactgcactc tagcctggtg acagagcgag actccatctc aaagaaaaaa agaaatcctt   11340
aattctaata agtcacaatg tctcaaactt accatctgtt gggtaaattt gagaaaatgc   11400
aataccttgc taccatcctt ttaaatcagc ctaccagact ggatttcctt attatggtt    11460
```

```
gtggcttttg attttttttt tttaatgtat agctctcttt gaattcttg gtggttatat    11520
atatatgtac tcgcaagatt cttttatctg tgggtctttc attctttttc taacactgtg    11580
agttgtatcc agagtacttt cggaacctct cctgagcgac ctatctctgc agatatcttt    11640
gtttatgttt cccttgtact gccctcctgg actcttcctc atccaccagc atttccatct    11700
agtgctttac cgtgccactg ctaacaggta atggctactg cagggctgaa atcagaggcc    11760
agagtaggcc cagcacttgg cgtttcctat ttgtgccttg ctgctcttgg tgcctgttca    11820
tgtgtgccca ctaccttgca ctcaatttct gtctttgctg gtacctggct cacttgcttc    11880
tttgttggct accttggagg gcagatagtg aattttcaga aatttcccctt tttttgtcag   11940
acagattgaa ataaacaggt ttgcattttg tttttttctac aagcggcaag cccatgaccc    12000
tagaagtctg acatctatgg aaccttcagt ttaaatgccc agggagaact tattttggta    12060
gatatgattt ctgacattgc aggtagcaag ttgaatataa ttttctaaa gtagcaccca     12120
cagcagccaa attatcagat gtatatagta gactagtttt aagaaaagca cttatgggta    12180
gaatatacat ctggatttt gaggcagttt tatttaggaa ttgtgtggtt ttctggaaca     12240
tctcagagac ctggtatgaa aagcactctt ctaatatata tgtgttttt tttatggatt    12300
tagtgatata tctatacaca cacacttttt aaaacctata gccggctggg cgtggtggct    12360
catgcctgta atcccagtac tttgggaggc caggcgggt ggatcacaag gtcaggagat     12420
tgagaccagc ctggccaaca aggtgaaacc ctgtctctac taaaaataca aaaatagctg    12480
ggtgtggtgg cgtgtgcttg taatcccagc tactcgggag cctcaggagg agaatcgctt    12540
gaacctggga ggcggaggtt gcagcgagcc gagatcgtgc cactatactc cagcctgggc    12600
gacagagcaa gactctgtca caaaaaaaaa aaaaaaaacc tatagccttc tagagaaatt    12660
tatatatgaa gtacacaact aacatagcta cacttcctaa atttggaatg gagtggttta    12720
gcttatgaaa agttgctatt tttcttaaca ggttataagc aatgccttga aagtttgggg    12780
tttagaacta atcctgttca acagtccaga gtatcagagg ctcaggatcg atcctatgta    12840
agattctgtt ttgcatttca tacatttctt ttcccaaatt tgattttaa agttgtaatt    12900
tcttaaagaa gagaaataca ttttgaatac ttttgttttg atgttccctg tttcattcac    12960
tcagactttc ctatttcacc tttgtgatgt ccatgacagt ctgccctgta gccttcctgg    13020
caccccagtg tctgtggcag cacagagctg accccataag tggcgcatga ggcatccttg    13080
tggcacagca tcactaagct gctgcagaga cgttcatatg gttgtgtgat cttttaaaaa    13140
catcagtgac acttaactat aaatataatc ttaaattatc acaattttta tataatattt    13200
gccagtagac aacataaata tgaattcaat atttcaagtt aatattgtct gttttctttt    13260
ttagaaatga aagatcattt atatgcaatt ataaggaaca ctggtttaca gttagaaaat    13320
taggaaaaca ggtaacattt cttacccttc cttgtctttt tttcttatat tgtacccccat   13380
ttaaaactaa aatgtgggcc aggtgtggtg gctcatgcca acagtttggg aggctgaggt    13440
gggggggatca cttgaagcca ggagtttgag accagcctgg gcaacaaagg gaggtcctg    13500
ctcttaaaaa aaaaataaaa ataaaaataa aaataaataa aaaaaaaac aaagagccag    13560
gcatggtggc tcacatctgt aattccagct tacttggaag gctgagtcag aaggatcact    13620
tgagctcagg agtttgaggc tgcagtgaac tatgattttg tcactgtacc ccagcctggg    13680
tgacagagta agactgttct ataaaaacata aaaattaaaa aaatataatt aaaaattaaa   13740
aaaaaaaaag gattgctgac tttaaaatta ggaaactgac cagtaatgtg tgtgtgtgta    13800
gcatggttta tccttcttga tagatagaaa ttgtcatttt aaaagataat atcagttttc    13860
cttataaatt tattgtgac aagtatatgc aatttaacta tatcataaga aaattctat      13920
attaaagata atacaaatgt ggttacttt aagtgggttt ttatgtgatg actatgttct      13980
gtcagttaat tattacattt atagatttgt atttagcata gtgctgtcac aaagcctgaa    14040
atagtgtcaa gcatgaataa agcattcaat tatgttgct ttagtgtaag attattcatt    14100
atgattccaa aagccatgta atacgtacgt ctacagaaaa tcacttctat tttttaaata    14160
aaacatgaaa tatgtcttga gcaagctatt ttaagaaaca atcatttaac gtccttgtta    14220
ttagaatttt gaatctttga aagagggtta ttgaaaacca gctaggacag taaaaagaa    14280
taaactagtg atacatgcag caatatggat gaatctcaaa ataattatgc tgaaagaata   14340
acccacaaac aaaatactac ctgctgtatg gtatcattta ttaaaagtct agaaaagtgc    14400
agattcatct gtagtgatgg aaagcagatt gaccagcggt tgcctgggga cgagaaggct    14460
atggaggagt gagaggggag ggttacagag aggcacggga aacatggcaa tgaggaatgt    14520
gttcactatc ttggttgtag taatggtttc atgggagtac agtatacaaa tgtgaaaaca    14580
tttcagaggc cagatgcagt ggctcatgcc tgtaatccca gcacttttgg aggccaaggc    14640
aggaggattg cttgagctca aggagttcag gaccagcctg gcaatggca caagacccca    14700
tctctaaaaa aaaaatgaaa gaaaaaaaaa ttggctaggc gtggtgatgc atggccgtag    14760
tcccaggtgc tagggaggct gaggagggag cacagaggtc aagcctgcag tgaatcatga    14820
tcgtgctact gcactccagc ttgggtgaca aaggagatc ctgtctcaaa aaaaaagttt     14880
caaattatac actttaaata tgtgcagttt attatatgtc acttataccc caataaatct    14940
gttttttta aaatgtaaat acaagccaaa aaaggtataa gtcaagaaaa tatattgaat    15000
taaatctgta agagtataatt caaaaacaaa aaccctattg ttatcttta agtcacccaa    15060
atcaaatttg ggaaaagtca cctacttagc ttcatcctaa gttggttctt tctttctttc    15120
tttccttctt ttgagacgga ttcttgctct atcgcccagg ctggattgca gtggcgggat    15180
cttggctccc tgcaacctcc gccacctggg ttcaagcaat tctcttgtct cagcctccca    15240
aatagctgta tctacagcca cgcaccacca caccagcta atttttgtat ttttagtaga    15300
gacggggttt cgccatgttg gtcaggctgg tcttgaactc ctgacctcag gtgatccgtc    15360
cgtctctgcc tctcaaagtg ctgggttac aggcgtgagc caccatgccg agccctaagt    15420
tggttctttc ttaaagttct tcctgaggag ccaagagcaa gttaaggaga tgtaacctag    15480
aagcttacag tggaggctag ctgggtgcag tggttcacgc ctgtaatccc agcactttag    15540
gaggctgagg cagggagatc actgaggcca ggagcttgag cccaacacag                    15600
tgacaccttg tctctacaaa aaaaaaaaa aaaaaaggca gcttacagca gtagaggctg     15660
atgcgagtgg gaatcacctc taggtaaaaa ccagtgtagc gtactgctga gattatttaa    15720
cctctgggtt ttatttatgt gttttaaaaa attatgatcc agtattttt acttttttt     15780
gtataaagta agcactgaat ttaaggtt gtattaattt gcaataaaat gtctatctta      15840
ttattttgag aagatttaaaa aatttagtt cttcaaaatt gatttttcac attttgaatt    15900
acgttatctt tgacaaatac agaagatgtc aaatttttggt ttattttctt tggttctaat   15960
ttatattttt gtttaaaact atattttca ctatagactc tttctgtctc tcgaggtccc    16020
tgtataatga aaagaaggc tggaaaaagt attaacattg tcaaaatcca ggaaaagtag    16080
ttggtcatga tattgatcgt taactttaga aactttttgt atcttgtggg ttaaattagg    16140
attactatgt ggtagtgata aatgatgtta attagggccg agtgcagtgg ctaacacctg    16200
```

```
taattccagc atgtagggag gctgaggtgg gaggatgtct tgaatccagg agtttgagac   16260
cagcctgtac aacatagtgt aagccccttc tccacacaa aaaaattaga aaatttgtca    16320
agcatcttgg tgcacacctg tagtcccagc tgcttgggag gatgaagcga gagaatcact   16380
taagcccagg tgttcgaggc tgcagtgagc tatgattgca ccactgcact ccagactaga   16440
tgaccatctc ttttaaaaaa atgtgtttat atgttatatg tgatagtgct ttttaaaaac   16500
atttttaaat tatagagaca gggtctcact atgttacagc ccaggctggt ctcaaattcc   16560
tgggctcaag caatcctccc accttagcta acctcccaaa gtgctcggat tataggcatg   16620
agctgcatgc ccagctaatt tagtgatttt taaaaactga gctggtaatt ataaattctc   16680
ttcctggaac ttctgacttt ctcacaattg gaatcttttg acaaaaatta tcagtaatgg   16740
gaaaactttg tgtagttgtc attttcctc ccatcagtgt gatagatatg attggagtta    16800
tgttggactg atattttgaa aaaagattta attatagcta ttaataaaga catttaaact   16860
actgactatg catttttatt cttttgggag ggtttaatgt ttatagttta aagcaaactg   16920
ttgttttaa aaaagtatct aacagggccg ggcgcggtgg ctcacacctg taatcccagc    16980
actttgggag gccaggcgg gcggatcaca aggtcaagag atcaagacca tcctggctaa    17040
catggtgaaa ccctgtctct actaaaaata caaaaaaata gctgggtgtg gcggcgtgcg   17100
cctgtagtcc cagctactcg ggaggctgag gcaggaggat ggcatgaacc cgggaggcgg   17160
agcttgcagt gagccgagat cgcgccactg cactccagcc tgggcgacag agcaatactc   17220
tgtctaaaaa aaaaaaaaaa aaaaaaaaaa gagtatttag cagaggccag gtgcagtggc   17280
tcatgttgt aatcccagaa cttggggagg ctgaggcggg cggatcattt gaggtcagga    17340
gtttgagacc agcctggcca atgtggcaaa tgtgctgtct ctaactaaaa atacaaaaat   17400
tagctgggtg tggtggtgca gacctgtagt cccagctact gggaggctg aggcaggaga    17460
atcacttgaa cctgggaggc agaggttgca gtgatccgag atcatgccac tgcactccag   17520
cctgggttac agagtgagac tcttctcaaa aaaaaaaaaa agtatttaat agtgataaat   17580
ctgcagtatt ctcttgtagt ttttaagatc atattattca gtcaaagaaa agagctcaac   17640
ttgaaatatt tccagagttt aaacaatctt actaagcttt gatgggttgt atctattctt   17700
aacatgtaaa acttccttat tacctataat atacactaac ttaaatattg acaattttt    17760
tccagtggtt taacttgaat tctctcttga cgggtccaga attaatatca gatacatatc   17820
ttgcactttt cttggctcaa ttacaacagg aaggtaagta acggctgaac attttgtaat   17880
gttacctttc gaagtagtta ataaccagg cacattagat gacagtgtga taaaactgtt    17940
tttctggcag tggcagtgaa acaatcttta gttttgacgt ggtgataggc tgtgatttgg   18000
gtgacgctgt tcagttagag ttctcactga cacctggccc ttcctcttct gaggatgctg   18060
cttttctttgc agcccttcta agtaatggct ttttctttta tacatcacat atcacacggc   18120
tgagaggagg gatagatgtt tttcttcttt gcctcttcta ggccactgtt cttccttata   18180
aactccagtt tctttgaaat acatgcccct aacggctggg caggtggct cacgcctgta    18240
atcccagcac tttgggaggc tgaggcaggc ggatcacgat gtcaggagat cgagaccatc   18300
ctggctaaca cggtgaaatc ctgtctctac taaaaataac aaaaaattag ccggggtgtg   18360
gtggcggacg cctgtagtcc gagctactcg ggaggctgag gcaggagaat ggcgtgaacc   18420
caggaggcgg agcttgcagt gagctgagat cgcgccactg ccctccagcc tgggcgacag   18480
agcgagactc cgtctcaaaa aaaaaagaa aagaaaaaaa aaagaaatac atgccctag     18540
attaaactat cccttgtcct tttgcactca tccacaagtc tctttcatc agtgatttta    18600
ggatctgact cgttgtcttt ttctctactt caactacttt tatcattctt aattattct    18660
gtatcgtcaa tcaatccagt acctgcctct tagtttcaaa atcacttact cttgcttagc   18720
tattaccagt aatcataacc actgtcaaat ctcaattgca agcatattac tctttaacta   18780
ccacctccta tctttaaacc atgttttgtc tgtttttta ttccagccat tctttaaacc    18840
ctactgtggg gcccaagcat ttccttata cgcattcttc ctttcttcta ctgcttattt    18900
tctgtaatcc gtcatcataa tcactccatt gcattcttca acgtgtttcc cctctctccc   18960
tccatcatac ttgaatgaca aaatctcaa ccctggttaa accacatctt ggccttgtcc    19020
attcctgtac cagagtagct ggacgtggct aaaaaataac ataaaacatg atgattggtt   19080
ttacttttt cttaaatgat ctatccatcc attcacccat ccatctatca aagtgactag    19140
gcctatttct gaagcccagg ctggagtgca gcagcataat cacagctcat tgcagctcca   19200
aactcctggg ctcaagtgat tctccttgcct tagcctgttg agtagctgag actacaggct   19260
tgtgctacca cacctagcta aggttttact ttaaatttat tataatcaca aaattcagat   19320
gagccttag tgctgtctga tatttctact atgttttctt agtgatgtac caccctccaa    19380
ggtgtttata aaaaattatg taccactctc caagaagttt ataaaaaata atgtgccacc   19440
ctccaaggtg actaatttca cagcttatgt cttttaaacct ttaagcactt tcctctcct   19500
tacacacctt ccttgtggct ttccgttaca ttctgctgag aacatagaag caattaaaat   19560
tatgttcttt ctaccagcaa atttatcaat ttgcttatat cttcacctgt gctttgagcc   19620
tatttaaata gatgaatggt cccctacctc taaccaaaac cagtccctca cttgtgggct   19680
ggatcccagc tcttctcacc tactcaagat gttcctgctt tcatctctcc actctcttat   19740
ataacagtt cccccccct ttttttgtaa tattcctata agcagtaaaa taagcttttt     19800
atttccattg attaaaaata aaaatcctc cttaattcca tgaaactcca gctgcctccc    19860
catttttatt ttttccttag gattgtctct agtgtgcctt ctcctttct tgaactctgc    19920
ctcctgggtt caagcgattc tcctgcctca acctcccgag tagctgggat tacaggcgtg   19980
caccaccatg accggctaat ttttttttt tttttttgg atggagttc cctcttgttg      20040
ctccggctgg agtgcaatgg cgtgatctcg gctcaccgca acttctgcct cctgggttca   20100
agcgatttc ttgcctcagc ctcccgagta gctggattta caggcatgtg ccaccatgcc    20160
tggctaattt tgtattttag tagagatgga aggggttttct ccatgtttgt taggctggtc  20220
tccaactcct gacctcaggt gagccgccca cctcggcccc ctaaagtgct gggattacag   20280
gcatgagcca ctgcgcctgg ccccggctaa atttttttt tttttttgg tattttagt      20340
agagacaggg tttcaccata ttggccaggt tggtctcgaa ttcctggcct cgagtgatcc   20400
acctgcctca gcctcccaaa gtgctgggat tacaggcgtg agtcaccttg cctagccatc   20460
ttttagtaat ggtatttgga gatcacaatt tgagtgctgg catgcttatt gctgctgggt   20520
ttgttatgta gttattgtga attcacattt aggaatatag ggttttttaat tctttgattt   20580
tagatacttg tatctttttt cttttatatt taaaaccttg gttcctgatg atatccctc    20640
ttagaaaccc tgtctacctt tggcttcag cccaccatgc tgtggttttc ctaacttgct    20700
gcctgcactt ttcagattcc tttcatggat cttaaatatc atctgtaaat aagatctatg   20760
tgtcaataat taccaaactt ttatcttag tcttgacatc tacccctgaac acctagcttt    20820
gactaactcc tagctttggc atctccactt ggaaatccaa aaagtgtttc aaactgaaca   20880
tgtctatgaa agacttattt ttttctctct atccatgcta tccatcaggt tttccatttc   20940
```

```
cataagggtg actcttgtac tctggttcct atatattata ccgacagagc agcccagagt  21000
gcttcttaac cagtgtaagg cctgttatgt cccaccctca ctctttgtcc ttcagtggct  21060
tcccagcaca cttagaataa aatctgaagt cttaggccgg gcttggtggc tcatgcctgc  21120
aatcccagca ctttgggagg atgaggggc agatcacttg aggtcaggag ttgatgagac  21180
cagcctggcc aacatggtga aaccctgtct ctaccaaaaa atacaaaaat taactgggtg  21240
tggtgttgtg cacctgtagt cccagctact cgggaggctg agataggaga atcacttgaa  21300
cccgggaggc agaggttaca gcgagccaag atcataccac tgcactccag cctgggtgac  21360
agaacgagac tctcaaaaaa aaattaaaaa aaaaaaatat gtgaagtctt gaataaaacc  21420
caagatcttt accatggccc ctgaacaggg cagagtatcc attcttcaga cactcttcat  21480
agaataccat ggtgagctgg catatttatt atacaataca gaaacaattt tactggcaga  21540
aaacacatta aaccgtctaa actctgaata cagttgtcct cataaaaaat gttcaacata  21600
ctattttgag gttttccatt aatagttctt ataatctttg tcccattatg tgttaatcca  21660
acaaaggata tccaataaca aacaccaaag tttaagaaaa atgtgctagg cgcggtggct  21720
cacacctgta atcccagcac tttgggaggc cgaggtgggc agatcacctg aggtcaggag  21780
ttcgagacca gcccagccaa catggtgaaa ccctgcctct cctaaaaata caaacattaa  21840
ctgggtgtgg tggtgggtgc ctgtaatccc agctactcag gaggctgagg caggagaatc  21900
gcttgaacct cctgggaggc agaggttgca gtgagctaat attgcaccac tgcactccag  21960
cctgggtgac agagtgagac tccatctcaa attaaaaaaa aaaaaaatt aatgatagag  22020
aaacttaaat cagttagatt gttttaggta tagcccatcc ttggttttg tgtgtagcat  22080
ctagcttggg gaaaccctgg attttctgaa tcatatttag acacagtcac actagactaa  22140
tgtaattctt ttgggatgca aaccacacgt ttgacacctt aaatagcttt taggtatttg  22200
gcttcccagc ccctattttt agttacaagg ggtgtacatg tgtgggtcag ggtgggggta  22260
gctcttttccg cagatgatta gttttagcca tgttactagt tattgcacac attatctgtg  22320
tcctcacagc agccctgtga gtaagtgtat tagggttctc tagagggaca gaactaataa  22380
ggtagatgta tatatgaagg gtaatgtatt aaggagtatc gactcgtatg atcacaaggt  22440
gaagtcccac aataggctct ctgcaggctg aggaaccagg aagccagtcc aagtcccaaa  22500
acctcaaaag tagggaagct gacagtgcag ccttcagtct gtggcaaaag gcctgagagc  22560
ccctggcaaa ccactggtgt aagttcaaga gtccaaaaga tgaagaactt ggagtctgat  22620
gtttgagggc aggaagcatc cagcatggga gaaagatgaa ggctcagcaa gtctagtact  22680
tccacactct tatttctgcc tgctttattc tagctgagct ggcagctgat tagatggtga  22740
ccacccagtt tgagggtggg tctacctctc ccagttcact ggcttaaatg ttaatctcct  22800
ttggcaaacac cctcgcagac acacccagaa acaataattt gtagccttca atccaatcaa  22860
gttgataata ttaaccatca caggaaggta ctagtatcat atgtttaaca gtagaaacca  22920
agacaaatgc agctaggaag tgggagaact gggatcagat gcaggcagtc tgattctaaa  22980
tcagttgctg ttaccccactc tgacaacagt aagtgagtag cctgctcagt caagtactat  23040
attagtaggg cccttttacag acatatttat ttcctcacagt cactcaatga gacggctctt  23100
ccagtcttac aatggagaaa gtgaggctca gagacttttaa gtaacttacc ttagacgact  23160
ttactagtaa gtataagaat cattatttgg actaaagtctg ttctgaatcc tcagcttgta  23220
ttttttttcca gtgttctgtg ctgccttttt atctactagt gttttacatc aattttgaat  23280
ctctttacta actggttagg ttgatttttg ccttttttt ttaggttatt ctatatttgt  23340
cgttaagggt gatctgccag attgcgaagc tgaccaactc ctgcagatga ttagggtcca  23400
acagatgcat cgaccaaaac ttattggaga agaattagca caactaaaag agcaaaggta  23460
aaaatgaggc ctgcagtatg gaatatatgt tagtatttca ttatgagaat taaattttca  23520
tgcttagatt gaatatgtgg tccttgtgtt gttggcgact ctattttgga ccttatattt  23580
tagtgaagtt tattagtta aacttgaatc aactctttga aatacttaaa tatattaact  23640
tagttagctg gtatggtata ttcctagcac ttcgggaggc tgaggcaggc tgattgcttc  23700
aacccaggag ttcgagacca gcctgggcaa catggcaaaa cctcatctct acaaaatagta  23760
caaaaattag ccagatgtgg tggtgtatgc ctatagtccc agctacttgg gaggcagagg  23820
aagaaggatc acctgaaact ggggaggtag agactacagt gagccataat cacactaccg  23880
cactccagcc tggtcgagag agtcagaccc tgtctcaaaa aaaaaaaaaa aaagaaacgg  23940
aaaaaaaaaa cttagttgga ttcaaattgc aacacaatca ttatattact aggcttatt  24000
tgccagaaaa catttttaagt tttgacttac ttaaagcctt tacattacaa atgcctttat  24060
gttatgtcta aaatagaaga ttggttcag ttattaccag tgcttttgtt ctttagagtc  24120
cataaaacag acctggaacg agtgttagaa gcaaatgatg gctcaggaat gttagacgaa  24180
gatgaggagg atttgcagag ggctctggca ctaagtcgcc aagaaattga catggaagat  24240
gaggaagcag atctccgcag ggctattcag ctaagtatgc aaggtaaaga cattctgatg  24300
tgtgttgtat tcattgctga agaattgatt ccaattattc ttagatttca tggaagttaa  24360
tgtactctta gaggtgtttt gacaattact gcagaagcaa tagctatata gtgggctttc  24420
cctttagatt tcttataatg gaaatcactt tttacaacct atatttttatt aggagtagtt  24480
atattttttac tcctggttat tttatttggt ttcaacactg tactaacaca atagtaaatt  24540
gtggtttaa tctttgtggg tatcagttga cccttatcca aatcagctgt tacataata  24600
tgtgccatta gacactatgg aagggcctgg acagggaata taaactgatt ttacaaaaac  24660
ccaacattta ttggctatgc aacttaaacc gtaagcccac tttggtgggc ccagttttt  24720
agtgatataa actatcaata gagaaaagcg aaaacatatc ccctagacaa tctaggcaaa  24780
gaaaaatgtt aagacatagc tcaaagtagc ttaattaaaa gtttgaagtg ggttttttgt  24840
tttatttttt tctaactcat atgtatttgc ttctactttc taatgaaatt atttatcagt  24900
tgatttcctt agatatctaa ataaaattga aatttcatta atgggaagat tatttttatc  24960
ctgaactttt cttgcctcta tgcatgcctc tgagtactcc atatgtgtg caatcccatt  25020
tttgattaat agagtcctgc tggattagca gggacagaaa tcagctttag atttctttct  25080
tttttttttt tctttcttttt tttttttttt tttttgag tcagagtctc actgtcgccc  25140
agcctggagt gcagtgatct tggctcactg caacccctgc ctccgaggtt caagcgattc  25200
tcctgcctca gcctcctgag tagctgggac tacaggcgcc taccaccacg cccagctaat  25260
ttttttgtact tttagtagag atagggtttt gccctttggg ccaggctggt cttgaactcc  25320
tgacctcagg tgatccacct gccttggcct cccaaagtgc tgggattaca tgtgtgagcc  25380
accacgccca gccagaagag tagaatattc ttaaagagaa aacgtttaa aggcttactc  25440
aaatgagtat aaacaaacat attgttgctt gaattggtaa atacagtgat tggttttgt  25500
tgtgttgtgt tttgttttca ggtagttcca gaaacatatc tcaagatatg acacagacat  25560
caggtacaaa tcttacttca gaagagcttc ggaagagacg agaagcctac tttgaaaagt  25620
aaagtagttg gtacaagtta aagtagcatg tttaatattt gctttggcta tttttgtctat  25680
```

```
ttgtaaatgg ttactgcctg aatcctgtga atatttgaat gtatttttta aaaatttaca   25740
gcaaatagga cgggcacggt ggcttacgcc tgtgatgcta gcagtttggg aggccaaggc   25800
gggcagattg cctgaggtca ggagttcgag accagcctgg gcaacacagt gaaaccccat   25860
ctctactaaa aatacaaaag aatcagctgg gcatggaagc gtgcgcctgt agtcccagct   25920
gcttgggagg ctgagccagg agaattgctt gaacccggca cgtggaggtt gcagtgagcc   25980
gagatcgcac cactgccctc cagactgggg acagagtga gactccgtct ccaaaaatat   26040
atgtatatat atataaataa aaataaaaat ttacggcaaa taacatgaaa caaaaaaacc   26100
ttgccccaat actggataaa ttttttaaac tgagtgaagg aaaccttata aaatttcatt   26160
tattaaaaga aaaatgaaat taggacaaga caagaagaat gccaattgat cctttggatg   26220
tacttcttgc ttacctgatt aaccctgcaa aattcctcta ccaatcagta cgaaaaacag   26280
ctttggaggt atgggagcgc attcccaaat agacgtggta gttcatttag ctgctcatgg   26340
ccgcttcagg cagtcctgta agcctgttag catcagggga atggatgcaa accataaatc   26400
tggatcaact cctaaaacct taccttgtgc ccagccttgt aagtgcttgc taaataggaa   26460
ttccaccata tgaaaataca ttcttttcaa gtaactatca ttcagacttt tgtcccccac   26520
tttttttttt taaagaaaaa taaaaggctg ggcacggtgg cttacgtctg taatcccacc   26580
attttaggag gccaaggcag gtggatcacc tgaggtcagg aattcaagac cagcctgacc   26640
aacatggtga aaccctcatct ctactaaaaa tacaaaaatt agccgggcat ggtggtgggt   26700
gcctgtaatc ccagctactt ggaggctca gacaggagaa tcgcttgaat ctgggaggca   26760
gaagttgcag tgagctgaga taacgccatt gcactccagc ctgggggaca agagcgagac   26820
tcgtctcaa aaaaaagag aaagaaaact tcatgttaaa gattacaaga taaataatca   26880
gacccactga tcctaggtca gaaaacagag tcatagctca atctgactta ctatttgctg   26940
tatttcatcc attctgagat gcacatagtt tcacatttca atgtctctga aattgagaag   27000
catcttacag tcataattga cagtatatta gcagcccta taaatattgg ctcattttac   27060
atttgatggt ataatgaaga aaatatttac cttttttttct gttttgtttt taagtcacaa   27120
ctcagaagta gatgaaggaa aattctgatc agctgacatc ctcttaatgt gagatatttc   27180
tagtcttttat tcagtataga ttaatggcta attatatgtt aaatttcaaa gtagtgctta   27240
ttagtgcttt ttactttaa gtttcaaaat taacttttt attataataa actccaaatt   27300
tatacaaaag tagaaaaact agcatactcc tgtttatgac ccagattcaa caaatactag   27360
cacacggcca atcttgcttt tttttttttt ttttttgag atggagtctt gctctgttgc   27420
ccaggctgga gtgcaatggc acaatttctg ctcactgcaa cctctgcctc ctgagttcaa   27480
gcgattctcc cacttcagcc tcccaagtag ctgggattac aggtacacac caccatgcct   27540
ggctaattct tgtattttta gtagacacgg gatttcacca tgtcgtccag gctggcctta   27600
aactcctgac ctcaagtgat ccacctgcct cggcctccca gagtgctggg attacaggca   27660
tgagccactg agcccggccc aatctcgttt tataatactc ccatctccca ttcttttccac   27720
tgtcccacct gcaagtttgg attattttgt aacaaatctc aatcatcata ttattctata   27780
accattttaa tatgtgtctc taaaatatat tagctttatt tttaacatag ttaaatgcta   27840
ttgtcataaa ataataatca taataattaa ttgtaattct atatcatcaa ttatctagtt   27900
aatgtaaaaa ataaatctaa ggccaggcgc ggtggctcac acctgtaatc ccagcacttt   27960
gggaggctga ggtgggcaga tcacctgaga tcaggagttc aagaccagcc tgaccaacat   28020
ggagaaaccc catctctact aaaaatacaa aaaattagcc aggcgtggtg gcgcatgctt   28080
gtaatcccag ctacttgaga ggctgaggca ggagaataca ttgaacccgg gaggcgaggt   28140
tgcggtgagc cgagatcgtg ccattgcact ctagcctggg caaaaagagt gaaactccat   28200
ctcaaataaa taaataaata aataataaaa aataacttaa atctacttaa ttagaaaaac   28260
taacattcta aaaattttat tttaagaaat atcaaaattg gctgggcacg gtggctcacg   28320
cctctaatcc ctgcactttg gaaggctgag gtgggcggat cacctgaggt caggagggtc   28380
aggagtacaa gaccagcctg gccaacatgg cgaaaccctg tctccactaa aaatacaaaa   28440
attagccagg catgatgatg ggcacctgta atcccagcta ctcaggaggc tgagacagaa   28500
gaatcgcttg aacccaggag gtagaggttg cagtgagctg agatcacccc actgcactcc   28560
agcctgggtg acagagtgaa actccgcctc aaaaaaaaaa aaaagagaaa agaaatatag   28620
aaattaaagc atacatggcc aggcgtagtg gctcatgtct gtaatcccag cactttggga   28680
ggctagggca ggcagatcac ttgaggccat gagttcaaga ccaacctggc caacatggtg   28740
aaagcctgtc tctactaaaa atacaaaaaa attagttggg catggtggtg cacacctgta   28800
atcacagcta ctttggaggc tgaggcagga gaatcgtttg aacccagagg tggaggttgc   28860
agtgagccga gattgtgcca ctgcactcta tcctgggtga cagagcgaga tactgtctca   28920
aaaagaaaaa aaaaaggctg ggcgcggtag ttcatgcctg caatcccagc actttgggag   28980
gccgaggcag gcagattacg aagtcaggag atggagacca tcctggctaa tacagtgaaa   29040
ccccgtctct actaaaaaat acacaaaaat tagctgggtg tggtggcagg cacctgtagt   29100
cccagctact ctggaggctg aggcaggaga atggcatgaa cccgggaggt ggagcttgca   29160
gtgagcagag atcacaccac tgcactccag tctgggcgac agagcgaggc tctgtctcaa   29220
aaaaaaaaaa gaaagcatac tctcacctcc ttcagtgact gatgttagta ttttggcaca   29280
ttctttttct gtgacatata cacacttacc ttgtaagtgt tgtactcatt tcctatgaca   29340
gtaaatagtc tttgtaacag gctgcatgat atttcataaa atgaatggat gtggcataat   29400
ttatatgtga gccttttgaa ttctgctatt ataattaata ttgcaatgaa caattcttat   29460
attgcctcta cacctcaaat gtcttatcat ttcttctagt ttttctgagg atgtcagatt   29520
attgggttaa aggatatgaa cattttttaag gccttgagaa agatttctaa attgctttcc   29580
agaataattc ccatgtgata cttttcaccat gtttatttca gacttttttt tttttttttt   29640
tttgagacga aatctcactc tgtcacccag gctgagtgt agtggcatga tctcggctca   29700
ctgcaacctc cgcctcctga gtttaagcga ttattctgcc tcagcctccc aagtagctgg   29760
ggttacaggc aagtgccctcc atgcctggct aattttttgt tctttttgtag acatggggtt   29820
tcaccatgtt gcccaggctg gtttcgaact cctgagctca ggcaatctgc ctacctcggc   29880
ctcccaaagt tctgggatta caggcgtgca ccaccgcgcc cagccatcag agctcttttt   29940
gtcaaaataa aatggtctaa agacatacat catagagaaa ctataataca aaatttacag   30000
gtatatctaa gaaaagaaaa gtatatttaa agcataataa taaactgctc ttttacttaa   30060
aattttttaa aaactgatt aaaaaatatga aacttccaac aaattggct tttttttttt   30120
ttttttttctt ttttgagacg aggtctcgct tttgtcaccc agtctggagt gcagtggcgc   30180
gatctcggct cactgcaacc tccacctccc tggttcaagc aattccctg cctcagcctc   30240
ccaagtagct gggattacag gcgcatgcca ccacgtcggg ctaatttttt tgtattttta   30300
gtagagaggg ggtttcacca tgttggccag actggtctcg aactcctgat ctcaggcaat   30360
ctgccagcct gggtctccca acatgctggg attacaggca tgagccactg cactcggcct   30420
```

```
gaacttttta tagtagtaac gataattcag taatgtccaa taatgactaa gtaagttata    30480
acaagtacaa tgtcagcaat aactagtgct tttagtaaaa cagggtcagg caaccttgta    30540
cccttttaaa aatgttcgaa tatcgatata cctccttcct acttggtgga ggattgattg    30600
aggaggaaag tgtgcagtga tggttaccag cttcagcctc ttggcttgac tttgcaaata    30660
ctggtgagaa tttggaaaga gcttgagaat atcttacata gtcacatgtt gctgagaaga    30720
gttaagaact aacttcttga tgttcatttt taacaatggc ttgcattcaa aaccttgtag    30780
agctcattag taggagctaa gaagctaata tttgcctttc actaaaaattc ctgattactt    30840
agcctaggta gttcgttgtc tctctaggtt ctgtctttgg gagcttgggt ctaaggttat    30900
caagctaact cttcttccc tctcacccct cccaaattga ccctggtgct gatttgttat    30960
tcatacgatt ttctagttt tcttttcct ttttgagtat ttgaagcttc atactgaata    31020
tagtaatcat agtattcatg cataaagaaa atcataaagt aattgcataa atgcataaag    31080
taatcatagt tttcatgcat taaaaaaact agttttggct gggcgctatg gctcacgctt    31140
gtaatcccag cactttcgga ggccaaggca ggcgaatcat ctgaggtcag gagttcgaga    31200
ctagcctggc caacatggcg aaaccctcttc tctactaaaa atacaaaaaa attagccgag    31260
tatggtggcg ggcgcctgta atcctagcta tttggcagge tgaggcagga gaatcacttg    31320
aacctgggag gcagaggttg cagtgagccg aggttgtgcc attgcactac agcctaggcg    31380
acaagagcaa gactccatct caaaaaaaaa aaaaaaaaaa aaaaaactcc ctattacaga    31440
ttcataattt atgagtcatt aaataatatt ttcaagccat gacattttt ccagcagtag    31500
tctctaaatc tgttttacca tcataaaaacc caagcaaaa ctctactaca tcagctgtgt    31560
cactgtaaaa cctgccttaa ctcacagaag catgaaatta agcaatgtgt gtgaaactat    31620
tttataaact gtaagtatt ccatacatac atgttggcag ttattaatgt cttctctagg    31680
tgtggctttg aaatggatgc agatgctttc tgttacaaaa aacataagtt gcaaatgttc    31740
tataacaagg agacacaa atatcttcat ggacatggat tgctatgagt gtttgattgc    31800
ctaatacttg agccaccact tcagtgatat ggtataattt atcaaacagt gttgagaaac    31860
agaaactact ggggatgttt taagaggaa aatacttaat atagaaatta ggggtttaca    31920
taatcttaag aaaggatgaa ggtgcagctc ttagccagac ctccacagta ccacaaacca    31980
acttgcagga agagctgtaa ccactgcccc agttgggaca atgggtaatg aggatattaa    32040
atttaagaac atactgctat agcaatgatc cttggcatag aaagctgcca ccacaattgc    32100
ctagagatgg gaacatgaag tctggccccc attgcaacag cagtgaagca gaattttggg    32160
actggcatct cccaaatggc tttgcttgcc accagagaac aaccaaagtg gagggagatg    32220
gctaggcctc atttctgcct attttatttt atttttttgag acggagtctt gtctgtcgcc    32280
caggctggag tgcagtagtg tgatctcggc tcactgcagc ctccgcctcc cagcttcaaa    32340
caattctcct gcctcagcct cctgagtagc tgggattaca ggcacccgcc actgtgccca    32400
gccaattttc ttattttag tagaggtggg gtttgccagg ctggtcttga    32460
actcctgacc tcaggtgatc tgcccgcctc agcctcccaa agtgttgtga ttacaggtat    32520
gagccaccat gcctggccca tttctccctt tttttttttt ttttttttt gaggtggagt    32580
ctcactctgt tgcccagact ggagtgcagt ggtgcaatct tggcgcattg caacctctgc    32640
ctcccagttt caagcaattc ttctgcttca gcctcctgag tagctgggac tacaggtgtg    32700
tagcaccaca cctggctaat tttgtttttt gttttgtttt ttttgagaca gagtctcact    32760
ctgtcaccca ggctggagtg tagtggcatg atctgggctc actacaacct ccgcctcccg    32820
ggttcaagca attctcctgc ctcagcctcc agagtagctg ggattacagg tgtgcgccaa    32880
cacacctggc taattttttt gtatttttaa tagagatggg gtttcaccat gttggccagg    32940
ctggtcgagc actcctgacc tcgtgatccg cccgcctccg ctcccaaag tgctgggatt    33000
acaggcatga gccaccgtgc ccagacaagg tttgtatttt tagtagagac agttttgcca    33060
tgttggccag gctggtcttg aactcctcac ctcaggtgat ccgcctgcct ggcctccca    33120
aagtgctggg attacaggcg caagccactg tgcctgaccc gtttctgctt tttaaagctc    33180
atgtgagcac ttaatttgta accagaatcac tacttgtaaa ataatctaaga acatgtagct    33240
tttagctttg taacctctat aatattgatg gcacagtggg agtggatgct gagtaccact    33300
tgaacatgtt ccacctcagt gtcttcacag ctggaaggtg tctacattgt ttcaaggtgg    33360
acaattgatt tacttctcat ttttcataaa ctaaaagtag aataaaggct attcctctaa    33420
aattgctatc tcacctgtca ctcccttgca ttctcacata ccttcttgag tggaggggca    33480
gagggcatgg agtgatagca gatgtgccga gaattctcca taactcagtc cgtccctctt    33540
gtgctatgtt gcagcatcag gatttgctaa tgggaggata ctgcccttac gtgcatcatt    33600
agccatgcac actaaggtct tacacctaca cacaggtcag tattctggct cagagaccaa    33660
caggggagaaa ttgcagttct cattagttga acttctttta ttgttcacag ttttaaaaca    33720
caaaattgag aggaactcta taaaaaatgt gccattctat taataattgt tgctggtaat    33780
ttaaaaatcc ttgttccttt tcaaattctt atataccttt ttttttaaa cacttgatct    33840
tagccaaaag accgagaagc aatcttttt ttttttttt ttttttttaa cctatagctt    33900
ctcactgaga ttgtcagctg tttgtaagtt ttggttttg gttttctgtg tttgtattta    33960
catatatgaa atacagattg agtatccctt atccaaaatg cttaagactg gaagtgtttt    34020
agatttgggg ttttttagga tttgtgaata tttgcactat acttaccagt taagcattcc    34080
aaaatccaaaa tttcaaatct gaagtgttcc actgagcacc tcttttgagt atcatgttgg    34140
tgctcaaaaa gtttctgatt ttggagcatt tggatttctg attctcggat ttaggatgct    34200
tgacctgtaa tttcagattt acataaagc agaaatagta cacagagctc cttatatcct    34260
tcacccagat tccccaatta ttggcctttc tgaaccattt gggaataata tgcagatatg    34320
attttccatt atgtctcagt tgttcagtgt atattttcta agtacaagaa tatattccta    34380
catatttaca tgataaccgt catgtttaaa catttttaaaa tggggatttg tattacattg    34440
tttctctttt tgaaaaaatt acagaggagc ttaatgcaat cagtattact taaaatctga    34500
taatgtgtgt taaatagtag tttcattta tttcatttat caggtgttca gtgaatgtga    34560
actatgtaac agcacagtta tcagcactgg ggaaatagat gagtaagata agatttgcac    34620
tttcattagc ttacatgcca taaagaggga aataaagaga acaccagatg atgataagtt    34680
tatgctgaga attaaaatga agtgatgaaa taatgggaat gtcaggtggc tacttttggt    34740
gggatggtca ggaaaggcat ctctggggag ataaattta agctcagacc tgagtgaaaa    34800
gaatgagcca gccatggaaa cattatgtta actcacatg tagtttgaaa tgcttttact    34860
gatcaaaggt acttatttt ggtgactttc aacaatatta agggtctata aaccaacact    34920
catttgcata agaataacta ccagtgaatc ttttttgtatg ataggttttt tgtttgttgt    34980
ttttttgaga cagagtctcg ctctgtcgcc caggctggag tgcagtggcg cgatcttggc    35040
tcactgcaac ctctacctcc ccggttcaag tgattctcct gcctcagcct cccaaagtag    35100
ctgggattac aggtgcctgc caccacgcct ggctaattt tgtattttta gtagagatgg    35160
```

```
ggtttcaccg tgttgtccag gctcgtgtca aacttctgac ctcaagccat ccacccgcct    35220
cggcctccca aagtgctggg attacaggtg tgagccacca ctcctggcca tgataggtta    35280
ttttgtgatg aaaataccta cctcttaatt tgtctgataa atttaaattt tatgtctaga    35340
tttcctaaga tcagcacttc catattttaa agtaatctgt atcagactaa ctgctcttgc    35400
attcttttaa taccagtgac tactttgatt cgtgaaacaa tgtattttcc ttatgaatag    35460
tttttctcat ggtgtattta ttcttttaag ttttgttttt taaatatact tcactttga    35520
atgtttcaga cagcagcaaa agcagcaaca gcagcagcag cagcagcagc agggggacct    35580
atcaggacag agttcacatc catgtgaaag gccagccacc agttcaggag cacttgggag    35640
tgatctaggt aaggcctgct caccattcat catgttcgct accttcacac tttatctgac    35700
atacgagctc catgtgattt ttgctttaca ttattcttca ttccctcttt aatcatatta    35760
agaatcttaa gtaaatttgt aatctactaa atttccctgg attaaggagc agttaccaaa    35820
agaaaaaaaa aaaaaaagc tagatgtggt ggctcacatc tgtaatccca gcactttggg    35880
aaaccaaggc aggagaggat tgctagaaca tttaatgaat acttaacat aataatttaa    35940
acttcacagt aatttgtaca gtctccaaaa attccttaga catcatggat atttttctt    36000
ttttgagatg gagtcttgct ctgtcaccca ggctggagtg cagtgtcgcg atctcggctc    36060
actgcaagct ctgcttcctg ggttcatggc attctcctgc ctcagcctcc tgagtagctg    36120
ggactacagg cgcccgccac atcgcctggc taatttttg tatttttagt agagacaggg    36180
tttcaccatg ttagccagga tggtctcaat ctcctgacct catgatccgc ccgcctcggc    36240
ctcccaaagt gctgggatta caggcgtgag ccatcacgtc cggccagaaa tcatgaatat    36300
tagtaggtga aaaataaaca catttacca cctggaaaat gaaaaatact tgagtataat    36360
ctaaataaca atgggaagtg cagagttact ttccaggtct cggtttaaat atgtcttaaa    36420
ctttggccaa ttagtagtag aagttgagag aaaaagtaac tatctgacaa agaaattata    36480
agcagaatat ataagaact cttaaaactg aataatcaga aaacaactca ataaaaaggt    36540
gaaggatttg aaaagatatt tcaccaaata agacataggg atgacaaata agcacatgaa    36600
aagactctca gcatcactag tcacaggaa atgcacgata aaaccacagt gagacaccat    36660
ggcaccccctg taggtatggc tttaatgaag aaataaaact gcaataccaa agtgttggca    36720
aggatccaag cagctgagac tcatatactg ttaatgggaa tgtaaaagtg tacagctttg    36780
gaaaacagtt tggcattttt ttgataaatg tatacttagc catgtgatcc agcagtccca    36840
atcatgtata taaccaaa agaaagaaa acttaggttc acataaaaac ttatatcaaa    36900
tgcttatagc tgaccaggca tggtggccca tgcctataat cccagcactt tgggaggccg    36960
aggttggcag atacctgaag tcaagtgttc gagaccagcc tggccaacat ggcaaaaccc    37020
tgtctctact aaaatacaa aaattagcca ggcgtgatgg caggcacctg tagtccagct    37080
attcaggagg ctgaggcagg agaatcacgt gaacccggga ggcagaggtt gcagtgagcc    37140
gagatcgtgc cactatactc cagcctgggt gacagagcaa aactctgtct caaaaaaaaa    37200
aaaaaaaaaa agggctggac acggtggctt acgcctgtta tcccggcact tgggaggcc    37260
aaggctgatg gatcacctga ggtcaggagt tcaagaccag cctggccaac atggtgaaac    37320
cccatctcta ctaaaaatac aaaaatttgc tgggcatggt ggtgggcacc tgtaatccca    37380
ggaggctgag gcaggagaat cacttgaacc cgggaggcgg agattgcagt gagccaagat    37440
tgtgccattg aactccagcc tgggtgacaa gaccaaaact ccttctcaaa aaaaaaaaag    37500
attatagcaat ctttattcat cattgcccaa aattacaaac tgcctaaatg tagaccttca    37560
tttagttaat gaatgcacaa actgtggtat atccaaacaa ttgaataaaa aaggaatga    37620
actggtactt ttttctattc ctcctgttta agtacagcca aaacacctca acatttgtat    37680
aaaacatgag ctgggctggg tgcggtggct cacacgtgta atcccagcac tttgggaggc    37740
tgaggcgggt ggatcacctg aggttgggag ttcaagaccg gtctgaccaa catggagaaa    37800
ccctgtctca actaaaaata caagattagt cgggcatggt ggcgcatgcc tgtaatccca    37860
gcttcttggg aggctgaggc aggagaattg cttgatcccg ggaagcgaag gttgcagtaa    37920
gctgagattg caccattgca ctccagcctg ggcaacaaga gcaaaactct gtctcaaaaa    37980
gaaaaaaaaa accattcagc tgaatctcaa aggcagagag aagacagact ggctagggac    38040
cttgaaacca gaggagcagt gtggtgggga gtggactgga ttttcttttt gcctcattta    38100
tcctggactt ggtgctggag aagctatggg ttcagaccaa gagaaacccc catgaaaagc    38160
ctgctctctc tagccaaaag aggcaaccta gcaagataaa aacctttaga taataagcac    38220
ttgactccag tcaaacaaaa cagaataaac tggcccatt caccctgtc agcaaaggcc    38280
aagtgggagc caagatatgt accccaacct ggaagtcata aggtacactt ctcccctttc    38340
ccagccaagt tggtgttaga gaaggctgac tggggagctg ggattctcat tccctccagg    38400
aggtgataac actcctttca catggtgtca gtggtcacga ggaggctgaa cttccaccca    38460
gtaatacata ggcatctctc tggctcctat atgggtgatg ttggagaaga ggccgagtag    38520
agaatccaga ctgttgctga cacccagcag taacaaggac acctccacaa tgtccgtgga    38580
ggccatgtgg agatcagtaa caaggcactg ctctcctcc cagtcagaga gatgtcagtg    38640
gaggactagg gggctagaac tcccatgtgc gttcagcagt aatccccatg accgccactc    38700
cttgacatca caggccttga agaaacctgg actttcactc ccctctggtt gtagcgaggt    38760
ggcactccct tttccctgtt gccagtgctg tgtcagtgga ggcttgctaa attgaagat    38820
gtaaataaga ttcacattct cataacataa taccccaaat tttcaggatt taattgaaaa    38880
tcactaagct gggcatggtg gctcacacct gtaatcccag cactttggga ggccaaggtg    38940
ggcaaacac ttaaggtcag gaattcaaga ccagcctggc caacatggtg aaaccctgtc    39000
tctactaaaa atacaaaaat tagctgggcg tggtggcaca tgcctgtaat cccagctact    39060
gggaaggcta aggcaggaaa atcactgaaa cctgggagac ggaggttgca gtgatccaag    39120
atcgcactag tgtactgcag cctgggcaac agagcaagac tccatctaaa tttgtgtcag    39180
gattcccaga aggagatgag aaagggtggg gctgaaaaga attgaggaag aagtcatggc    39240
tgaaaatttc ccaaatttgg caaaagtcag aaacctacag attgaaaaag ctgaatgaag    39300
ctcaaatatg ataaactcaa agaagttcac acagagacac atcacagtca gatttctgaa    39360
cactgcagac aaaaaatgaa gatctcgaaa ttagcaagaa atgaccttac ctaagcaatt    39420
tgaatgacag cagatttccc atcagagatc ataaaggcca gaaggaaggg gtacataaa    39480
catttttct agtgctgaaa gacaaaaact ctaggctggg cacggtggca cacacctgta    39540
atcccagca ttttggaggc tgaggcaggc agatcacctg aagtcaggag ttcgagacca    39600
gcctggccaa catggggaaa ccctgtctct actaaaaata caaaaattag ccaggtgtgg    39660
tggcacgcac ctataatcct agctacttgg gaggctgagg caggggaatc gcttgaacct    39720
gggaggcgac ggttgcagtg agccaaggtc gcgccactgc actccagcct gggcagttga    39780
gcgagactcc atctcaaaaa aaaaaaaatt atccaggctt ggtggtgggc gcctatagtc    39840
ccagctactt gggaggctga ggcaagagaa ttggttgaac ccaggaggtg gaggttgcag    39900
```

```
tgagccaagc tcatgccact gtactccagc ctgggtgaca gagcgagacc ttgtctcaaa   39960
aaaaaaaaaa aaaaaaaaaa acaagaaaaa aactctaaac ccagagttac atatccagtg   40020
aaatatcctt caggagtgaa gggaaaatta acgatttgtc ttcaggagac ctaccctaaa   40080
agaatggcta aaggaatttc tctaaacaga aagaaatga taaagaagt aattttggaa    40140
catcaggaag gaagaaagaa caataaaaag agtaaaatat gggtaaacac aatagacttt   40200
cccctccttt tgaattttct aaattgtatg atggttgaag caagaattat agcactgatt   40260
tggttttcag tatatatatt ggaaatattt aaggcattat gttacagatg aaggagggtc   40320
aaaggatata aagggaggta acctttctat atttcttttg tactgatgca ggcactttgg   40380
aaaataattt cactatttgt ttaaaaactg aacatacccct gaccatatga catagcatct   40440
atactcctgg gcatttatcc cagagaaaca gaaatttatt tatttttttt ttagtattac   40500
actccgtaag tgctgtaata ctagcactta gggaggctga ggcaagcaga ttgcttgagc   40560
ccaggagttc aagaccagcc tgggcaatgc tgcacagtca aaaagaaaa acaaacattt   40620
agaaaactat tttaaaagtc tttaattgct gaatgcctct ttggctaata tttggaagat   40680
cattattatt atttttcttt tttaggcaga tgcttgctct gtcactgagg ctgagtgca   40740
gtggcgccat ctcggcttac tgcaacctct gcctcccggg ttcacgccat tctcctgcct   40800
cagcctcccg agtagctggg actacaggcg tgtgccacca tgcccggcta atttttgtg    40860
tttttagtag agatggggtt tcactatgtt agtcaggatg gtctccatct cctaacctcg   40920
tgatccgccc acctcggctt cccaaaatgc tgggattaca ggcgtgagcc actgtgccca   40980
gcctggaaga tcattattta gtcctacaac tgacacattg ttccactgac gcaattgccc   41040
aggctggtct tgaactcctg ggctcaagca atctgcctgc ctcggcctcc ctaagtgcta   41100
gtattacagg cttgagccac tgtgcccagc caaaatagaa aatttatatt ctcacaaaaa   41160
catgtacatg aatgtttata gcagctttac ttgtcataat caaaaactgg aaacaaccaa   41220
aatgtcctac agtgaaacaa actgtagtac atccatagca tgtaatactc tactgtcagg   41280
attaaaaaga aacccactgt tggcacaggc agcaccgtgg ctggatctca ggggcattat   41340
gctgagtgca aaaagcctc aaagggtctt acactgtatg attccacttg ttcaactaaa    41400
aatgacagct gtatagagat agagaacata ttagtggttt ccactagtta ggagaaagtg   41460
gtaaaagata ggtgggtggg aatataaatc gatagcaggg agatctttgt ggtattataa   41520
cacttctatg tcttgattgt agtggtggtg gttacatgaa tacacgtgtg ataaaatgcc   41580
atgtagaact acatataacg ttgtgccaat gtcaatatct aggttttagt ttgatctttta  41640
gttacataag atgtaactat tgggtgaaat tgggcaaaag agtacacgaa acctctctta   41700
aatatcttta caacttcctt tgaattgaca gtttttcaaa atagaaagtt gggttttgt    41760
aaatacatga attgttgata tacaacaa atctcaaatg cattatgcta cgtgaaagaa     41820
gccatattca aaaggctaca tacctactga tgcctttat atgacgtgca ggaaaagata    41880
aaactgtagg acagagaata tactggtggc tatctgggat taggaaatgg ggatcgacca   41940
caaggggca gcatggggga attttctggg gcaatggaat ggttgtgtat cttgatggtg    42000
tatttgtcaa aatatataga actataaaag taaattttgc tttatatgta ttaaatcaaa   42060
aaaagaaact cgtgctcaaa tagaaataca ttttctgaga acttgccttt tgatgacttt   42120
gagaattttc tggaaatttt aaagaaatgt ggttttgttt cccaacaggt gatgctatga   42180
gtgaagaga catgcttcag gcagctgtga ccatgtcttt agaaactgtc agaaatgatt   42240
tgaaaacaga aggaaaaaaa taatacccttt aaaaaataat ttagatattc atactttcca   42300
acattatcct gtgtgattac agcatagggt ccacttggt aatgtgtcaa agagatgagg    42360
aaataagact tttagcggtt tgcaaacaaa atgatggaa agtggaacaa tgcgtcggtt    42420
gtaggactaa ataatgatct tccaaatatt agccaaagag gcattcagca attaaagaca   42480
tttaaaatag ttttctaaat gtttcttttt cttttttgag tgtgcaatat gtaacatgtc   42540
taaagttagg gcattttct tggatctttt tgcagactag ctaattagct ctcgcctcag    42600
gcttttcca tatagtttgt tttcttttc tgtcttgtag gtaagttggc tcacatcatg     42660
taatagtggc tttcatttct tattaaccaa attaacctttt caggaaagta tctctacttt   42720
cctgatgttg ataatagtaa tggttctaga aggatgaaca gttctcccctt caactgtata  42780
ccgtgtgctc cagtgttttc ttgtgttgtt ttctctgatc acaactttttc tgctacctgg   42840
ttttcattat tttcccacaa ttcttttgaa agatggtaat cttttctgag gtttagcgtt    42900
ttaagcccta cgatgggatc attatttcat gactggtgca ttcctaaact ctgaaatcag   42960
ccttgcacaa gtacttgaga ataaatgagc attttttaaa atgtgtgagc atgtgctttc   43020
ccagatgctt tatgaatgtc ttttcactta tatcaaaacc ttacagcttt gttgcaaccc   43080
cttcttcctg cgccttattt tttcctttct tctccaattg agaaaactag gagaagcata   43140
gtatgcaggc aagtctcctt ctgttagaag actaaacata cgtacccacc atgaatgtat   43200
gatacatgaa atttggcctt caattttaat agcagtttta tttatttttt tctcctatga   43260
ctggagcttt gtgttctctt tacagttgag tcatggaatg taggtgtctg cttcacatct    43320
tttagtaggt atagcttgtc aaagatggtg atctggaaca tgaaaataat ttactaatga   43380
aaatatgttt aaatttatac tgtgatttga cacttgcatc atgtttagat agcttaagaa   43440
caatggaagt cacagtactt agtggatcta taaataagaa agtccatagt tttgataaat   43500
attctcttta attgagatgt acagagagtt cttgctggg tcaataggat agtatcattt     43560
tggtgaaaac catgtctctg aaattgatgt tttagtttca gtgttccta tccctcattc     43620
tccatctcct tttgaagctc ttttgaatgt tgaattgttc ataagctaaa atccaagaaa   43680
tttcagctga caacttcgaa aattataata tggtatattg ccctccctgt gtgtggctgc   43740
acacatttta tcagggaaag ttttttgatc taggatttat tgctaactaa ctgaaaagag   43800
aagaaaaaat atcttttatt tatgattata aaatagcttt ttcttcgata taacagattt   43860
tttaagtcat tattttgtgc caatcagttt tctgaagttt cccttacaca aaaggatagc   43920
tttattttaa aatctaaagt ttcttttaat agttaaaaat gtttcagaag aattataaaa   43980
ctttaaaact gcaagggatg ttggagttta gtactactcc ctcaagattt aaaaagctaa   44040
atattttaag actgaacatt tatgttaatt attaccagtg tgtttgtcat attttccatg   44100
gatatttgtt cattaccttt ttccattgaa aagttacatt aaacttttca tacacttgaa   44160
ttgatgagct acctaatata aaaatgaaa accaatatg catttttaaag ttttaactttt   44220
agagtttata aagttcatat atacccctagt taaagcactt aagaaaatat ggcatgtttg   44280
actttagtt cctagagagt tttttgttttt gttttgttt ctttttgaga cggagtcttg    44340
ctatgtctcc caggctggag gcagtggca tgatctcggc tcactacaac ttccacctcc    44400
cgggttcaag caattctcct gcctcagcct ccagagtagc tgggattaca ggcgcccacc   44460
accacacccg gcagatttt tgtattttgg tagagacgcg gtttcatcat gtttggccag    44520
gctggtctcg aactcctgac ctcaggtgat ccgcctgcct tggcctccca aagtgttggg   44580
attacaggca tgagccactg cgcctggcca gctagagagt ttttaaagca gagctgagca   44640
```

```
cacactggat gcgtttgaat gtgtttgtgt agtttgttgt gaaattgtta catttagcag   44700
gcagatccag aagcactagt gaactgtcat cttggtgggg ttggcttaaa tttaattgac   44760
tgtttagatt ccatttctta attgattggc cagtatgaaa agatgccagt gcaagtaacc   44820
atagtatcaa aaaagttaaa aattattcaa agctatagtt tatacatcag gtactgccat   44880
ttactgtaaa ccacctgcaa gaaagtcagg aacaactaaa ttcacaagaa ctgtcctgct   44940
aagaagtgta ttaaagattt ccattttgtt ttactaattg ggaacatctt aatgttttaat   45000
atttaaacta ttggtatcat ttttctaatg tataatttgt attactggga tcaagtatgt   45060
acagtggtga tgctagtaga agtttaagcc ttggaaatac cactttcata ttttcagatg   45120
tcatggattt aatgagtaat ttatgttttt aaaattcaga atagttaatc tctgatctaa   45180
aaccatcaat ctatgttttt tacggtaatc atgtaaatat ttcagtaata taaactgttt   45240
gaaaaggctg ctgcaggtaa actctatact aggatcttgg ccaaataatt tacaattcac   45300
agaatatttt atttaaggtg gtgcttttt ttttgtcct taaaacttga ttttcttaa     45360
ctttattcat gatgccaaag taaatgagga aaaaactca aaaccagttg agtatcattg    45420
cagacaaaac taccagtagt ccatattgtt taatattaag ttgaataaaa taaattttat   45480
ttcagtcaga gcctaaatca catttgatt gtctgaattt ttgatactat ttttaaaatc     45540
atgctagtgt cggctgggcg tggtagctca cgcctgtaat cccagcattt tgggaggccg   45600
aagtgggtgg atcacgaggt cgggagttcg agaccagcct ggccaaaatg gtgaaacccc   45660
atctgtacta aaaactacaa aaattagctg ggcgcggtgg cagtgcctg taatcccagc    45720
tacctgggag tctgaggcag gagaattgct tgaaccctgg cgacagagga tgcagtgagc   45780
caagatggtg ccactgtact ccagactggg cgacagagtg agactctgtc tcaaaaaaaa   45840
aaaaaaaatc atgctagtgc caagagctac taaattctta aaaccggccc attggacctg   45900
tacagataaa aaatagattc agtgcataat caaatatga taattttaaa atcttaagta    45960
gaaaaataaa tcttgatgtt taaaattctt acgaggattc aatagttaat attgatgatc   46020
tcccggctgg gtgcagtggc tcacgcctgt aatcccagca gttctggagg ctgaggtggg   46080
cgaatcactt caggccagga gttcaagacc agtctgggca acatggtgaa acctcgtttc   46140
tactaaaaat acaaaaatta gccgggcgtg gttgcacaca cttgtaatcc cagctactca   46200
ggaggctaag aatcgcatga gcctaggagg cagaggttgc agagtgccaa gggctcacca   46260
ctgcattcca gcctgcccaa cagagtgaga cactgtttct gaaaaaaaaa aatatatata   46320
tatatatata tatgtgtgta tatatatatg tatatatata tgacttcccta ttaaaaactt   46380
tatcccagtc ggggggcagtg gctcacgcct gtaatcccag cactttggga ggctgaggca   46440
ggtggatcac ctgaagtccg gagtttgaga ccagccggc caacatggtg aaacccccatc   46500
tctactaaaa atacaaaact taagccaggt atggtggcgg gcacctgtaa tcccagttac   46560
ttgggaggct gaggcaggag aatcgttaa acccaggagg tggaggttgc agtgagctga   46620
gatcgtgcca ttgcactcta gcctgggcaa caagagtaaa actccatctt aaaggtttgt   46680
ttgttttttt ttaatccgga aacgaagagg cgttgggccg ctatttttctt tttctttctt   46740
tctttctttc tttttttttt tttctgagac ggagtctagc tctgctgccc aggctggagt   46800
acaatgacac gatgttggct cactgcaacc tccacctcct gggttcaagc gattctcctg   46860
cctcagcctc ccaagtacct gggattacag gcacctgcca ctacacctgg cgaatatttg   46920
ttttttttag tagagacggg cttttaccat gttaggctgg tctcaaactc ctgacctcag   46980
gtgatctgcc tgccttggcc tcccaaagtg ctgggattac aggtgcaggc caccacaccc   47040
ggccttgggc cactgttttc aaagtgaatt gtttgttgta tcgagtccctt aagtatggat   47100
atatatgtga ccctaattaa gaactaccag attggatcaa ctaatcatgt cagcaatgta   47160
aataacttta ttttcatat tcaaaataaa aactttcttt tatttctgcc cccttttataa   47220
ccagcatctt tttgctttaa aaaatgacct ggctttgtat ttttttagtc ttaaacataa   47280
taaaaatatt tttgttctaa tttgctttca tgagtgaaga ttattgacat cgttggtaaa   47340
ttctagaatt ttgattttgt tttttaattt gaagaaaatc tttgctatta ttattttttc   47400
caagtggtct ggcattttaa gaattagtgc taataacgta acttctaaat ttgtcgtaat   47460
tggcatgttt aatagcatat caaaaaacat tttaagcctg tggattcata gacaaagcaa   47520
tgagaaacat tagtaaaata taaatggata ttcctgatgc atttaggaag ctctcaattg   47580
tctcttgcat agttcaagga atgttttctg aattttttta atgcttttt ttttttgaa    47640
agaggaaaac atacattttt aaatgtgatt atctaatttt tacaacactg ggctattagg   47700
aataacttt taaaaattac tgttctgtat aaatatttga aattcaagta cagaaaatat    47760
ctgaaacaaa aagcattgtt gtttggccat gatacaagtg cactgtggca gtgccgcttg   47820
ctcaggaccc agccctgcag cccttctgtg tgtgctccct cgttaagttc atttgctgtt   47880
attacacaca caggccttcc tgtctggtcg ttagaaaagc cgggcttcca aagcactgtt   47940
gaacacagga ttcgttgttgtt agtgtgaatg ttcaatgagt tgtattttaa atatcaaaga   48000
ttattaaaata aagataatgt ttgctttttct a                                48031

SEQ ID NO: 43          moltype = DNA   length = 300019
FEATURE                Location/Qualifiers
source                 1..300019
                       mol_type = genomic DNA
                       organism = Homo sapiens
SEQUENCE: 43
gatgtcccga gctgctatcc ccggctcggc ccgggcagcc gccttctgag cccccgaccc    60
gaggcgccga gccgccgccg cccgatgggc tgggccgtgg agcgtctccg cagtcgtagc   120
tccagccgcc gcgctcccag ccccggcagc ctcagcatca gcggcggcgg cggcggcggc   180
ggcgtcttcc gcatcgttcg ccgcagcgta acccggagcc ctttgctctt tgcagaatgg   240
cccgcttcgg agacgagatg ccggcccgct acgggggagg aggctccggc gcagccgccg   300
gggtggtcgt gggcagcgga ggcgggcgag gagccggcag cagccggcag ggcgggcagc   360
ccggggcgca aaggatgtac aagcagtcaa tggcgcagag agcgcggacc atggcactct   420
acaaccccat ccccgtccga cagaactgcc tcacggttaa ccggtctctc ttcctcttca   480
gcgaagacaa cgtggtgaga aaatacgcca aaagatcac cgaatggcca tatcttttg    540
cccgaacccc agcagccgct gcgcctcccc ctcctccccct cttccaggct              600
gggagagaga cccgggggtt gatgggaggt ggggaggagg ggggtcttcc agggggctggg   660
agaggggggca ccgggaggag tgtgaaagaa tctctccacc ccgagctggg ttgagctacc   720
ctggaggctt gggaatgggt ttgtgggggg ctggggggtg gcagcggag agtggatcct   780
tcccaaggac cgactctaga atgagatctg ggccctgggg tcgtgcagga gccttggtgg   840
ggctttcga gccaagtccg gagggtttgg agttctacgg agtgagcttg gagcgggctc    900
```

-continued

```
gggcctgggc gcttctggcc agggcagggg aactatgggg gccttggttg ggttttcttg  960
gccgtcgctc actggagtcc acgcagggga agctggacag cctctccact actgctttcc 1020
ccaaggtggg gggccgccgc acttttaggg cagggcgctt gggggctccc agggctaaga 1080
gcaagaggga gtccatgtgg ccttcacact gagaagccag cactggccga agtgagtacc 1140
ccagggtggg ccgctgttcc tatctggaga ggatagtgat gggctggggg gcgcttatgt 1200
ttccctcatg tgtgcaggtc ccattgcctt taaccgctga ttggggaacc tcatcatctt 1260
tggggggtgtc gagaaagaga tcccacttgc tttatctggg cccctggcct gggaagacct 1320
gatctggaca ctttcagtaa gaaagacagg gcaacagcaa atgaggtggt gggtccattt 1380
tagagcacca tgtccagctt ttcctacccc gagtagccga gagggaacac caggagaatc 1440
agcacccatg tggacatctt aggtaggtaa atgccttta aattttttt tttttaatca 1500
aagatccaga ggaaaaggt gaagcccaca ttttcttctg tggagatgct atcaaaatgc 1560
agatcttctg tgtttcttta aatccctgcc tgcttgaaat aaaccttgag gagggcttaa 1620
catctatcga gatgtaggca ggcaagggtg ggtaattagt cgggctttct agcagttatc 1680
taagcatgac ccagattcca ggagggggga cacaccctgc tgcccaggct ggctggccac 1740
tgtgccatgc ccagatgtgc cgcttctccg cacagttcca accagctgcc ctctgtgtaa 1800
aaatgaacgg gctggatggg tccctggggc tcagcgatga gtcccctatc ccttttgtat 1860
gtggttttgc agttatagac taaacggggc tgggccctgt gtggtctccg ggggttgctg 1920
tttgaggagc atggcggtg gtagagggac tcacttcagg gggttcaaa atcgagcctg 1980
gcgcttggat cctgggtgct gggattgcaa cagagggcac tgaggttttg gagtgtgtga 2040
gtggtctact ttgagggtgg ggaaaattaa gaagttcagc agaggtgctt ttgagggggag 2100
catacctcta actacgatgc catctccgtt ggtgcccaaa gcaggtgcca ggtctttgct 2160
tcctaagttt cagactctta aagaggctgg ttcttaaggt tagcaattcc tcaccatcc 2220
aggcccattg aagtgctcag gggtggcttg attactctgc ctatcaacag agtgaggagt 2280
gggagtgcct tgcaggagga cagggtattc atgggtgcac acccagttag ctccaggagt 2340
gagagggctt tgctcggctg acaggtttcc tcattgaaaa tggctttaga tcgccttctg 2400
gagcctggat ttggagactt ctaagaggaa aggaaggagg tggggagccc ttctgctggg 2460
tccttagctt acctctgtcc agcctgaatc ctgcagattg gagggctgtt ggggagagg 2520
gggattgcag tggcccctcg gaaggggaa tcgtgggaga gggaggcagg tgaattgcga 2580
gtgttgcttg ccacttcatc tattctctgg ccagctcgcc cggggctttc ttgctcttat 2640
gatgagtttg tgcattatgc tctctgcaga ctgttttttgt tctcttttgac ccgaggtaac 2700
aaacacatta tacagcccta ctctggaagg gaaaactccc cacctcacaa tctgtcatcg 2760
agctgggtca tccaggactg agctttctct gtcctggatg gagcggaggg cggtggcggg 2820
gtgggtggga gggttggaga tgagagggga tggacagaga cctggggagg gaggtagtga 2880
ataaaagaat tcaggccagt gtaaagagaa agacacgtgg aatgtcagag tcacgatacc 2940
agggcagaac attctacttt ttaatctaaa tatttctgcc attaaaaaaa aatgtttcag 3000
catatcctga gagtgaaaaa aaagtgtgt aggtacttaa ataaagtcta atatatgtac 3060
aggcaagtac atatattcag atgcatagat ttttacaaaa tgaacacacc cacgtatcca 3120
gcacccaggt cccgatcagt gccctggaag tccccctccc cataccgcct cctagttgct 3180
cccccaacaa gggtaccgct cacctgactt ctaaggttca ttttgcctct tttaaacatg 3240
taaatggagt cacacagtac gttcttttgc cactggcttc ttttgctcac atctgtgtat 3300
gtgactctac tacaatctat ccattctact gttgatgggc atttgtgtca tttctgtttg 3360
tgccactggg aacattcttg tgtcttctat tattttttc ccacagttct cttagatagg 3420
agtggaatcg cccctgctac tttttgatgc atgtgttgtg ggatgtgtat ttggaaatgg 3480
tgttgactaa gggttgcagg tcgatatgga aagcaggttc ctccctgtct tgtttaagag 3540
aagtgagtga atgatccatg aacttgtcgg tatgctcaca gggcctaaga gtgctacttc 3600
caaatgtaaa ttctggcatg gtacactggt gaaggatgca gtcttgcttt ctccacactc 3660
ggggcaattt gtcactatga tttcttcctc tttcatccct cagtgggtca aacttgaagc 3720
catcaatgac aattaagaat cctcatttat ttcattttt cccctcttcc taagtgagga 3780
aacccaaatg gaagtctttg atgttcaaat ttacattgcc gtgttttct catgccaggc 3840
agcaagccgt cttgaccaca caccttggtt tcatgttttc attgactgga attgtgattc 3900
aaatagggcc atgagggtct ctgatgattg ccgaagagct cagatctgtc agctcaaaaa 3960
ggagcatctg tcagccttcc tagagttccc tccccactta atgccactca ctccttctac 4020
caagtgccaa ggtgaatgtc atcttttccag ccctccctgt gccaccaggt ctcccactga 4080
acatgatgta gaaactcagg ccatcggagg aacactggaa gcaggtcagt gtattatcac 4140
gcacagttgc ctgaattaca cgtagaattc cagcttttca tccggttttgc agaaaatctta 4200
acaagacacc taaagtcaca ttgacatcag gtgacatcac tttgacatct gtggacattg 4260
gctgattggc actcctctca tttttttttt tttttttttt tttaagaaaa gctctctaaa 4320
gagaaacttt ctgcatgaga agcgctggga gacatgggag caggttatca gactcttggc 4380
ctgtcctgag agatagaatg ttctagaagg tactgccgta gagggcagga tggtgtcact 4440
tacgtgatcc ttgtactaga ccggcttggc tggtatttcc agaggagcaa aattctgcga 4500
agtaaaattt agcacggctt ttccaatggg agtattttca aaaagggtgc aatttcttat 4560
ccacaattcc ccaatccaaa aagctccaaa aaccaaaaga cgagctcata tagaggtaaa 4620
acctaacctg aactgacttc agtttgaagt cttaatttac agttttcatt cattctactt 4680
gtgtgcatt tgagtatgtt ttgcagcaga aatgttaagt gtgctgtgat atgaggtgct 4740
gcttcagctc ctgactgtta ggtctgcatt gtagtcctgt caaactttca ggtgtatgga 4800
agttgtcttg ttaacaggat ggtctggtc cagcaggatt tgggtggggt ctgggattct 4860
gcttttctag ctagcttcta gggattcccc atgtggtaag ttcatgggct agggttggag 4920
tatccaggtt agatcataga gacatcttgt tatcattttt ctttccctta aaaatcaggt 4980
ttataggggc cgggtctggt ggttcacgcc tataatccca gcactttggg aggctgaggc 5040
cggtggatca tgaggtcagg agttcgagac cagcctggcc aacatggtga aaccccgtct 5100
ctactaaaaa tacaaaaatt agccaggcgt ggtattgtgc gtctataatc ccagctactc 5160
gggaggctgg caggagaatc atttgaacct gggaggcaga ggttgcagtg agccgagatt 5220
gcaccactgt acttttttt gagactctgt ctcaaaaaaa aaatagattt attgatgtat 5280
aatttattgt tagcaaaatt caccctttg acatactggt ctgcaagctt tgacaaatgg 5340
atgtagttgt ggccaccacc caaatcaaga tatgggacag tttcatcaac cctaaaatac 5400
ccccacagtg cccctcttga gtcagcaccc cacttctcca gccccttcaa ccactgatct 5460
gttctccatc cctacagctt tgccttttgc cgaaggtcat ataaatgtaa tttcacgta 5520
tatagccttt tgaatgtgga ttcttttact cagactttga gattcattca tgctgttgcc 5580
tgtgacagta gcgccttcct ttttggtgtt gagcaggatt ccatgatatg gatggaccag 5640
```

```
agtttgcttc ccagccgaag gacattggga tgcttccagt ttcaatgatt atgaatagag  5700
ctgctataaa cattggctta tgggttttag tgggaacatt tcatttcata catttcattt  5760
ctcttgggta aattaaccca ggagtgagat tgctgagttg tgtggtaggt gtatgtttaa  5820
ttttataaga ggctctcaaa ctgttttcct aagtggttgt accattttac attcccatct  5880
ttgcaatgcg tctaaaagcc ctgagttctg aattccaaag cacgtctggc ctcgatggct  5940
taggattaag gatgtggatc tatgaaaggt agtggaagta atagtgttaa atcccggtca  6000
gagaaataag aaagattaag gatgtcattc aaagctatgt gcctgcacta gagagagaga  6060
aagaaggggt tctcttgggt ggggttccac ccctccctgg tagttctacc attcccagg   6120
aaaaagtcaa gctctgaggc tgtgagaccc atgatctttt ccctgttctt caccactgca  6180
accccagtgt gtgggacaaa gcaggcgtcc tataaacgtt tgctgagcaa atgagaaaag  6240
gtacctgtct tcacccatta actaaattgt ataacatcta tctgatctac ccttgtgcca  6300
acgtttagg attttgatgg gttttagttg caggggttg agagactgtc catgagatta    6360
tcagaccaat gaaagtttct gaaatgttag tgcttgagta gattggatgc agcggcccct  6420
tgagaatgaa gtctttcttc agggacttgg agtgggaggc atctgttggg tgcgtagggc  6480
ttatgcttcc ccctccctgt ttccccccca gtagcaagca cacatataca ctttctcagc  6540
aataaaaagc accgccggga aggtggactc catccagaaa tgatcagagc ctaagagccg  6600
tgcagtaacg catttccgag aatgccagct cagctcctga gaaaagggcc ggatgggatg  6660
gtgcctgctc tgaaagaggg cagagaggag agggaaaaca ctccggactc tgggtcagac  6720
tggcccaggt tcacattatt caccagccat gttatcttgg gcaccagagc ctatttcttg  6780
acatgcatga tgaggatatt ccttctagta gcatctccct tggagggctc tcaggagatt  6840
aaatgggggtc gtgcgtgaaa aatggccagc acagtctcca gcacagagaa aaaccccaaa  6900
acgccagagc cgtaatacta tggagtcatt taggttccag tgttcttttt ttggaaaccg  6960
gccagaaaag aggctttctg ggtgggaatg ggagcgaagt gcccccccc accaccccct    7020
gcgactggtc agtgtggatt gattaacctg atcgtggcgc tctttaaagc cacctttgga  7080
cattttgcat tctccgttct ctctggaagc tttcaggggg aaaaaaattc gtggccactt   7140
gacccatttt tctattccct tgagtctaag gtaaaaatta atttctcttc ctcctttggt  7200
ccctccctct ctctgtgggt gacaaggtga gggagtttta aagtatataa ttagcttccc  7260
tcttcccctt ttgcactccc tgtctcttcc tttggggccg gtcgagagtg cagcccagga  7320
tggccacccc aggtgtccac tgcaaactcc acagaaaaac tttgctcaac ttttggttta  7380
gaatttaggt accccccctcc ccttccaaac tttggtcttc tttctcctca ctccctaaaa  7440
aaataggaaa aacaaggaac attcctggcg agggaaccat gagtgggcac agcaacttag  7500
gtttcaaaaaa ccactgggcc tcagttctta tctgagtagg gtgacccttc agccagggtt  7560
gcctgggact atcctgggtt tagcatctct ggaaactcac agtcctgggc aaactgggac  7620
gctggtcacc ctaatggtga gttcttaaca cctgagagag aagaatggtg caagagtgg   7680
tgccgttgac caagaaaggg ggagagtcag ttacttattc cctctgaaaa gccaagactt  7740
tttattggaa tgaatgcagc ttttagaagc cgtctttaag gcagctaata caagagagat  7800
tccagctatg aagggaaatg cctgagttaa gtccggatca agtttgaca tctcgcttcg   7860
gtcagacacg gctttatctg ccgttcagac tgggagcagc cgtgagtctt ccttaaaggt  7920
gcctgttgct caggcggcac ctgcagttag aaattagcag cctcccaccc ccagcccca   7980
aataacagga ttcaagagtc ccctctctga agccatgagg gaaacccaac ttagtcaccc  8040
acttgccagt aaataatatt catgctgtta agttctgttc tcatttagg cctatgtgta   8100
aaaaatatat gtaatttttaa actgattttt aaagtatttt catacgaaca gcatttgcag  8160
gaggggcgaag tctggatgtt acctttttgt aaaagtggat tgattttgtct tcaatgagac 8220
tctgggcag acttaaaact tggcccgcag tggtgttaca tggattctga tcttccagag   8280
tctgtcacgt tcttttatct ccatgatctt tattatcttc tttattgaga atgatgggca  8340
tggtgtgtgt gggtgggagg gctatgctga ccatcactgc agtgaaatgt gttcgtggca  8400
tgttgtggcg tctgcatagg aatgtgtctg tttgattaac agcacaagca gtggaggctg  8460
taaggaggaa aagaggaggg aaggtgtatat tggatggagg ggagacatat agagcttggg 8520
aacagtccac cctggctgca aatctcagct ccagctcaca gttgtggagc ctcagtcttc  8580
tcctctgtaa aacggggaca gtagtccat gtccgaggaa ttgtaagaag gttaaaagat   8640
actgtaccca gaaagcacat ggcatatata atcatcctgt gaagtagcca actcaatgaa  8700
tttttatttta tttattttga gtcagagtct cactctgtca cccaggctgg agtgcagtgg  8760
catgatcatg gctcactata gcctcgacct cctaggctca agcgatcctc ctgccttagc  8820
ctcccgagaa gctgggacta taggcatgca ccaccgtacc cagctttaac aacataaatt  8880
tatatatata tatatatata tatatatata tatatatata tatatatata tatatatatt  8940
tttttttttt tttttttttt ttttttttt ttgagatgga gtttcattct tgttgcccag  9000
gctggagtgc aatggcgcga tctcggctca ctgcaacctc cgcctcccgg gttcaagcag  9060
gacgatgggc atttgggatg tttctagttt ggggtggggg attgtttgtt tgtttgctgt  9120
tatgaacaat gctgctgtaa ggaatcaata atttttgaatg aatgaattcg aggtgttaat  9180
tttagtctgt gtacttggaa atctagcttc acctagaatc agctgagatt catccagcatt  9240
tatgccagga gctaagacat ttcacagctt actcatcatt ttctctaaga ggctgggtca  9300
accggttagc tcttggtcct gcttgtattc tgagagtcag aacctgtggt ttagacactg  9360
gcaattgata tggttgtaga gaagcagcat ggttgagttg agagcatgga ttctggagct  9420
aggtgctgg ggttcaaatc ccagctctac tagtcactgg ctgcgtgatc ttgggcaagt   9480
cacttaagtg ttctgtgctt cagtttccca gtctgtccca gtggtgattc taatagctcc  9540
atggggatcc taatagctcc tatctgggag gattaaatga gttaatacat ctgatgttta  9600
gagtggtgcc tgcacttag gaagcactat atgtgtttat acatggaaga gtggatagat   9660
ggatggactt atgtgggtgg ccatatttgg gcttctctga tccactgctg agaatagtgt  9720
gtggcacaca gtaggtgctg cataagtgtt aatattctgc tcttctctcc caagtctctc  9780
aactcccttg atctctgtta tttttggcgt ctgtgttgtt aacccattct tctgaatgat  9840
cagctgaatc actgttgctc caatatataa gccaaggaga acacaatcac aaggtctcat  9900
tgattgtcca tactagaatt ccatgattcc taggcccaag taggattttc cccacgtctc  9960
agcaatcctt cttccatgtt tctaatcttt ttctctcatt tgttatgccc cattgccaga  10020
ctctccaatc tccccacagc ttcccccttcc tctaactata ctgtctctag tcttacccttc 10080
tccctaaggg caccgtcttt gaagacatca aatacttcag agcaccaaat ataggttagc  10140
ttctctgagg gccttacaag gacatggagt gtttgggtct tacacaaatt ggaatggtca  10200
gaaatgttta gagacttgag ttgtctttga aagagttgtc agaatgcaaa ttttttgactt 10260
gtggcctgtt tctgatcaca acgcagtctt ttaagttatg gatcatagct ggatgtttgt  10320
ggtttagagg ggatggaggc atcctctgca gttagtgttg gatgtctggg tggatggatg  10380
```

```
gatggatgga tggatggatg gatggatgga tggatggttg aacagatgca tggatgagtg   10440
gatggatggga tggatgggat gaaggaagga aggaaggatg ggtgattgga gggtaggtgg   10500
gtggataagt agattggtag atgactcgat gggtgggtgg acaaatggat gggtgaatgg   10560
atgactggat ggatgactgg atggattggt gtatgagtga atatatggct ggatgaataa   10620
ataggcagat gactagactg gattgagggg taaaaatatg gatgactgga tgggtggatg   10680
agtggatgat agatggttga atgggtgggt ggatggtgg  atgttggata taagggtgta   10740
tggtagggta gctgtctatg tgtgggtctc cctgatattt ggtgttctgt ttgacttggg   10800
aatgaccaag tctctccgct taccacctta tttgtacctt ttccagtatc aagtgaattt   10860
tgcacacttt tgtaaaaatc aataagattg tatgtttagg actttgggag gccgaggcag   10920
gcagatcaca aggtcaggag atagaagacca tcctggctaa cagggtgaag ccccatctct   10980
actaaaaata caaaaaatta gccaggcgtg gtggcgggca cctgtagtcc cagctacctg   11040
ggaggctgag gcaggagaat ggcatgaacc cgggaggtgg agcttgcagt gagccaagat   11100
catgccactg cactccagct tgggcgacag aacgagactc catctcaaaa taaataaata   11160
aataaatatt atatgcttag gttttaccta tgtaattaga aagctccttg agggtagggg   11220
acagtgattt gccttcctca catcccccca aagttcctgc actatatcat gcataagtat   11280
ttaattgagt aatggtgagg aaagtaaaca gtgttattga acaaagatta ttaaaattct   11340
ggaaacacct ggttttgttt cagcactggg actgaaagtg gaattccttg gattttgctc   11400
cattggtgga taggatagca tgtggtggtg gactggtaga ctctttctct tccaagcaga   11460
ttgggtaaat gccccagatt cttacccact agtcagagat tacagattac tgattgatat   11520
ggttttttctc tgtgtcccca cccaaatctc atctcaaatt gtaatacccca catgtcatgg   11580
gagggacctg gtgaaggtga ctggatcatg ggggtgattt cccccatgct gttcttgtga   11640
tagtgagttc tcatgagatc tgatggtttt aaacttgtgg ggcctcttc  cctctctctc   11700
ctctcctgct gccatgtaag acgtgccttg ctttccctt  gccttctgcc atgatttgta   11760
agtttcctga ggcgtcccca gccatgcaga actgtgagtc aattgaacct cttttctttta   11820
taaattactt ttatagcagt gtgaaaacgg actaacacac tgatgtagca aggtccttta   11880
aggccccatg tgatctggtc cctgttttgt ctttgatctc atctcttca  ttgtctacct   11940
tcctttcatt gtctattctg tctcagccct gctgaccatt ttactcacac ccatgtcatt   12000
tgcattacat gacattcctt ctgttcagca taagctatt  cctctgcctg catcactgtt   12060
tctccaggtc tccccatggc taactccttc tcttcattta ggtctcagcc caaaagttac   12120
ctcctccaag aggcctatcc tttttcattta ctgaacatct catgtacaaa aaagaatata   12180
aaatatatgt atactctctc atccacaaaa aaatctctga agacatttta atgtatttca   12240
tcccatacct ttttatgcat gtaaactttt aggaacacat ttccatgcca ctaggtatcc   12300
ttgaaaaaat aagggccacc atgtatagtt gcacaggttg tgcactgcac aaagatagca   12360
tgtcacatat cttaagtatc atggagcttg tatgtctact atttcagtac cccagctgat   12420
aaaagcttaa gtatcttgtt ctagcaagat gaagctatta tgacattttt tgacagagaa   12480
aggggtgttt tgtttaagtt cacaatcaga gaaatgggtg tcttgtttaa tttcacaacc   12540
agagaaaggg gtgtcttgtt taaattcata cagtggtgct gtatgggttg gtggcaaccc   12600
cagaaaagac tgttgttaat atctgataat gttccacttt atacgtgtat tatattcatg   12660
taacaatctc tggctgtttg ttttgccatt ataaataaca gtgcagtaaa catctttgtg   12720
tgtgaatctc tgtccaaggt tctgatagtt ttctgaataa aattcctgtc tatatatggc   12780
actccaagcc cataattgaa actgctgtgt taccactttc tttgaatctg tagaaggaat   12840
tttgagaaca ggtgactggt atattcagga tgttgatgac aaggaacaga gaagaacag    12900
ttaaatggtt tggaattttt cctgggctgc atgtaaagca gtgcttttga actgggagca   12960
attttttcccc caaggggact tttggcaatg tctggagacg ttttttggttg tcacgaatgt   13020
agggggaggg ggcaagatgc tactggcatc tggctggtag aaaccaggga tgcagttcag   13080
catcttaaaa tgcacaggac agccttctc  agtaaagaat tatccagctc caaatgtcag   13140
taataccaag gttgagaaat cttgatgtaa tcgatgtcat gggtttcttc aagaggagtg   13200
ggtggattta gggttttttgg gtgacttaaa tttaatttac agtttgtctt cctagctggg   13260
tgtctaagcc agctttctgt gaactttaga tcccacacaa gaagcaacag gcttgctacc   13320
gacagattcg ttgatgtaaa tatagatgag tgtatagaag gaaatctcac ccagagctgg   13380
aaaatgttgg aatgaaaact gcggcggcct ccccttctct ctccttcccc ttctgttgcc   13440
ctgtttgaaa atcgtgcctt actttctttg gtctcctggc atggtgaatg ctgctggtat   13500
ggactgtgtt tctatatccc cttgatcccc acacccttag gaacgtacag gagagagacc   13560
ctggagcata tcagcttaga gatggagggg aatgggaagg agtgcgttca ttcattcata   13620
aatgttgact gagcacctac tgtatgctag gtgaatgggga ggacgtgagg gcagggaggt   13680
gacaaggttg gctattctg  ggctttgtga actatggtga ggattttgtt tttttccaaa   13740
ggaaatggaa taaccactcc ttttttcccc ccgatatacc taaactttt  gattttcata   13800
acaaaaatgg gcttccttt  gtatatttgt tttgagacca gccgttttc  caccaacact   13860
gatcacactg cagtgagcat cctggtgagag aagtcttgc  acacttctgt cactgtttcc   13920
ctaggacaga ttcctggaaa tggtatggca aggttgtatg tcaggctttt gggccaggtt   13980
gcaagaaaca ggaagtctgt gcccttcaa  attccaaggt cccctttccc tgacgacgtg   14040
gcccaatcag gcttgccctc ccttgatttt acatcttcac caatcagata agtgaaagtg   14100
aaatcctgtt gtggtatcct gtgcatttct ttggtgactt aagacataga gcatttttcca   14160
gatctctgtg ggctgttttgg atatccttt  ctctgttttc tcaggcacat tcttttaccga   14220
tgtcttttgag ggattgagca gtttctgttt gaaattgagg catgtcatgg ctctgtgtgg   14280
ggcttgaggc agtccagtgt agtggaggga gggaggctgt ggagcctggc tgcctaggtt   14340
caaataccaa ctctgcttat ttccattcat atcatttag  gcaaatcact tagccccctg   14400
ggcctgcctt tcctcatcag taaaagtggt ataacattag tgcctgcatt gtggggtggt   14460
tgtgaggaaa gcagcactca aaacagtacc tgacacacag tgggtgccaa ataagagtct   14520
gatgtattag tgttataggt atcggcctcc tccctcccca gtgcaatagt gtgtgtgcgc   14580
ctctgtgtac ctctgttggt gctgacaagc cttttttaaa atttagaggt gaggtctcac   14640
tctgtcccct aggctggagc acagtggtgc aatcatggct cactgcagcc tcaaccgcct   14700
gggctcaagc aatcctccca gcttagcctc ctgagtagtt gggactatcg gtgtgcacca   14760
ccacactgga ccctagaca  gcccctttat tccaaagcga aatgcagcc  acaagattta   14820
gtgcaagctc tccaagcttt aggaccagct gcaactcctc taactgacca aacaggatcc   14880
cccatgtccc caacccccaa aacctgatga aaagcaaaca gaccattttc cacattcatg   14940
acggaaaggc ccttttcttg gctcctgccc ttgctcatgt caggatttca ctccatccct   15000
gataaagagg aagcaccatg tcccaggagg acatggaaac tctctgcttt gtggtgaata   15060
gttacagtaa cagtagctcc tctctgtggg gagcttatga gccctaagc  tttatagaac   15120
```

```
tgccctggca gtttatgaga acttcatccc agcccccaga gctcatggca cttattttg   15180
cccccagttt gcagatgtgc acactgagac tcagagagct aacactgctt gccaaggtca   15240
cacatctagc aaatggagaa actttatgag acaggtgaag gcacagcaag gataaaaacc   15300
cagagggaaa aatactcaag ttttctccgg gaaaccattt gcattccaga gaggttggtg   15360
tgcgagtggg caagagatgt cgcgggacga tggttaaggg acagagtctg agctcaacta   15420
ggactaggtt tcttccttc cttccttcct tcctttcttc cttccttctt cctttccttt   15480
gtctttctct ccctccctc cttcttcctt tccttccttt ccttttcttt tccctccctc   15540
cctcccttcc ttcttccttc cttactcctt tccttccttc ctcctttcct tccttttctt   15600
tctcttttccc ccttcccctc cctccctttct tccttccttt cttttccttcc ttcctttctt   15660
ctttctcttt ccttttcttc ctttccttcc ttcctctctt cttccttctt ttcttttctt   15720
cttttctctt tctttcttc ttttcttctt tctttctttc ttttctttcct ttcttttctct   15780
ctctctctct ttctttcctt cttctcctt ccttccttcc ttcttttctt ttcttttcct   15840
ttcttttctt ttgttttttg agatggagtc tcgctctgtt gcccaggctg gagtgcaatg   15900
gcacaatctc agctcactgc aacctctgcc tcccggttca agcaattttc ctgccttggc   15960
ctcccaagtg gctgggacta caggcacgcg ccaccacacc cagctaattt ttgcattttt   16020
agtagagatg gagtttcacc atgttggcca agctggtctc gacctcttga cctcgtgatc   16080
ctcctgcctc agcctcccaa agtgctggca ttacaggcgt gagctaccac gcctgggcta   16140
ggactaggtt tctatcggtg tgtggctttt ggggaagcta cctaatctta accactctgt   16200
ttcgtcatct ataagataag cagtgtagca ttttcttgca ggaatgttgc aaggattaag   16260
tggatggtga ctgtaaaaca tcatgcgtgg cacatagtaa attctcagca ggtagtcatt   16320
gctggtcatt tacttttctc taatgaccag caagctctta atttcctcct tggcatgggc   16380
actgggacgt agatggacaa aacacagaga gaaataaaca cacggacaaa aatccccgcc   16440
ctggtgtggc tgatattctg ggtggggaga gagagggagt ccaaggacca gataaacagg   16500
taaaggatag tttgagtgtg gtaagtacta aggctcaaaa ataaagatct cccaggtgat   16560
cttagctgca tttggaggtg acaggagata caactgagaa actgagatag gaggaaaccc   16620
aagggagat gtgggcttga tttagggtga tctgaggagt aggagaagtc agggctggt   16680
gtggggaggc tctgatggtt ctctctgggg agtgaagcag ggattcgttg gggagacccca   16740
aggggacagg tgaaggcccc tgaacaggtg gccagtgctg agaaaggaaa ggtggaggac   16800
ccaagtgagt tcctaatttc ttcattgctc ccctaaggtg tttgtctcac ccttggccat   16860
agtcttggat cacttacaga tgcagaccag gctgggctca atggctttgtg cctgtaatcc   16920
cagcactttg agaggctgaa cccaggagtt tgagagcagg ctgggcaaca tggtgaaacc   16980
ccgtctctac aaaaaaatac aaaaattggc cgagggtgtt ggcacatgcc tgtagtccca   17040
gctacttggg aggctgaggt aggaggatct cttgagcccg ggagacctat gctgccaaat   17100
aaggtaggca gtagccacac atggctattg caattttaga aattaattac aggccacatg   17160
tggtggctca cacctgtaat cccaacactt tgggaggccg aggcgggcag atcatgaggt   17220
caggagatcg agatcatcct ggccaacatg gtgaaacccc atctactaaa aaatacaaa   17280
aattagctgg gcatggtggt gcacaccccgc agtcccagct actcgggaga ctgaggcagg   17340
agaattgctt gaacccagga ggcagaggct gcagtgagct gagattgcac cactgcactc   17400
cagcctgggc aacagagaga gactccgtct caaaaaaaaa aaaaaaaaaa aaaaaagaa   17460
aagaaaagaa attaattaca ataaaaacag tccctgagtt tcactggcca catttgaagt   17520
gcccgatgac cctgtgtggc ttagtgacca ctgtgctgaa tagtgcagat ctagagcatc   17580
ctactggaca tgttgccagg gtccctgaac caacagaatt agcatctcct gggagcttgt   17640
tggaaatgca gaatctcatc ccctacccca gacctgctca atcccaatct gctcttcagt   17700
gagattcctc aggtgatctt gactgcacct tctaatcact tggaagcttt aaaaatgctg   17760
aggctgggca cggtggctca cgtgtgtaat cccagcactt taagaggcca aggcgggtgg   17820
atcacctgag gtcagaagtt tgagaccagc ctggccaaca tggtgaaact ccatctctac   17880
taaaaattac aaaaattacc caggtgtggt ggcacacacc tgtagtccca gctacttggg   17940
aggctgaggc aggagaactg cttgaacctg ggaggtggag gttgcagtaa gctgagatgg   18000
cactgctgca ctccagcctg ggtgacagag tgggactctg tctcaaaaaa aaaaaaaaaa   18060
aaaaaaaaaa gaaaagaaaa aggaaaatgc tgatgccccca agctccaccc ccacagatgc   18120
tggagagatt tgtccagggc ttcccctgga gtggggaatg tttgaaaact ccccaaggt   18180
ttctaaagtt cagccagagt tagcagaaag cccattaggt ggctaagcag gtagactgaa   18240
gttggagctg tgtgaccttg ggcaagccac ttaccctctc tgaaccacaa gctccctct   18300
ctctaaaact agagacctgc tggcacctcc ctcccagggc tgtgagaagt aaatgatggg   18360
atgattcaaa gtgctgagta gggtcagatg cagtggctca cacctataat cctagcactt   18420
tgggacgctg aaatgggagg attgcttgaa gccaggagtt tgagaccagc ctgggcaaca   18480
tttaaacatt acccaggtgt agtggtgcat gcctgtagtc ctagctgctt ggggaggccga   18540
ggtgggggga tcccttgagc ccaggagttc aaggctgcag tgaacaatga tggtgccact   18600
gcactccagc ctgggggaca agagtgagac cctatttcta aaaagaaag aaacccaaaa   18660
tgctgagcga gtgccttgga ttgatagtaa gcagtgcctg tgtaataagc atgaattta   18720
aaaaatgagg tcagcagcct tagagctaat ggttaatggg tttgggtgtg ggattttttt   18780
ttttttaatt tttaaaacat tgagataaaa ttcccataac ataaaattga ccattaacca   18840
ttttaaagtg tacagtttgg tggcatttaa tacactcagt gttgtgcaac catcacctct   18900
ctgtagttca aagacccaaa aaaggagacc ccgtactcac tgaggctca ctccctgtct   18960
ctccccgctc cccagccccc tggcaactac taatcttctg tctgtataga ttgacctatt   19020
ctgattttgg gggttttttga actcgccttc cctggctgac aacctctcgc catccaggtg   19080
agactgtgtg aaagcccagc tccctgcatt tctgggtctt cctctcccca ctgggggctg   19140
cccccacctg tttccccctc tgggcaccct ggttctactc atcagcctgg cttaatccca   19200
gcagcaggtc catgttctgc tctcctgtgg ctgccacaaa tgagaggttt catctcagct   19260
gggtttctcc tagttaaata tttaataaat aagacctaca acttgtgatg ctgggagtgt   19320
ttgatagtga aattaatgat ggggagagag tggcaggcgg cccacaggtc catgctggag   19380
ctgggatgag gcgccctggg caggcgtccg tgccactgat gctgggaac cacggtgggc   19440
catgccatcc catttccccc agccagggcc tcttttttag cactgtgtcc agcacagggt   19500
agccacctga taataagtg ttaaaagaaa aggagcctg gtgtgtaggg aagaaggaag   19560
agacagagga gacaaagagg agacacagag agagagaga agatgagaga gaaagaaag   19620
tggaaggtga gaaagagaca gagatggaag gggagagaag gacctggatg gaggagtgc   19680
aaggaaggca atggtgaggg aaagagaga gacaaagaga tggaagggat gaaggagagg   19740
gagagatatg gaggtagaga aagagagaca gaaagagaag agagaatatt gcttcttgta   19800
tcttcccctt ctcctgttat ccttgaccat cttattattt ttttcttttt tctgtctctc   19860
```

```
cagttctcat ttccttaccc tcgccgtctt gccaactcgt catctcttttt catttcctgt  19920
gtctatgtta tcttttaatt ttctgtctgg gtattttccc cttttctctt tctcagcata  19980
aactgttggt tggtgtatgt gtcttctttc tttttttagtc tttaactgac gtgtgtgtgt  20040
atgtgtgtgt gtgagagaga gagagacaga cagacagaga gagagagaga gagacagaac  20100
aaacctagag agcagtgtag gaacatagat gaacatttta aagaccaaac catgaagcgt  20160
acacccattt tacccaggtc aagagccaca gggccaccat cagattctcc ctcatgctca  20220
tcctcaatca cagccactcc ttccctcctg gaggaaccac tattggagat tgtatgggaa  20280
ccattcgctt gctttcttgt gtggttgtac caccttaagta cgcatcctga agcaatatag  20340
tcagatatta tgtggttttg agttttatat gaataaaaat atgtgagagg agttgttttg  20400
tattttgctt cattggtttg cagttacctt tgtgagattt catcctcatt gtgtgtcactg  20460
cagctccttc atgatcttgt ttattcattg atgatgagca tgtgactttg ttctcttttg  20520
ggcactggca taagcagctt tgttggttgt ttatggattc tgctgctcgc ttgcaggggt  20580
ctctctggag cacatcgctc tgtgtgaaat tgttggatac taagatttgt acattttcac  20640
cttgactaaa cactgccaaa caattttcca aagtgcttgt gctaatttac actcctgccg  20700
gtggtgggtg agcattcaag atgcttcaca accttgccaa cacttggtat tgtcaggttt  20760
ttaagttata gcctttctca tggtgatttc tcattgtgat tttagtttgc atcccccgat  20820
tgcaaattag agtgaacata gtttaaaata tttattgact attcaagctt gctttttgt  20880
gaagtgcctc tacatgctct gtccatttt gattaggtca ctttttaaaaa aaaaatattg  20940
atttgtgggt gatccttaca tagcctgaa actgattctt catcattata tgttgtgcaa  21000
tattttctct tggcttggct tttgatcttt tttataatgt cttttgatca ccaacagttc  21060
ttaattttga tgtggttgat tttagaaatc ttttcctta tagtttgtgg gctttgtatc  21120
ttatttaaga aaatcatttc taccctgagg ccatggat atttatgtt atttctgaaa  21180
gttttacagt tgtgttcact gtatgtcttt aatcagcttg ggattgatt ttatatgtgg  21240
tggtaggtag gggtccaatt tccttttat tccataagaa ttgtcccagc atcatttatt  21300
aaaaagccca ttcttgcccc aatgatcgc aagacaacct cttgactgtt taacttttac  21360
cttctttcat ctggtctgtt tttatactca acctttgaag ccacaaatat ttattgagtg  21420
ccaactgtgt gccaggcact gagttacagt gacggatatg acagatgcaa tcatggcttt  21480
catggagttt acagtctggc aaggatgaca tgtaaatagt tattactact tataatttaa  21540
aatgttatag gccttgcaaa aagggacaag tctggcttgc tctaaaagaa acatgtgaaa  21600
caacatcttc cagggaagtg ctgataaact gagtctttag tgggcctctg ctattgtagg  21660
ggtgggaatg gtggaaaaga tgttttggcc acagggaaca gcatgtgcaa aggtcctgtg  21720
gaaggtgctt aggagtttga tatttatcct aaaggcactg tcaggctact gaagcagtaa  21780
tacaatgatt ttatgtctgt gaatagttcc actggttgct gcatggagaa tgtattggaa  21840
tacagcaaga ataaaaagcc atgagactca ttaggaaatg attcactca ttcagggaag  21900
tgtgccttgg gctggcatgg tggctgtgga gatggaaatc attgatcaga ttaaaagaaa  21960
ttttgagctg gcatgatttt tcccctctct ccctctctc tatctctgtt tcttttctgg  22020
ttgtgttttc tgggtgagaa aagcagtttg tgatcctgcc aagggtatgt gctctggagg  22080
atgtatttgc cacagatggt ctttggaatt ctggccaaga gagtcactgg acagcccctg  22140
gccccaggg tttctggagc caattcaaca atgactgttt attaacaaca gcaaggatga  22200
gttgctagcc tttccttcag agcacctttt aactgttacc ttactttgtt acccaaaccg  22260
acactatgga attggtgggg gagaagtgga agggttttta tctccatttt ttatagaacg  22320
ggggaagtta attggcactc ttgaaatcat acaaagatg ttggtttcag gattggtttc  22380
tggacttca gcccaatccc aattactcaa gctcacacac ccaatcccca aacatactct  22440
tttgcaaata atttccctac tgaggtgctc ctggccaatt taaaaggtcc ccatttcctt  22500
gcctataaaa tgggaattaa agtaaaaata tctacctgtt gacttgctgt gaggtcagtg  22560
ggcctgacac atggtgtgga ctcattatat ttacctatgt gaatcccta gttcccttta  22620
cttggaagag gtggaaaact caaagggct taaacaagaa gtgggattg tattggctca  22680
tgagactgaa gagtctcagg agtgtccagc ttcaggcttg tttggatcta gggatcagat  22740
aacaccatta ggcctctgtt tctgtttctt ggctctactt tttgcagctg gctccattat  22800
ccatgactta gctgcacttc cagccctcca gtctgcccaa gaccatattc agagagagat  22860
tcttctctct ttttcagcta tctttcccgga attttcagca aatgctttct tgcttttgan  22920
tggctgttgc tgaggtcgtg tgctcatgcc agaaccaatc actgtgggga aatgggaggt  22980
ggagaacggg gtgctctgat tggcttaggc ttgggtcaca tgactttatg gagttggggt  23040
ggagccaact tctccaagtg gggaagagca gtcttcttaa aggtgtatta ggatatgctt  23100
gctgctgtaa caagcaaccc ccaagtctgc agtagcttaa ggcaatacga atgtacttct  23160
cactcaccct aaatccaatc agataatcag caagtggcat tccatgtggt gatttcagga  23220
cccggctctt tccatctgtg gctccaccat ccccctaagat cagaaagtcc ttcacttccg  23280
gcctgtagga aaagagtatg aaggctcaca caggaagttt tgggaggcca catatagaag  23340
tagtgaacct tacttctgcc tgcattctgt ggactggaat ttcatcccat ggtgtatgag  23400
agagggtccc agtaggaaac ggaagacaca gaccaagaat caaattaaga gatagcttaa  23460
gaatcaaatt aagagatagc ttacaaaggt gtgggccctt actgaaatag agaaggagga  23520
agagaggaag gaggcagaga cagagagaga ctgagactca caaagacaca cacacacaca  23580
cacacacaca cacacacaca cacacacaca caagttgaga gaaagaaggg gggagagaaa  23640
gagagagga gagcattcc taacaggaag ctggcagaat aaatgtcccc cattgtccaa  23700
agccagaggg ctgggagccc agtgagccca tccacacagg tcagccccc atgtgacagt  23760
cctagaaggg taaagaagga aggagagtgg atttggggta atggaagaca gccaataccc  23820
atggtccatc tgactgcagg gggaactgag aaattcagtc catggagaag aaggtttagt  23880
ggacacgtca ctttgtcttt ttcacaaagt gaaactaggt tctcaggtgg aaaaaagaaa  23940
aagaaggttt gccttgctgc tattctttt tttttttga gacggagtct cactctgtca  24000
cccaagcggg agtgcagtgg cacgatctcg gctcactgga agctctgcct cctgggttca  24060
cgccattctc ctgcctcagc ctcccgagta gctgggacta caggcaccca ccaccacgcc  24120
cggctagttt tttttgtattt tagtagagac ggggtttcac tgctagccag gatggtctcg  24180
atctcctgac ctcgtgatcc gcccgcctca gcctcccaaa atgctgggat tacagacgtg  24240
agccaccgca cccggcctcc ttactgctat tcttattatt ggtggtagca gtggtggtga  24300
tggttattgg ttcttagttc cctctacatg ccagtatctg ctctcttctt tttttctccc  24360
ttacttcttt cctgttctg caaattcttt cccttttaagt gaaaatcttt ccgtgttctc  24420
caagggagat aaattctatg ccaagcttga gtgtggggtc ctctgcttgg atagctgtct  24480
tctccaggag atgaggtaga actgagatag tggggtctc tgcaggcagt ctgtgcccct  24540
ggcaagcccc tcaccttaac ctgaggctgg gtggggaaag atgccttgat ggagtcagaa  24600
```

```
cagaaagcaa gtgatcgctg cctgaaccaa gcagtcactt tcctggaggt gaaacctaga   24660
aacggtccct caggctgggt ccagggaggg ggacttgggt cccagggggca ggaagcaacc   24720
tgcccctcac ctgctcctac ctctttgtag cctatcttgg caaccagaag taggtataca   24780
agtgacgttg aagctgggca tgttaacaat ggtgtgagcc cgcctgactc caatctggtc   24840
cagctgtact ggccgtgcat cctcatctcc agccccagg gtcagcccag cggctgtaac    24900
aatggtctgt cccctccccg ccccaccacc ttctttgaac tcctccaagg atctgtgatg   24960
ataggggctgt cactgtctta gcttccacca ttcaagctta accggccttc ttcccctcca  25020
tggagaacgg aagagcaacc cctcattgcc tctggcagct gaccagcagg tccctgcctt   25080
ctgcccactc ccaggtctag gacaatgagg tgagaggtag acaggaccaa gttccccagt   25140
gctgtcttct aggtccacct atcatgagag ccgtgattcc tagttttttat caccctctcc   25200
ccaactttgc cagctctcca cttctggcag tggtggctgc ccatgacttc accttcccgt   25260
gcctcagttt cctcatctgt aaaataagga cagccatggt aatgagagtt ctggtcaata   25320
tgccaggcac ctcgcttgca tcaatttagc tcatcctttc agtgccctga ggggtgggta   25380
tcgttatcat cccgtgtaac aaaaagagaa aaccgaaaca ggagagagta tctcactatct  25440
gaggtcttgc accccctcaag caacaaaagt gggattcag cctaggctat ctagattcgg    25500
agtccacggt ctcaatgaat aataacaaca ataataatat tgtcctaatc tgatgagttt   25560
ttgatcagat tcaatacaag agcataggca gaaaagctta gcccagtgcc cagcacatgg   25620
taagaactca gcatgttatt tataatagta ataaaccatt ttatgttatg taattatata   25680
ttcatagata aatatagttg actcttgaac aacataggg ttggggcaat gacctcctgt    25740
gcagtcaaaa atgtgtgtgt aacttttttt ctctattttt tagaaattt aaaattagag    25800
acaaggtctc gcttttgttg ctcaggttga tctcgaactc ctgggctcaa gtgatcctcc   25860
tgcctcagcc tctcaaagtg ctaggattac aggtgtgagc ccccgcaccc agcctgtgta   25920
taacttctga ctccccccaaa gcttaactac taacagtcta ttcttgacca gaagccttac   25980
cagtaacata aacagtcgat gaagacagat tttatatgtt atatgcatta tatactgtat   26040
tcttacaata aagtaagcta gggaggagaa agtattattt taagaaaatc ataaggaaga   26100
gaaaatatat ttactattca ttaattgaaa agggatcatt ataaaggtct tcatcctcat   26160
tgtcttcaca ttaagtaggc tgaagaagag gaggagttgg tcttgttgtc tcaggggtga   26220
cagaggtgga ggtggaaggg gaggccagaa agacaagcac gcttggtgta actgttattg   26280
gaaacaaatc tacataagtg gacccataaa attcaaacct gagttgttca ggggtcaact   26340
atatatgcta caaatacgta atatgctaat atagttgtat gttattgtta tagtacgggg   26400
atcagaaaat gttttctgca aaggattagc tagaaaatgt ctagtaaata ctgtctctttt  26460
gggaccactc tactctgcca ttatagcaaa ggcagctaca ggcaatacgt aaatgaatgg   26520
gcatggccat ttgccaataa aactttgttt acacaaacaa gccatgggcc agagtttgtc   26580
aacggctggt atagtatatg ttattatata ttagctttta tttttctgtt gctttgttta   26640
tgttcttctt tgcccttcct tcttaaagg ccagccttttc tttctctctg ttggtctgtc   26700
tttttaggaca gcatggcagg ccactgggac atgggctctc ctgactccag gcttgtttgt   26760
ctgataagac atgaagagtg aaggtggcag gactctgagc tcaggcctgt cctcctcctc   26820
ttccctctct tcgtttttttc ttttcctcttt cctctttct tcccaagctc cagaagttgc   26880
catttccttt tcccattgct gattttctct gccttgggag aaagcccgag aagatcactt   26940
ggaaaagccc acgagcatct ctggcctcac tcacccagct cctgccattg tctttactct   27000
tcctcagaca caccaggcac agtcctacct caggggcttt gcactggctg tttcctctgt   27060
ctgcattgtt cttctctcag gtgacctcat ggcttctccc tcctctcctt caggacttca   27120
ctcaaaggcc accttctcag catttgcctc ccgcccttct gccttatttt ccccttttga   27180
acttttcacc ttcttactta ctcatctgtc tgctatctgt caccctacat cactatgatc   27240
tccacaaggg aaggtgattt tattcgtttt ttgttctgtt tgttgaaga tgaggttttg    27300
ctcttgttac ccaggctgga gtgtggtggc acgatctggg ctcactgcaa cctccacctc   27360
ccggattcaa gtgagtctcc tgcctcagcc tcctgagtag ctgggattac aggcacccac   27420
caccatgcct ggctaatttt tgtatttta gtacagatgg ggtttcacca tgttggccca    27480
gctgatctca aactcctgac ctcaggtgat ccacccacct cagccttcca aagtgctggg   27540
attactgtga gccaccacac ctgatctttt ggttttaccc accaatgtgg actagaacag   27600
cctagatcag caggtggcat gcagtaagca gttgataaat atgtgttgga tgagtgagca   27660
ctgtggcttc tgtcattctg ttgctcaata gcattcatct ggaaataacc acagtttgtt   27720
tatccatttta cctgttgatt ggcatttctg ttgattctcg tttgggccat tatgaacaaa   27780
gctgctgtga aatacttata cctttgccca attcttcact tggtgaaccc ttataaatcc   27840
tttaggccag gtgtggtagc tcacgcttgt aaccccagca ctttggaag ccgaggtagg    27900
aggatcgctg gaggccagga gttcaaaacc agcctgggta acatagcaag acccgtctct   27960
acaaaaaaat aaaaaattgg ctggacgtgg caatgcatgc ctgtagtcc agctacttag    28020
gaggctgagg tgggaagagt gcctgagccc aggagttcaa gaccgcagtg agtgatcgcg   28080
tcctgcactc caggctgggc gatagagtga gaccctgtct gtaaaaatga cagcaacaac   28140
aacaataata aaacctttag gtttcctctt aaaaggaaca tccttagagc ttttcctgac   28200
ccagcaactc accccaagtc tgaattagac ttcaccccat ttctttcata acatttatca   28260
caatgacatg tttatttgt gggggcgggt ggcattctgg ccagaactgt cgacttccag    28320
agtgaaaata cggaagaacc aaataaaaca caacacacac atttgcacag cagctcgagg   28380
gaggtgctta gttctttgag tttccaagaa cagagaggag aagatttgtc tggggaggaa   28440
aaatcaggga ctgcttcttg gaggaggtgg actgttgctg cccatccac ccacacattt     28500
gcagatgtgg tgatgagaag atgactgtca cgaggtctct gagcccaggg ggcccatggt   28560
tgagtgcaaa gatagtgggg ttgacaaata atcgtcgtat aacaaagaa aagccaccac    28620
agttgcataa tggaaaggcg gcttctatag aacattcaga tcatagttga aggcatgtca   28680
cactgtgtta ctcagaggcc actgtcagag ccaaagtga gagtggatga gagtttgggc    28740
aggaaacaac tgaaccagat acagcatcac ctccatgagg gctcagcttt atctattttg   28800
tcttctgttg catcccagcc ccttagaaca ctgcctggtc catctttgct gtgtgaataa   28860
taataaggaa cgatcgctgt gttgagtttg ggctgtgaat tcagacagtt tgctgctgca   28920
tacctgatta tgagtctcag ttttcctcct ccataaaatg ggcaaaacag tccttgcctc   28980
atggggctgt gcatttgttt agcaaacact gaaggagtat acatggtggc caaggcactc   29040
ttcaagacac aggaagcaga caaaagtccc tgccctctgg gagcttacat gctcatgggg   29100
agagatgtat gataagaaac aaaaaatagta ggtaagttgc atagtacttt agaagattat   29160
aagggtaatg ggaagagaac agcagagaaa gggctgggga ggcagttgct gtattagata   29220
gagctttatc gaggcgatgg cattggagcc aagacttgag gaagctgtga ggatgtctag   29280
agaaagaagg aacagctggt gcaaaggccc tgaggtaggg gtatatgtga catgtgtgac   29340
```

```
agtgaggagg cagatgtggc tgaagccagt gagcaagaga gagggaaggt gcaaggataa   29400
ggacagagag gtgacgggac aggttttgga gggccttatg ggctgcgggg aggactttgg   29460
cttttgctct gagggagctg ggagccacgg agggcttttg agcagaggag ggacgtgacc   29520
tgactcagat attcataggc tcctctggct gctgtgaaaa aacagactt tgaaggttgg   29580
gggcaggcag ggcagaagct ggggaattag gaaggagtg acagtgttgg tcctggcagg   29640
taatagtggg ggtggaacca ggttgttgtc tgtggagata ataatgagtg gctggattct   29700
ggttataatt tttaagtttt tttattgtga taaaatgaat ttttttattg tgataaaatg   29760
aaatttacca ctttgaggtg tgcaattcca cagcacttac tacagtcacc ctgttatgca   29820
acagtcacct ctatttaatc tcagaacatt tcatccccc taaaggaaac cctgcaccca   29880
ttagtagtta cttccagttt ctcccttccc ccagcttctg gaaactacta attctggata   29940
taagttgaaa gttgaccagt aggatttcta ggcagacagg tggtgagggc tcaatgcatt   30000
catgcacaga aagtactcag gtggcatatc ataggtgctc aaaactgaaa tggtgatgat   30060
gagttggcaa tgatggtgag tccttccaga atccctgctc tagtgctaaa ctgacctacc   30120
tggctgtgta gaattctcac ctgctggccg ggagggtggc agaaccagga tcccttctta   30180
cttccagtct ggcttgggtt agggataggg gaggaatgat cagaagaacc aagctagcac   30240
catctgttct ggaacatcat ccaactcttg tccagatttc ccagaactga gcaggaaaat   30300
gtccagggag gaacagtgca gctgatgaa gtcctggtaa gccctggccc cagcttcctg   30360
agctgctgtt gcaccaacta gcatttgttg gaccttcagt ctgagccaag atggcagctt   30420
cagaggaaga acaagaagtg tacaagtttc tttcatggtt gtgtcccccgc ctccttatat   30480
agcctcatat aaacccctgc actatcccgt tactgtttgc ctctccctga aaagagtgta   30540
aaactccccc acttttttccc tacttttcac aatgtgtttt ggtttctaaa gatgaaactc   30600
ctttaattat gttctggttg taattttctg gctcctttta tttctccctt acttgatgta   30660
ttattttccc ttgttccttc tgccccctgc ctccattgat gttctcttc actgctatct   30720
agatttaatt ctcaactcct gccaagttca gggtgatagt gcaaaaagac atggaccatt   30780
tagtcttgaa ttcaggtccc acttctgaca ccttcaaagc tgctttactt tgggcaagtc   30840
atatgatctt cctgaggggg tatccttac ctttgttcagc taacatttct tgttttttctc   30900
tgggcacaga gtagagtgtc attttcccca cctccctgaa gttaggtatg gctgtgtgat   30960
ttggtttcat caatgaaatg tgaggggaag tgacgtgagt ccttccggac agaagcctta   31020
agggtgagca tgggattcac catgtttcct ttttcctgcc tccactgtca tggatgcaca   31080
aagatggacc ctctctcaaa gtaagtgctg gagagaggat gacatagatc agtccccatc   31140
ccacttcata gcatgagtag aaaaatagac ctgggggtgtg ttcaaccact gagatctggg   31200
gattgtttgt tactgcagca ggacatagac taggctgact gtataacctca ttatctgcat   31260
tttgggggctg atatctaatc acagtgtctc caggaagatt atgttgatgt atgttttagg   31320
gatggatatt catatttttcc tataagggct caataggttt ggaaatgtca catgcatgta   31380
aacttctgat taacaaatat ttcttgcttt ccaatttctt cctatagtgc ttctaatttt   31440
cctgtttttc aatcttgaat aaaatgtgag aagtgtttga cttctccttc gaggagatta   31500
atggtttcta aagcctgggg cattgattta gtcattctca acctccttgt ttctatgacc   31560
ttttttctc ctttctggt cacttagtgt ctgctaaggg gtgaaggaat gtctgttttta   31620
actcattgca ttttttttt ttttgagacg gagtctccct ctgttgccca ggctggagtg   31680
cagtggtgtg atgttggctc actgcaacct ctgcctcctg ggttcaagtg attctcctgc   31740
ctcagcatcc caagtagctg ggactacagg tgtctgccac cactcccggc taattttttgt   31800
attttttagta gagacggggt ttcaccatat tggccaggct ggtctcgaac tcctgacctt   31860
gtgatccgcc cgccttggcc tcccaaagtg ctgggattac aggcgtaagc caccacactc   31920
ggcaaactct ttgcattttt aactcttgac atcttcatct tcttttttccc acctccccttt   31980
tgcctgttcc tcccctgctc accccaccag ggagtttata atcaggttct agaacctgca   32040
atgttttct gttgttgtct tccatcttcc ttgagtctta tgggaatcgg ccatagtcgc   32100
aaattaacaa atagctctga agcgcctcaa gcttggaggc atttccttt gctcacctaa   32160
gcaagatcct ggagctgttg caaatatcct gccccctact gtaaatctgt cttcatggtt   32220
gtaagagatt cagtcggggt cagtgaagac ccgagcagga gatcttggcc gaggctcctt   32280
gatgttctgt ctgcgctggg tgttgtcata ttgattaagc tcctgggact gctgccagca   32340
gcctctagga ttaaatcaat agagtttgca aaagtaaaag cttcttttgg agacacagaa   32400
tatgtgggtt tatttttttaa tgataaagct tcaaggagaa tcttcatgga tggcagaacc   32460
agtgatggaa aaggcgaggc agacccaaat atttggggaa gtgcagtggg gagcaagtga   32520
gggaggtttc attgggaggc cggggctttc cagaaaatct gtttaactgg agttgctaat   32580
gcaacagctc agagttagaa gtgaaggtgg aagatgcaag aaggactgcc gctgagatgt   32640
aaagagaaat gaaggagagg tggatccatt tgctcattca ataaacattt tgggaggcag   32700
gggggtgggg gggagcctgc catgtgcctg gaactgggat gtacatggtg gggacatgac   32760
agtgggcagg acagatgtgg ttcctcctgg ccctcctgga acttgtaaca ggaaaagaag   32820
gcataaaata aggaataggc aaatacagac ataattacta attgtggtaa gtgtttggga   32880
gaaaccagc agggtcctgt gtttgttttcc tagggctgcc aggacaaatt gccatgaact   32940
atatggctta aaacaacata aatatattgt cacccagttc tgaaggctgg aagaccaaaa   33000
tcaaggcatc agcagtgctg agctcccttg gacggctcta gagaagaatg cttccttgat   33060
tcttccagtt tctggtagtt gttagcatac attggcttga ttggcttgtg gctgcatcac   33120
tgcagtctct gcctctgtct tcacatgcc ttctccttca tgtcagtgtc ttctcttctc   33180
cttctctctc tctctttttt ttttttgt cagggcctca ctctgtcacc ctgtacaaga   33240
gtacagcagt gcaattatag ctcactgcaa ctgctgcttc ccagcatcaa acaatcctcc   33300
cacctcagcc tcctgagcag ctgggactta caggcgtgca ccaccatact cagctaattt   33360
ttaaattttt gatagagatg ggatctcact atattgccca gactggtcgt gaacttctgg   33420
gctcaagtga tcctccctcc tcagcctccc gaagtgctgg gattacaggt gtgagccatc   33480
gcacctggcc tcttctgtct cttataagga tcttgtcga tggattttga gcccgtcaga   33540
taatccagga caatctcatc ttgagatctc taattttaatt atacttgcag aggccgtttt   33600
actaaataag gtcatggcca gaggctccag aggctaaagc atgggtatga ttgcaccact   33660
gcactttagg ctgggtgaca gagcaaggcc ccatctctga aaaataaaat aaaataagta   33720
acctactaca ggcccttgc gtagaggata attagaagta catgggtacc acgtaagtga   33780
agacctgaag gttgttaagc acagagcaga gtgtgaacag aatgagacag agggaggaag   33840
agaatcccag gcagagggaa cagcatgtgc aaaggccctg ggaaggaac aagttcatca   33900
tgttaaaaat gagccagtgt agctagagtc tgatgagcaa agggactcac aggtgggaag   33960
acacccaaga agttggcaga gacaggtcac acaagacctt ctaggtcaag ttccggaggt   34020
gaactttatt ctacatgcaa tgagaagtcc tcagagaagc ttaagtggga tgggacagaa   34080
```

```
ctgctttact ttaaatatat atacatatat acaaacatat aatattacat atataaagca  34140
tatatatgta tacatatata catatctatc tacctgtcta tatattttt agctgggcat   34200
ggtggctcac acctgtgatc ctagcacttt gggaggctga ggtgggagga tcacttgagc  34260
ccaggagttc aagaccagcc tgggcaacat agggagaccc catcactaca aataaaaata  34320
aaaattaaaa attagctggg tgtgatagtg tgcacctgta gtcccagcta cccgggaggc  34380
tgaggtagga ggattgctgg agccccaaag gttgaggctc cagtaagccg tgattgtgcc  34440
cctgcactct agcttgagca acagagtgag atcctgtctc aataaaataa tttttgtatt  34500
gaggtgaaat tcatgcaaca taagttaacc attttaaaat gagcaattca gtggcattca  34560
gcgcattcac aatattgtac aacctccacc tcttttctagt gctgaaatat tttcatcacc  34620
accccctccag aaaaccctgt atccatgagg cagttgctcc tcatcctccc ctcccggtat  34680
cccccaacc cccaccactc ctggtaacta caaatttgtt ttctgtttct atggatttac   34740
ctatactggc tctttcatat aaatgaattc aggcactgtg tgacctttcg tgtctggctt   34800
cttcactta gcataatgcc ctggcttctc tctggagaat gaaatggata gaccactttg    34860
gagtctactg agattataga tattctgtg ggaaggagca gtggcttgac cttgggtggt    34920
gctgaagagg caatgctgag caggaggatt caaagtctaa tttcggaagt agaattggtg  34980
gggtctgatg atacatcagc tgtaggggga ggaagatgta ggaactggga aggtctctta  35040
gggtaacctt acctgattga gctccttact aggcagctgg tggtacaatt cataacaaag  35100
gttaatagag aaagagacat gggattaggg agggaatgga agagtttggg ccttggacag  35160
tgtagtggtt tgaatcctgt ccaccaaaaa ttcagatgca tttggaactt cagaacctga  35220
gacctcattt gaaagtagga tctttgcaga tgtcattgag tcaggattg agatgaggtc    35280
atcctggatt acagtggact cgagattcca tggtaagtgc ttttatatga gaaggtacag  35340
gggagaaagt catgtggcaa tagaagcaga gaatggagct ctgcagccac aagccaaaag  35400
acatgtagag gcaccaaaag cgggaagagg caaggaagga tcctccccta gagcctttga  35460
agggaaaccc cctaatttca gaaccttgcc tccaggatga cgagagaata aatttctgtt  35520
gttttaagcc acccaatctg tggcaatttg tcatgactgc cctaggagac taatatagac  35580
actcctatga gatgctcaa gaagcacacag agtggtatag ctattgctaa gaccacacac   35640
tgtagcaggg aggaaatcaa atggagaaat gccccaactc cccctcctct ctgatctctt   35700
gctggtgcct cccgttggcc aagccaaccc agaaggcaga agatgtgtg gagggcagcg    35760
ttgcagggct tggatgatgc agtcacagaa gtcagccctg cctctaccag gatgccaaac  35820
agggcaatga gtggatattt tagggagaaa gggcaacaag agaatggcaa aatacatcga  35880
aatgcatgca agctctagaa aaggatagag atagataaa gggtgattac ctaggattaa    35940
gccccaggga agaccaacat ttagagattg gatagaaaaa gaggagcaaa aagggaagat  36000
tgagaagtag agaccaggag gataggagga aaactagaac aacattaaga agggcatggt  36060
caagtaatct gggcacagaa aaatggccct gggatttggc agcctggggg tctttggtga  36120
tcctctttgg aagagttttg gttgagtgat ggggctaga aaccagcctg gggaggtag    36180
gagaagaatg tgcagtgagg aagtggcagg aacacgtgaa ggcaactctt catgaagggg   36240
agtagagaaa ttggttggtg gctgaaggaa aattttcagt caagggtgga ggttttaatg   36300
atggaagaat attgatttct gtaaattggg tcattcccat ccattatacc aatatgcacg  36360
ggtgtcttct ctgatatagg atgctgggat tctcaaatgc ccttgagt ttagcatcat    36420
gaatttaatg tcaccagccc agatagttga tctcattcag gaatgctcca ctgcccaggt  36480
atggggaagg caactagttg agttcatgca gggatggatt ttttccagga gagaaacagg  36540
aggcaagaaa gtgcgatata atcaacctat gtaaggttga caaggcagga gagggtcctg  36600
agaaatggcg gggtcagtgg gttgcagggc tcgatggagt ggacgttggt ttgcatttaa  36660
gggagttagt gagctgggag gtggttaaag aggaggtggt tcagccgggc gcggtggccc  36720
acacctgtaa tcgcagcact tgggaggccc gaggcgggcg gatcacaagg tcaggcgatc  36780
gagaccatcc tggctaacac ggtgaaaccc tgtctctact aaaaatacaa aaaaaaaaa  36840
aaaaattagc caggcgtggt ggcgggcgcc tgtagtccca gctactcagg agcctgaggc  36900
aggagaatgg cgtgaacccg ggaggcggag ctgctgtact ccagcctggg cgacagggcg  36960
agactccgtc tcaaaaaaaa aaaaaaaaa aaaaaaaaa gaggtggttc aagacaagga   37020
tgctggaaac aggtgttttg gaggtggctg gtgtagcttc tgagcatgca tagctggagt  37080
ggcttgggag agacattggt tattgatgaa gaggtaggga catcctccag tgatcaagga  37140
agcaggggac cagcatggac aatggtctct ccacagggaa attggaggtc atcaaatgtt  37200
aacaggttcc gtcggagtct tagctcccag ctttctgtttt cctgtggatc tcaggatctt  37260
ggctgctggt gctacctctg actttggact tcccattgag cccagcagca ctgggaggga  37320
cctcatggc attggctggt ttaaggaaga cttccttggc tttgctgatt ttcttgggag   37380
ccttcttggc tacacctgct tttgaggag ccctcctcac ctcacctgac ttcttggggg   37440
cacctttttcc accttatctg agttgggaag gtctttctt gattctcttg ctttcttggg  37500
gcccttctca ctggttttc tgggggccat gatggtggac atattccaga gctgagcttt  37560
cctttttgttc ttaggaacta atttgaggct gccagtggac ccaccttggt cttagagttg  37620
atggtctgca gggaatttcc aggttaaagg ttttttattt gtttgtttaa ttttgagaca  37680
gagtcttgct ctgtcaccca ggttggagtg cagcggcacg atcttggctc actgcagcct  37740
ccgcctcctg ggttcaaaca gttttcctgc ctcagcctcc taagtagctg ggattacaag  37800
cacgcaccac catgcccagc taactttgt atttttagtg gagacagggt ttcaccatgt   37860
tgaccaagct ggtctcaaac tcctgatctg aagtgatccg gccaccttgg cctcccaaag   37920
tgctgggatt acaggtgtga gccactgcgc ctgacctcca ggtttaagtt taaccatga   37980
agtagatgga ctgtgtagag agagaccagg gaaatggagg attttactga ccactgaaca  38040
gggatgtcac tattgccaga gaggaaaagg attccccctt ggtagagtga acatataagg   38100
gaaagtggtt gaaaattgaa tcaggagaca gagacctcac accactggtc ggtccctaga   38160
gaactttact gacctagaaa aaaagataaa cagggagaag gtcttcagtt cttgtttgga    38220
atctgacact gaagcatcct cactcctcac tctcttcccg accccgagag tctgaaattg  38280
attaatactt tttgtttaaa acttggcttg ttgttttgtt ttttctttct gttttcatca  38340
agggatcttt attttacttt tgtgtatttg tgtgttttcc atgagtcatg ttaattcttc  38400
catgtttaaa cttttggcc cagagaatt tatacattta aattatggat ttaatttcag   38460
aaggtacata cacacacaca cacacacact cactcactc acttttaaa aactgtaaaa   38520
tatagccctg taaatatcca gaaaatatct aatgtgggcc gggtatggtg gctcatgcct  38580
gtaatctcag cactttggga ggccgaggtg ggtggatcac ctgaggtcag gagttcgaga  38640
ctagcctggc caacgtggtg aaaccctatc ctcactaaaa ataaaaaaat tagctgggca  38700
tggtggcagg tgcctgtaat cccagctact cgggaggatg agacaggaga atcacttgaa  38760
cccaggaggc agaggctgca gtgagccgag atcacccac tgcgcccag cctgggcgac    38820
```

```
agactgagac tctgtctcac aaaaaaaaaa aaagaaaaga aaaagtcagt gtgcatcccc  38880
tctgacatcc agcaacttca catcttggaa tttatgctgc aggaaaatta tcacaagtgc  38940
acaaggatgt atggtgagat agttattatt atcattttaa aagatagggt ctcactgtgt  39000
cacccaggct ggagtgcagt gaagtgatca cagctcactg cagccttgac cttctgggct  39060
cgagtgatcc tcgtgcctca gcctccccag tagctggact tacaggtgtg agccaccatg  39120
cctggcatcc cccttttttt aaaaaaaggt tttaattatg aaaagaatat gggcttgttg  39180
ttttgtgtgg ttttttaaaa gcttaaaaaa tgtgtagtgt gtcatttaga aggtgaaaag  39240
cccttacccc atcccacctc ccagagataa cctctgctag caatttcgtg tttgtctttc  39300
aaatttttc ccacacacat tctttgtact ggctgcttcc cctcctgggt tactcttctc  39360
ccagacagaa acagggctca ttcccttgcc cctccagct tttattaaaa cattaacttc  39420
cctgtagctg gatgcagtgg ctcacgcctg taatcccagt gttttgggag gtggggaggc  39480
aggaggatag cttgagccca ggagtttgag actagcctgg gcaacatagc gagacccatc  39540
tctacaaata aataaataaa taaataaata aataatataa taatgaaat ttaaaagaga  39600
gagggaagga ctcttgaaaa ccgtccatat catgcttctc taaatggttg agggctcaga  39660
ggaaaaaaaaa tcagcaattt cacatcacgg aatttattct gcagaaaaat tctcacaagt  39720
gcacaaggat gcgtggtcag atgatgatga tgatgattat tattattatt attgaagaaa  39780
gtagcagcag cagcagcagt attttaaaag acagagtctc ggatgggcat ggtggctcac  39840
gcctgtaatc ccagcacttt gggaggttga ggtgggcaga tcacttgagg tcaggagttc  39900
gagaccagtc tggccaacat ggtgaaaccc caactctact aaaaatgcaa aaattagcca  39960
ggtatggtgg tgggtgcctg cagtcccagc taccagggag gctgaggcac gagaatagct  40020
tgaacccagg aaatggaggc tgcagtgagc caagatcgtg ccactgcact ccatgcactc  40080
cagcctgggt gctgacccag gttaggtgca agactccgtc ttaaaaaaaaa agaaaaggaa  40140
aaaaaaaaaa aaaggacaga gcctcactgt gtcgcccagg gtaaagtgca atgagtaaag  40200
gcccatgatg ggaaccctga ggagagagtc aaggggaaag aaaaaaaaaa aagcaaaacc  40260
aaaatggaat ttaaaaaaaa tcaggtgcaa tttgcataac agaaaattaa ccattttaaa  40320
gtgaacggct ctgtggcatt tactgcactc caactgttat gtaactacca cctctgtcta  40380
gctccagaac attttcacca cccctaaagg agaccttgta cccattaagc agtctctctc  40440
cttctcccct ccccaccacc ttcctccagc ctctggcaac cacccatctg cattctgtct  40500
ctatggattt acctattcta ggtagtcaac aggatgagat atcccaaaag tccatccatg  40560
gatgaacaga taaaccaagt gtgatatgcc ttcctcagat attagtctgc cttaaaaagg  40620
aatgaaatac taatctttgc tacaacatag atgaacctca aaaatatgat gtggctggac  40680
acagtggctt acacctgtaa tcccagaact ttgggaggct gaggtgggcg gatcgcttga  40740
gcccaggtgt tcaagaccac cctgggtaac atagcaaaac tccatctcta caaacaatt  40800
tacaaaaac tagccaggtg tggtgacatg tgcctgtagt cccagctatt caggagactg  40860
aggcagagg atcgattgag cccaggaggc cgaggctgca gtgagccatg atcataccac  40920
tgcactccag cctaggcaac agagtgagac cctatctcaa aaaacaaaac aaaacaaaac  40980
aaaaaagttg atgctgagtg aaagaagcca gacacaaaag gcaacatcgt gtttaattcc  41040
atttacatga aatgtccaat gaagatttt tttggcaaca tttattttga gtataatatt  41100
cagtgagtgg accacacata tgcatgcact gcagtatgtt cttggaaaca tttcagattt  41160
gagaggtctg ttcagctatg atgacgtag gtattgtccc ttcctccct ccttgaagaa  41220
aaggaactaa ggctggacgc ggtggctcat gcctgtaatc ccagtacttt gggaggctga  41280
ggtgggcaga tcacttgagg tcaggagttc aagactagcc tggccaacat ggtgaaacca  41340
tgtctctact aaaaaaatca aaaaattagc caggtatgt gctgcacgcc tgtagtccca  41400
gctactcggg aggctgaggc aggagaattg ctcgcaccca ggaggtggag gctgcagtca  41460
accgagattg caccattgca ctccagcctg ggtggcagag caagactctg tctcaaaaag  41520
aaaagagaag agaagagaaa agaaaagaaa ccaaaagaaa aggaaagaaa agaaaaggaa  41580
ccaagaccta gaagggcaaa aataggaaga gttggccggg cgcagtggct cacgcctgta  41640
atcccagcac tttgggaggc caaggtgggc agatcacaag gtcaggagat cgagaccacc  41700
ctggctaaca cggtgaaacc ccgtctctac taaaaatact aaaaattagc cgggcgcggt  41760
ggcaggcgcc tgtaatccca gctactcggg aggctgaggc aggagaatgg cgtgaacctg  41820
ggaggcggag cttgcagtga gccgagatag caccactgca gtctggcctg ggcgaaagag  41880
caagactcgg tctctaaaaa aaaaaaaaa aaaaaattg gaaaagttat ttactattag  41940
cagcaattgt cataaagtaa tgaacattta ttgcatgatt acaatgagat aaattgtatc  42000
ctgtttttat aagcatatta agttttcttt tttaaaaaaa tgtatgtatt tatttatttt  42060
aagagatagg gtcttgctct gttgcccaga ctggagtgcc atggtatgat catagctcaa  42120
tgcagcctca aattcccagg ttcaagcaat cttcttgcct cagtctctcg agtagctagg  42180
actacaggca tgtgccaaca tgcctggcta gttttcttat ttttaaatgt attttttgtag  42240
agacaggatc ttgctgtgtc gcccaggctg tcctcaaact cctggcctca agcgatcctc  42300
tgccttggcc tcccaaaggg ctgagattgat aggcatctac ctctgcattt ggcccacatt  42360
aaattttcta gtcatcatgg gaaccaaaat aaacaataa aaacactcac attccttgag  42420
cacttactat atgcagggcc ctgtaataga ttattgtgtg tatcagctca ttccattctc  42480
acacaaccta tgaggttgat gctattttct acctttata tatgaggaaa ctgaggctca  42540
gagaaggaaa ctgccttgcc caaggtcaag gccacgtctg atccccaaat cctttcaact  42600
cctctgcact actatttttt agtgcagata ttgccagtt tctaagcaga agcatgattt  42660
agcagccctg agtagacttc tcatttcaga accaaagtgt tggacattgt tggataatat  42720
gaaaaacaaa tgcacacaa acctatttga tactgttttt aatttttctct tcatttgatt  42780
ttcctgatga catgattaat ctttttgcc tctaccctgt atgtgaaatg taggtctttg  42840
cagatgtctc agagagtgtt aatagttgct gctggtttta ttttctctcc ccggggattc  42900
ccatccctgg gtgcaagtga aattaaactt gtgcctcttt gccgctgcc gtggtgctga  42960
aaacatcccg ggcagcgcta gggttgccct tgttagcatg ccatccctgc taagagtctt  43020
aggctgatca gcgagtggag agatcttttc caggcttcat tttggttaga actgtgtgtt  43080
gaagattta aagcccatgt ctgggaactg agactgttt ggattgtttg aagttgaaat  43140
agtcatgaat aattcctact tgagatgggc ttatgagggc gtggactagc atgcaatggt  43200
tggcctttac taaactgtgg tcattggttg ggactgtggat tgggtgggt gtgaac cattttggt  43260
taatccatat ggttagggcc ccaagtgcac ctgcattcta ttttttttttt tttttaaata  43320
aaggcaaacc catctatctt ctaaccagga tagctcctga gtggtctttg gggaccacca  43380
gcttaaaagc atagactgtg ggctgggcac agtggctcat acctgtaatc ccagcacttt  43440
gaaaggccaa ggtgagagga tcgcttgagc ccaggagttc aagaccagcc taggcaacat  43500
ggtgagaccc tcatctctac aaaaatgtta aaagttagcc aggtgtgttg gcatgcacct  43560
```

```
atagtcccag ctactcagga ggctgaagtg ggtggatcgc ttgagcctgg gaggtcaagg   43620
ctacagtgag ctgtgatcgt gccactgtat ttcaccctgg gcaacagagc aagaccctaa   43680
ctcaaacaaa caaacaaaaa aaggcataga ctgtggagtt gggcagacct gggtgtgagc   43740
cccagctctg ccagtacctc ctatgtgacc ttgaaaattt gtttaatctc tctgagcctg   43800
gattttcttg tgtggaaaat gaggcttacc acagaaccca ccttgtagaa atgttgcaag   43860
gaattaactg aaacaaagtg cttaccacgg tatctgccca agaagcagt tggaaacaag    43920
gcagctgtaa ttatggtcgc tgtgcttgtt aatggcccca taatagttga tcatattgca   43980
gagtgaaatt ggggtatgtg tttaatggac caaggaatat gtcttaaacc catatatcta   44040
gggttctggt accctctact ctttttcctg gtgattgtga tgagcatgga acttacatga   44100
aaatgaggtc tgtttggctt cttcacacaa gctcaatgac ctggctaact gctacaagta   44160
tctgtttcct tagaacccac ccatcagcag tccccatagt ggagacaagg tcacaaagag   44220
ttgacaaacc tgatttgatt tccgcaccaa ccacaggagg cttgaaatga gatgagggtg   44280
aagggcacca cagagggatg caaggattac ttggacactg caaggtcttg ctaagggatg   44340
ggaaccatca gccacgccca ctttgagaat tttccttcat gttctgaatc tgaagagcaa   44400
ggtcctgttc tcagatgcaa gccctccttc ttccctacgc agagtcaaac ttggtctttt    44460
ccagggtcac atacagcctc tctctggggc ctctgcaggt cctgatcaat ttcattgtgt   44520
atagagctct gtgtctcctc acctgcctgc agggctgtct gctatcctga cttccgagag   44580
ccatttcgga agccagcttt tcctcccatc agggatgctt ctcttctttc agccccccgc   44640
ccgctttggc ctcctaggat ggctgatttt tctggatccc gctgacacag gtgctttctc   44700
tccgagccaa tcagggagca gaaaggctca gctcagctaa cagaggcatt gctcaccgca   44760
gctgtgagtt agaactcagg ctttctaaat cgggaggatc aggcatgact tgaggttggg   44820
ctgagaaagc ctcgcctgcc cccagactcg actacccagt gaaaccttttg gcttctgcct   44880
cgggcgaggc atctcttacc atgccaagaa ctcagcagcc catctttctt tcatctgggc   44940
accaagtaca tcattgcata tttcaggggg tttcattgtg tccttaacat gctcatggag   45000
acttggcttg agatgaagtc gggggtttcta ggcagcagga cccatgtccc cttccttcat   45060
ttcctccacc ggtgattttt gttttgtttt gttttgtttt gctttttgttt gttttgtttt   45120
tgagacggag tctcgttctg ttgtccaggc tggagtgcag tggcgttatc tcggctcact   45180
gcaaactctg cttcccgggt tcaggtgatt ctcctgcctc agcctcccaa gtagctgaga   45240
ttacaggcgt ctgccactat gcccagctaa ttttgtatt tttagtagag acggggtttc    45300
accatgttgg ccaggctggt ctcgaactcc tgacctctgg tgatccaccc gcctcggcct   45360
cccaaagtgc tgggattaca ggtgtgagcc accgcaccag gcccttccac tggtgttttt   45420
tgagcatcta ctatatagag aatgctctcc tgggcacaga ggatgaagca gtgaacaaag   45480
tagacaaaaa atccccacgt gcatagagtg tgcagtctcg tgggagagac agggaacaag   45540
ataaagaagg aaaaaaatag cagatgcttg actggggacg gggactaaag aaagaaaaaa   45600
ataagcaggc taaggggggtt gatgatgtg acctttgagt aaaggcctaaa aggaagtgag    45660
ggagggagtc atgtggatgt ctggggaaag actattccag gagaatgaac agcaggtaca   45720
aaggcccctg ggtacaaatg tgcctgggga gtttggggaa taaagggag gccggcgttg    45780
ctgtagctga gtgactaagg gagagaatag aggagatgag gggagggagg taatgggagc   45840
aggtcatgca ccttgctggt gctggaagga cttgttttt gcttttgagt gagatgggat    45900
ccatgggaag gctttgaata cttccacatg cattaggctg aaattttctt ttctgctttt   45960
gtcgcattcc aacattgctt ttatttcatc aaaatcttcg gtttcttctc aggctctttta   46020
cccaagtggg agcagaaggc tggtaccag ggctgttcag ttctcccct ggggtcagaa      46080
cgtggaggag aaagcttgga ggagaaacag gaaccccccac ctcttttctgg atgactcaaa  46140
accgcaatta cctgagctcc tcctcctatc cctgaaatag aggcacttag cacttcctaa   46200
acttcccggt gcacacaaat cccctggcga tctttttaaa tgcaggttct gactcagcag   46260
gtggatgcaa ggtctaaggc tgcattccta accggtgctg gttctgggac cacactttga   46320
gtagcaaggg tctgaggtca ttgttgcaga tgtccatctg gggcatgtct gtggacactt   46380
gcggggggtgc gggtgagcag agggaggggg gatgatgttg aaaagcagt gtgagtatct    46440
gtgtttgata agaagtaaga aaatgaagca aggtgggaga gtagaacctc tttattttttg  46500
cctacgtgct aaggttttat tgccataccc agagagccct gggtctgaaa tccaggcaac   46560
actggccagt tgaaacctg atattgcagc ccataaaagt gctgcatgct gcatggtgga    46620
cttctgggac tcttcctgga accttcagtg ccagagccgg tccaaaggaa gtcacatccc   46680
tgccattgag gggcaggaga ccagggaacc ggaggagtgg gatggcagaa gcgcgtgtaa   46740
ggaggctgag ttgcaggga gagaaagcga agtcagcttc aaatcatagc gagaggagac    46800
caggggagg cttggcgttg ctgctctgtg tacaaatatt gtctcttatt ttccaggctg    46860
caggtgaggg cagagtggag tatttgtgca acacagccca gctttgttct ctgggctcct   46920
aatgcctgtc agctcagagg cagaaagcca atcagagatg atcgtcggca aggccggctt   46980
ttgttggctc cccaaattgc cctgagtctc ggattttgct tttcagagtg tgctttcagc   47040
tggaggcaaa ggctgaagct ggtgacaaaa ggaagcctgg ttttcctggc tttccggagac  47100
ttttactgag ggggtttcta tttcagactc cgttttccca cctggaaagc aggttccact   47160
ctccctccgg cctggaaggg atggtttat ggtgcttcca aaatgccaaa cctaactcca    47220
gggcagaaga ggagactgaa accaattaat ttttccaaagg ttagagctac gaggaggga    47280
gaggtttagc atggtcaagt tccccaagac atactaattg atctctctac agaatgcggg   47340
atttcagtgc ccccagggga cactcagcaa tgtttagaga ccacttgagg ttgtcatcac   47400
tggacaggag gggctgctac tggcatctag cacacacagg ccaggatac tgttgaacat     47460
gctgcagtgc ccagacagcc ccaccaagga gaatgatcca ccctaaacc tagtgctgag    47520
gttgggaaat cctgctccgg agtaaccaac acccatatgcc ttttcactc aagcagccgc    47580
ttctccagcg cttacacctc ctcagagatt gccagatcca tatgcagage ctgttggcgt   47640
gggacacttc tgagggggtgt ggcagggaga cagcggacat tccccattac cagctgatca   47700
gcaggttagg agctaatatg aaatgaacaa gatagaccct ccccacctgc cctgcagatc   47760
ctctggtggg acactaggga gggaggcctc ctaaacccaa atgacagttc caggatgca    47820
gggaggagtt tacctatgca aactggagag aatgcaaatg gggcatctag agatacttac   47880
tggacgaccc ctcccctgcc tcgggtcttg gaagaacaga ttctcagagg tctgccctga   47940
tcactgtaat tttttttta ttgaggtaaa attaatataa cacaattaac cattttaaag    48000
tgacatttag ggctgggcac agtggctcat gcctgtaatc cccgcacttt ggaggctgaa   48060
ggaagaaagg tcgcccagga gttcaagacc accctgggca acaaagtaag actctgtctc   48120
ttacaaaaaa aaaattaggc acacatggtg ttgtgcacct gtagtcccag ctactcagga   48180
ggctgaggca ggaggatcgt ttgagcctag gaattcaagg ctgcggtgag ctatgatcat   48240
gccactgcac tccagcctgg gtgacagagc aaaattgtgt ttctttaaaa aaataaaagt   48300
```

```
aaaaataaat aagaaaagaa aggagagggg aggggagagg cgtttagtac actcacaatg   48360
ttgtgtaact gtcaccttca tctagttcta aaacattaag cagccactcc catttccctt   48420
gccattcccc aggaacaaca aatctgctgt ctgtctctgg atttgcctgt tcgggatatt   48480
tcatatacat ggaatcatac aatatggggt attttatgtc tgcttcttc gcttggcata    48540
atgttttcaa ggttcattcc tgttctatca tgtatcagta cttcattcct ttttttttt   48600
ttttttgaa acggagtttt gcttttgttg cccaggctgg agtgcaatgg cacaatcttg    48660
gctcactgca acctccgcct cccggttca agcaatcctc ctgcctcagc ctcctgagta    48720
gctgggatta caggcatgcg ccaccacacc cagctaattt tgtacttttt ttagtagaga   48780
tggggtttct ccatgttggt catgctggtc ttgaactccc aacctcaggt gatctgcctg   48840
cctcggcctt ccaaagtgct gggattacag gcgtgagcca ctgcacccgg cctacttcat   48900
tcctttttat ggctgaatac tattccattc tatgagtaga ccacattttg tttatccatt   48960
cacccactgg tgaaatttag gttgtttcca tcttttggct gttgtgaata gtgctgctgt   49020
gaatatttgt gtatgagtgt tcgttggaat acctgtctta cgatccttt gtgtttatac    49080
cttggagtgg agttactgtg tgtcacatgg taactctgta attaacttt tgaggaacca    49140
aggaatggtt ttctatggca gttgcactgg tgttttttg ttgttgttgt ttttgttgtt    49200
gttgttttga gacagggtct cactcccatt gcccaggctg gagtgcagtg gtgcagtcat   49260
ggttcactgc agcctcaacc tcctgggct caagcaatcc tctctcctca gcctcccaag    49320
tagctggcac tacaggcctg cgccactatg cccggctaat ttttcatatt ttttgtagag   49380
atagagtctc agtttgttgc ctaggctggt ctcggactcc tgtgctcaag taatcctcct   49440
acctcggcct cccaaagtgc tgggattaca ggcatgagcc accgcatctg gccagctaca   49500
ccattttata ttcccaccag catgagggtt tcaatttctt cacatcttca ccaacacttg   49560
tttctgtttt gtttgtttgt ttttaatagc tatcctagtg gatgtgaagc agtatcccgt   49620
tggggtttga tttgcacttc cctgatcact aatacctca tgtacatatt ggccatttga    49680
ctgtcttctt tggagaaatg tctattccag cctcctgtcc attttcaat tggattatct    49740
ttttgttgtt gtgttgtaaa tgttctctct ttatttttta tttttttgag acagagtctc   49800
gctctgtcgc ccaggctgga gtgcagtggc acgatcctgg ctcactgcaa gctccgcctc   49860
ccaggttcac gccattctcc tgcctcagcc tcccgagtag ctgggactac agatgcccgc   49920
taccacgccc ggctaatttt ttgtattttt ttagtagaga tagggtttca ccgtgttagc   49980
caggatggtc tcgatctcct gacctcatga tccacccgcc ttggcctccc aaagttctgg   50040
gattacaggc gtgagccacc acacctggcc gtaaatgttc tttatatagt actagaccct   50100
tatcagatac atgatttgca aatagcttct cctattctgt tacttgcctt ttaactttct   50160
tgataacgtc ctttgatgca caaaaggttt aaattttgat aaagcccagc atatctgttt   50220
tttcttctgt ggatcatgca ttaggtgtca aatctgatca taatgtttta tttattatt   50280
tacttattta ttattatttt tatttatttt tgagatggag tcttgctctg ttgcccaggc   50340
tagagtgcag tggcatgatc tcggctcact gcaacctcca cctcccaggt tcaagcgatt   50400
ctcctgcccc ggcctcccaa gtagctggga ctacaggtgt gtaccaccac gcctggctaa   50460
tttttgtatt tttagtagag acagggtttc accatgttgg ccaggctggt ctcaaagtcc   50520
tgaccgcaag tgatccaccc accgcagcct ctatcctttt ttaattatc tcttttttt    50580
tttttttttt tgagacaggg cctccttctg tcacccaggc tggagtgcag tggtatagtc   50640
attgtacact gcagcctcta cctcctcggc tcaagcaatt ctctcgcctc agcctcccaa   50700
gtacctggga ccacaggtgc ctgccatcat gctggccctg ccaccatatt tgaaattgca   50760
gccctgaccc cttccactgt ctatagtctt caccatctta ctacataaca tagcatatat   50820
gatgtactgt ataacatggt atatgcagtg tactgtatag acagtatac atgatgtagt   50880
catctcattt atttgcttct cctctggaa gcaggaggaa gcttctcctc ttgtctgctt    50940
tgctctcaac tgtgtcccta gcccagaaca gagtctggca cacagcaggt actgaatgaa   51000
tatgtgttca gtgaatattg tgggtgagat agaaggtgaa tatccacatt tcccttaga    51060
agtcacctga tctgggtttg agatctgcag ggatctactc cagacaggag aacgaataat   51120
tccacctgtg ctgatgagtt ggaaggatct agagggcttg agatctttcc actgggtca    51180
gtggggtgg gtgcacctcc aacacccttc ttttctttga acaagatttt tccttaattc   51240
cccaatactc ccctttgaata tatgatttta gccaccatca tagcgaattg catcgtcctc   51300
gcactggagc agcatctgcc tgatgatgac aagacccgca tgtctgaacg gctggtgagt   51360
gatgtcttt ctcagggtct tctccttggc tttagcagga cattaatttt tggggagtg    51420
gagcagggca cagaggaggc tctcagtcct ggagcccaga gccagatcat gggaagccta   51480
aatttcctt tcatttttc ttgaaccaga gtctcgctct gtcacccagg ctggagtgca    51540
gtggttcagt catagctcac tgcagcctcc acctcctggg ctcaagccat cctcccactg   51600
cagcctcctg agtagcaggg actacaggtg ccaccatgcc cagttaattt tcttattttt   51660
atcttttttt gtagagatgg ggtctcact aggttgctta ggctggtctc aaactgccca    51720
ctttggcatc tgcataatt tcaggcagta tactcaaatg aacattgtta atgttaataa    51780
ttatgtcttg gccagacact gtagctcatg cctgtaatcc cagcagtttg ggaggccaag   51840
gcaggtagat cacttgaggt caagagttcg agaccatcct gaccaacatg gtgaaagccc   51900
gtctctacta aaaaaataca aaattagctg gatatggtgg tgcacacctg taatcccagc   51960
tacttgggag gctgaggcag gagaatcgct tgaacccggg aggcagaggt tgcagtaagc   52020
caagatcgca ccattgcact ccagtctggg caacaggagt gaaactccat cttggtgggg   52080
gggaggcgaa aaaaaagaaa caagaatatt acaaaggata cagatagaaga gatgcaaagg   52140
gtgagatata ggagaagggt gtggctggca gcttctaggt agcttcagga ggggactgg    52200
tcaccagaaa gaccaaggca tgattcgagg gttgcgactt tcagcccac cccccaacct    52260
ctgggagggc agagggctg aaaatcaagt tgatcaccaa cggtcaatga tttaaatcca    52320
aacctctaat catgccttgg ttttcccggt gaccaaccc catcctgaag ctacctagaa    52380
gctgccagcc atcagtcaat ccttagcctg caaaaagaca tcccttggga gatcccaagg   52440
gttttaggag ctgtacacca ggaaacagtg tcaaagacca aacatacatt tcacaatgtc   52500
acagtcttct aaaactata actagcctag caaacctatg atttctagat cttgcatttt   52560
tcacttaaaa taaagctaaa taaaaagcgt ccattgaaag actggtaagc aagtagaagt   52620
accagtggca agctaatgtg gaaaaaaaaa atcattcagg cagagtgaaa atgattgtag   52680
aaagggttgc tgctgtaa cagatgggaa aacattcaca ttgggggtct gatggagaag    52740
agcttgtagc ttaatttcaa atatgataga ttagcagctg gaagccagaa ccagccggag   52800
gttctgcaga ggaactggag gtgaggtac tggccactta tcagccagta cagaagtcct    52860
attccaaacc tttaacaatc tacatgccag ctgagaacca tcctaagggg tcagatttag   52920
gagtgaggtc aatgcacaag ctctagcctc aaataccttg aacgctgcat gtgacaagta   52980
aattctctaa accaatgctt tccattagaa cttttctgcag tcacagaaat gatctccatc   53040
```

```
tgccctgtcc aataggattg tcacttgaaa tgtagccagt gtgactgcag aactgtgttt    53100
tttattttat tgcatttaaa ttaattttaa ttgaaatagc cacatgtggc ctgtgactgt    53160
cgtattgaat aagacaggtg caaacaaata attctgttta gctgagtgat atgtgaggtt    53220
ggcccaaaag gaatgaagga ggaaggtgcc ttctctaggc attggctttg ctcgcaaaag    53280
gctttggaca agagaactct gcaagaggca gtgagggtg gtgagtgcag gagggtcagg     53340
ggaagtgaga gggtgatagg tactgatttc taggtgggct ggttccctga tcttgtcaac    53400
atctgcccag cccaagacgc tgaccttgcc ttctctccct tccaggatga cacagaacca    53460
tacttcattg gaattttttg tttcgaggct ggaattaaaa tcattgccct tgggtttgcc    53520
ttccacaaag gctcctactt gaggaatggc tggaatgtca tggactttgt ggtggtgcta    53580
acggggtaag tggcgcgtgc tatacgcttt ggatttaact agctgaagga ttacgaggct    53640
tttggttggt gtggtccggg ccaggctcag gaaggctgag cccttgtgtt ctccctcccc    53700
ttgttatgcg cctgcctcct ttctgccaac acccccacctc catgtctcag ctgtatatta   53760
cagcagatgc tttctgttac aattaaaata atagctcatt attgttggct gcttccagag    53820
tgctttatgc ccattctcta atttaatcct tgcaacaacc cactgaatta ggaaatatta    53880
atattcccat ctgaccactg aggaatcaga aactcagagt gtaacttgct taaggccacc    53940
cagcaagtaa gtgatggaac tgggagatga acagaagatt atgcattcca gaactcaagg    54000
ttttaagtgt tgtacgtgca tgggtctctt gatttgcttg aggatatctt gcttttattt    54060
caacttggtg aatgtttttt gagaatgtct gggtgcaagg gattgtgatt atgacaaagg    54120
agaaaagcaa gctaaataag gtacagttac tgtcttcaag gagttttcag atccatatat    54180
gatgaactgt ggttgaaatg tgtatatgct ttccctctaag cacccctgtat gaggtagcac   54240
ttgctggtat aacaaaagat ccaaagctag gaaatgactt aaacacggca gaagtttatt    54300
tgtcactcat agaaaattca aaattgagct gggtgtggtg gtgcatgcct gtaatctcag    54360
cactttggga ggctgaggtg ggaggatcac ttgagctcag gagttcaaga ccagcttggg    54420
caacacagtg agaccaccccc cccatctgta aaacataaaa taaaataaaa attaaccagg   54480
catggtggta catgcctggg agaattgctt gagctcagga gttggagggc acagtgagct    54540
atgatcatcc aaccgtgctc cagcctgggc aacagagcaa gaccccatct cgaaaaaaaa    54600
aagtccaaaa taattgttcc tagttgacag gctcatctcc tccaatgact gacggacccc   54660
gacccttgcc atattgtggc tcttcattgt cagcccacat catccaataa ctccatgctt    54720
gtctgtatca aaccaggaag gagaagtgag catagaaggt gatacttgga aaggtttatg    54780
agtttggaag gggtgtgacc cataccgtt ccattcatat cctattggct agaactcggt     54840
cacatgacca cacatcactg caagggaagc tgggaagtaa cagattgtgc ttagaagaaa    54900
agggaaatgg atttggagaa tgacctacta gtctgtcagg gaccttaaaa acttttatta    54960
gattccagta gggacattag tatctggtac caatggctgg ttcctcctct tcccactctc    55020
tactcctctc tcagctaagt ctgggctctt ctattctaag acccttcttc actgacacc     55080
tttttcatag taatcattta caggatcata gctttccatg ttttgttgct gctccaggtt    55140
ctgtctctct tggcgatgt gatggttgc agcacccaca ctgtgctggc cgggctctca      55200
caatgcagat ttgtttcaga gcaatgttgc ctctcacaga aggagctgtg gcctattggg    55260
ctgtttctgt agaggccttc agatgtcagc agtctgttgt aaggactctg ggctagctct    55320
catgggcttg ggtgttcaca gagggatctt tgttggctgt gctcacagtt cggtggcttg    55380
ggaccttggt gggttccaag ggcatattat ggtactgggc acttttctct tagtctacta    55440
ggaaactcat ctagaaacag cctagtggct aacttttttta ttgtttaaaa aatgtaaagc   55500
tgggcagggt ggctcatgcc tgtatcccag cacattggga ggccaaggtg ggaggattgc    55560
ttgggcccag gagtttgaga cgagcctgag caacatagca agaccacatc tccacaaaat    55620
aaaaattaaa agtgtataaa gctgggtaca gtggcacatg cctgtaaccc caattactca    55680
ggaggctgga gagagaggat tgcttgagcc taactagttt gagaccagct tgggtaacct    55740
agcaagatcc catgcaaaac taagtagaga ataatagagc aaacacctgt gtatacattc    55800
atttattcaa tgactattta ttgaacactt ctgtgtgcca ggtcctgttc taggctctgg    55860
gacacagcag taaacaaaat agaaaaatcc cctgtcctca tggagctgag agtctactga    55920
tggagatgga cacaattgat gaatgaatct agtgtgtcag atggcggtga ggggtacaga    55980
ggaaaaataa agcaggggag ggatggggatg tgtggcaggc aggggtgagg ggtgctgaa    56040
gccagggaag acttcactgg gcatgtgaca tctgaatgaa aacctaaggg aggtgagtga    56100
gtgagccatg aggagagctg gaacagagtg tcaggcaaag ggaacagcca gtgcaaaggc    56160
tctgaggctg gactgtatct gacatgtttg atcaacagta agaagaccca catggctaga    56220
gaaggtgacc agaagaatgg ggagaattgg ggatagagaa gtaatggagt aacctgctat    56280
caaaacacaa cctttctctt ttttttttttt tttttttttt tgacaagagt ctccctctgt    56340
cacccaggct ggagtgcagt ggtacaatct cagctcactg cagcctctgc ctcccagttt    56400
caagtgattc tcctgcctca gcctcccaag tagcttggat tacaggcgtg taccacaaca    56460
tctagctaat ttttgtattt ttagtagaga cgggtttacg ccatgttggc caggctggtc    56520
ttgaactcct gacctcaagt gatccacctg gcatggcctc ccaaagtgct gggattacag    56580
gcgtaagcca ctgtgcccag caaaacaaaa cctttctaac cttctaatc cctgttttct     56640
ccctccctag acccattcct ttctctcccc catccagggg cactttcctg aattttatgt    56700
ttattattg catttatgta ttcacacttt ggctgcctaa gtatataaga aatatatgct     56760
acctattttt acacttcaaa atattttta aatagcatca gagtgagaat agtttacact     56820
ttgactacat gcatagataa gaaatatgtg ggctgggaat ggtggctcac acctgtaatc    56880
ctagcaattt tggaggcaaa gatggaagga ttacttagg ccagaagttt gagaccagcc     56940
tggccaaatgt agtgaaaccc tgtctctaca aaatgaaata aaatgtaata aaatattcag   57000
ctgggcatgg tggtgtgctc ctgtggtccc agctactcag gaggccaagg cgggaggatc    57060
acttaagccc ataaggtcga cgctgtagtg agctatgact gcactccagc ttgggcaaca    57120
gagcagacc aaaatgtttt ttgttgttgt tgttgttttt tgttttttg                 57180
ttttttttaat aaaggccagg tgtgatggct cacacttgta agcctagcac tttgagaggc    57240
cagggcagga agactgcttg agtccaggag tttaagacca gcctgggcaa catggtgaaa    57300
ccccatctat aaaaaaaatg caaaaaatta gccaggcatg atgacgcacg cctgtagtcc    57360
cagctactca ggaggctgag gtgggaggat cacgtgagcc caggaggtcg aggctgcagt    57420
gatccgtgat tgcaccactg cactccaggc tgggcaaaa gtaagacct tgtctcaaaa      57480
aaataaaata aaataaaaaa taaaaaaag aaaagagaaa gaaaaaaaga gatatgtggt     57540
actgtttttc aaacttcaca tttctctaac ctgactttg tgttcaacat gagataaatc     57600
tgattaataa aaatagtttc catgcatcca tttttcatgac tgcatagtat tctgtggtag   57660
gagtatgctg ccgtgtattt atctatttgg attgtttcca gctttgggct attttgaccc    57720
aaagtgtccc tgctttctcc caagtgagtt tctctagggc acgtacccag gagtggaact    57780
```

```
gctgagttgt atactgtgtg catcctcagc cccactaggt attgccaaat tgctctgcaa   57840
agtggttgtg ccaattcatg ctccctgggg gctggcttct gctggctgag gctggcttga   57900
ccttgctggc aggaaggagc cttaaaaatc cctgtgtggt ttttttttgtt ttacttttat  57960
tttaagttta ggggtacaag tgcagatcta ttacatgggg aaacttgtgt cttgggggtt  58020
tgttgtacag gttatttcat cacccacgta ttaagcctag tacccattag ttattttttct 58080
tgatcatctt cctcctcccg ccctccaccc tccaaaaggc cccagtgcgt gttgttcacc   58140
tctgtatgtc catgtgttat catcatttag ccccactta gaaacacgcag tatttggttt   58200
tctgtttctg cattagtttg ctaaggataa tggcctccag ctccgtccgt gttcctgcaa   58260
aggacatgat cttgttcttt ttcttggctg catagtattc catggtgtat atgtaccaca   58320
ttttctttat ccagtctatc attgatgggc ttttgcagcc ctgttttttt ttttttttca   58380
taataacacg gttatgggaa cacttaggga agctcatata ttattgagca gtgtgatggt   58440
taatattgag catcaacttg atcagcttga aggatgcaaa gtcttgttcc tgggtgtgtc   58500
tgtgagggtg ttgccaaagg agattaacat ttgagccggt gaactaggag aggcagactc   58560
acccccaatc tgtgtgggca ccatctaatc agctgccagt gtggccagaa taaaagcagg   58620
cagaagaagt tggaaagagt agacttgctg agtcttctgg ccttcatctt tgtcctgtgc   58680
tgaatgcttc ctgccctcta aaatcagatt ccaagttctt cagcttttgg actcatggac   58740
ttacaccaat ggttagccag gagctctcag gcctttggcc acagactgaa ggctgcactg   58800
tcagcttccc tacttttgag gtttgaggac tctgacggat ccaccactgg cttccttgct   58860
cttcatcctt cagatgggct atcgtgggac tttaccttgt gattgtgtga gtcaattctc   58920
cttataaact ccctttcata tatacatcta tcctgttagt tttgtccctc tgaagaacct   58980
tgactaatac agacacctag tgggtcccaa taagtgatca ttaaactgaa ggcagtcatt   59040
cagtaggtca gtttgtcact tgtgtttgta tctccctgct tacaacaagg tggcctttct   59100
tctagtttcc tgtcatctga tggaagagat tctagactca ttcctctaga ggagaaaatac  59160
ttcatctaga acagataggt cctaagggtg agagctcatc gttgggatga atgaacccac   59220
tgaaatttta tgcaagaaga aaattgtgta tatgtatatt tttttttctg gtctgtagtt   59280
tttattagat tctcagggaa tcctgatcct atcatgaaga cctctattc tagattgggt   59340
tcctttcaca tccccttctc ctttcttgtt gaattctcca tgcatttctt tcacttgctt   59400
ttcttgctct tatttctctg gtagtcagtt atcctttttg tctggtggtt ctatctcctt   59460
caaatgaggc acattgctca aattttatta ctccaaattc caaggtgctg tttagtgtcc   59520
tgttgggttg taagctagga acagggaggg gaaagtaaaa cattctgcat gagctgggtg   59580
cagcgggcaa gcacctgaaa ttccagctac tggaagctga ggtgggagga ttccctgagc   59640
ccaagggttt aaggccagcc tgggcaacaa agtgagattt tgtcttaaaa aaaaaaaaaa   59700
tcccagctgg gctctgtggc tcatacctgt aatcccagca ctttgggagg cagaggcggg   59760
cagatcgctt gaagtcagga gttccagacc agcctggcca acgtggtgaa accccatctg   59820
tactaaaaat acaaaaaaaa aaaaaaaaaa gcctgagcatg gtggtgtggt gtgcactgtg   59880
aatcccagtt atttgggagg ctgaggcagc agaatcactt gaatccagga ggcagaggtt   59940
gcagtgagct gagattgtgc cactgcactc catcctggat gacagagtga gactctgtct   60000
caaaaaaaaa aaaaaaaaga aagaaaaaac acgcgcgcac acacacacac atcatgcaga   60060
cctagccttc tgccaatgtc aatggtagag aaacacagta gacacttaat tctatgtttc   60120
agagaggagg ggactcaaat atattaattt gacattgaga cagtgatgac tttaatgagt   60180
actttctttc ctttttttttt tttttttttt cgggacagag tgcagtggtg ggattttggc   60240
tcactgtagc ctccacctcc tgggttccag cagttctcct gcctcagcct cctgagtagc   60300
tgggactaca ggcatgcact gctgtgcctg gctaattttt gtatttttag tagagacggg   60360
gtttcacact atcagccaga ctggtctcga actccggacc tcaggtgatc tgcccacctc   60420
ggcctcccaa agtgctggga ttacaggcat gagccaccgt gcccggccta atgagtactt   60480
tctgattaac ctgttgccct tcagattcc tgaagcaaac cacagcgtta aaacgtgatt    60540
cattttgtgt ggaccaccac ggtgtttacc ttcttgttgg gtgaagtttg gtggaaaaga   60600
tcttaccccg gacatctgtt tgttctttgt aactcagagc ctcagagaaa tcctaacttt   60660
ataatgttgt caaaccccttg taaggcatgt ttttattgta tttgtgttct gatcatgaaa  60720
ctgaaaatgt gtaagaggaa gatttcagaa gcttggctgt atgtctgaga tgacagttcc   60780
tttactgtca ttctcaaata tatataaata ttgaagagat caaataacac aaatcgtgca   60840
tgttaagaaa agagactgtg aacctcacca gagagggggtg agcacaattt tttttcttt    60900
ttattcacag ggttagcact gtcccttca cataataaat gctcagtaaa ataaatggtt    60960
gttaagccga aaaagggtaa cacttctgat aatgagtgtc ctgggaaatt tactaagctg   61020
tttagaagat gggaccaaca cactgataga aatagtcaga tagtccagaa gtctatggca   61080
gatgccctga acatcagatg agatatataga cagagaagct ctgggtcttt gccagctctg   61140
acatttttatg actctatgaa acggaaggtt cctttttaga agggtctata aactgtctca   61200
ggctttgggc cattttgttg aagatcagag gcaaggaaaa gacacaacta cacaggaacc   61260
atcagggaaa gatgttgttt tttggtcttg aagcatcatt gaattttttt tttttttttt   61320
gagacgggagt ttttctcttg ttgcccaggc tagagtgcaa tggcatgatc tcggctcact  61380
gcaacctccg cctcccaggt tcaagtgatt ctcctgcctc agcctctga gtagctggga   61440
ttacaggcat gtaccaccaa gcccgggtaa tttttttgta tgtttagtag agacgaggt    61500
tctccatgtt ggtcaggcta gtctccaagt cctgccctca ggtggtccgc ccacctctgt   61560
ctcccaaagt gctgagatta caagcgtgag ccaccgcatc attggatttt                61620
aaggctccat ggattctggc aggtccagcc cttctgtttt actcacaaac aagtggtttg   61680
tccaaagtca cacagagatg gtggcaagag atctagaata agaaggtgtc ttcaagtcat   61740
ggagccagga accctggctt ttgggcaat ggaagtggta taaatgttta atatcacccc    61800
tcaggttctg ccactagagc ccagctctct cttccttcct cttgccccct gactagcta    61860
tggcctcttt ccagagaata agaaagggat cctcagagaa taatcccagt tcctcgcttt   61920
ttattatata gttgaggaaa ccaagtctca gaggggtcag tgtcttgacc atacacctct   61980
catgtcctct ctccttttttg attaattgaa taaatacatg tagttgcttc ttacctcctt  62040
tctttcttca ccccctgcccc atgcacctgc tcttagttgc cttcacatgt aaacagcatt   62100
ccaacaacaa caacaaaaca caaccagcat tctaactcat gagaccagca acagttccta   62160
taaatacccag cagcatttta ttttaatgtc tctctgcagt agtttctccc ctccatggat  62220
cagtcatcct tggtaccaaa aggattcccc actgtgcaca aaatgctttt tgtcattctc   62280
agtgagttat accattgaga gagcatcgat ctttttattg ttcaaagctt ttggttgtca   62340
tgatatttgc tggaccatgt ttcaccagga accacatcac ttcctagcag caggagctat   62400
tttcttccat cttctaacaa caccagcagt gacagtgata taatgatgt tagctgccat    62460
ggtcgttatt cttatcattt attgagtact tactatgtgc cagggactac attaagagtt   62520
```

```
ttatgtgtat tatcacattg agcctcgcta gcctttgtac agatgaatct gaggctcaga   62580
gaggttaagc tgctcacaag ggagtcacac agctggtaag gggtggatca ggatctcagc   62640
ctctctgcta ggacacttct ctaaacctag aataatactg ggcctgtgtt aagttcagca   62700
aagagctgta ttcaacccag tgtccttagg aatgtaatgc ctgttattaa caacagtggc   62760
aacattgata agctgaaact tatgaggtgc ttacaatatg atatactata tattatatac   62820
atacataggc acccacctat aatctcagca ctttaggagg ccaagtcagg aggatcactt   62880
gagcccagga gttcgagacc agcctgagca gcatagcaag atcctgtctc tgtaaaaagt   62940
ttatttttc agttggccag gtatgttggt acatgcctat agtcccagct aatgaggagg   63000
ctgaggcagg aggattgctt gagcccagga atttgaggct gcagtgaact atgatcacac   63060
cactgcactc cagcctgggt gacagagcaa gactgtctct aaaaataaaa ataaaaataa   63120
aattatttca actctcaagg ttaaatataat actattatta ttcccattta cagatggagc   63180
aactgaggct caaagacatt aaatgcttac tgtcttagtc tgttttctgt tgcttatagc   63240
agaacacctg aaactgagta atttataaag aaaaagcaat ttatttctta cagttatgga   63300
gactggaaag tttaagatca aggctgcatg agctataatg cacacacact attgcactcc   63360
aggctgggtg acagggtgag accccgtgtc aataaaataat aatataaaat aaataaaaca   63420
aatttcaaca tgagttttgg aaggtttgaa atattcaagc cagagcatct gtctcataag   63480
tggtggaccc aggatttgaa ctaaggcaga tctggatcta gaaccccattt tcttgaatcc   63540
tacgctatt ctctaaggtc aagtttgcca aggaaaataa acttgagaat ttgaatagag   63600
ctctctgaca tgggaagtca gggtgatcct tccttcccct ccctgatctt gggttccact   63660
atggctgggg gaaaacagga gcagaagaga tttcaagaaa tgagagattg gcctagcgcc   63720
atggttaaga cctggacttc agagtcagag gaagctcctc cctctatgac agtgagaatg   63780
tgggttgaac tcactgaacc tcagttttct cacctggaaa aagggagtaa aactagtgca   63840
tagctcctag ggtttgcatc acacacgaaa gttggtgaac tgaaggaaaa aaacttaaat   63900
tcttgtgggg gagcatgtga tagatgctac aaattctcca tgccttattt acctagctta   63960
cgtctaagtt cacctgcagc ttcctcttgg tacactccca tctctctaca tctctgttgg   64020
agggcagtct ctggcatcac agagtttgct gagccagatg cttaacaacc tcggtagcat   64080
ccctcaacca gtgagctagg gagtcagtgt ataaatacccc tggcttcccc attgctcagt   64140
gggaaaaaac tgaaatatgt tatacagcat catagaggtg cctcagtaaa attgaatcct   64200
agttgttcac ataaaacccca ttcactagtg tacccttttac caatctctct cttcctcatt   64260
cctcacttgt aattccttgc attaccttccc aaattaacca ttggacccta gttttttgcct   64320
tggggtctac tcggcgctaa ctcaaggagc ggaagttgga agcttagcgg gttacaggtt   64380
tcagcaccct ggacagctcc cagcacaccg tattgtgcta aaatgttctc ttccctccct   64440
ctgcctccag ctggggtgga gagggactga gtaaaggcca gatggccagg tgaccttgtt   64500
ccatactgag cttcttggcc attttccctg tggggctgga gaagaccttg ccatccatct   64560
ctccgcaggt ttgggggccg actgaggtct tgttttctcg aattgctatg acaaatgcca   64620
gcctgcctcc aagggggcatc tgtcccactg cctctacagt ttgcatgcct aatgactcct   64680
ctcctctcac cagggcaggg aggtggctgc ctggtgggcc gcttgaagcc gggagaccaa   64740
gatcatgcca ctggactcgc aacaaaccga gactcttttt tttttttttt tttcctcgag   64800
acaggtcttt gctctgttgc ccaggctgga gtgcagtggc gcgatcttgg ctcactgcag   64860
cctccgcctc ccaggttcaa gcactccac ctcagcctcc caagtagcgg ggattacagg   64920
cgcacaccac catgcctggc taatttttgc atttttagta gagaggggggt ttcaccatgt   64980
tggccaggct gatctcgaac ttctcccctc aggtgatcca ctcgcttgg cctctcaaag   65040
tgctgggatt gcagctgtga gccaccatgc ctggccaaca gaataggact ctgtctcaaa   65100
aaataatttt ttttaaacat tgctttgcaa cccagctgct tcttgtgcag gcatctctaa   65160
atgaggacag ccagtctaca tagacacgta aggaagcata gtggttaaga cctggtcttt   65220
gggggttagag tggattccca acctgactcc actgtttcca agctgtgtga ccttgggcaa   65280
gttactgtac ctccctgaat cttccatttc ttcatctgga aaatgagagt agtagcatcc   65340
cctgacttgg tgggggcatgg tggctgatgc ttgtaatcca aacactttgg gaagccaagg   65400
tgggtgaatc gcttaaactt gggagttcaa ggccattctg gcaacatggt gaaactcca   65460
tctctacaaa aacaaaacaa agcaaaaatt atctgggtgt gatagtgtgt gcctgtaatt   65520
ccagctactc aggaggctga ggtgggagaa tcacttgaac ccaggaggtc aagtctgcag   65580
tgagccgtgc ttgcaccact gcagtccaac agagcgagac cttgtctcaa acaaacaaaa   65640
caaaacacaa aacaacaaca aaatactacc accttatggaa gttgttttca aggttcaatg   65700
agttaatgtc tgacccatgc tgggctgggt ttatggatgt tacttgccca gggacagtct   65760
gaagaaagag aaagtgatat agtccattgg gcctcagctt cctcatctgt ggaatgggaa   65820
taataattgc acctacctca aaaggtaaaa gtcagtgaga tacatataag gcattcagaa   65880
caaaactgg cacagaataa gtgctcaatt atattagcta ttgtaagact aataactatc   65940
attataatga tgataataat tattactact tccccaggcc cagttccata gaccagttag   66000
ttaactgtag ggaacgtttg ctattattag ttgggttccc aatatctgac ctcccctttcc   66060
aatttaggga gaatcctccc ctttctataa agtactgctg gtctatggga tcccacccctc   66120
actaataagt tgaaggtgaa agggattcat tgtcacccca tcacctggta gtcagggcat   66180
gtgatttaaaa caaccaggggc caggcgcagt ggctcacgcc tgtaatccca gcactttggg   66240
acgccaaggc aggaggatag cttgagccaa gcccaggagt ttgagaccag actgggcaac   66300
atagtgagac ccctatctct taaaaatttt ttaattagct ggggtggta gcacaggctt   66360
gtagtccccg ctactcagga ggctgaggca ggaggattgc ttgagcccag gaggtcaagg   66420
ctgcagtgag ccgtgatagt gccactacac tccagcccag cctgggcaac agggcaagat   66480
cctgtctcaa aaacaaact aataaaaaac tcaaccagtc acgttttcct acccaggaat   66540
ttgaaatgg accaagtgat ccaaacatga tggtttggac tctttcatgg cctcctgcta   66600
caggagaagg tcaggctggc tacattgttc ctgctgattt cccaaatcct ctcttctggc   66660
cccctgttga ttatctgagt ttcctaaaaa tcccttttat gcctaagata gccggtcagt   66720
gtttggtttt gcaatcaaga acccagactg gccaggcac ggtggcccac gctgtaatc   66780
ccagcacttt gggaggccga ggcgggcaga tcatgagatc aggagatcga gaccatcctg   66840
gctaacgtgt gaaaccccg tctctactaa aaatacaaaa caaaaaaaaaa aaaattagcc   66900
aggcatgatg gcggtcacct gtagtcccag ctactgggga ggctgaggca ggagaatggc   66960
gtgaacccgg gaggcggagc ttgcagtgag ctgagatggc accactgcac tccagcctgg   67020
gcgacagaac gagactccgt caaaaaaaaa aaagaaaaa agaagaaccc agaacccaga   67080
ctgatcctga gacaaagatt tgagggcaac gaatcacgag gtcaggaaat cgagaccatc   67140
ctggctaaca tggtgaaacc ccgtctttat taaaaataca acaaattagc tgagcgtggt   67200
ggtgggcgcc tgtagtccca gctactcggg aggctgagga aggagaatgg cgtgaacctg   67260
```

```
ggaggcggag cttgcaataa gccaagatcg caccactgca ctccagcctg ggtgacagag    67320
caagactcca tctcaaaaaa aaaaaaaaaa aatttgagga caagtggttt gtttggcaat    67380
accaggaaac aggggaacag gatagtcaga aaagaaagag aaagctgggc atggtggctc    67440
actcctgtaa tctcagcact ttgggaggcc aaggcaggtg gatcacctga ggtcaggagt    67500
ttgagaccag cctggccaac atggtgaaat ccctgtctctg ctaaaaatat aaaaattagt    67560
cgggtgtggt ggcgtgcacc tataatcaaa ataaaataaa atcaggatat tttattttaa    67620
aactctgtct tagtgtaact catatttacc tcttctgtat gctcctttgc atcagttata    67680
tattgccata atacgctgt gtaacaaaca atccccaaga cccagtggct tataatgaca    67740
agcatttatt tagctcatga ttctgaaggg tggcagttta ggctgggcgg agttgggtgc    67800
tttatctggt ctcagttgag ctcattcatg catctttggt cagctgcggg tcagctgggt    67860
ggctcttctg tttggctgtt agctggctgc agactggtcc aggatgacct cggctgaat    67920
gactgtgctc cactccctat ggtctttcac cctccagcag gctagcctga gctagttcac    67980
atggcagctt ttcatcctcc agcaggctag cctgagctag ttcacgtggc agcaatggga    68040
ttctaagaga aagaggaagt gttcagcctt cttaaggagct agtcccagga atggcacaac    68100
atcgtgttgg ccactgttgt ccaaagcaag caatgaagct ggtccagatt caaggaatgg    68160
ggcaacagag cccatctggt atttacctgg ggccactggg gccccattcc tgttccctgg    68220
ggccttttgc cctgacttct gtgggccctc agagcatatt ttcagattcc tttccatccc    68280
tgaccctcag caatcaatgt agatgacgtg tcattactgt gtcacttgca cagagaaaag    68340
gaggaaaaaa tgtcagcaaa aactctgctg agagcagagg gcccatcata cagcaagctg    68400
gaaagaaaag tgggaatgat tacacagcct cctcagatgc ttccagcttt tatcaaatct    68460
cactgtgata tctgagttct gaaccctcac aggtggttgg cgtgcaaggg aagagatttc    68520
ttgtctgcca tgctgacatg cacagacacg caacctgtcc ccctctgtcc actggggctt    68580
tggattttgt ttgttgaaat gttacccact cctgatcaga gctggatgga aacctggctc    68640
tgattccatt ggctcagggg ctcagtgggg ggcagaggcc aggctggttg ggtgtctatg    68700
tggagacctt aactcttctc cctcccgccc caactctttt tgtttctttt ttttttttt    68760
tttttttttg agatggggtt tcactcttgt tgcccaggct ggagtgcagt ggcgtgatct    68820
tggctcactg caacttctgc ctcctgggtt caagcaattc tcccacctca gcctcctgag    68880
tagctgggat tacaggagca cgccaccata cctggctaat ttttgtattt ttagtagaga    68940
cagggttttcg ccatgttggc caggctggtc ttgaactcct gacctcaggt gatccaccct    69000
cctcagcctc ccaaaatgct gggattagag gcgtgagcca ccacacctgg ccctttttctt    69060
ttcttagctg cctccacctc tcttcccttc tgcagtgtta ggtttatgga aaccgaggcc    69120
ggcgtagaga tcaacttcag agagcatgaa ctgagcatct gctgggtctt agatcctta    69180
catagcttat catcttcaaa ccttctcaca gttctgtgtg gctagagcca ggatttggac    69240
acagctctgc cccactgtag aaccaggctt ccttctgtcc actgtcaaat tttagaggga    69300
gaaataggg aaagggacac cagccttctc cacgagcagc ttctgcccac tcaccccagg    69360
gactttgcac atgctgtgtg cctgtgtctg agatatgctc cctcctctgt atctgcttaa    69420
ttcttaccca gacatgatac ataaagtatt taacatccag gtggcaggga caccagctaa    69480
cctgaaaaga ggttcccctg ttgtgccaca tgtgtactca ttgtttgctg cattgtgggg    69540
gcagtccagg ggccttgaag aggggccaag tgccaaagg ggcactcctca ggcctcaagg    69600
aagtacatgt ttactgatat gatactgtct cttcctccag gaaggaagcc ttccctgatc    69660
tccccactgc atgcccacta tgataccagt ttaggtcccc tctttatggc catctgtggc    69720
atcagtgtga atcctcttaa tgttgtctat ttggttaatc atctgtctcc ttcctctggg    69780
gggtaaagac agaaccacag agcctcgtgt agaacttgag aatggggttc agtaaaaatc    69840
tgttgaatgc ataaatgggt gattgagtga atgaatgaat gagtgaatga atgagtgagt    69900
ggatgaatga atgagtgaat gaatgagtga gtgaatgaat gaatgagtga attaatgaat    69960
gaattcatag ctgataatac aggcttcatg gcttttgtta ggcttgccca gacattgcta    70020
ggggatggac agaaggaaga agagctatac ttaattccag tcctgtttgtt ctgtagcagg    70080
aggagaaaaa cagggactgc ccagcctgct ctgggtggat tcaggagcag ctgaggttcc    70140
tctcttattt gcaaacaggg aattcaaaaa gccccaacct cagaatcaca ctcgcctcag    70200
cagctgtacc agcaaggggg acaatgtggg aagccttggg caccaggaat gctgagtgct    70260
tcgaaaaagc gaaggctcag ggaacaatcc ctgattttc attcccttgt cctttctgaa    70320
gaaacaggca aaggcaggcc aggcacggtg gctcacacct gtaatcccaa cactttagga    70380
ggccgaggct ggtgaatcac ttgaggtcag gagttcaaga ccagcgtagc caacatcatg    70440
aaatcccatc tctactaaaa atacaaaaat tagctgggtt tggtggtgca tcctgtaat    70500
ctcagctact cggaggctg aggcatgaga atcacctgaa ctgggaggt ggaggttgca    70560
gtgagctgag tctgcgccac tgcactccaa cctggatgac agagtgagac tccatcttaa    70620
aacaaaacaa aacaaaaaca agtaaagcct tgtgtgtttt taaattgtag gttcagcagc    70680
aaagctctgt aataaggagc tggaccctgc agtcagacag tcatgggctt ctccagtgcc    70740
cagccgagtg acccgaggga gttatgataa acaccaacat tcatccacaa tttgtaccta    70800
gtgctattct caatatcttg agtaaattat ctcatttaat cctccaggca catctttctt    70860
ggtaggtgcc gtcattgtcc ccagtgtaca tctgggaaaa tgaggacagg ctggcagagc    70920
acccttcctg ctcacctctg ctgctctgct gacctctggc aagactgttg tctctctgag    70980
cctcagtttc cccatctgaa aatttgggcc tgtattagcc cgttctcaca ttgctataac    71040
gagatgcttg gctgggggctg ggcgtgatgg cttatgcttg taatcccagc acttttgggag    71100
gctgagttgg gcagattggg agtgtgagac cagcttgggc aatatagcaa gaccccatct    71160
cttctaaaaa aaaaaaaaaa ttagccaggc atggtgatat gcacctgtaa ttccagctac    71220
ccaggaggct gaggcaggag aattgcttga acccaggagg cagaggttgc agtgagccaa    71280
gattgcgcca ctgcactcca gcctgggaga cagagtgaga ctccatctca aaaacaaat    71340
tattttttaaa aaattaaaaa aaaaatgcc tggctggca cagtggctca cacccataat    71400
cccagtactt tgggaggcca aggtgggaag attgcttgag cccaggagtt ccagaccagc    71460
ctgggcaaca cagtgaaaatc ctgtctctac taaaagtaca aaaattagcc aggtgtggtg    71520
gcacgcgcct gtggtcccag ctactcagga gggtgaggtg ggaggattgc ttaagcctgg    71580
gaggtcaagg ctgcagtgag caatgattat gccactgcac tccagcctgg cgacagagt    71640
gagaccttgt aaaaataata ataataataa taaataaata aaaacccctga gactggggta    71700
atttataaag aaaagaggtt taattgactc acgattctgc aggctctaca gaaagcatgg    71760
cagcatctgc tcagcttctg ggaaggcctc aggaaactta caatcatggc agaaggtaaa    71820
gctggagcag gtgtcctcac atggccagaa caggaggaag agagagagtg gggagatgct    71880
acacacccttt aaatgtccaa tctcacaaga actcactcac gatctcgaga atagcaccaa    71940
ggcggaaatc tgcccccatg atccaattac cttccaccag gccccacctc caacattggg    72000
```

```
gattacaatt cgccataaga ttttggttgcg gacagacaca gatccaaagt acattaaaag  72060
taatggcaaa aaccacaatt acttttgcac caacctaata tctcaggggc tcattgtacc  72120
tatttcacag gacaaatgaa ggtatcagta ataacagtag cctgtagtcc cagctattca  72180
ggaggccgag acaggaggat cacttgaacc caggaggtcg aggctgcagt gagctatgat  72240
cacgccactg cactgcaccc tgggtgacag ggcgaaaact tatctctaaa aataataata  72300
acaacaacaa tagtgaacac agatataaca tgtgtgtggc caggctgtgc ccttagggct  72360
ttgcagggat tatttcattc actctcaatc tccccatttt acagatgaga aaactgacgt  72420
tcagaaaagc tagaggactt gccccaagcc acacggctag gaagtggtgg aattgggggtt  72480
taaatgagga agcttgactt cagtgtcgaa gctcttaact gccacactca atacatggag  72540
tagaggttgc tgattctgtg attatctgat tctggaaagt aaagaccctg tttccagacg  72600
tttgctgctt gacttagttc ccaggggatg gccactggat gatgcagtgt tgcccaggag  72660
aggttagcta gacacactgc aaccattcca ttgctaatac ttatacttgc tcttgttctg  72720
ctgggtgcta tgcagggaag ggctgtctga gcccttgcca agaattctcc cattggtgcc  72780
tcccagagat tctgaggttg gggctttttg catccctat tagcagatga gacaccaaag  72840
cccaggtcaa taatctgacc tgcatcccc gcctaccagc cagaccaagg tcacttcccc  72900
acaatgcagg ccctgatcca aggctctggg tgcaaaccag tttccatgtc cctgggggtc  72960
catcttcttc agctgacttt ttttttttt tttttttt gagacagcgt cttgctttgt  73020
tgccgaggct ggagtgcagt ggtgtgatca tggcttattg cagccttgac ctcccaggc  73080
caagcaatcc tcccacgtca gcctcctgag tagctaggac tatgggcaca cgccatgatg  73140
cctgggtaat ttttttttt tttttttga gacagagtct cgcactgtag cccaggctgg  73200
agtgcagtgg cgcaatctcg gctcactgca agcccatct cccaggttca tgccattctc  73260
ctgcctcagc ctctcgagta gctgggatta caggtgcctg tggctaattt  73320
tttgtattt tagtagagac ggggtttcac cgtgttagcc aggatggtct ccatctcctg  73380
acttcgtgat ccgccacct cagcctccca aagcgctggg attacaggca tgagccagat  73440
gcctggctaa tttttaagtt tttttataaa ggcggggtct tgctatgttg cccaagctgg  73500
tctcaaactc ctggcctcaa aaagtcttcc tgcctcgcc tcccaaagtg ctaggattac  73560
agacatgagc cactgcaccc agcctgactt tttttctaac tgaaaaatta attatatata  73620
ttcatggagt acaatgggat gttctgatat atgtttacat ttttgaatga ttaaatcaag  73680
ccaattaaca tatccactac atcgcatact tatttttgt ggtgagaacg cttaaaatct  73740
actctttag caattttgaa atatacaata ccttatgttg tatattacat tatgttgtat  73800
agtacgttga aacatacact acaatacgtt atcattaatt gtggtcacca tgctgtgcaa  73860
aagatctcta aaacgtattc ctcctgtctg actgaaactt tgtatccttt gcctaatatc  73920
tccccaatcc ctccaccacc agccctggt aaccaccatt ctctctgctt ccatgggttc  73980
aaatttttta ttttttgaaa tttttaattt ttatttattt atttatttat ttatttattt  74040
atttttgaga tggagtctcg ctctgtcacc cagtctggag tgcaatggtg ccatcttggc  74100
tcactgcaac ctccgcctcc tgggttcaag cgattctcca gcctcagcct cccgagtagc  74160
tggggttaca ggtgcttgcc accaggcccg gctaattttt gtatttttag tagagacggg  74220
gtttcaccat gttggctagg ctggtctgga actcctgacc tccagtgatc cacccactcc  74280
ggcctccaa agtgctgaga ttacaagcgt tgagccactg cacctggcct aaaattttt  74340
tttttttt ttttttgag acggagtctc actctcttgc taggctggag tgcagtggca  74400
tgatctcagc ccactgcaac ctcagcctcc cgggttcaag cgattctcct gcctcagcct  74460
cctgagtagc tgggactaga ggtgtgcacc accacgccca gctaattttt gtatttttag  74520
tagggacagg gtttcaccat gttggccagg atggtctcaa tctcttgatc tcgtgatcg  74580
cctgcctcgg gcttcaaaag tgatgggatt atgggccacc acgcccggcc tcaaatttt  74640
tagagctcac atataagcga gattgtgtac tatttgcgtt tctgtgtctg gcttgtttca  74700
tcttagtata atgtcctcca ggttcatgca cgttgtcgca aaagatggaa tttgctcctt  74760
tttaaagact gaatagtact tcattgtgta catatacacg ccatattttc ttcatccatt  74820
cctttactga tggacatttg ggttgtacct gcatcttggc tattgtgaag agtgctgtca  74880
tgaacatggg tgtgcagctg actctgaggt gttagaggga ttacagctcc tccaaaagac  74940
caccgtcacc caaacctgct cctcctgccc tattttctgt ttaggtaaag gcgggcttaa  75000
ccccctgcag tgctctggcc tcagacctcc agatcttcct ctatgcctct atgcctcttt  75060
ttctccaccc cctgcatcca atctgttagc acatcttatt ggctctacct tcagaatcta  75120
cccagaatcc accaccacc tctcaccacc ttcacagccc caccccgtc cagcccccat  75180
ctttgctggc ctggactaaa ccagttgccc ctccacccca atctggtctc ttaacttcag  75240
tccttgcccc acccccagga ctgttcccca cacagcagcc agagggcacc tgtgagccac  75300
tgagtcagga cctggctcct ctttgctcac aacctcactt ggagaaaag cccaaattct  75360
cctcacaggg acccacaaac tctgcccctg tgatccccca tccccctcta ttcccactct  75420
cctctccact cactcggctt cagctacaca agttccctgc tgtcccttac acaccaagca  75480
ctcccagcc tcagggcctt tgcacaggct gttccctgcg cctggaacac tcttccccca  75540
gatatctgct tggctcccccc ctcacttcct ttgggtcttt gctcaagtgt ccttctaaca  75600
tgtaactgcc tcacctgcac tgtgccaccc cactcccgc ctctaggctt aatttccctc  75660
tacaccctg aagagcatct gccaagctat atttacttgt ttattggtta ttgccaatcc  75720
cctgcccca ctagaatgcc agctccatga gggcagggac ttctgtctgt tttgttcact  75780
gctattcccc cagagcctag aacacagcct ggcacatagt aagtattcac taaataattt  75840
gtaatatgaa ttgtgccagt aaaatcttcc aggggcatca agccctgcc atgactaggt  75900
ggtaacatcc tcacccctg tccatgtgct atctcctcct gacctgcttg tctcattgtt  75960
ctaatggtgg ctcacgcctg taatcccagc acttggggag gccgaggcgg gcagatacct  76020
gagttcagga gtttgagacc agcctggcca acatgatgaa accctgtctc tactaaaaat  76080
acaaaaatta gctgggcgtg gcattgcacg cctgtagtcc tagctactcg agaggctgag  76140
gcaggagaat cgcttgaacc cgggaggtgg aggttgcagt gagctgagat catgccattg  76200
caatccagcc tgggccacaa gagcgaaact ctgtctcaaa aaatatatat atatatttca  76260
ttgtggtaac atatgcataa cataaaatgt accattttt aagtgtttag ttgagcggcg  76320
ttaagtacat tcatattgtt gtgcaaccag gaccgcatc catctccaga acttttgcat  76380
caaaac tgaagctcg ccccaggaa atctccacga acctgcccc cgctcccctct  76440
ccccgactcc cccttccccc ctcccccactc ccccaccct actccacact cccacactc  76500
ccagcccctg gcaccgccg ttctagttc tatctctgtg aatttggcta ctttgggtcc  76560
cccctgtgag tagaatcata cagtatttgt cttttgtga ctggttttgtt tcgtggagca  76620
taatgtcctc cagtctcatc catattgtag catgagtcag aatttccttc ttttccaggc  76680
cgaatcgtat tccattgtgt ggatggacca cactttgctt atctgttcat ccagatgggc  76740
```

```
acttggcttc cacctttttgg ctattgtaaa taatgctgct gtaaacctgt gtgtacaaat   76800
agctgagtcc ctgctttcaa ttcttttgga tatagaccca gaagtggaat ttttttttaaa  76860
tcaagatttg acccactggg gcccttagag gtctcattgg ctctgaagct ttttttttttt  76920
ttttttttttg gacgctttga aactaaaaat aggagtgagg ggcacagtga gggggggcaca  76980
catctctcgt gtcagcgttt tttaaaaaca ccccgggagg aagatgtgtg aaatccctcc   77040
cttcccccccg ctcccacccc ctccaagatc tcaaaatacc tcttgttttta ggaagcggct  77100
gtgacatcag gcaggcagcg tgtggcatct gagacacaat atcgcaagtg gctgggagcc   77160
cagagaaacc aggacaggcg tgctggggat gtggactaga gatggagcta attttagtgg   77220
ctgaagaggc tgcaagaaga gagagaaaga gggggtgtgtg tgtgtgtgtg tgtgtgtgtg   77280
tgtgtgtgtg tgtacgcaca gtgatagagg ctggaggggg agaaatgaca gataaatcag   77340
cttgggcaaa gaaagctaat gggcagagga gcgagaccca gctcagaagg tggtcagcaa   77400
atctaaagat gtgtgcccga gggtcaaggt ggtggggggga ttcataggca agtggtagag   77460
aggctattcc atttgcagag gctctctctg tttgaggcgt gattcacctg tgccgtcctc   77520
aaggccattc tgagaacacc actgttgttt tcctccttt atgagtaggg aaactgaggc    77580
attgaactgc ttctattctt cagtaagaag caggggggaac atatggtaga agcaaagaaa   77640
tacaaacatg agggctctcg gggtctacgt gattggctgt gacatccatg agagcggatc    77700
gcaggttgaa ggaaacactg gtggcagaaa gtagctgaac attttggattt gggaatccca   77760
gtggacgtgg cgaaaattct ggcttttccc ttcacaggct gcggggccac tctgacctgc    77820
ggtttcctta tctgtgaaat ggaacgatgc cacctgtctc agcgttgttt tgaggatgcg    77880
aggagatgat ccgtgtaata tgcccactag ggggcctgct ccagggtaga ttctcagcaa    77940
atggtagtca tggttttttgt tacatttggg gatattggca ggtaaaaagg aaatacttca   78000
ttcattccaa aattgctcac tgaggttcta ctatgtgcta gggccctgatg acacatcggt    78060
caacaagaca ggcctgcttt ctgcccttgt aaaacttcag ttcaactgca ttgcactcat   78120
cagcctaata atccaggtaa attgtgatga gaataacaac tagcatttac tatgagccct   78180
ttacaaatat taacccattt aatcttcaa agagcctata agataagagc tcttgccctg   78240
cgcagtggct cacgcctata atcccagcac gtcgtgaggc caaggcaggt ggatcacctg   78300
aggtcaggag ttcaagaata gcctgaccaa cagggtgaaa ccctgtctct gctaataata   78360
caaaaattag ccaggcatgg tggcaggtgc ctgtaatccc agctacttgg ctgaggtagg   78420
agaatcgctt gaacccagga ggcggaggtt gcagtgagtc gagatcactc cactgcactc    78480
caagagtgaa actctgtcac acacacaaaa aaaacaacc tgttattatc cacattttca    78540
ctatgaggaa accgatgcc agagaggtta agtaactgtc caaaggtcac acagctacgg    78600
agtggtagag ctgggattca gacccaggag tgtgatccca gagtgtgtgt gtatgtttgt   78660
ttgtttgttt gtttgtttgt ttgttttttac cactgtgttt tcctgcttct gcaatagaag  78720
taatcaccag taacactgag cagttgttat gtgccatgcc cttaacacac atctccttgg   78780
atctttggaa agaatcctaa aagggttgtt tttcatgatc cacatttttat ggagagagag   78840
agatcaaagc atagagagag gaagtaactt gcccaagatc ctgcagctga agactctagg    78900
gttgcaaatt tgggacggcc ctggaccctg cattccagct tctagcagct cataggggga    78960
actctttatt tatttattta tttatttatt tatttattta tttattttga gatggagttt    79020
cgctcttctt gcccagcctg gaatgcaatg gcatgatctc ggctcactgc aacctccgcc    79080
tcctgggttc aagtgattct cctgcctcag cctcctgagt agctgagatt acaggcatat    79140
gccaccacgc ctggctaatt taatttttt tagtagagac ggggtttctc catgttggtc     79200
aggctggtct cgaactcctg acctcaggtg atccgcccca ctcggccccc caaagtgcta   79260
ggaatacagg cctgagccac cacgcatgcc ctggggggga ccacttttat cggtgcattt    79320
cttccatttt ccctgtgtct gtgtaaagat aaacaccccc aagcccctg actatgaact   79380
gtgggccata attagttaat ggaaggtaaa tgttttagag acggaaattg ctgtgccatt    79440
tttccccgct aggcattgtt gcctgcatgc taatgcaaca caatgtgcct ttcttctgtc    79500
aggcattttt agacaaattc tattttccct aaaatatttt gccaaagaaa atagcaaatg    79560
gggaagacat tcagaggctc aggcagagag aggacaccat tcccttgggt ttaaacagaa    79620
tggcagagtg gataacagca cagatcttga gttaggtgga tgccaatttg tgatttattt    79680
cccagcaaac caagatgctg gctctctgtg tgcctcagtt tacttatttg tcaaatgagg    79740
agaataatgg taccgtctc tcaccagctt accagttgcc tcttttagcta tgtctaatct    79800
gctattaacc acgcccacta tgtctttaat tccaagtatt agaattgttt tcttcctaca    79860
agctgtctga tctttttttaa tcctgcttca tcttttgcag tattgttttc ctacagcagg    79920
atttctcaac cttggcacaa ttgacatttt gggctaggta attcttggcc gtgagctacc    79980
accctgtgct aagatactta gagcatccct ggcctctcac cctactaaat gccagtagca   80040
gccccctcccc agttgtggca gccaaaaatg gctcagacat tgccaaacga aatgtcccat   80100
ggaggggtaga aacgccccca cttgagaatt gttctatagg tattttcaag catgtcttac   80160
atttctttaa gtataatatg caaagaaaa ggctaaatct aaaaaaagcc cataatatgc      80220
gaagaatttt tataatcagt gtccaataac ttaagtatct aaaattgtta tggctttttt     80280
tctgctgtct cttgtttcct gtgattcctc attctggtgc cttgttttct tgaatgtctt    80340
gttatctttg gttgtgtgaa gctcattttc catgggacac tatttttttgt tttgttttgt    80400
tttgagacag agtctcgctt ggttgcccag gctggagtgc agtggtgcaa tatcagttca   80460
ctacaacctc agcctcccag gcccaaatga ttctcctgcc tcagcctcct gagtagctgg    80520
gattacaggc gtgtgccacc acacccagct aatttttttgt tatttttagt agaggcaggg    80580
tttcaccacg ttggccaggc tggttttgaa ctcctgacct caagtgatca acccgcctcg    80640
gccccccaaa gtgctgggat tacaggtgtg agccaccgtg cccggcatcc atgggacact    80700
gttgaaggga gttcattgag gcctgcgatg aaggcgaacc ctccatggac aatttgcatt   80760
tacttttttcc aggtgtctgg gaaactccca gtctaggaac atcttagact tttagaccaa    80820
caatgtcttg agaattttagg tcaccagtgt ctgcaaaagc cagctctgtg tgttataattc    80880
tcaaaaactt ttgttttttct cctttctcgc aaagtgccaa agtaacttcc tcaaaaatct    80940
ctgggaatgg aaagacggga gtaaattaac ttcaggtttc ttacctgaaa gtgatagcct    81000
attgggcccc catcctactt ggggagtggt gtgtctcctt tgagactttc taacacgtgt     81060
gtaccctgga ctttgcccca cccctgctcc ctaggaggcc ataaaacttg aagcagcagt     81120
tccggtt agacagatgc ccttggggca aaagtggttt taatgctctg gtagatgctn      81180
aggttaccte tgggaaattc ttgacttcac ttatttattt ggggctgata actactaatt    81240
gtcaggcctt tcttgtttca acaacatgga cttcagtttt tatgcaggat ttgtcatcgt   81300
tttcagcaag agagtcagtc ttattaccca gcttactgca ttagaaatag atgtctggc    81360
caggcgcagt ggctcacacc tgtaatccca gctgtttggg aggctaaggt gggcggatca    81420
tgaggtcagg agttcgagac cagcctggcc aacatggtaa aaccccatct atactaaaga    81480
```

-continued

```
tagaaaaaat tagctgggtg tggtggtgcg tgcctgtaat cccagctact tgggaggctg   81540
aggcaggaga attgcttgaa cccgggaggc agaggttgca gtgagccaag atcgcaccac   81600
tgcactccag cctgggtgac aggacgagac tctgtctcaa aaaaagaaat agatgtctgt   81660
tgtgtggatt atttaaaaga gtagatggcc aagaactatg acttatgcct gtcatctcag   81720
cactttgaga ggctaaggtg gagggatcac ttgaggccat gagttagaga ccagcctggg   81780
aaacatagca agaccccccat ctctgcaaaa gtaaaataaa ataagttagt gtgcatgatg   81840
gtgcaggcat acctctagtc ctagctactc aggaggctga ggcaggagga tcacttgagc   81900
ctaggagttt gaggctacag tgatctatga tcatgccact gcactccagc tgggtgaca    81960
gatcaagacc ctgcctctaa aacataaaaa taaatacaaa ttaagttaaa aaataaaata   82020
aataagtaat agaacatcca gcacagttcc tggcatgcat tgactgttgt tgtttgtttg   82080
tttgtttgtt tgtgacggag tctcactctt gttgcccagg ctggagtgca atggcatgat   82140
cttggctcat cataacttcc acctcccagg ttcaggtgat tctcctactt cagcctcctg   82200
agtagctggg attacaggca cgtgccacca ctcctagctg ttttgttttg tttgtttgtt   82260
tgttttgtat ttttagtaga gatggggttt ctccaagttg gtcagctgg tctcaaactc    82320
ctgacctcag gcgatctgcc agcctcggcc tcccaaagtg ctgagattac agacgtaagc   82380
caccacgcct ggccagctgt tttgattgtt aaatgaaggt ggtatgaaag ggaaggaaga   82440
acagtgacat ttgcaaggga cactccctgg agggcagggc aagggggctg tggaggggag   82500
aagtcagaga gtatgataca ggttgccttg ggtgatgttt tagattttag ccaacattgg   82560
caaagagcct catttatctc tcagagtagc tctggctact ggaaatgctg cacaacttca   82620
gcggactttt ctagaagaaa actcttggcc aggtgcagtg actcacacct gtaatcccaa   82680
cactttggga ggctgaggca ggtggatcac ttgagctcaa gagtttgaga ccagactggg   82740
caacgtggca aaacctcatc tctacaaaaa aaaatacaaa aattaaccag gcgtggtggt   82800
gcatgcctgt atcccagcta cttgggaggc tgaggtggga ggattgcttg agcctgggga   82860
ggtgaggtg gtagtgagcc aagattgcac cactgcactc ccatttgagt gacagagcaa    82920
gaccttgtct caaaaagaa aaaagaaaa gaaagaaaa gaaattctc tctgggattc        82980
aatcctggcc cacacagcat tggcttcact tcacctcctt ctcccctgag atacacagca   83040
ccattccccc aagcttcatc aacttaatct ctgatctggg tgctgtgact tgtccccatt   83100
cctggccaga atttaaggta gggatgaacc cactagccct ccatcacgca ctctgccata   83160
aaagcacacc acgtgctgat tgctgtcttt ggtctccttt ctgccttgcc ctctagactc   83220
tgagctgctt ggagacagag gccagttttg tccatctcca aatcccctaa agtcctgctg   83280
ccagcaagca ggtaggacat ctgaaagttc gtcagagagg gaattgcttt tctcttgaga   83340
tgcaactaga acaagaatct tattgacctg gagtagcttc aaggttgtaa gagtatgtgt   83400
cagggttctc caagaccact ctcaggtttg aaggtttgct aaaagggctc acgggaccca   83460
gaaaagctgt gaaattcagt tatggtttat tacagtggaa gaatacagat aatacagatt   83520
aaaatctgca aagcaaaaga tgcacaaggc aatgtccagg ggagatcagg catgagcttc   83580
cagctgttca ctcccagtgg agttatgcaa acagtgctca attctcccag caatggtgtg   83640
tgacaatgta cagtgtaccg ccaaccgag aagctcacct gagccttggt gtccagggtt     83700
tttattgggg ctcagttaca ttgacatgga gcacccatgt gactgacttt aactgctggg   83760
tctccagcac actccaagat caaactgata ccgtgtgtcc caggccccca gctgaacaca   83820
aacaggcagt caccatagat cccattgtga gcataagcta ccaggcatgg cccaaagccc   83880
tagatataca gatattcttt ccaggagcca gccaagggcc agtccttcct ttggaatatg   83940
cagagtttga actccccaac cccaaggagt taactcttta ctacacagaa tataaatctc   84000
accaagtctt tcttcttgtc aagtcctctc aaggtgaccc attgctttta gcagtgtctt   84060
tgagaccctg cgtcatctgg ccttgaccca tatcaccgt gttatctctc cactctagct     84120
acattgaact tttctttttt gagatgtggt ctcactccat cacccaggct gaagtgcagt   84180
ggtacagtca cagctcactg cagcctcaaa ctcctgggct caagtgatcc tcccacctca   84240
gcctcctgag tagctgagcc cacaggtgca tgccattaca cccagctaat attttttattt 84300
ttagtaaaga tgggttctca ctatgttttcc caggttggtc tcaaactcct gggctcaagc    84360
agtcctccca tcttggcctc ccaaagtatt ggcattacag gggttagcca ccacatccag   84420
cccattgaac ttttttaagga tccctagca tcctatactt tctgtcactg gatagccttg    84480
gaattatttt tccttcttt tgaaatactc ttcttcttct caccctttgc tgtcaagtct     84540
cagaataggc attatttcct ccaaaaaccc tctcctgacc ctccaaatct ggatgaggac   84600
acttcctttg cccagagagc acctgtttta atcctctcag gtggctataa taaaataccct   84660
taaactgggt ggcttataca cctcagaaat ttattttcca cagttctgga ggctgggaag   84720
atcaaggcac tgacagattt ggtgtctgat gaggggccat ttcttgtttc gtagaaggg   84780
tcttcctact gcatctttcc atggtgaaaa gagttgaggc agctctctga aacctctttc   84840
atgagagcat gaatccctct gtcttcatga tctaatcacc tcccaaaggc cccacttcct   84900
aatatcttca cattggtgac taggtttcaa catatgaatt tgagaaagac acagacattc   84960
agaccatagc agtgctcttc caccaggttt tttatcccc tgtattataa ttgaggttta     85020
aattatctgc tttccttccc ttagattgta agctccatga gagcagggcc ctacccatcc    85080
agtcattgtc ctatccccca tgactacaac ttcctgggta cataattaat atttattata   85140
ttatgtagca aaggtatgct gccatactaa gagacccaaa aggccaccgg attaaaacct   85200
taaagaaaaa aaaataattt ctcctcctata atagctgcaa ggttagccat gcaggttggc   85260
agggaagctc acttccacaa agtcactcag ggattccagc tcctgttgcc ctcttctttt   85320
ctaccaccaa atgatcttca gcaccatttg cacaatcaaa acttaactgg tcttgaatag   85380
gcagaccttg aatttctgaa gtctcagacc caaaagtggc agctgtcact tccactgaca   85440
tatcactgat ggaaacttaa tcatgtgatc ataccaaact gctagggatg ctgggaaatg   85500
tagttttgtt gggaactcca tgacttggct aaaattccat tactgtagaa gatggtgggg   85560
gatgggggag tggtggacat ccagtggttg ctaccatatt tattgaatca aattgtcaaa   85620
caggacctat ctgataaggg gttcttttcc agaattaact gaagtattaa atcagggcca   85680
aaggcatgtc acctcatctt tctctcccta tattggcttt ctagggctgt tataacagag   85740
taacatgaac ttggcggctt aaaacaacag aaatttattt tctcttagtt ctggaggcta   85800
gaagcctaaa atcaaggtgt cagcagagcc acctgacaa ctgctctagg aaagaattct     85860
tccttgcctc ttctggttgg tcctggcaac ccttggtatt ctttgtctgg catccacttc   85920
aatcctgcc tccatcttca tttgccttttt ttctctgtgt gtctatgtcc tttcctcttc    85980
ttagaaggat accagtcatt gaatttaggg cttactctaa atccaggatg atctcacctc   86040
aagatcctta attagttaca tctgcaaaga gcttatttca aaacaagatt gcattctgag   86100
gtttcggtaa acacgaattt gggggaaata gtattcaact caattcactg ctttacttaa   86160
gaaaagagac catgaagtga gcctccttct gcttgagaga gagagcgagc ctttctgtgc   86220
```

```
aataggtcaa tgaatggatg cagctgaatt ccacataact ttataaaaat agatggccag   86280
cccatggggt ttgctgaccc ctgcccaaaa attccaaagt caacagcagt ctcttttta    86340
atcatttctc tatttttaa  tttatttta  tttttatgtt gagatagagt cccgctctgt   86400
cgcccaggct ggagtgtagt agtctcggct cactgcaacc tctaccttcc agatacaagt   86460
gattctcctg cctcagtctc ctgagtggct aggagtacag gtgtccgcca ccatacccag   86520
ctaattttg  tattttaat  agaaacaggg tttcaccatg ttggccaggc tggtctcgaa   86580
ctcctgacct caagtggtcc acccacctcg gcctcccaaa gtgctgggat tacaggcatg   86640
agccaccatg cccggccagg attttcttca ttttaacagc attcttactt gtcccacatc   86700
cattctatcc tgggtctaat tagataacaa aatctacaga tcttgtttaa ctgacattgt   86760
cctgggggat actttttatc ttttgagaca aggtctcact ctgttaccca ggctggagtg   86820
cagtggcctg ataacagctc actgcagcct cgaccacctg ggttcaagcg atcctcccac   86880
ctcagcctcc agagtagctg gaaccacaga tgcatgccac cacacctggc taattttaa    86940
atttcttgta gaggtgggt  ctccctatgt taccaaaggc tggtctcaaa ctcctgggct   87000
caaaagagcc tcccaccta  acctcccaaa gtgctgggat tacagatatg agccactgtt   87060
tccagccttg gaaatatagt ctaagaactg agtcaatagg cgattttgtc attgtgtgga   87120
catcatgtag agaacttaac acaaacctag atggtataaa ctactgcaca cctcagttat   87180
ggggcatacc ctattgcacc taggctgcaa acctgcacag caggttactg tcttgaatac   87240
tgtaggcagt tgtaacacaa tggtaagtat ttgtgtatct aaacatatct aggccgggca   87300
cggtggctca cgcctgtaat tccagatcac ctgaggtcag gagttcgagc ccagcctggc   87360
caacatggcg aaactcctc  tttactgaaa aatgcaaaaa ttagccaggt gtggtggcag   87420
gcacctgtaa tcccagctat tcgggaggct gaggcaggag aatcgcttga acctgggagg   87480
tggaggttgc agtgagctga gatcatgcca ctgcactcca gcctgggtga cagagcaaaa   87540
ctccatctca aaaaataaa  aataaaaaa  catatctaaa cagaaaaggt acagtaaaaa   87600
tacagttata accatatggg accaccattg tataggcagt ccgctgttga tcaaaacata   87660
tcaaaacatc gttatgtagc acatgactgt accataaacc acacggcttc aaacaaggga   87720
aatgtattct ctcactgttt tggaggccat aggtctgaaa tcgaggtgtc accagggtcc   87780
ctccaaagga tccggggag  gatccttcca ttggatttgg agttgcttca ctccagtctc   87840
tgcctcagtg gtgacagggc gttctcctct tccctctcaa agttccctct tctgctgtgt   87900
cataaggata catatgactg catttaggcc ccactcagaa aatccaggaa taaactcttg   87960
ccctcatatt cttaactaaa tcgtacctgc ataccttatt tttttctaaat aaggtagcat  88020
tccagggatt aggacatcaa cataacttct ggagggttca ctgttcaacc cactacagcc   88080
agaatgcgct ttgaattcag gttctgacat ctgggactgc ctcccacgta cacacaccac   88140
taccttgtac tgaatgcctg aagggttctg cccccacctc cactccccca aatatttgct   88200
gtggacctga gaaagctgac ttcatggaag cttcattcca ttgttctcag gacttttcat   88260
acattaacaa atgtcttctc tctatgggga aaaccacaga gaaatcaaga cagagtgggg   88320
ttaagtaact cacctgagga ggaacagtaa gtggcagagc caggattcaa accaacatgg   88380
ttttgcacag ttttgacatc atttgcaaca caaatattgt cacagatacc ttttgagca    88440
tctactgtgc taaccgccag gaaggaaaag aacatggggc cgggagagct cttgacaggg   88500
gacagggctg gccatggagg tctgtgtctt ggtggaagat gctatggttc tctttttttt   88560
ttttttttt  tgagatggag tcttgctctg tcacccaggc tggagtgcag tagtgcaatc   88620
ttagctcaca gcaacctcca cctcccgggt tcaagcgatt ctcctgcctc agcctcccaa   88680
atatctggga ttataggcac acaccaccac gcccagctaa ttttgtatt  tttagtagag   88740
atggggtttc accatgttgg ccaggctggt ctcgatctcc tgacctttgt gtgatccagc   88800
cgcctcggtc tcccaaagtg ctgggattac aggcatgagc caccacactg gcaactatg    88860
gttctctttt aactccttgt gctgaaatta ttgcagaagc ccaggccagt tcatcccag    88920
aaagtgaggc ataaacaggc agagctctac agaaacagag aatccacgac tggtttgatg   88980
gaggcgcct  cactacctac agaatgggct ctgggtggat tgttctatct ggggagccag   89040
cccacccacc agtctcagcc cttggcgact cttctcctgc gtcacagcag ctggacattc   89100
agaaaccgaa acatgacagc cttccctccc tgttcctgcc cagtggagtg gaaacccctc   89160
gggacccaca taccgagcgt gcacagcagc acagagttgc acagttaaca cagcgcttct   89220
tctccagccc tccggatgca agctgacaga ttggcagctg gctgacttcc aaggtccagt   89280
gagttcttgg cagtcgctt  ctgacctgga cgagtggctg ccacctcctg gaacatcagg   89340
ctgccccctt ggggagaggg tgacggtctc tctggaaaga ctgtgagctt tgaggtggtc   89400
atcaaaagcc attcttggaa acattctttg agctgtaccg tgcaattcgg tcaccaattg   89460
cacgtatttg gatattaata tccgtatgtg gatattaatt tggttttggg tttttgttttg  89520
ttttgattgt ggcaaaatat acacaacaat cctcctgcct cagcctccca agtagctaca   89580
ggcatgcacc accatacca  gctaattttt ggattttta aatttgtttg tttgttttg    89640
ttttttgaga tggagtgtag cactgttgcc tgggctggag tgcagtggcg cgatctcagc   89700
tcactgccac ctccgcctcc tggattcaag tgattctctt gcctcagcct cctgagtagc   89760
tgggattaca ggcgcccgcc aacacgccca gctaattttt tgtatttta  gtagagatga   89820
ggttttacca tgtcggccag gcttgtctcg aactcctgac cttgtgatcc acccgcctca   89880
gcctcccaaa gtgctgggat tacaggtgtg agccaccgcg cccggccgat ttttgtagtt   89940
ttagtagaga cagggtttca ccatgttggc taggctggtc ccgaattcct gatctcaggt   90000
gatccaccgc ctcggcctcc cgaagtgcta ggattacagg catgagccac ctcacacagc   90060
ctaaatgctg tgcctcacgc ctgtaatccc aacactttgg taagctgagg ccagaggatt   90120
gcttgagccc aggagtttga ccagcctgg  gcaacatag  gaagaccccca tctctataaa  90180
aaataaaaat aaaattagcc ggcgtggtgg tgcaggcctg tggtcccagc tactcggag    90240
gatgaggcag gaggatcgct tgagcccaag aggtcaaggc tgcagtgagc tgtgattgtg   90300
ccactgcact ccagcctggg tgaaaagaca agaccttgtc tcaaaaaaaa ttaagcgaaa   90360
tttaaaattc tgtttctcac tcacacaggc tgcacttcaa gtgcttaatc atcccttgtg   90420
ggtggtggct atcatattgg acagcatgga tagagaatat ttttatcagc gtaggaagct   90480
tcatcagaga ggaccgctca gaggcctgtg ggaccagca  cagtgcagta aagacacag    90540
gccagctggt gagagactgg tcttctgatc ccagatctgt ccctcacttg ctaggtgacc   90600
ttggacactc ccctcagtcc tctggagtt  ttctcttcat tgttaaatca ggaaattggc   90660
ctcagtgaat tctgaggccc catctacttt tttttttttt tttttttt   tttttttaat   90720
tgagacagag tctcgctctg ttgaccaggc tggagtgcag tggcatgatc ttggctcact   90780
gtaacctccg cctcccaggt tcaagcaatt ctctgcctca tcctcccag  tagctgggac   90840
tacaggcgtg caccaccatg cctgggtaat ttttgtgttt tcagtagaga cgggttttgt   90900
ccatgttggc caggctggtc tcaaactccc aaccttgagt gatcctcccg cctcggcctc   90960
```

```
ccaaagtgct gggattacag gtgtgagcca ccacgcctgg cctcatctag ttctaaatgt   91020
tatgacccac tcagctctga agacaaggga ggaacatcct ctcagtctag ctctgacatg   91080
cagaagcctc tcaccctgtc ccccaggtca taaaggcagg cgtgttgtga agagcacaga   91140
atgggctgag aaaaatatgc agggattgcg tctatctccc ttccttccgc acgtttcctt   91200
gtcggcacca cctgcctcta ttccgcgccg cacacacacc cgccttctct ctgtctcgga   91260
ggaagacagg atcttccatc ccccaaatcc tgccctgatt cctactctga agcctctgcc   91320
ctgactcctt taagctccct gggaatacag cccatctcct atgccctcct catcccagta   91380
gttcctacct tccccaaaat cgctttggga aagtccccca atgagtaacc agctgtccta   91440
catgggcatc tcagaacttc tcttctgttg ttgttgttgt ttgttttgct tttgttttga   91500
gacaggatct ctctttttca cccaggctcg agtgcagagg tgtgatctca gctcactgca   91560
gccttgacct cccaggctca ggcgatcctc cccctcagc ctctggaata gctgggacta   91620
caggcacacg ccaccacacc cgggcaaatt ttttttagga cttttggtag aaatggagtt   91680
tcgccgtgtt gcccaggctg gtctctaact cctgggctca agcgatccgc ccactttggt   91740
ctctcaaagt gctgggacta cagacgtgag ccaccaccac cggcagagct tctatttctt   91800
gagtgtgttc tcagccatgc taagacattt tctcttctca gcctgatgat gcttttggct   91860
tgtgtttctt tgtttttaat taccccttcc cagtcgctgt catgggatca tgagggtctt   91920
ctgtccatct agatgacacc tttcttgtgc cacgtgtctc caacattccc tggttttaa    91980
acccttattg ctttcaagat actatccaag ctccttaatg tggcacattg tccttcgctg   92040
ctatctgcct gcttttttt tgagacagag cctcgctcta ttgcctaggc tggagtgcag    92100
tggcgcaatc acagcttact ctgcagcctc gacttcttgg gctcaagcaa tcctcctgcc   92160
tcagccttc gagtagctgg gaccacaggc atgcaccatc atgcttggct aatttatttt    92220
tatttatttt tatagagaag gagtctccct atgttgccca ggctggtctc aaactcccgg   92280
actcaaagtt cattgcagtt tcaattttt ccttggctca aggatcctcc cacttcagcc    92340
tcctgagtag ctgggactac agacgggcac caacacacct ggctaatttt tgtattttt    92400
gtagagatgg ggtcccacta tgttgcccag gcttctatct gcttttatct caccttccac   92460
tcttccatcc ttcctttctt ttcttttatt tcctttcct ccctttgcct tccttttctt    92520
tcttttcttt cttttctttt tcttttcttt tcttttcttt ttctttttctt tcttttctttc  92580
ttgacagagt ctggctctgt cacccagact gaagtgcaat ggcaagatct tagctcactg   92640
caacctccac ctcctgggtt caagcaattc tcctgtctca gcctcccgag tagctgagat   92700
tacaggtacc tggcaccaca cccggcaatt ttttttttt ttttagtaga gacgggtttt    92760
cgctatgttg gccgggctgg tcttgaactc ctgacctcag gtgatcctcc cacctcagcc   92820
tcccaaagtg ttgggattaa caggtgtgag ccactgtgcc tggccttttt tttttttttt   92880
tttttttta agacaggacc ttgctctgtc actcaggcca gagtgcagtg gcactataat   92940
cactttctgc agccgtgacc tcctgggctc aagggatcct cttgccttgg cctccctagt   93000
agctgggact acaggcatgt gccaccacac tggctaattt ttaaaacttt ttgtaggccg   93060
ggcacggtgg ctcacacctg taatcccagc actttgggag gccaaggcgg gcggatcacg   93120
aggtcaggag attgagacca tcctggctaa cacagtgaaa cccatctct actgaaaata    93180
caaaaaatta gccaggtatg gtggcgggcg cctgtagtcc cagctactcg ggaggctgag   93240
gcaggagaat ggtgtgaacc tgggaggcgg agcttgcagt gagctgagat cacgccactg   93300
cactccagcc tgggcgacag agcgcgagac accatctaaa aaaaaaacaa aaaaaaaaa    93360
caaaaaactt tttgtagaga tggattcttg ctaggttgcc caggctggtc tcaagcttct   93420
aggctcaagc agtcctcttg cctgtgcctc ccaaagcctt gggattacag gcgtgagccc   93480
ccacacctgg tcctaaccca cttttctgaac ttccaaccac accatttgt cctaatattt    93540
aagtcacacc ataacatgtc ccacttcaga aatgcctacc aaagtagtct tcaaatcttt   93600
ttaaatcagt ggacccttc taccaaacaa atgttatttt ttaaatattt attttagagt    93660
aatttagact tttagaaagg ttgtagctgg gcgcagtggc taacgcctgt aatcccagca   93720
cttgggagg ccgagacagg tagatcacct gaggtggac gtttgagacc agcctgggca    93780
acatggtgaa accccgtctc tactgaaaat acgaaattag tcaggtatgg tggcacgcgc   93840
ctgtagtctc agctactcgg gaggctgagg caggagaatt gcttgaaccc aggaggcgga   93900
ggttgcagtg agctgagatc gcgccactgc actccagcct gggtgacaga gtgagactcc   93960
atctcaaaaa aaaaaaagaa aagaaaaaaa agaaaggtta taaatatatt ataaagagtt   94020
cccacatacc cttcacccag tttctcctgt tgtttgtatc ttatattatc accatatgct   94080
tgtcaatgct aaggaattgc tgggtgcaga gtggcacatg gctgcagtcc cagatactca   94140
ggaggccaag gcaggaggat atcgcttgag cccaggagtt caagtctagc ctgggcaaca   94200
cagtagaacc tcttttctgc aaaagaaaac aaataaaaac tctaaaaaag aatacactgg   94260
aggcggcgtg gaaacaagga tctcatttgg gagttgtctg caatgttctg agcaagcagt   94320
aacgaggcc tcaagtcagg gctgtggtca tggaggtggg gaggggtggt tggtttcact    94380
atctgtgttg acttaatttt agatttgcag actcaactga gtatgaactt taagagaaag   94440
agagaggcca ggcacggtgg gtcacacctg taatcccagc actttaggag gccaagtggg   94500
gaaggccgct tgagcccagg agtttgacac cagcctgggc aacatagtga gaccccgtc    94560
tctacaaaaa aaaattttta aattagccag gcagggtgat gtgtccctgt aatcccagct   94620
actcaggaca gtgaagcagg aggatcattt gagcccagaa agttgaggct gtagtgagct   94680
gtagttcac cattgtgctt cagcctggga gacaaagtga gaccctgtct caaaaaggag    94740
aatgggtagg agagagagaa gagagaagga aaaagagaga gagggaagtc                94800
aaggagaacc ccacattttt tgacatggtg tattagtctc ttctcacact gctaataaag   94860
acatacctga gactgggtaa tttataaagg aaagaggttt aatgcactca cagttccaca   94920
tggctgggga ggcctcacaa ccatggcaga aggcaaagga gaagtaaagg catgtcttac   94980
atggcagcag gcaagagagc ttgtgggtat tataaaacca tcagatctca tgagacttat   95040
tcactaccac aagaacagta tgggggaaac tgccccatg attcagttat ctccacctgg    95100
cgccgccctt gacacgtggg gattattaca attcaagttg agatttgggt gggaacacag   95160
ccaaacccta tcacatgggc aagtgaaagg atgggtttgc catcaaataa aatgggaag    95220
gagactgact aggtgggcag attaggaact cagcttctta tgaagtgcct actgatggat   95280
agagatattg tgttggccat ctattaggtt ggtgcaaaag taattgcggt tttgccatta   95340
aaagtaatgg caaaggaaat aaccttttgca ccagcctaat aggaaattgga gtctaaaatt    95400
caaaaaaggt aagtcagagc tggagatcca aaggcaggag tcagcctcct gtggaggcta   95460
tttaaggaac tgaataaggg catagatgca ggagagcacc caggactgag cccagggctt   95520
actctccatc attaaagagg ttggggaaga tgaggaggag ccagcagaga agactgaatt   95580
ggagcaaatc agaagaatgt gggtgctggc tgtcatgcaa ggaaagtgct aagccatttc   95640
aagtatgagg gaatgatcaa tgatgtccac tgatgctgat gtgttgactc aaatgaaaaa   95700
```

```
tgagaatcaa ccattggatg tagtggcatg gagatctttc gtgacctgag ccagagctgc   95760
ttaggtgaag aggtgaaggc aagaggctac tggaaggatt actactagct cttttaaaga   95820
gttctgctgt gaagggtaga ggaagagaga tggggcatgt gttagctggt ggggaagtg    95880
gatttcagag gtttgtttcc cttaaaaaaa aaaaaaaaa gaaaaagaa taagaaaaa      95940
aaaaaggcca ggcacaatga ctcacacctg taatcccac attttgggag gctgagacct    96000
cgggaatttg agactagcct ggacaacata gtgagacccc atctctacaa aaaaaatttt   96060
tttttaatta gctgggcatg gtggtgcatg cctgtggtcc tagctacttg ggaggctgag   96120
gtgagaggat ctcttgagcc tgggaggtcg aggctgcagt gagctatgat cacaccactg   96180
cactccaggc tggacaacag agcaagaccc tgtctcaaaa aaaaaagatg gggagacctaa  96240
cagcagattt tatgctgata ggaataacct attaggggag aaaaacatga ggatgctgga   96300
ggaagaagag tgtcaggagg acatctcttg gtggacgaga ggggatggca tttggtgtac   96360
aggtggaagg tttcacttta gatgacagca cacacagtta tctatagaaa caggagaaaa   96420
tgcactatat gggcatacat gctgggaggt agagagtaaa taatagtggt ggttgcttgt   96480
ggaaattctc ttctaatgtt tttatatttt tatggtttat caaggacaat ttatatttt    96540
acagtttact gcaaacaaca agttctaatt tattcaataa ttatttgtgg gtagaccgag   96600
tgcagtggtg catgcctgta atcctagcac tttgggaagc caaggtggga ggattgcttg   96660
aactcctgat tcacttctga gcttgaatca ggagttcgag atcagcctaa gcaacatggc   96720
aaaacactgt ctctacacaa aatacaaaaa ctagccaggt atagtggcat gcacgtagtc   96780
ccagctattc gggaggctaa aacgggagga tcatttgagc cctgaaggtg gaggttgcag   96840
tgagccaaga gcgagccact gcactccagc ctgggtgata gaataagacc ctgcctcaaa   96900
aagaaattct tattcttctt cttcttatta ttatttgagg agacatttac tttgtaccag   96960
gcgctgtgct agatgctgga gatacagaca tcaacaatga caaggctaag tgcctggcgt   97020
atttgtactt tgagtctaat aaaagacatc acacagacac acaacacaca cacacacaca   97080
cacaggattg tcaaaggatc aaccatttca catgtcaaga tcaggaatga tattggtcta   97140
ctactgcctt accatatctc ctaccatgac ctcatcttcc tcttgccaga ttttaagtct   97200
ttatacctca actcccagaa ctctcttcgc ctcacaccct atacaatgt catccgtacc    97260
ccacggccaa tactccatca ttcgggaaag caaagttcca aagcgtcaag attgtatcaa   97320
tggacctgtc tctatggcaa cagtcctgaa tgagccaagc aaggtaaccc tggagatggc   97380
gtgaatgaga agtggcctg ttgccacgga gacgtgctga atgggaaggc ccccacgagc    97440
caggctatgt cacgaagccg aaacagtcag catgaagtcg gtatgtctat tttcaactcg   97500
gaattacaaa aatacatttt aatagagctc atgacccatc tccttcctcg tccctgcctc   97560
ccacccccact cttcagcctt catcctacaa cacaatcgag cctcaccagg aacccttcaa  97620
acccctcaag gacaccttac tgttccttca gtacacagtc cccttcctgg gctgaggtgg   97680
tattccttg accaactact gtctccccctt tgggaccaac agtattctca aaagccatga   97740
gcttatggga agaacattaa ctacattctt tggggcaaga acagttgctc acctgtgaac   97800
cagctcagct tgcatctgtg agaatgattg caatgggtag accagttctc catcaaagaa   97860
tggcctage accccacaca cagtggtata atctgatcat gctggtgtat tgaacatata    97920
atgttagtgc cacatgaaag gaatttgtaa aaggacttag tgcctagaaa ggtaccttg    97980
aagatcttgg aatctctgaa acttacccag gttccttata ccctgctcaa agtattcctc   98040
catttatttc ttcattcatt agttctttg tttcaccaca tatatatttt tgaaacgggg    98100
tctcactctg ttgcccaggc tagtgcag tggcaagatc gtggctcact gcagcctcaa     98160
cctccccatc tcaagcagtc ctcccacctc agcttcctga gtagctggga caccacaggt   98220
acaagccacc acgccaggct aattttgta attttttgtag agacggggt ttgccatgtt    98280
gcccagtgta ttcgtttgtt ctcacattgc tataaagaac tacctgagac tgagtagttt   98340
ataaagaaa gaggtttaat tgactcacgg ctccacaggc tgtgcggaag gcatggctga    98400
ggaggccaca ggaaacttgc aatcatgcg gaaaatgaag gggaaacaag cacatcttca    98460
catggtggca ggagagagag agtgaggggg ggagtgctac aaaaccaggt ctcacgagaa   98520
ctcactcact gtcatgagaa agcaagggg gaaatctgct cccaggatcc aatcacctcc    98580
taccaggtcc ctcccccaac attggggatt acaattcaac atgagatctg ggtggggaca   98640
cagagccaaa ccatatcacc caggctggtc tctaactcct gagctcaagc aatctgcctg   98700
ccttggcctc ccaaagtgct aggattacag acgtgaacca tatttattaa gcattgttac   98760
agcaaagaga agcattgttg cagcataaca attggaagac tccattgatg gacgtctcca   98820
tcaacaagaa ctgtcggata aactatggta cacccatccc ttagcgtgtt atgaagtcat   98880
tacaaaaaga agaagcagat ctctgagtgt caataagagc tagtacttat agggtgtcta   98940
ctgtatacaa gtgctgttag aaagtgagta ttaactcatt taattcttgt aacaagcctg   99000
tgaggtggat tctttcatat ccccatttta cagagaagga aataggaatc tctatatcca   99060
agatatgtta tcaggtgaca aaagcagttt ttgaatggtg ccgccatttt ctcgtaagag   99120
caaatctgga agattccatg agaaattaat aattgtgttt gcctctgtag cggcaccctg   99180
aaagatttgg aagtaggtgt ggaaaggaaa cttactttct tgtgtctttc tgaattttgt   99240
actgtctacg cgttttgtct ttcacaaaac caaacagaaa atgaccattt ggtgcattt    99300
gtgtgtcagg cattcttcta gtctagaaa gcacaggaga gcaaaatatt ttactgacga   99360
gaaaaatgag gcatggagaa gttaagtgac ttgcccaggt agcagagctg ggattccaca   99420
tcatagggtt tatacaggaa acaggtaaac agagctgtgc ttgtgtgtgg gtatgtgtgt   99480
acacatgcat acatgtgtgc atgtgtgtgt gtgtttgtgt gtgtgtgaat gtgctggtgt   99540
gttgggagag ggaaatggca agagaagaac ctacagaagg tcagcaggaa ccaacccatg   99600
ttttgaggag tttggacttt atcctgaagg cacaagggag ccatgaaagg atttagacaa   99660
ggggtggttg tgcttagctt tttatttaga aggatgactc tggctgaagg gtgatggccc   99720
agaatacagg tatatgtgaa ggactcctcc tgccctagta ggaggatgcc cacccaccct   99780
ctctgcccag tgcagtatca aagggcaaat tgggtacaga gaattctcac caagctgggt   99840
agaatccact ctgatgctgg ggagtggaca ctgaatgcac cagcctctcc tcctgctcaa   99900
tccctgaatt gaagctgttc cactaatgtt agggatcaga ttcccttcat atatatatat   99960
atatatat atatatat atatatatat ataatttt tttttgaga cagagtctcc           100020
ctctgtcacc caggctgaag cccattgtcg cgatcttggc tcactgcaac ctccacctcc   100080
caggttcaag caactcttgt tcctcagact cccaagtagc tgggattaca ggcaccccgcc  100140
accacacctg gctaattcta tatttttagt agagacaggg attcaccat gttggccagg    100200
ctggtcttga gctcctggc tcaagtgatc agtctgcctc agcctcccaa agtgctagta    100260
ttacaggcat gagccaccat gcccgtcctt tttatattac ctttttttat agagatgtgg   100320
tttcactatg ttgaccaggc aggtcttaaa ctcctggcct caagcgatcc tccctcctca   100380
gcctcccaaa atgctaggat tacaggtgtg agccactgca tctgtccaga ctctgttctc   100440
```

-continued

```
cataaagctg gcatatggaa agagggaaga ccatccaggc aatatcgaag tcccattggt   100500
gctgatgtgg ctgctgagac cacatgaatg gatgcattct gactctgcca cctctcagct   100560
atgtgaccct gggccagtca gcaagtccct ctataactca gttttctcat ctgtaaaatg   100620
gcgtcaacag tagccaaccc cagcaaatac tgtgaaatat acagaacatc attataatgg   100680
tgaggatgat agagatgcta tgttatcaga ataccctggg ttgaaccagc tccccttctt   100740
gcaagctgtg tgacttggag ctgatgccca aacctctgtg ggcctcattt gtttcatctg   100800
ttcaatgggg ataataacac tcttacttca tacagttatg gaggatttat tgaaataatt   100860
gacatacagc tcttagaaca gtatccggct ccttgtaagc gctcaagaaa tattacagac   100920
tgttgataat aatgcaatac tactaccaat aatatggcca ggagcaatgg ctcacacctg   100980
taatcccagc actttaggag gcagaagcag gctgattgct tgagcacggg agttcgaggc   101040
cagcctgggt aacataggga gactctgtct ttacaaaaaa taaaaataaa aatacaaata   101100
attagccagg tatggtggtg catacctgta gttccagcta cttgggaggc tgaggtggga   101160
ggattgcttg agcccaggaa gttgaggcta cagtgagctg tgatcacacc actgcactcc   101220
agccagggca acagagtgag accctatctc aaaaataata ataatggccg ggcgcgctgg   101280
ctcatacctg taatcccagc actttgggag gccaaggcgg gcagatcact tgaggtcagg   101340
agtttgagac cagcctggcc aacatggtga accccatct actaaaaaca caaaaattag   101400
ccgggtgtgt tggcggggtg cctgtaatcc cagccactca ggaggctgag gcaggagaat   101460
cgcttgaacc cgggaggtgg aagttgcagt gagccgacca cacaccactg cactccagcc   101520
taggtgacac agtgagactc catctcaaat aataaatatga gtaataataa taatatcatt   101580
tttatcatca ttcttactaa cagtctctca ctccttgccc tgcagttttg cctgttttct   101640
tggaataaca ctcttccaca cctttcccct cagggatggt tcacgtttag catcatgacc   101700
caccctggg gattagttag ctcatttctg gaaagcactt tggagctgta ggtgctttgc   101760
aggctggaaa catcacggga cttgtaccat atttaagcaa tgccagatta ttctgcctgg   101820
caggggagag acacagagga tacggccctg gtatcttttc tccctgccta cctcagcttt   101880
gctctgaacc atttttctgtc ctgttcaggg cagcctgggc cacttgccac ttccagcttt   101940
ctcgggagag gatgccttcc tgatggcacg cctcttaaca cacacctggt gctgttgttg   102000
aaaaagcaac aattgactcc agcgccagca ctgagaggct tgtccttaaa attagcagga   102060
gctgttggaa ggtcgctgtt agctcttttg actggaacac actgttcccc aggtggcatg   102120
aggctgaata cagtgcaggg attggctctg ctctcaggtg gcctgctcca cgctcctgag   102180
ctccgggtgg aagctgtgac cattatttcc ttaacagaaa catatatagc agcattaact   102240
atgaacctta ttactgtgtg tgtgtgtgtg tatatgtgta tatatatata tgcacatatg   102300
tgcatatgtg tgcctatgaa cctgttctga gcacttaca aatgtcaatg tattttatcc   102360
tcccaacaac ccattttata aataagactt gaggcacaga gaggttacgt tactgcccca   102420
agatcacaca gctggagagt ggtgaggcca agatttgaca atatgtacca ttgtaccata   102480
tgtaccaact tttttttttct tttgggatg cattcttgct ctgtcaccca ggctggagag   102540
cagtggcatg accacggctc attacaacct caacctccag gttcaagcta tcctcccacc   102600
tcagcctctc aagtagctag gaccacaggt gcataccacc atgcccagct aatttaaagt   102660
tttttttttgt ttgtttgttt gtttgtttgc agagatgggg tctccttata ttacccaggc   102720
tggtctagaa ctcctaggtt caagcaatcc ccccacctcg gccttccaac atgctgggat   102780
tacaggcatg agccactgca cccaggtcct ccctccttat aaaggtcgcc aagcacaatc   102840
ttgtgagcct ggccctatcc acacccatac gcaacatggt gtgtatttt caaacaaaaa   102900
ctgaatgaac acctctggtt tgggttcccc tcacacttgt cccgggtttg ttgactctgt   102960
gttgtgggcc tagacaaagc agtgtctgga gctcctagac ccagggacca gacagtctgg   103020
gttcaaatcc tggctcttcc acttctgcct gagtgctctc tctgaacctg tcttctctta   103080
tctataaaat ggagataatt tttttaaact catcacttgg tcaaactgct ttgagcatgc   103140
aaaatgagttc atatgtataa acctcttaga atgtcccagg caaagaacaa cacttcactc   103200
agatcaacat ttatttagca tctactgtgt acccatgact attctaggtg atgaggagac   103260
cctctggttc ttatgaggta gtgaggtggg ggagggtgag aacccctaaac attaacgatg   103320
gtgtgttcgc aggtgggaaa atcagtcaaa tcgggtaaag ggaatttggg agtgctgtgc   103380
tcaagtcctg gccctgccac tttctggggt gcaagataca gcattgaata gggtggtcag   103440
ggtaggcctt attgggaaag tgatatttga gcagacgatc tagatgtcgg cacatattgg   103500
tactgtttga tggtactaat atgagtttga gtttcacttg caagtatata tatatatata   103560
tatatatata tatatatata tatatatgtg tgtgtgtgtg tgtatatata tatgtgtata   103620
tatatgtata tatgtgtgtg tatatatgta tatatatatg tgtgtatata tgtatatata   103680
tatatatata tgtatatata tgtgtgtata tatatgtata tatatatgta tatatatata   103740
tgaaatttgg tccatttatt tatgctgatc aattaattga tgttgaaatt ataattgaat   103800
gttttattaa taaacagata cccacatact attttttcag aaattgttag gttttggggt   103860
tttcttttaga ttttgattat ttttatttgc ttaatttttct ttttctttt ttttaatttt   103920
attttttccat aagttattgg ggtacaggtg gtattttggtt gcatgagtaa gttcttcagt   103980
ggagatttgt gagaacctgg tgcacccatc acccgggcag tatacactgc accatttttg   104040
ttgtctgtta tccagtgctc acctcctact cttccccca agtctctaaa gtccattgta   104100
ccattatttt actcacccac attctttggc ctgagatgct gagtggtcat gactcccaga   104160
tcccttcttg tttctgtatc aaagatctt actaagatcc tggcctaggg aacctattcc   104220
ctttcctcat ccccaatggg agaagggct tcttcccccag cttatttgcc aactcataggg   104280
aaaggtatga aggagaggac tgtagttgtc ttgaagctgc tcagatgttg aagagatgat   104340
aatatttgct gatcaagaga gacaaagcaa tgctggaaga gaggctgtg ttagttaaca   104400
ccagctgcaa taaccaataa aaccaaaaat ctctggctta agagtatgca tgagtgagaa   104460
atcaacttct aaagtacaac tggtggccgg atgtggtggc ttatgcctgt aattctagca   104520
ctttgggagg ctgtgtgggg aggtcgctt gaccccagta gtttaacgcc aacctggca   104580
acacagtgag acaccatctc tactaaaaat aaaaaataat aaagtgaaac tggtgagggg   104640
tgcaatgagg tggagtggtg ggtgactcaa atatggctcg actccatgca gtcactcagg   104700
gatccaggct gttggaggct ctccctgctt aaacatgtgc cttccaaggt tgttctaaga   104760
gcctacattg agacagcagc tggggaaaag ggaaagtgga gtgggaggta cttatgaggg   104820
ttcctggaag tggtgaacaa cacttctgcc tgcattctat tgggtggaat ttagtcatgt   104880
ggcccaggct agctgcatgg gaggctggga aatgtagtct ctgattaggc tgccatttcc   104940
cagtcccact tgtgaatctt tagtgggaag ctcaccatgt ttgcaccagg gattcagtct   105000
acctcccact catgcctcaa ctatgtatca ggcactgtcg taagtacttt acatatcagc   105060
ctacctaatg caaacaacta ctcagtgggt gcttattgg tcacatgtat tagtgagaac   105120
atggaaaccc agagccgtta aatatcttgc ccaaggtcac acagctagga agtggcagag   105180
```

```
ttggaatttg aatccaggaa atctggctgc agagccccac gcttagtata aattcattgt    105240
agtttagaaa gaggcagaag gaccctaaaa ttggcataat ccatttttg gtccctaagg     105300
aactgactga attgactact tgtaaaagtg agtcctggac aggcaacagt ggctcaggtc    105360
tgtaattcca ggactttggg aggctgaggc gggcagatca cctgaggtca ggatttcaag    105420
accagcctgg ccaacatggc aaaaccctgt ctctaaaaaa atagaaaaat tagctgggtg    105480
tggcggtggg tgcctgtaat tccagctact caggaggctg aggcaggaga tcgtttgaa    105540
cctgggaggt ggaggttgca gtgagcaaag atcacgccac tttactccaa cttgaatgac    105600
agagcaagac tctgcctcag gaccgccatg gcccctggg ttctaggtca gagtttctcc     105660
gccacagcac tgatgacttt gggggctgca ttattagctc caaaatggga gctatcctgt    105720
gcactgcctc aacttacttg atgccagtag cgcccgcgcc ccagttgtga gaaccaaaaa    105780
tgtctccaca cattgccaaa tgtccctgg gaggtgaaat caccctggt tgagagtcac      105840
tgttctagat tgttaaatat tatcttacac tctagcacaa gtccaaggca aactgactta    105900
gaaattacca accttgcaaa aaatagaaga tttcttaaag tcagtgagca tgatggtggc    105960
aagctgctga aatcacaccc ccagacatta gcagatggga tctggacagt attcatctag    106020
ttaaaaattg acaaggactg ggacactgca ggctcttcaa aagagaatca tttgaataac    106080
aagggggtcaa gacaggggta attggtgaaa gcccctgctc ataatttgaa aatataaata   106140
ggcatcatga aaattcatcc tgcaaaagtc aaaagtcgaa tgtgcagtgt tatacatgat    106200
cagttgattt gggagggaa attgcatgca cacacatgga agcttgcaca cccacacaa     106260
cacacctgtt caagtgtgtg tgccagtgct cagtgaggac catctcccca acctgtctga   106320
tcatcttgct ttggggtgac cctatgggtg aggcagaaat tcttggatca tagttttcta   106380
atgaatatta taattgttaa cttctgatgg gtgctgactt tttcatcttt gcaacactgc   106440
gtaggtattt ttactctccc cattttacag atgagacaac tgaggctcag aaagattgat    106500
tagctctaca cgaagccagg atccaggctt agcctggctc caggaatcat gttttgagtt   106560
acgtagcttc cctgattctg agggacctcc ccacttctga aatcttctac tgttactccc   106620
catgcccctt tcctattgac cggaggcacc ccagctcctc actcgtccct tatcttatga    106680
aacatgacca tgatgtctga attcaaagga gagcctggcc tttgtgggga aaacgaaatg   106740
gaaaaagaaa ggtggaggtt ggtggttgtt tttggcatgg tgaggagcct gtcgttgctt    106800
gaggaaagca agaaaggaga ttgctggggc ttggatccat ctctgggtgc ctgtgggtct   106860
gtctgtaaaa atgagaactg gtcgtgctca ttagaggatt tgaccgttag gccttgggat    106920
agcgatttgg gaacttttt ctgctaagac aaagaataat attggttcagg ttcattttgc   106980
tcctgctttc ccaagcccta catctcttct gggcttttt tttttccttt ttctctcctt    107040
cttcttcttc ttcttcttct tcttctcatt tttggatctg gacttctgct gactcatctc   107100
tctgagcaag gaaggaggga ggaagtcaga attgctcatt aaccgttttc tttagtgact   107160
cagctgtgat tcacatttta attaatggag gagaaaaacc tgatcagtca taaggcatct   107220
gcccaatcac gcataactcc aggctggtga taataataat acttgaaaaa agtggggtgt    107280
cctgaattaa actatggctc attccccaca ttagtcttga ggactccacc aggccctcta   107340
agttccaggt ctcaatgggg ctccctgaac cagagcagct agtccaagcc ccgagcagca   107400
tttctgcaga gttagtctga ggtcaggaca agaaacagag gctcaagccc tcctgggatc   107460
gcaggaggat catgggaatg taatattgtt tcctgagctg gtcttttggct ataatcccag   107520
gctcaagcct ggcctccctc ccctcggggc ctgaaatttg tcagagccta ttgcaggggc    107580
agcttctgtg cttttttgttt gcccagagaa tgagaaaagt ccagataatc atgaccgcta   107640
cttcctgagc acttactatg catcaggtgg tgtgctcagc acttctcatg aatgatcacg    107700
ttgaatcctc actctgtcca caaaaagaaa gagcttttat ataattctcc aacctcccta   107760
tgaggaaact gaggcttggc aattgccaa tgtagacaat tagtaaataa tcaggcagga     107820
tataaaccca accctttccc acctgggagc cagagcttgc atctactata cttctctgct   107880
ttccagtcag ctgcaaagaa aaattggaag ctgatagctc attcaacaaa cacttattga   107940
acccttccac ttgctcagcc ctgttctaga caccagagat ccatcagtga accaaagagg    108000
caaatccatg gtctcatgaa actgacaatt tacctgccca agtgtattag ttactgttta   108060
taagttccta ttaagtgtat tagatatgct tgcagctgta acaagaatc ccaacatgca    108120
taagggctca aaacaataaa aatttcgttc ttgcacagat aaagttcaaa aggtgtattc    108180
tttttttttt tttcttttgc gacggagttt tgctcttatc ctccaggcat gagtgcaatg   108240
gcccagtctc ggctcactgc aacctccacc tcctgggttc aagcattctc ctgactcagc    108300
ctccccagta gctggaatta caggtgcccg ccaccacacc tggctaattt tttgtatttt    108360
tagtataggt gggttttcac catgttggtc aggctggtct taaactcctg acctcaggtg   108420
accctgc ctcggcctcc caaagtgctg ggattacagc cgtgagccac cgtgcctgcc       108480
caaaaaaaa atgtattctt aaacagcagg cacctctcct ctaagcagta agtcaggggc    108540
ccaggcttgt tccatattgt agctcctcat cttcaaccca tggcttccaa agtctccatg    108600
cttcttgata tcaagccaca gaagggaaa gagcatgaga agggcacagg agaaatgttt    108660
ctgggacaga cccagaagta gtccatatga cttccatcta cctcccactg gctagagctt   108720
acatggcggc acccacttgc agagctggga aatggagtct aactgagcat ccaggaagga   108780
gagacagaca tgagtctttg cgtgggtcct cactgagaat caagctccac attttgatcg    108840
atgtcaccag agcgtacatg gcggcgccca cttgcagagc tgggaaacgg agtctaactg    108900
agcatccagg aaggagagac agacatcagt ctctgcgtgg gtcctcactg agaatcaagc    108960
ttcacatttt gatctgtgtc acctccttgc aagccctacc ttaggacaat tttaagggac    109020
attcctatct tcttccaccc ttaggacagt tttaagggac actcctgagt tcttccaccc   109080
acctcctctg tttcttgggc ttccagctct caggatttgc ctttgcctta caatgggtg     109140
aagcaagaat ctgaagaat gtctctcccc acaatttgaa gtcttattg aaaaaaagca      109200
gtagagcatc cctccctctt gaggtaggga aatctagaat caaatcctgc ttctccagac   109260
tttgacctca gaaactgggg ggacttcaag gtcttcaggt gggcagcttt catgaaccat    109320
tcattcctcc cacctcatac caatcagggt cctaacagga aaagaatta acttctagat    109380
ggttcaaaag aagaccatgc catgaagaga ctccttaaag agataggaac aggtgagaga    109440
aatagataac ggctgtttga ggtcctcaga gagaagccat cgcgagccct acatttcctg   109500
gaacccagtg gaggcagagc tgtgcagaag ggactactgt cagaaccagg gagggagcag    109560
ggaagcaata ttccaatctc tttccctccc ctcatcttct gccacgcgct tccctcagcc   109620
aaaccaaacc ggaaacggag caaagcattc tgggagttga gtcttcaag ggtccgcctc     109680
gagggcacag agcccgctgg agcattgacc tagagggcac acagggaatg actagtttgc    109740
accatcatgt gacggactgc acgccctcga ttatgtaatc cactctataa ttcaactgca   109800
gagctgcatg gtacagcagg atagccacta gccacacgag gctatttaaa tataaatgta    109860
cattcattaa aatttaacca aatgaaaatt ttagccactg agcccatttt caaatgctca    109920
```

```
ttagccacac gtggctcttg gctaccatat tggacagatc agaatagaac atttccatca 109980
tcccagaaag ttctagggc cggcgcagct gtggtgtaac ctgagcccat gcatgttatg 110040
gaatggagaa gagagaaaac agcacaagag gcagttttga agggagacag agagctgtgg 110100
atcagtaggg aggagactct ctaggcaaag gagcagttga gaagcaagaa agttgagtga 110160
gctgctttgc tgcgatggag gcttccctca cggggaagag tagagtcaga aagctttagt 110220
tcaagttcag ctctgaaatg aaccaatgag tgttctgaca agacacctgg ccttccggaa 110280
ccttggtttt gtagtggcca agggcttgac cctctgaagg ttcactgaaa aaaatcaact 110340
cacaaggcat attaattgga gaaaaggcag gcagatttat ttaatgtgtt tgcacgagag 110400
ccttcagaat gaagacccaa agctgcaggg gaaattgtcc gttttttaag cttaggttca 110460
acaaagtatg gacagcgtg tagaaatatg attgaacaaa aagtgtacaa tgtaaatgct 110520
aatagactga gtgggaaac ccaaaaaggg ctgtcttgat tctccttggt ctctctgagc 110580
atgcatttct tccgggtatg ggacaagacc ctctctggaa tggagggggg gctctcttgg 110640
ttctccttgg tctctctcag catgcattcc ttccgggtat ggggcaggac cctctctgga 110700
ataagggggc tgtcttgatt cttcttggtc tctcagagca tgcattcctt ctgggtatgg 110760
ggcaggacc tctctggaat gggatcctta taacctacgg tcaaataacg taagttagat 110820
aatttcttt tttttttttt cttttttttg agacagagtc tgattctgtt gcccaggcta 110880
gagtacagtg gcacaatctc ggctcactgc agcctctgcc ttctgggttc aaatgattct 110940
cctgcctcag cctcccaagt agctgggact acaggtaagc accaccatgc ccagctaatt 111000
tttgtatttt ttagtagaga cagggtttca ccatgttggc caggctggtc tcaaactgct 111060
gacctcaagt gatccaccac ctgggcctcc caaagtcctg ggatttgtaa tcccagcatg 111120
agccactgtg cccagccaga tcattctttt ttctttttct ttttctttc tttttttttt 111180
ttttttgag atggagtctc actctgttgc ccaggctgga gtgctgtggt gcaaactcag 111240
ctcactgcag cctctgcctc ctgggttcaa gcaattctcc tgcctcagcc ttccaagtag 111300
ctgggactag aggtgcgcgc caccatgccc agctaatttt tgtattttta gtagagacag 111360
tgttttgcca tgttggccag gctggtctta aactcctgac ctcaagtgat ccacccacgt 111420
cggcctccca aagtcccggg atttgtaatc ccagcatga ctaccacagc tggccagata 111480
atttttttat aactagtttt tacaaagaaa ggtggaggga aagttagagt aacattttta 111540
ggtgttaggg ctgactttgg ggaaaagagg tctggtttct acgacccgcc ttagggaaga 111600
gggattctag tttttgtggc tagccccagg ggagaatggg actaagagat agaagggcag 111660
gagaaggtca gagaaaaact tttgcttctg tggctgcttc ggagaacttc atttttggggt 111720
attgttttct gagccccaac agtttgctta tcagtgaagt gggtataggc gcccacctcc 111780
cacagtgacg atgctgtgaa caggggctttg gaagagtaga actatgaaat atttgttgtt 111840
gccttgtggg gaaatggtcg ttaaagccaa aattgttcaa gagaagaagc aggaagagtt 111900
cctttcttc ctgcaggtat cctcttaagc tgagtcttca gaatccctg acaacgttta 111960
atcaacactt tattaaattc accccaaccc tgcttcaaac cttcacctgg tcctcgagat 112020
cttccaactg ttttcttgatg aagttagcag gcaattgtat ggcgggatca tcatctcatg 112080
ttttgttttg ttttttttcct ttttaccctc tgactttgag aaatccttgt cctttactt 112140
ttccaaacct gagagcattg cagagaagtt agaattgagc aggacatggg cttaagaccc 112200
agcccagcca tgtgctagct gtgtgaactc gaagcagtga ccccaccctct ctgacctgga 112260
aagtagaggg aatgatagga cccaccaccg ccacacttgt agggtcatca tggggattga 112320
ataaaataat gcataagact tggcccacag caagcactca agaaatgtta gctacttcct 112380
aaatatattt ttaaccttt attgaatata acatacatac agaaaagcac atgtatcata 112440
caagtagagc ttgagtgatt ttcaaaaact gagcccagtc atgtaaccag cgcctagttc 112500
aagaaacaga acatgccga gtgaggctga ggcaggagaa tcacttgaat ctgggaggca 112560
gaggttgcag tgagcagaga tcatgctatc gctcccagc gtgggcaatg ggggcggagg 112620
ggaagagaga gagagagaga gagagagaga ggaaggaggg agggaaggaa ggaaggaagg 112680
agggaggag gagagggaagg gaaggaaggg gagagagaga aaaggaaaga aaagaggaag 112740
acagaaagag agagagaaag gtaaagaaag aaaaggaaag aaagagaaag aaagaaaaga 112800
ggaagacaga gaaagaaaga gaaagctaaa gaaagaaaaa aaggaaggaa ggaaaatagg 112860
gagggaagag gaggaggaag aagaagaaga agggggggag ggagggaaca gctgcagctt 112920
cgaggaggga ggagggaagg gaaggaaggg aaggaaggaa aaaaacagca 112980
ccaacgttta gaaaccccct tgtgcctctg aggtcaccag taactccatc ctgacttcaa 113040
acagtctaga ttagtttttgc ttgttttttga acttaagca catggggtca tacagcatgc 113100
atgcattgac ttcttttccct tgacgttgta tgtgtgagat tcatctgtgc tgttgctgtt 113160
catttgttct catcgctgtg tgtgctgaac cacctgttca tttactctca taatggtggg 113220
cagtttggtg cttttctactt tgggctatt ccagagaaag ctactttgaa cacactcaga 113280
tatgtctgtg ggtgaccact cttcatattt ctatgggaga tattcctagg accggaacat 113340
ctgagtcaga gggaggaatt ggtttagctt tggtaggaac tgcctaacaa ttggccgggc 113400
acagtggctc atgcctgtaa tcccagcact ttgggaggct gagggggggca aatcacttga 113460
gctcaggagt tcgagaccag cctggccaat gtggcaaaac ccctggccaa catgccaaaa 113520
ccccgtctcc gcaaaaaaat acaaagatta gccgagcatg gtgcgtgtg cctgtaatct 113580
cagctactca ggaaactgag gcaggagaat tgcttgaacc tgggaggcag aggttgcagt 113640
gagcagagat tgcactactg tactccagcc tgggtggcag aatacatgaa actccatctc 113700
aaaaagaaga aaggaaggaa gggaggaagg aaggaaaagg aaactgccca acagttttcc 113760
caagtgtttg ggatggaagg aaggaaggaa ggaaggaaaa gaaactgcct aacagttttc 113820
ccaagtggtt ggaccagtta aaactcccac cacctgtgaa tgagagtttg ttttattttt 113880
gctcctggag tgcctctcct gtagcaggtt cccactgaat gtctgggaat tcaaatgtaa 113940
tgcacttgtt catttcctca agagcttcac tccatcaatt ggattcatcc attggctctc 114000
ccatctccac tgacactatg ttctcacctc tatttggag acatcctgcc tccacctgcc 114060
caagtcacat tatcttctca ttccagcctc tcaggagag ttttctcttt caccacctcc 114120
tctagccctg gtgattggca aggtctcgca acagtaccct tcaaacact catgactgtg 114180
aatgcactgg ccttcactaa gtttcccatt cttctctttc tttcttttt cttttctttt 114240
ctttttttt gaacagagtt tcactcttgt tgaccaggct cgagtgcagt ggcacaaaca 114300
cagctcactg tagcctcaac ctcctgagct caaggtatcg tcctgcctca gcctcctttag 114360
tagctgggac cacagacatg caacgttgtg cccagctgat tttctttttt tcttttttt 114420
tttttttttt gagacatggt ctcacccgtgt caaccaagtg cagtagcatg atcacagctc 114480
actgcagcct tgacctcccg ggctcatgcg attctcccac ctcagcctcc cgagtagctg 114540
gggctacagg cacaagccac catgcctggc taatttttgt acttcttgta gagaccaggt 114600
ttcaccatgt tgcccaggct ggtcttgaac tcttgggctc aagcagtcct cctgcctcag 114660
```

```
cctcccaaaa tgctgggatt acaggtgtga gccagcacgc ccggccatgg ctaatttctt   114720
cattttggt  aaagacaggt ctcactttgt tgcctaggct ggtcttgaac tcctggactc   114780
aagcaatcct cctgtctcag cctcccaaag tgctaggact accgatgtga gccaccgcac   114840
ccggcaattt ccccttcttg acttctccag agctctcatc cctctcgagc tcctgtctct   114900
tctagaatca cttacctcac caccttatgg ggtttttgcc tctgttccta ctcctctta    114960
tttaagaaaa cactgtactt taagagggct tcagaaacca cccgaaatag aaacatgtcc   115020
ttttgttcaa tcctttactt taaaagacaa ataaaatgaa gaattgctct ccatgtagaa   115080
ggttaaggag cttgggagga ccttctgtga gtggggagaa cttacatta  aaggaaaaaa   115140
aatgctggag aatagctgtg aacccaggaa gggagaagga cttcctccac tgaacttgta   115200
aagcacaaac tctaaggcaa aaaaagacat gattacatga aaactaagat atttgttcaa   115260
ataaagatgc aattgggcc  aggtgcggtg gctcacgcct gtaatcccag cactttggga   115320
ggccgaggca ggcgaatcac gaggtcagga gatcgagacc atcttggtca catggtgaa    115380
accccatctc tactaaaata caaaaaatta gccaggaatg gtgtcacgtg cctgtaatcc   115440
cagctacttg ggaggcttag gcagggggaat tgcttgaaac agggaggtgg aggttgcagt   115500
gagctgaaat cacgccactg cactccagtc tagcgacaaa gcaagactcc gtccaaaaaa   115560
aaaagatgca atagcaggtg gttcgggaac caaaccttac atccagatgc tggttgtccc   115620
atttcctgtg aatccttggg tgagttatca acctctctga gcctcagttt cctcgtcaat   115680
aaaatggaga aaatagtatc tacctatgga attgttgtga gttttgaatg agttaatatt   115740
tataaatcat ttagaatagg aattagcaca tggtaaatag tggatagaat cataaaaaaa   115800
aaattgatca ggggttaact tctaactgct gtttgttata gaggtcccta gcactgtgtg   115860
gtcattttaa atttagatga tttagaatta aatgaaattt aaaactcagt tcttcattca   115920
cactagccac attttaagtg ctcaaaaccc acaggtgact agtggctacc atatttggca   115980
gcacagattg agaacagatt tatcatccag aaagttctgt cagacagtgt tgatcaaggc   116040
tacatgaggg tctgggtgca gtggctcaca cctgtaatcc cagtgctttg gaaggccaag   116100
gtgggaggat cactggaggc caggggtttg agaccagcct gggaaacaga gagacctcat   116160
ctctaccaac attttaagaa ttagccaggc aaagtgttgc atgcctgtag tcccagctac   116220
tcaggaggct gagacaggat tgcttgagcc caggaatttg aggctgcagt gaactatgag   116280
cgcaccgctg cactccagtc tgggtgacag agtgagacct gtctctaaac ataaaaaata   116340
aaaatgtagg tggggcatag tggctcccgc ctgtaatccc agcactttgg gaagccgaga   116400
tgggcagatt gtgaggtcag gagatcgaga ccaccctggc taacatggtg aaaccgcgtc   116460
cgtactaaaa ataaaaaaaa attagccagg catggtggcg catgcctgta gtcccagcta   116520
ctcgagaggc tgaggcagga gaattgcttg aacctgggaa gcagaggttg cagtgagctg   116580
agattgcgcc actgcactcc ggcctgggcg acagagcgag actctgtctc aaaataaata   116640
aataaataaa taataataaa gtaaaaataa aaatgcaaag actacctgag ggaatgtctg   116700
caagtcaacc agaataacac agcaacccca ataggaaaac aggccgaaaa tgtgaacagg   116760
cggatcaggg aagtgaagtc tgaaaagcta atcagcctat gacatggtac tcaaagtcat   116820
ttgtaaccag aaagatggaa atgaaagcag tatctctgta caccttttaat attgggggaaa   116880
aaatatgtga ataagccaag ggtttccagc gatgcgggca cagaggaaag tcttgcacca   116940
ctcaaaggtg tgtgcccag  ggaggccact ctggagacat atcggtagta ctcagtccag   117000
tgaggtccag caccatcagc gcttatgtcc ccaggcatcc atcccaggga cattcttacc   117060
aggtctgtta ggggcaggta cgagaatgct tactccagca ccatctatat aaggggagct   117120
gaaggccacc tggtgtccct cctggagacc aggaggcggc atgtgacagc ggcacccatg   117180
gagcaccaga atgagtgaga gctccagacc gcatatccga cagatactac gggatgggc    117240
ttttagaaat atggttgttg ccgggcacgg tggctcatgc gtgtcatccc agcactctgg   117300
caggccaagc cgggtggatc acctgaggtc aggagttcga gaccagcctg ccaacatgg    117360
tgaaaccctg tctctattaa agatacaaaa attagctgga cgtggtggcg ggtgcctgta   117420
atcccaacta ctcgggaggc tgaggcaaga gaatcgcttg aacccaggag gcagaggttg   117480
cagtgagccg acatcgtgcc actgcactcc agcctgggtg acaagagcaa aactctgtct   117540
caaaaaattt aaaaaacaaa aataaaaat  atggttctgg gtgaaaacag gaaacaacag   117600
aatgtgtcta acttcatcct gcttatgtca gttaaaaata gacacactca aaatatcgca   117660
cgtgtttttg cgagaatgca ctcctataag gccaaattaa acattctctc agttgtctc    117720
gggagggaga agaatgaaag tagggtatag agagatatag gggaattaat gcatgaatga   117780
atgaaggtat aaacaagaga caggcgtcat acagaccaaa ggtaaagata tcccgtaacc   117840
tgaggagagc aaagaacttg actctgcatt tgaagattca gaaatgaatt tcagaaata    117900
gttttctcgc caggggggtgg ctcacgcctg taaccccacc actttgcgag ggcgaggcag   117960
gtggatcact taaggtcagg agttcgagac cagcctggcc aacatgatga aaccctgtct   118020
ctactaaaaa tacaaaaatt agccaggcat ggtggcatgt gcctgtaatc ccagctactc   118080
aggaggctga ggcaggaaaa tcacttgaac ccgggaggca gaggttgcat tgagctgaga   118140
tcacaccatt gcactccagc ctgggtgaca gagcaagact ttgtctcaaa aaaaaaaaa    118200
aaaaaaaaaa aaaaagaaga ggaagaaatc gttttttcaa gaagggaaa  gctgggtgat   118260
ttaagaatga acttgaagag gatcactcag tcctcaacct aggagtggca agaatataga   118320
ctgtatggga agtggttctg ctccttggta cccatcttag aaatatttgg cctgagtctg   118380
taagaggcag gtactttatc taacctgagg ttagggggcc actacatccc catccctcc    118440
cctgctttct aaccatgcta acatcttctc actctcctga ctcctctctc tctcactccc   118500
ctaatctgcc tattcacatt ttgggcctgt tttcctattg gggttgctgt gttattctca   118560
ctgatttgca gacattcctc tgtgtcatct tttaatttt  gttttaattt ttagaggcag   118620
gatgtcattc tgttgcactg gctgtagtga cgtagctcac tgcagcctca aactcttggg   118680
ctcaaactcc tgtcctctgc ctccacttct caactggtaa cctcacttct cttcatgagg   118740
tctctccagc cccagggcct ttgcacatgt tcccctctct tctgagtggc atatggtagt   118800
tgctcctctg taaatattta ttgacatcct gacttccaac cagcagagaa ttgacctcct   118860
tcccatgctc aggctagtga aggcatgagt ttggctgagg tcccagtggg gaaggtgagt   118920
ggggtggcag agttaaccag gagcagcatg gtagaatggg taaaccagag cgtagcacgc   118980
aggcaccaca tgttagctgg acaagtagtt taaccccatg ggtctcaatt tccccatcaa   119040
tgaaggagg  aatagaacaa gtcccggta  agcagcataa aatgagctct cagaatgtaa   119100
agtaacaagc acacaacctg gaagagaata catttagtga atattggctc ctttaatcag   119160
caggttctga tatgacttag ctacaattaa gaaaataaaa atgaggccgg gcgcagtgg    119220
ctcatgcctg taatcccagc actttgggag gccaagacgg gtggggtgga tcacctgagg   119280
tcaggagttt gagaacaggc tggccaacat ggtgaaccc  atctctacta aaaatacaaa   119340
aattagccag gcgtggtggc gcacgcctgt agtcccagct actcgggagg ctgaggcagg   119400
```

```
agaaacattt gaacccagga ggtggaagtt gcagtgagcc cagattgcac cactgaactc   119460
cagcctgggc gacagagtga gatttgtctc aaaaacaaaa gaagtctgga ggccaggagg   119520
ttggttgcag ggttggttcc ttggctcaac aatgtctcca aagagtcctt ccatctttcc   119580
actctaacat cgtcactgta aggacttttt ttaacattta ccactcacag ccccaagacg   119640
actgcgtcag ttcttttctt ttttccttca gacagagtcc cgctctgtcg ccaggctgg   119700
agtgcagtgg catgatctcg gctcactgca acctctgcct cctgggttca agcgattctc   119760
ctgtctcagc ctcccgagta gctgggatta caggtgcctg ccactgcatc cggctaattt   119820
tttgtatttt ttttagtaga gatagggttt caccatattg gtcaggctgg tctcaaactc   119880
ctgacctcag gtgatgcacc tgcctcggcc tcccaaaggg ctgggattac aggcgtgagc   119940
cactgtgccc ggccgatgac tgcctcagtt ctaaggtact tacccagcca tccacgtaga   120000
cagacacaaa agcatccggc caaagaagag ggagaggaag ggctgtctct taccatgtga   120060
ctcatctcac ggggaaaaaa tccttttcca gaagcaccca gcagattttt cacccagatc   120120
ctgttaggcc tacgaatggg tcatgtgaca agtgctctta ttgcaaggaa tcttgggaaa   120180
aagagactat taggcatttt ctgcctcttt gatgggaggt gggctctgcc agtaaggcgg   120240
gtagtggtgg tggctcttgg atggacaact gtgtcttcca ttcttcttct tctttttttt   120300
tttttttaa gagacaaggt ctcactctgt tgcccaggca gaaatgcagt ggcacaatca   120360
cagctcactg ctgcctcgac ctgccaggct caggtgatcc gcccaccta gcctcacgag   120420
cagctggagg agtgtaccac catggccggc taattttat atttttgta gagatggggt   120480
ctctttatgt tgcccaggct ggtcttgaac tcctgagctc aaacaatcct cctgcctcag   120540
cctcccaaag tgctgggatt acaggcataa gccaccacgc ctggactctc ttctttaaat   120600
actgagcctt ccacctcttc tagaatatac tctgttaatt atcaaccaca cttttctaca   120660
tttttgcttc attattcatt cagtaaacat ttattgagtg cctactgtat gccaggcaca   120720
gcttaggtg ctggagatgc tatgaacaaa acagatgaaa atttctaaaa aataaaataa   120780
aaaataaaaa taaattttgc aaagccaggc acagtggctt aggcctatag ttccacctac   120840
tcaggagtcc aaggcagtag gatctcatga gactgggagt tgagtccag cctgggcagc   120900
atactaggac tctgtctcta aaaaagaaaa gaaggccggg cgcagtggct gcacgcctgta   120960
atcccagcac tttgggaggc cgaggcaggt gaatcgcaag gtcaggagtt tgagatcagc   121020
ctgaccaaca tggtgaaacc ccgtctctac taaaaatgta aaaattagcc aggcatggtg   121080
gcaagtgcct gtaatcccag ctacttggga ggctgaggca ggagaatcgc ttgaacctgg   121140
gaagcggagg atgcaataag ccgagatcgt gccactgcac tccagcctgg gcaacagaat   121200
gagaccctgt ctcaaaaaaa aaaaaaaaa gaaagaaaga atagaaaata tctgccctac   121260
ggggatggac atgctagaac atcaaagtcc aatggaactt tctgcactga tgaagtatgt   121320
atgtatgcac cagccacatg tggcttggga gcacttaaaa cgtgactggt acaagcgaat   121380
ttttcattta atttaaatga atatttaaat agccatgtgt ggctagtggt   121440
tactttattg ggcggtgcag ctctctaaag gccaagagat acatcatcaa cttctctccc   121500
ttgacccata ttcagttctc tcccaccctg aaaatctcct ctcctaccca ggctcacatt   121560
tccagttctt ctcctcttgt tctccctcaa ccatcagccc ccgcaagact gacgtgaccc   121620
tgatgccgta tgaaatgcat tcttcatcct ttactcttac tcacctctgt gcggccctgg   121680
agaccagtga cctctccttt ctcaaaatac tttatttctg tgtgtttttg ttgttgctat   121740
tgttttggg gggttttctt gagatggagt ttcactctca tcacctaggc tggagtgcag   121800
tggtgcgatc tcagcttact gcaacctctg cctcccaggt tcaagcgatt ctcctgcctc   121860
agcctcccaa gtagctggga ttacaggctc ccgccaccac ggctggctaa ttttcttgta   121920
tttttggtag gacggagtt ttgccatgtt ggccaggctg atctcgaact cctaacctca   121980
ggggatccac ctgcctcggc cttttcaaagt gctgagatta caggcatgag ccaccgcacc   122040
cagcctcaaa atgctttga acttgactgt caggtatgcc attctccaca ccagtctcct   122100
cccatgtctg tgtcttctcc ctctccactg ggacccttg gcttttttcca cttcactcat   122160
ctaccctggg ttatctggtc ttccataacc ctgtcctctg ccacacctca cttattcacc   122220
caccacaata tttattgagt actcactagg ccatgaaaga tgctatacaa aaaaagcccc   122280
tgtcctcgtg gagctgacat tctagaagaa agcatgaata ataaatacga cttaataaac   122340
agtacgcca ggcatggtgg ctcacgccta tcatccaaac actaagagac caagatgaga   122400
ggatcacttg aatccaggag tttgagacca ccttgggaac cgtactggga ccctgtctct   122460
acaaaaaaaa tattaaaaat tagctggata gggtaatgca tgcctgtagt tccagctact   122520
tgggaggaca aggtggaagg attgcttgag cctgagaggt caagtccgca gtgagctgtg   122580
actgtgcact gcacgccagc ctgggtgaca gagtgagatc ctgtcttaaa aataaataaa   122640
taaacaaaca aacaaacaat ataattccag agagtgagaa ggcaggatct ctttagctag   122700
gaagttgagg gatgttctct ctgagaaggc agaatctgag tttcaacctg aagaattcga   122760
agaggccagc taggcaaaag atgagagttg aaggaatggg gacggcagag gagacagcca   122820
atatagtaat tctcaataaa gcagaaagtg agctttttcct gctggcagaa cagaaaggaa   122880
gtcggagtgg ccagggtgtt gtgggacaag gtggtcagca ggagtcacat cagcaagggt   122940
catgtggtca tggtagactt taaatttttac tccaagcctg atggaagcca ttggaagatt   123000
ttaactaagg agtgacggaa aactggcatc tcaaactcaa catgtctaca acccagttct   123060
tgatctttga aaccttcttc ctccatcttc cccatctcca ttgacagcaa cttcatcctt   123120
cagttagctc aggccaaaac cctggagtca cccttgatac ctctctcctg ctccacactc   123180
agtcttttcca ttggaagccc taggggctgc catattgttc tccatagcac ttcacaccgt   123240
ctgacatact atatctttc ccactattgc tttgtccttg gtagcatctt taggcactct   123300
ctgaatatct ggcacatagt acgtgctcac taaatccttg ttgaataaat gaatgaacat   123360
cactccgtgt tcctttcaga accagagcca ttcttctctt tcttccaccac cgttgcccct   123420
caccccgccc aactagtcac aggagttgaa ggatgacaca gtagagaact gggattctgg   123480
agtcctgtgg ctggtctggg gttcgagttc ttactcagtg gtaggaacct ccatgtggga   123540
ttaacttatc tggtctttag tttcctcctc tgtaaaatgg gcctcaaact gccaaccgct   123600
gggatgcagg gaggatttga tgagcccagg caggctccct ggagcacagc aatcaatggc   123660
agctatatat aaaccggggc ctcttttgta ctcccactgc ctttgtccta gttccagccc   123720
tcattacacc agcctgctct tgcggctccc tcctaacttc tgctccatca ccaccaatct   123780
tttcag ctgtcagtgc tgtcttctga acgccaatcc taatcacatc ccttcctgct   123840
ccaaaaccttt acatgactct cactgtccac aggacaagac ccagcctcta gttgacagcc   123900
tccactgtcc agcttaccca acctctcccc taccacatac cctgagtgga gccttctgcc   123960
tccataggc tttcttagcc agagaagcct cccttatctt cctgttctcc tcctaattcc   124020
ttcttatcct tccaggagg aggctgtgag gtaatgcatc ttgggagcca gctgggattg   124080
cacagggtgg tgagattatc tgcatttccg aggcttgaac aagttaaggc aatgggaaag   124140
```

```
gtcacacaat gagaaaatgc agggccagga tttaacccgt ctgagatgtt ctgactgtgc   124200
tatgctgcct ccccggacat gagctctgcg ataatgctgt ccccaggctg taatcattcc   124260
ctctttcatc cctgcctcct ctatccctgg ggtcagaggg acttgtagtt gaatctctca   124320
ctcactcatt ggtgtggtct ctccctaaag cagggtggga tttgtcttag cgttatcact   124380
gcatccagca caacctccct ggtccaggct tatcagccgt caactgcgtc aatgcagttg   124440
cctcctcctc aatctcccag cttccggcct tgcccctag agagatcata ttttaataca   124500
agtcagatta catccctcct cccctcagaa ccctccatgg ctcacacctt actcagagaa   124560
aaagccaaag tcctctccac aacccacaaa gccctgcacc atccatcacc tcactgcctt   124620
cgtcccctca caccctcccc cttgctcgct ctgcttcagc cacaccaact catctctgtt   124680
tctcaaatac accaggcatg gcctagctat taaatgcacg gtccagcctg gtgcatttga   124740
agaacacgga tgaattggtg tggctggaac agagtgagtg aggggagag cgggaggagg   124800
acctttgcac cagctggacc tttgcaccgg ctgttccatt tgcctagagt tttccctgac   124860
atattcatat ggctcactct cttgcttccc ttgctttctc ccagtctta ttcaaatgtc   124920
tatttctctg cacttgtgct gtttgataca gtcaccgctg gccacatgtg gccttgagc    124980
acttcagttg aaaacatga aagtgtagaa tattgaccag attccaagga aaaccatgtg    125040
caaaatatct tttatctctt aagatacagg gtctcgctct gtcttccagc ctggaatgca    125100
gtggcacgat cacagctcac tgcagcctca aaatcccaaa ctcaagtggt cctcccacca    125160
acagcctccc gagtagctgg gattacaggc acacaccaca atgccccgcc cattttttta    125220
attgttatta ttttttttaa tagcgacaag gtcttgccat gttgctcagg ctggtctgga    125280
actcctggcc tcaagcgatc ctcctgcctc agcctcccga gtagctgaga ttacaggcag    125340
gagcttttgt gcccagcagg tctacgatct tcttagaatg cttcaggctg ggcatagtgg    125400
ctcatgcctc aaataccagc actttggag gccaaagcag gcagattgct tgagctcagg     125460
agttcgagac cagcctgggc aatatgtaa aaccctgtct ctccaaaaaa aatacaaaaa     125520
ttagctgggc ttggtggctc ccacctgtag tcccagctac ttaggaggct gaggaaggaa    125580
gatcacctga gcccaggagg cggaggttgc agtgagccaa gattgagcca ctgcactcca    125640
gcctagacaa caggagacc ctgtctcaaa ataaataaat aaataaataa ataaataaat      125700
aaataaataa acaaacaaac aaacaaacca ataaatgaat tttacctgtt tctttttact     125760
tttttaatgt ggctactagc aaattttaat ttttttttt tttttttttt tttttgagac     125820
agagtcacgc tctgtcaccc aggctggagt gcagtggtgt gatcttggct cactgcaacc    125880
tccacctcat gggttcaagc agttcgcctg cctctgcctc tgagtagctg ggattacaga    125940
tgcccaccgc cacgcccagc taattttttg cattttagt agagatggag tttcgccatg     126000
ttggccaggc tggtctcgaa ctcctggcct caagtgatct gcctgcgtcg gcctcccaaa    126060
gtgctgggat tacaggcatg agccaccgcg cctggctata aatttcata agtagctctt      126120
aatagatttc tcctgggcag tgctggtcta aacacttttt tttttttttt tttttttga     126180
gacggcatct tgctctgtca ccaggctgga gtgcagtggc gcgatctctg ctcactgcat    126240
cctctgtcac ccgggttcaa gctattctcc tgccttagcc tcccaagtag ctgggactac    126300
agacaccgc caccacgccc agctaattttt tgtattttta gtagagacgg gttttcacca    126360
tattggccag gctggtctcg aactcctgac cttgtgatcc gccagcctcg gcctcccaaa    126420
gtgctgggat tacaggcatg agccaccgca cctggctata aatttcata agtagctctt     126480
aatagatttc tcctgggcag tgctggtcta aacactttt ttttttttttt ttttttttga    126540
gacggcatct tgctctgtca ccaggctgga gtgcagtggc gcgatctctg ctcactgcat    126600
cctctgtcac ccgggttcaa gctattctcc tgccttagcc tcccaagtag ctgggactac    126660
agacaccgc caccacgccc agctaattttt tgtattttta gtagagacgg gttttcacca    126720
tattggccag gctggtctcg aactcctgac cttgtgatcc gccagcctcg gcctcccaaa    126780
gtgttgggat tacaggtgtg agccaccgcg cccggccctg taacactttt aacactgaac   126840
tgtttgcctt ccaggtggta aagagcaggt gcctttactg atagaaatgt caccactccc   126900
ttcatcccgc cagcccatg tcactgacgc gtcctttccc cttgctctgt ggtaactttc    126960
tcctaagcac tcatcgccct aacatctgtc atacaggtat acctcagaga cactgctggt   127020
ttggttccag gtcgccataa caaagcgaat attgcaataa agggagtcgt gcctttttg    127080
gtttcccagt gcacataaaa gttatgctta cactatagtc tgttaagtgc atgatagcat    127140
tatgtctaaa aaaaaatgta catccttaaa ttttaaatc catcaaggct gagcacagtg    127200
gcttgtaatc ccaacacttt ggggaggcca ggcaggagga ttgcttgagc ccagggattt   127260
gaaaccaggc aacaaagtga gaccccgttt ctacaaaaaa attctttta aaaatagctg    127320
ggtatgctga cgcatgcctg tggtcccagc tacatgagag gctgaggtgg gaggctcact   127380
tgagcctgag agattgagac tgcagtgagc tgtgatcaca ccactgcact ctagcctggg   127440
ggacagagtg agaccgtatc tctcaacaaa aattaaaaaa aaaaaaaaaa aaggctgggc   127500
acagtggctc atgcctgtaa tcccaacagt ttgtgaggcc aaggtgggtg gatcacttga   127560
ggtcaggagt tcaaaaccag cccagccaac atggtgaaac cccgtctcta tgaaaaatac   127620
aaaaaaatag ccgggtgtgg tggtgcacac ctataagcca gctactcgg gaggctgggag   127680
cacgagaatt gcttgaacct gggaggcggg ggggagattg cagtgagcgg agattgcact   127740
gctgcactcc agcctgggtg acagactgag actctgtctc aaaaaataa taaataaata   127800
aataaataaa taaatgtttt attactaaaa aagttaacaa tcatctgagc cttcagtgag   127860
tcctcatctt gctggtgaag ggtcactggc tcagtgttga tgggtgctga ctgatcgtgg   127920
gggtggttgc tgaagattgg ggtgcctgtg acatttttctt aaaataagac aagaaagttt   127980
tccgcatcca tcgactcttc cttttcacgaa agatttctct agcatgagat gcttgttgac   128040
agcaatttta cccacagtag aacttttttt aaaattggag tcagttctttt caaaccctgc   128100
cactgctttg tcaactaagt ttatgtcata ttctaaatct catgttgtca ttttaacagt   128160
gttcacagaa ttttcaccag gagtagaatc catctcaaga aatcacttt tttgctcttc    128220
cataacaagt aacgcctcat gcattgaagt ttgatcatga ggctgcagca attcagtcac   128280
atcttcaggc tccactttcta actctagttc tcttgctagt tccatcactt ctgcagtgtc    128340
ttcctccagt gaagtcttga actcctcaaa gtcatccatg aggatcggaa ttgacttcct   128400
caaaattcct attaatgttg atattttgac ctgttcccac gaatcacaaa tgttcttttt   128460
gttgtttgtt tgttgtggat tgttttttta ttttaattg agttgaggtc tcactatgtt   128520
gcccagactg gtcttgaact cttggcctca agtgatccca ctgccttgat ctccctaagt   128580
gctgggatta caggcatgag ccactgggaac agccacaaat gttcctaatg gtatctagaa   128640
tggtgaatgc ttttcagaaa gttttcaatt tcctttgccc agatgcatca aaggaattta   128700
tctatgcag ctatagcctt atgaaatgta tcccttaaat cataagactt gaaatagaga    128760
attacttctt gatccatggg ctacagaatg aatgttgtgg ctgggcatgg tggctcacac   128820
ctgtaatccc agcactttgg gaggctgagg caggtgggta acttgaggtc aggagttcaa   128880
```

```
gaccagcctg gtcaatatgg tgaaacccca tcactactaa aaatacaaaa attagctggg   128940
catggtggcg tatgactgta atcccagcca cttgggaggc tgaggcagga gaattgcttg   129000
aaccctcttg aagacagagg ttgcagtgag ccaagatcac accactgcag cgacagagtg   129060
agactctgtc tcaaaaaaaa aaaaaaatgt tgtgttagaa gtcataaaaa caacattcat   129120
cttcttgtac atgccatta gaggtcctgg ataaccagtc cattgtcagc agtaatattt    129180
tgaaagaaat ctttttttctg gctgggtaca gtggctcgca cctgtaatcc caccactttg   129240
ggaggccgag gcgtgtggat cacctgaggt cgggagttca agaccagcct ggccaacatg   129300
gtgaaacccc aactctacta aaaatacaaa aaaattagcc aggcatggta gcaggtgcct   129360
gtaatcccag ctaccctgga ggctgaggca ggagaatcgc ttgaacctgg gagtcagagg   129420
ttgcagtgag ctgaggtcgt gccattgcac tccagcctgg gcaacaagag tgcgacttca   129480
tctaaaatac atatatatat ataacatgtt atatgtaata taaattatat ataacata     129540
tatgtaatat aaattatata tcacatataa catatatcat gtgttatata tatcacatat   129600
aacatatgtg ttatatatca catataacat gtgttatata tcacacataa catatattat   129660
gtgtatatat gtcacatata ttatgtgtta tatatgtcac atataacata ttgtgttata   129720
tatatcatat ataacatata ttatgtgtag tgtatcatat gtaacatata ttatgtgtag   129780
tgtatcatat ataacatata ttatgtgtag tgtatcatat ataacatatg tgtagtgtgt   129840
tatatataac atatattatg tgttatatat ctcatatgtt atatataaca tatattatgt   129900
gttatatatt atatatat tttttttctga gtagatctca acagtgggct taaaaatca     129960
gttatccatg ctataaacag acgggctgtc attcagtctt cattgttcca tttatagagc   130020
acaggcagag tagattcagc ataattctta agacctaggg actttaggaa tggtaagtga   130080
gcattggttt caacttaaag tcaccaggag cactagctcc taacaagaga gtcagcctgt   130140
cctttgaagc tttgaagcca ggcattgact tctcctctct agctatgaaa gtcctagatg   130200
gcaacttctt ccaatagggc atttcatcta cattaaaaat ctattattca gtgttgccag   130260
cttcattaat aatctcagct agatcttctg gataacttac tgcagcttct ccatcagcac   130320
ttatcacttc accttgcact tttatattat ggggacacct tctttcctta aacctcatga   130380
accaagatct tctagcttca gattttttct ctgcacttcc ccacctctc cagtcttgct    130440
gtgggcttgc tgtggattag gctttggctt aagggaatgt tgtggctggt ttgatcttct   130500
atccagacca ctaaaacttt ctccatgtca gcaagaagcc tgtcttactt tcttatcatt   130560
catgtgttta ctagagtagc ccttttaatt tccttcagta atttttcctt tgcattcaca   130620
actggctaa cctctagctt atggcctttt gtttgtttgt ttgtttttgt tttgagacag   130680
ggtctcactc cgttgcccag gctggagtgc agtggtgcaa tcaccgctca ctgcagcctt   130740
gacttcctgg gaccaagtga tcctcccacc tcagcctcct aagtagctga gaccacaggt   130800
gtgcaccacc acacccagct aatttttta ttttctgtag atatagggtc tccctatttt    130860
gcccaagcta gtctcaaact cctaggctca agccatcctc tcacctcagc ctcccaaaat   130920
gctcggatta caggcatgag ccaccatccc tggccctatc tcagctttg acacgcttc     130980
ctcactgtgt ttaatcattt ctagcttta attaaaagtg agagacgtgc aactcttctt    131040
ttcacttgag cacttaaagg ccattgtaca gttatacact gacctaattt caatattgtt   131100
atgtctcgg gaataggaag gcccaaggaa agcgggagag atggggaaat ggccagttgg    131160
tagacagtc agaacacaca caatatttat cgatcaagtt tgccatcttc tatggatgtg    131220
gttcgtggca ccccccaaaca atgactatag tcacatcaaa gatcactgat cacagaccac   131280
cataacagat gtaataatta tgtaaaagtt tgaaataccg taagaattac cagagtgtga   131340
cacagagacg caaagtgagc acacgctgtt ggaaaaaaaaa tggccctgat agacctcctt  131400
gacacagggt tgccacaaat cttcaatttg taagaaaac aatatctaca aattgcaata    131460
aagcaaagca caatgaaatg aagtcttcct cggccggtgt ggtggctcac gtccataatc   131520
ccagcacttt ggaggccaa ggcaagagga tcccttgagc ccaggagttg gaggccagcc    131580
tgggcaacac agggagactc catctctaga acaaaacaaa acaaagcctg cttatattta   131640
ttgggtttac tctcagtctc ccccacacag agataggcc tggcttgtta ttagtgctca    131700
gttgatgttt gtgaagtgaa atactaagga cttaaccact gcctgttctt tgctgttcat   131760
gcctgacag cttttatgtg ccagcacaga agaaaacaag gtgcaagaag agaatagtga    131820
tctctaagtc agaatttgag gaacccaaat tagtaccaga aagctgggag gagaagaaa    131880
aaataagta aatcaaatta aaagttgaat ggggcaagtg cagtagctca tacctataat    131940
cccagcactt tgggaggctg aggtgagagg atcactgag gccagaggtt ctagaccagc    132000
ctgggcaata tagcaagacc ccatctctac aaaaaaaatt ttttaattt ctgaatatgt    132060
tgttgtacac ctgtagtccc agctgcttag gaggcagagg tgggaggatc gcttgagccc   132120
aggaggttga ggctgcagtg agctgttgtt gcaccactat actcaagcct gggtgacaga   132180
ataagtccct gtctccaaaa ataaaaataa ataaattcat ttttttgtaaa gttgtatgtc   132240
atggcccctg cctactctgg cttcatgact tgctgcttga acctcaccat ccaaatccca   132300
gtggtgacac catgtcattt cttgaatttg ccaagccctc tttcagtccc aagctctctg   132360
tcatggccac tctcagcctg gaaagttctt tccccactgg ccagatttct ccccctcatc   132420
tatgggaact tgacttgaag tagggggtat cccaggccct ggactagtta acacgacctg   132480
ctgtgtgccc ctcaaagcca ttgtcttcct agctgagaag gcatcacacc tgcaacagat   132540
tcactcattg tgtgcatgtt tttcttaacc acttctcttc tgcatcagct ccatgggca    132600
gggatagtct catatgtcac tctacccagc acataggata cgctcagacg cccacttgtg   132660
gatggtggaa aaggtcagcc caacctaata tgcccatctc tcctctaggg gtaatcttga   132720
gaaaaaaagt tgggaacttg ctttgtgtta gttaggatg acccagaata gatcctgaaa    132780
caagaattta gggcaatcct tgtgcaagta gttcatctga gaggtgaccc cagaagggtt   132840
ggagaaggag agggaggtg gggcaaggaa gggtgagttg tcctgtaggc aactgagctc    132900
cgtcctactg ggagcccacg tggaactcac ctcttaagtg atccagaatg aagggtgagg   132960
gagctgcggt attgatccac caactcccag caatctttaa ttgagggctg ctcccttaaa   133020
gttcattccc tgggcctgcc ccagatttgg agacagccct aaggcaagag gtacagatac   133080
cagttggcca cagactgaag tgttaagacc caagcccctg gataaaactg aaaaatcaag   133140
ccagatgtgg tggttcccac ctgtaatccc agctactcag taggctaagg caggaggatt   133200
gcttgagccc aggagttcaa tgctgtagcg agctatgatt gcaccactgc attccagcct   133260
gggcatgaga gcaagacccc atgtctaaaa taaaaataaa ctgaaaaatc cccaagttat   133320
ttgctgtgac caaccttcca ttaaccacag acccctctggt attcagcatt tcttgtccat   133380
tatatgaagt tctgatgaca gtctctttta ttgtattgtg ccttgaccac gcactgtaca   133440
tcacttagct ctgaaatgga catgttcagg aaacagggcc aggtgggacc ctgtgtttca   133500
acagcaatac ttttacaaat gaggtctcat gacagggtct tgctcggagg gtttctatgg   133560
aagcctcatc ccacctactg ctatcatcct tactaacttg catttacaaa agggactctt   133620
```

```
tttgaccaga ggcttggggt ctgtagctgc cttctagcca gctgatgctg gctggtccac   133680
acaagcagga tcacacccat ttttttgttt tcttatttat ttctgaatag gttagcatac   133740
cggtaacctg tgtgcctggc attgtgctga ccacttttttg tcaacttact gaatcctcac   133800
aacccttgga ggtattgata ctattgttat ccaggttata caaaggggg aaactgaggc    133860
acagagcagg gatgtccctt gcccaaggtt acccaactgg aaagtggcag atctgggatc   133920
tgaacccatg caggctgggc tcttaacact gaactacttt cctgccattt gttaaagagc   133980
cacaaaccag gccaggcacc atggctcacg cctgtaatcc cagcactttg ggaggccgag   134040
gcgggtggat cacctgaggt caggagttca agaccagcct ggccaacatg gtgaaaccct   134100
gtctctacaa aaatacaaaa aaaagtaccc gggcatgatg gcgggtgcgt agtaatccca   134160
gctactcggg aggctgaggc aggagaatcg cttgaacccg ggaggcagag gttgcagtga   134220
gctgagatca caccattgga gatcgcactc cagcctgggc aacagagtga gactctgtct   134280
caaaaaaata aaataaaata aaataaagag ccacaaaccc cgaaaggtct gccattcccc   134340
cagggcccca ggccaccccca caatctattg tcattgtagg ttgtgaaata tactgaatgt   134400
caccccaacc ttgagccatg gggaagattc catttctctc attgcaacat ttgtgcaaca   134460
tgaaccatct gttgggggtc ttcgtaaatc accttttatc ccgtgaggca ggtactgtta   134520
agaccatttt acaggtgaca aaactgaggc cagtggtgtc gagtcacctg cctgtggtca   134580
cccaaccaat acaggacagc ttggaatccc aagcaccccc gccctgctgt ctgaccccca   134640
aaacccaccc tctgttctcc attctggctt ctttctttca gcatcttggc gacagttggg   134700
acggagtttg acctacggac gctgagggca gttcgagtgc tgcggccgct caagctggtg   134760
tctgaatcc caagtgcgtg agtttccgac cctgacaagg ggtttgctca cgggcccag    134820
gagccctcag tttcccctat gcagagcatc tcaggaggcc acatcctgcc accagcctgt   134880
gtgagggcag tctcttcttt gggactccct atagggaacc cctaggaat atgactgtag    134940
ctccccatga gctcctgaaa gcaaactagg agccacaccc attttattgag cacctactgt   135000
ctatcgggag ccatgctaag caccacgtgt gatctcattc agtactcaca gcccatgaa    135060
gttgatagga ctgatgtctc tattttatgg aggggaaac tgaggctcag agtggctgaa    135120
acattggagc aggggttttgt ggctgagaag tggcagaact aggagtgagc aagtgtgact   135180
ccaagcctgg gccgtaccac tggtggcaat gaccattccc attttaatgag tgcctgctgc   135240
gtgcagggca ctacagaagg actttacatg aattaccta tttcatcctc acagtcaccc    135300
agcgaacacc cattttacag atgagacggt tgaggcttaa ggaggttaaa ttactcacct   135360
gaattcttag agtggacagt aatgactct aaaattcata ctcattcctt gctgcttct     135420
cattctccac agatacatct agtccccgtt taagggtggc tgccatatgc agggtcaaga   135480
ttaagtgtag gttgagccaa aaaaaaatgt aaaaagcaaa aataaaacag ggctgtcctt   135540
tttctatctt cttgtcttgg ttaataataa taatttagcc aggcatggtg gctcatgcct   135600
gtaattccag cactttggga ggatcacttg aggccacaag ttcgagacca gcctgggcaa   135660
cattgtgagg aacaccaccc ccaccccccc gccaatatct acaaattttt ttttttttt   135720
tagaaattag ccaggttgac tgggcacagt ggctcacacc tggaatccca gcactttggg   135780
agaccgaagc gggcagatag agcgagctca ggagttttaa gaccagcctg gcaacatgg    135840
cgaaaccctg tctcaaaaaa aaaaaaaaat tagcaggcat gatggtgcac acctgtagtc   135900
ccagctactt aaaggctaga ggcaggagga tctgagccca ggagttcaag gctgcagtga   135960
gctgtgatag caccactgca ctccagcctg acaacagag tgagaccttg tctcaaaaaa    136020
acagacaaca aaaagtttaa aaacaaacaa tttataggct gggtgcagtg gctcatgcct   136080
ataatcctag cactttggga ggccaaggtg gatggtgga tcacctgagg tcaggagttc     136140
gagacctgcc tggccaaaat gggaaaccc cgtctctact aaaaatacaa aacttagccg    136200
ggcgtggtgg cgggcatcta taatcccagc tactcgggag gctgaggcag gagaatcact   136260
tgaacccggg gggcggaggt tgcagtgagc tgaaatcacg ccactgcact ccagcctgga   136320
tgaaagagtg aaactccgtc tcaaaaaag aaaaaaaaaa attaaaaagc acttactatg    136380
tgccagacat tattctaagt attttccattt ttttaaagtc ctttatcctc ccaacaagcc   136440
tgtgaagtag tctctctttat tatcaccatt ttacatttta ttggcttcgt tcttccggtt   136500
cattgctacc caggttttaaa gagtaagatt tcccagagga tcaccagcag gatctttttg   136560
tagaaagaag acacttctat ccaaggtctc tgcaagatcc cagcagatgc ctgcatcata   136620
ttaaattaag ggccatccca aatctaatag tcaaaagagc caggtgcagt gctcacacc    136680
tgtaatccca gcactttggg aggccaaggc aggacgattg cctgaggcta ggagttcaac   136740
accagcctgg gcaacaaagt gtgaccctgt ctcaaaaaat atatgtatat tataatagca   136800
gtagtaacaa gagtctctgt ttaatgacca cctatgactt accaggtact tcactgtgtg   136860
tgaactctct catctaatcg tatgagggag gtactattgc agtccccatt tacagatgga   136920
gaagctgagg tttggaattc actagtaagt ggatgactag gtcaggttcc cttgaagcgg   136980
atacttaggt gggtgttcag atgcacctgc tttattgggg gacggctctt gggagagaca   137040
gcaggagatc agcagggtgg ggctgggaa tggatagagc agggacgcaa tttcagctgg    137100
agtgtgtgtg acaccagagt tgtcctccaa tgcatggcaa ggatgccggc cttttgtact   137160
tctatagtca gtcactgtgg atgggaggta gagacgcagt agctcccagg tgagatagct   137220
tttgatcacc aagggcaatt ctactaagaa gagaggcagc tgggaggcat tagcaaccaa   137280
catccatagc agctggaggg cgggtacacc agaaagaaa tgggatcttg gccagacacc    137340
aagagtatcc agcaccttaa ccactgcacc acactgcatc tgttagcacc cacattacat   137400
tttttttttt tttttttttt tttgagacgg agtctcgctc tgtcgcccag gctggagtgc   137460
agtggcgaga tctcggctca ctgcaagctc cgcctcccgg gttcacgcca ttctcctgcc   137520
tcagcctccc gagtagctgg gactacaggc gcccgctacc acgcccggct aatttttgt    137580
atttttagta gagacgggt ttcaccgtgt tagccaggat ggtctcgatc tcctgacctc     137640
gtgatccgcc cgcctcggcc tcccaaagtg ctgggattac aggcgtgagc caccgcgccc   137700
ggccagcacc cacattacat ttttaagccc ttggagtgag atggccctc gagctatcc     137760
gacagcttcc ctctcttact gtggtctcca cccatcaaga gccatgggaa gttcctgcaa   137820
tcaagaagca aagcctcagg ctatatgttt gaacttcat tttgatcata gacttttccta    137880
gtagatacca tagtggttac aaacatagga tgttgtcatc gttcagacct gagttaatag   137940
cctcaagaaa aaaatggtag tggaaccagg tatggtgaag tgtgcctgta gtcccaccta   138000
tcgggagga tgaggcagga ggctcgcttg tgcccaggag gtcaaggctg cagtgagccg    138060
tgatcatgcc actgtattcc agcctgggtg acagagcaag cccatctcaa aaaaaaaaa    138120
aagccaatga taggcagaga aatactaact aaggctcttg ctctgtcgcc aggctggagt   138180
gcagtggtgc aatcacagct cagtacagcc tcaacctccc cagactcaag caatcctacc   138240
atctcagcct cccaaatagc tgggactcca ggcacacagc accatgccca gttaatttt    138300
ttgtattttg tagagacagg gtttcaccac gctgctcagg ctggtctcaa actcctgagt   138360
```

```
tcaagtgatc cacccgcctc agcctcccaa agtgctggga ttacaggtgt gagccaccac  138420
gcttggccag ctattattat tattaacatt cttcgagtct tacaacagtg aacttttag   138480
tgcaggatgc gaatttcagt attaaccct tcctctccca aaaggatttg aagcccagag   138540
taattcagcc gccatgaatg aaccattgt tagatgagag gctactggag gctgagcttg   138600
gtaggataag agcttgcatg gggtccctga ttgatgacaa tacccccaga tttaggtctt  138660
cagatgccca gttgggtgtg tcttctgttc cactgtgtcc cttcggggac tgttccctgc  138720
cttctttctt tttgagatgg aatctcgcac tttcacccag gctggagtgc aatggcgtga  138780
tctcagctca ctgcaagctc cacctcccgg gttcacacca ttctcctgcc tcagcctccc  138840
gagtagccag gactacaggt gcccgccacc acgcccagct aattttttg tatttttagt   138900
agagacgggg tttcaccata ttagccagga tggtctcgat ctcctgacct cgtgatctgc  138960
ccgcctcggc ctcccaaagt gctgggatta caggcgtgag ccaccacacc tggcccctg   139020
ccttcttatt caccaccatc tttctgaatt gggttgctca gaacagagaa agcaacatca  139080
gcacatgggc aaacatgggg cttcatttca gatggacctg ggttcaaatc ctagttctgc  139140
cttttttttt tttttttttt tttttgaga cagagtcctg tctgtcacc cagactggag   139200
tacagtggcg tcatcttggc tcactgcaac ctctgcctcc caagttcaag caattctcct  139260
tcctcagcct cccaagtagc tgggattaca ggcgctggcc accatgccca gataatttt   139320
tgtatttta gtagagatgg ggtttcacca tgttggccag acttgtcttg aactcctgac   139380
ctcgttaatc cgctggcctc ggcttcccaa agtgctggga ttagaggcgt gaaccgccgc  139440
cgcgccctgc ctagttctgc catttctcat gcattctctg ggtgaatcac agcatctctg  139500
ttagcctgc ttcccacttc tgtaaaatga gagtgactt acatgtatgg ccacctcagg    139560
ggcttgtcac tagaagccag tgaaataatg ttgagtctgg ttccttgggg ttgaaattgg  139620
gaccgccaac cgcttccta cccagagcag caactagcct atatgccggc cttttatgaa   139680
tgaggaaaag acaccgcctc ttggcagaaa aaaaaaatta agaaaatggc tccctcttct   139740
gggtgcaagt tgcccaacac ccaggaatat ggctccaaaa gcaatggact cccacccctt  139800
tcttgcccaa aagatcatca aatggaacag catgtcaaat acctttatta agtacttaa   139860
agttggctgg gctctgtggc tcatgcctgt aatcccagaa ctttgggagg cagaggctgg  139920
aagatcgctt gaggtcagga gttcgagacc agcctggata acatagtgag acctgtctc   139980
tataaaatat atatatagat ttatttgaga cagcgtcttg ctctgccact caggctgggg  140040
cgcagtggca caatcatagc tcactgcagc cttaacgatc ctcctgcctc agtccctaga  140100
gtagctagga ctacaggcat gcaccatcat gcctggctaa ttaaaataaa taaataaaata 140160
aatactttaa agttaaaagt gcttttttaaa aaataataag gccaggcgtg gagactcacg  140220
tctgtaatcc cagaactttg gaagaccgag gcgggtggat cacgaggtca ggagatcgag  140280
accatcctgg ctaacacggt gaaacccgt ctccactaaa aatatgaaaa attagctggg   140340
cctactcggg aggctgaggc aggagaatgg cgtaaacctg ggaggcggag cttgcagtga  140400
gccgagatga caccactgca ctccagcctg ggcgatataa caagactctg tctcaaaaaa  140460
aataaataaa ataaataata ataataatag gggccaggta tggtggctca cacctataat  140520
cctagcactt taggaggctg aggagtttga gtccttggag accaggggtt tcaggccagc  140580
ctgggcaaca tagcaagacc ccatctctac aaacaagttt taaaacttag ccaggcatgg  140640
tggtgcatgc ctgtagtcct agctattgca gggactgagg caggaggatc acctgagccc  140700
aggaggttga ggctgcagtg agctgtgatt gtgccactgc actccagcct gggcagcagt  140760
gcaaaaccct gtctcaaagg aaaaaaaaaa cctaggaagt gttgttccca tgataaggat  140820
cagcctccgt gtggtgcttc cttcaccatt gcccaatccc caggctcctg ggtgcttaat  140880
attccctcag gaacacacct gcttgtctg ggagagaccc ggtgcgggt gtggcgggt    140940
ttggggtac ttgctcatgg gcttatgggg cctctctctg tgtccccca ggtttacaag    141000
tcgtcctgaa gtcgatcatg aaggcgatga tccctttgct gcagatcggc ctcctcctat   141060
tttttgcaat ccttattttt gcaatcatag ggttagaatt ttatatggga aaatttcata  141120
ccacctgctt tgaagagggg acaggtaggt ccacggacgg tgatgcatct ttccagtttt  141180
ctccttcagg gacaagctct tgggaggatt aggcaggggt gtgcttcttt ctcctggcag  141240
ctgggaggac cgtctccttc agagagcact acaggagagg cagtgagtga aatagcctct  141300
gagatcttag ctgttgaaag gggtggggtt ccacagaagg tgacccagca gagaaagagt  141360
ttatttggga atgatcccag gaagcaccat cgggggaatg aggaagtgag cagagaaaga  141420
agggatcttt taaagagtgt gctatcaagc gggttaccac ttaaaactgg gactggatcc  141480
ccctgggcac ctctgggaga cagcaaagaa cacaaactc agctggtcac ggtggctcac    141540
gcctgtaatc ccagcacttt ggggggccaa ggcgggtgga tcacctgaga tcaggagtca  141600
gagaccatcc tggccaacat ggtgaaaccc catctgtact aaaaaataca aaaattagct  141660
gggtgtggtg gcaggcacct gtagtcccaa ttactcagga ggctgaggca ggagaatcac  141720
ttgaacccgg gaggcagaag ttgcagtgag ccaagatcac accactgcac tccagcctgg  141780
cgaaagagtg agactccatc tcaaataaat aaataaataa aaatataaat aaaaaaagaa  141840
cacacacctc agagccgtcc cagccaaggg gcaagggagc tggggtattt atacactggc  141900
ttcttttttga cattggtgag gactgctcct agagtgggaa ttaatgcctg gcacatctgg  141960
ctgagtggaa caggtattct gggtgctttc agacctcgac cagtcctgac ttctaaagca  142020
agcaagaagt ggggagagtt gggccagaaa agggttattg cctcaatgca ttgtgagtgg  142080
taccttgtgt aaggtgagag acagagaaga ttccaggcac aggtgccatg ctaaacgata  142140
gttctcattt attataggaa cccatgaatt tattttgttc tcgccctga gtgctgggtg   142200
agagtactgg atgagtcctc ctggtctccc ccaaccccca ggatgtacca gagatacccc  142260
aattgggagt cctggcacca accaatcaga acctagcact cagcagcatt ctgcccctcc  142320
ctgactatgc ccacattaac ccttcagtgg ctgggtctgg gggtagggtg agccccggaa  142380
aagccaggca gcgcagagac actctcccag ggctcagctc tgaaccagca gtgtggaagc  142440
agtgtgtcca ccacgatcca cactcaggaa ccaaatagcc cttggatacg ttttcagtta  142500
aatctttgcc atccaaactc tagctgcttg ctctctaaag ctccagaatg aaatggaatc  142560
aagtaggaag ggatgccttc agtatttcag tatttggacc actggccatc tgggtgcaga  142620
cagactgaat agcagttctg gttctgatga tttgggtcaa gggagctgtg aattgaagga  142680
gtggatagaa ggaatcaaga agcccaaagg ggaacccagg tgggcagaga aagaggttc   142740
aggccctta tttgggaaag gcagccacag aagaagattc tgtctgggag tggattcca   142800
cccaccctct ccaccagtg accccaagt ggatccgcga aggcagcccc tgagccctcc    142860
ctccccactc ctcccacgg ggagggaaaa cccactgggg aagtttatt tgcaatggtt    142920
ggaggtttgg gttttttgt gggttttggt tgttggttt ttttttcct cttttctct     142980
tgctcctcct gtctctttct ctcctgggct tgtgaagttt gctcaatatg gaatgtccta  143040
attatttctt tccccgatga agaaggtgtt aattgaggca gagctatttc tgctcctggc  143100
```

```
ctcgtcaccc aggcggaaat gcgagagaga gagagagaga gagagagaat gaatatgggg   143160
cagggcctct tggaaaaatc agccgtgagc agagaaacca ggactcctgg atcctaggtt   143220
tctgtgaagt tttattttat gtttttctac cctagactag ctaaaggaga agaggccatg   143280
gggttggctt gggtccgagt ggggttttga ggggacagat gtgggtggtg ccaccagagg   143340
ggaggaagcc tcgatttagg agaaagactg aaaagctagc tcacgattaa aaatataaga   143400
cgtgtgagta agagacagat atatacagac acccaggcag tgggttaatt ttaaaatgta   143460
tttataaccg aattcctcag acactctgga cgcttgtttt tctagaagca acgctcagag   143520
tgtttcgtgt cggtggttgg ggggttgagg gggattgcaa agctgctaaa gatagacccg   143580
ttttcagtag cattcctcag tgtcgggagc ccagttcctg tgtgcccagc accgtgccaa   143640
tcgcttagaa ggaagcaaag ataaagtgga aggcttcctg ctttctaaga gcttccaaaa   143700
tagttagagg aaacaagacc cctcatttgc agccattttt aacagtgaag gctaatgtgt   143760
gattataccc acgccccct aaatatgaaa attcagtagc tatttgtatgc ctgaaagggg   143820
ccaggtgcag tggctcacac ctgtaatccc agcactttga gaggctgagg tgggagtatc   143880
ccttgaggcc gttagtttga gaccagccta ggcaacatag ccagaccctg tctctgctaa   143940
aataaaaatt taaaaattgg ccgggtgcag tggctcacgc ctgtaatccc agcactttgg   144000
gaggccgagg caggcggatc aaaaggtcag gagttcaagc ccagcctggc caacatagtg   144060
aaaccccgtc tctactaaaa atacaaaaaa aataaaattag ccgggcatgg tggcgtgtgc   144120
ctgtagtacc acatacttga gaggctgagg caggagaatc acttgaacct gggacataga   144180
ggttacagtg agccgagatc acgctactgc actccagctt gggcaacaga gtgagatttt   144240
gtctcaaaat aaaaaaattt aaaaattagc catgagtggt ggtacatgcc tatagtccta   144300
gctactcagg aggctgagga agaaggatca cttgagccca ggaattggag gctgcaaggc   144360
tgcagtaaagc tatgatggtg cccgcactcc agcctgggtga acaaagtgag accctgtctc   144420
aaaaaaaaaa aaaaaaagag agagaggaag gaaagaagga aggaagggag ggagggaggg   144480
actgggggctg tgttaactgg gctacacaaa gaggctacat ggagggtggg aattgagcca   144540
gacttggaca tggcgtggag acagagaaga ttccaggcac aggtgccatg ctaaacgata   144600
gttctcattt attataggaa cccatggatt tatttttgttc tctgccctga gccttatgtt   144660
taaaagattt ttgccttcca acctgtattt atcaaataat agttcatgta ccaagtccag   144720
cataagtgag gaaggcgttt ccaacaactt aagttcatgg cgaggctaga cttggagttt   144780
ctattcagcc agagcttgaa aggccaacaa gattcattca ttcagcattg gtttatttcc   144840
ctctgctgtg tgctcagtca agggagcaga gaattggtgc tgcgaagtct gtagcacata   144900
cattgagaga tattttttgtt gagtaggaag cttgagttta cacacactca gctgtttgtt   144960
ttcttgtccg acaatgccac ggtcgtcttt gaaaaccttc aaaagcatcg ctcacagaat   145020
aaggtcctct cagacccgct gtgctggtaa aatgaggaca ctcccagatg tgagcttttcc   145080
tgcctcccta ccccatcaat accttaagat ttggactgac ctttagcgtt cagcctgact   145140
gccacctccc caggaagctg tctttggttt ccagcaaaag gggtgtctgt tggcacgttt   145200
ctctctcctt gtggcatttt cacagcctgc ctcctgctat ttggggagaa agctcagctc   145260
ctgttcctta cccttaggca agggtaggaa ctgtgtgtac tggtgtccct cacccccaga   145320
acagctccct gagcccagta catcccaaga agaaaaaaat cagcaaggct tataggagaa   145380
taacaaatg cgcttgacaa attttgtccta atggatgtcg gaagaagct gcacttacca   145440
gctacaccat gcacacggca catttactaa aactgactat attatggacc ataaagtttg   145500
tctcaacaga ggtcaaaaag ctgaaaaaaa tacaaataca aaacatattt tctgaccgta   145560
atgcaattaa gctggaaatc agtaacaaaa agagaactct aaaagtgttt gcagattaac   145620
agcatgcct ctcatttatg gatgaaatga tatgatgtct gagcttttgct ttaaaaatat   145680
tctaggctgg gtgcagtggc tcacgcctgt aatcccagca cttggaggc cgaggcgggc   145740
ggatcacttg aggtcaggag ttcgagacca gcctggccaa catggtgaaa ccccatctcc   145800
actaaaaata caaagattat ccaggtgtgg tggtggccac ctataatccc agctacttgg   145860
gagcctgagg caggagaatc ccttgaacct gggagtcgga gattgtagtg aggtgagatc   145920
atgccattgc actccagcct gggtgacaga atgagactcc gtctcaaaaa aaaaaaaaa   145980
aaaaaattct agtggcaagg caaagtgttt ggagggggata cagaggaata gatgaaacaa   146040
aatttgccag aagtaaatag gtaagtgtct aaattggtga taggtacatg gtgaatcatt   146100
atattgtttt atacttctct ctcgctctct tctctcccccc gttctctcc tgtcttcctc   146160
tccctctgt cttcatatat atatatatat atatacacac acacacacac agacacctaa   146220
taagttttttt taaaaaacaa atacatctaa attacccata ggtcaaagaa gaaataataa   146280
tggaaattag aaaatatttt acttgaacaa taatgataat gcatgacaaa atgttgagat   146340
gcaggtaaag ccacacttaa aggcaattta tagccttaaa ggcagttaat ccatccatct   146400
caaaagttta ggaaaagaat agaaaaaaaa aaaaactca tggaaaacat aaagagaaaa   146460
gtagtaaagc tcagagaaga aattaatcaa tagaaaacca ataatagacc cccaaagcca   146520
aacattgatc tctttgaaga ctgatcacgt ttgtcccaaa agttattcgt tccaacagca   146580
ttatagagtc actggtccct attttctcaga gctggttttc cctgctcctt ccctgacttt   146640
ttctccctt cccttttgta gatgacattc agggtgagtc tccggctcca tgtgggacag   146700
aagagcccgc ccgcacctgc cccaatggga ccaaatgtca gccctactgg gaagggccca   146760
acaacgggat cactcagttc gacaaacatcc tgtttgcagt gctgactgtt ttccagtgca   146820
taaccatgga agggtggact gatctcctct acaatgtaag tgatgctggg acagtgtgtg   146880
tggacaatca agctcagg gaggtggcct cctgggacca gtgagactcc aaggctgcaa   146940
tggagggacc ctgagctggg aaaggcagcc caaggacaac acagcccac tgaagctggc   147000
ctgaggctca ggcttttgaa gattacaggg gctcatgagc agaactctaa ctatagggca   147060
tagaagtctg gagggcccccc agatgcaaca tcatttttca ttgtgcaagt gtttagatat   147120
aattttagat ttttgaatac ggaaaggtta tgtgatccaa aaaccaacac agataaaaga   147180
tagagtaata tctttggacg taggcgaggg gtccctgccc tgaggctcac ccagtccttc   147240
tccagccata ccactccccg tgggatgaga agttcctgga gccaagggga tgtgtctacc   147300
aagagcttgt gccccacttt gtaggccatg tttaagttaa ccaggatcct ggaattccct   147360
gcccatggcc agattccatg aacttgcgtg caattctcat atggatctgt tcgtaaccca   147420
actgagggcc aaggacatcc gaggggtggc tgttaacaca aatgtggcca gagcttggat   147480
gtacaagctg gaatgcccac acatatgtgt ggagcccctc tggcaggaca gagccatgac   147540
taagaagaga aagggacagg acagggctgg ctctccccac accttgaccc agtgcagata   147600
tccggattct aaattccacc ctgaccttcc aaagtgtaaa ggaaggtata tttgcaaagt   147660
agaagcacac agcatgtttt atttagttac ctttttcaata ttccccgta gtatgtggtc   147720
tgcttttgta ctcttgccct agatcttaaa aatgttaggg atgtttctgg aaagatgtat   147780
ccctgccccc acttgcatgc tacttcctct tcccacaata tgcaacccct ttagttcctc   147840
```

```
agaatatcct tccaatgttt atttatgcaa ttataattat aagcataatc gaatctatgt   147900
cctccccct ctttcttatc ccaaggagta gcattctata catgctgttc aattctgtga    147960
ttttgtttt ctcataacca cacgttctag agatctttcc actgcaggac atggacagtc    148020
tcttcacggt tgcacactag tatgcccagc taatttttgt agagacaggg ttcttccgtg   148080
ttgcccaggc aggtctggaa ctcctgggct caagcaatcc tcccgcctct gcctcccaaa   148140
gtgctgggat tacaggcgtg agccaccacg cctggcctttc tttattcttt tgcacagctg  148200
catagcattc tattgtgtgg ctgcccatag ttttatttgt ttgccattaa gagaaatgct   148260
tgactggctt cctgtccact gacatggaac atgatgctgc tctgccagga gcatgttgca   148320
cgtacctctt catacttttg cagatatagc taggggggttg gagggtctcc attcccagaa  148380
gtgggattgc aggatcaaag actaaatgca tttataattt tattttttggg gaagattttt   148440
gttttgtttt tttggagaca aggtctccct ctgtcgtcca ggctggagcg cagtggtgta   148500
atcatagctc actgcagcct taaactcctg ggctcaggtg atcctcccac cccagcctcc   148560
tgagtagctg ggaccacagg cacacaccac catacctagc taatttttaa gaacaattttt   148620
atagagatgg ggtctcacta tgtttcccag gctgctctca gactcctggc ctcaagcaat   148680
cctcctgcct cagcctccca aagtgctagg attacaggtg tgagccactg cacccagcct   148740
aaatgcattt ataattttga tagatattta ggtgtgcaag ttttaaaccc cactctgtcc   148800
tcaccacagt tcaccttccc tcacctacta tgcaggtaag cagtccccag gcaggtcact   148860
tgtcagcagc tggagtgggg cagagccaag gattcaggat caaacacaag gatgccacaa   148920
ctgtagtgac cccatagagc accctggggc tgctccatac acacagctct gttgaccagt   148980
ggaggtctcc tcttcacctg ccctaagggc tgaaattacc attgaagttt aggccagcgg   149040
ttggcctgac ccgggagcaa tacctggctt cctcctcctg tacatagaga agctgaactt   149100
tcctcttggt cctagtgtat gttccttaac aacccattta tgcctagtgt tccattattg   149160
gaatgctaat cctgtgggag ttatttacat cctgctgctc aaggtcatca ctaaggtcgg   149220
attttttcaca cacacaaaaa ttgcaacctc cggcataaat gggttaagga atttccccac   149280
ttgtgggtgg agggagattt gcaaaaactc atccttgtaa tcctgatcaa caaaggcccg   149340
ttttagttgg gagtaggcag caaaaggagc cacatgaggg tcacgcactg                149400
cacaagaatg tcattcatat catagacaac atacgatttc tactgttatc ctgataattt    149460
attgacagaa aaaaggatgt ggggaaggga catggtgttc taatttgcat gaaaacctcg   149520
tctgagtgta gcatctctgg gaacatgcag cagatccgag ctcaggccct ctcttggccg   149580
tcacctgcaa acagcttgga caaaggtcaa gcccaattgg ccaaaactca gctggggaatt  149640
tttgtgggtt ctaggttttt acttttgcaag gctggtgtga gaggaggttc cagcaggaaa   149700
tgaaccctcc tgagagggaa agagactggg aaatggagaa ggctgggaac tcagggagag   149760
aatgggagtg gggaatggga gctgaaaaaa attgtgagca taaaaagggg atatgtcaca    149820
gggttggatg accagagaaa gcgtctgggg gttcagatta agatgctggg ggcgtgccca    149880
gtggtgggac aggaagcatg aatttccaga gggctcggtt ataaacatca ttgtccaatg    149940
ggtgtttccc ttggaagcct ctaagcttag agctaagcca cctctgggga cacaaactga   150000
gtggttaaga gcagagactc aggtgtcagc ctgtctgggt tccttccgac tcttccactt    150060
ccttgctgtg cagccttcgg caaggtgctt ggcctctctg tgccactatt tccacatgtg   150120
caaaacgaag agaagctatg tcccacctca caaggcacga ggactaagta aggtggattc    150180
gcatgaagtg tttagaactg atcctggccc ggggtgaccc ccgtgtaagt caaattcccc    150240
accctgcatg gtgttccttt tagaaatgtg catgaattttt tcattagaac agctccagca   150300
gtgcctgagg aagtggagtg aggtgtgaga ggtcttactt tattccccct gctggccctg   150360
ctattaacca ctaactcaga gtagctttct agcactttcc acacatttac atccacccct    150420
cgtcctttgg ttagcagccc atgcaatgat ttggccttaa tgtgaaccta gaacacagct   150480
tctcgcccag ggatgatttc tgcccccagg ggacacttgg cagtggctgc agacattttt   150540
ggttgtcaca actggatggg aagaaggagg atgctattgg catcaagtgg gtaaaggcca   150600
cggatgctac tcaacattct acaatgcaca gcatccccca cctctgccca accatagaga   150660
atgatccagg cccaaatgtc agtaaggttt ctgtcaggaa accctgggtc agaagaccaa    150720
ggttccttga ggacggggat gccttatact gcaatcagct gtcactctct gcctctctct   150780
ggggctgctg tgatcacctg gcctgcatgg acaacccctta ggagcagccc ccatccagtg   150840
cctggagaag tcagtggata aatacccag ctccctccgc gtcgggcgtt ttgctctgca     150900
ctgcatctct ccagtgggat caggctctgg ttgcccgcag ggttaacctg gtcacgtaca    150960
cacccttcac ttgccacctt cccttccctg tctggtattt cctgggatga acttttagat    151020
ttatttcctg gggctgctat aatgaagcac cacagactga gtagcttaaa acaacaggaa   151080
tttatggtct gacagttctg gaagccagaa gtccaaccc aagatgttag cagagctgac    151140
aacacgcccc tcaaaagcct ccggggggagg atccttcttt gcttcttcct ggcttttgct   151200
ggtttcccac aatctttggg attccttggc ttctagagcc ttcattctcc attccagtct    151260
tctgtcatct aatagcatcc tcccagcccg ggcacagtgg ctcacgcctg taatcccagc   151320
actttgggag gccgaggcag gcagatcact tgaggtcagg agtttgagac cagcctgacc    151380
aacatggtga aaccccatct ctactaaaga tacaaaaatt agccaggcgt ggtgggcggg   151440
tgcctgtaat cccagccact tggaggctg aggcaggaga atcacttgaa cccgggagat     151500
ggaggttgca gtgagccaag atcatgccac tgcactccag cctgggtgac agaatgagac    151560
tccgtctcaa aaaaaaaaaa aaaaaaaaaa agaaaaagaa aagcatcctc ccttcgtgtg    151620
tctgtgtgtg ttctcctctt cttagaagga catcagttgt attggatcag aacctacctc    151680
actccagtcc aacctaattt taactaatta cgtctgcaat tacccctattt ccaaataaga   151740
tcacattctg aggtaccagg gggttaggac ttaaacatttt ttgtgtgtgt agcaggagga   151800
cgtaattcca tttataactc ctcctaaata aaacgacttg catgtgaact cttgtctggg    151860
gcttcccaaa gtgagataac ccctctctct acccctaaaa caacgagtag cgtctgtcaa    151920
tgccagggtg caggggctaa ggtgcccatc tttgagtttc tgctgaggag gacacagctg    151980
ctacgttgga gcactcttgg gttctgcctt cgtgcccagc catctccctt gggctagccc    152040
tgccctgggt ctatcctaga atgagcctcg atctgtttgg ccataggcaa gcagagtgtc    152100
tggaaatctt tgtcctccat gactggtgct ggagccgaag ccagtgggtg tggccttgcc    152160
agccaactcc atttacccag ctctgaacaa gctagtagtt gagatcaacg gagagtccag    152220
acagtcgctc caagcatctt ggaatccatg gacacaggtg taccgcagag gcttcccacc    152280
tgggtaggca gcccttttgta agatcctggc accacatttta ttctcttaac atcctttcag  152340
ttatccagta atcatttatt gagcacctac tgtgtgccag gcaatgatta ggtgattgga    152400
gacactgcaa cgaagaagac agactaaaat ctccaccctg gtaggagaga cagatgcaaa   152460
tggtaaacat gataaataat caatcaccca gaaagcagga gacactaagc aaatgtgtat   152520
gtactatggg aagcccaata ggaacgaaag ctacacaaga gaacaagtga tgggtggttc   152580
```

```
cttagtctag gtcaggcaat cagggagggc ttctcagagg aggtgatgtt tgagcagaga 152640
aggagggagc caggcagatg tttttggaaac agcattctca gcatggagaa cagtggcagc 152700
tcacctacag gatgtgtttg attcccttcc agatttgta ttcgtttctt gtttttctcc 152760
cttggcttcc tggtttaaat gccttttgaa gaaatctaag ctcaactaat cagcgatgct 152820
gttgaaggtt tatatcagga tatgcatccc agagttattt acaaaattag aacaaaactg 152880
gaagcaattg aaagcctgac aataggagat cagttaaata ccgtatggtc cttccgtatg 152940
atggcatatt atgtcatcat taaaaatcgt ctgctgggag aatattaagg atacagggga 153000
aaggctcacc atataatgat gagtgggggt gctgggcgca gtggttcatg cctgtaattc 153060
cagcaatttg ggagtctgag atgggtggat cacttgagcc caagagtttg aggccagcct 153120
gggcaacaca gtgaaaccca atctctacaa aaaaaaaaaa acaaaaatac aaaaatcagc 153180
caggcatagt ggcgtacatc tgtagtccca gctactcagg aggctgagac aggaggatag 153240
gatcacttga gccctgggagt cagaggtggc aataagccgt gatcacgcca ctgcactcca 153300
gcctgggcaa cagagtgaaa ccctgtcaaa aacaaaaca aaaaaatga tgagtgggag 153360
aaacaagttt ttaaacaggg atcaaggagg ccaggcatgg tggctcacac ctataatccc 153420
agcactttgg gaggccaagg caggcagatc acctgaggtc aggagtttga gaccagcctg 153480
gccaacatgg cgaaacctca tctctactaa aaatacaaaa attagccagg catggtggcg 153540
ggcgcctgta atcccagcta cttgggaggc tgaggcagga aaatcgattg agccaggag 153600
gtggaggttg cagtgagctg tgatcatgcc actgcactcc agcctgggca acagagcgaa 153660
agctgcacga gagaagaagt gatgcatggt tccctagtct aggtcagcca atcagggagg 153720
gttcctaaga ggaggtgatg tttgagcaga aaggaggaa gccaggcaga tgttttggaa 153780
acagcattcc cagcatggag aacagtggca gctcaccctg tctagaaaag aagaaatgat 153840
aagaggggaa aatgagtttt taaaaaggaa tcaagggaga gtaaaccttta tgatctcaaa 153900
ggtacaaata tgaaaatata agtaaagaaa aactggagga cactgtacca agctgacctt 153960
cgggtggtgg gatttgggaa tcttgatatt ctcaatactt ctttgtatct tcaaatttct 154020
ctatgatgat cacagtttac tttttttttt tttttttgag atggagtctc actctgttgc 154080
ccaggctgga gtgcagtggt gcgatcttgc tcacttgcc tcacctctgg ggttcaagca 154140
attctcctac ctcttcctcc caagtagctg ggactatagg catgcaccag catggtcagc 154200
taattttttg tattttttagt aaaaatgggg tttcatcatg ttggccaggc tggtctcgaa 154260
ctcgtaagtt caagtgatcc accaacctca gcctcccaaa ttggcttgag ccaattaaac 154320
ttgtcttgct aaatggttag cggggagaaa gaagaaagtc tcgggtcatt cctagaccag 154380
gaggcaggga gaaagggagg agaatgaacc tttcttaggc aaacagtgtc ctaggtgtcc 154440
ttatcttaca taatctgtcg agagagtcac actaaaataa atcattgatt gattgattga 154500
tacatcaata ataaatggcc agccttggtg gctcacatct gtaatcccag ctacttagga 154560
agctgaggtg ggaggattgt ttgagacaag gagttcaaga ccagcctggg aaacacagca 154620
agactcatct taaaaaaatt tttttttttta attagccaga tgcggtggct cacgcctgta 154680
atcccagcac tttgggaggc cgaggcgggt ggatcacgag gtcaggaatt cgagaccagc 154740
ctggccaaca gggtgaaacc ccgtctctac taaaaataca aaaattagcc aggcgtggtg 154800
gcacacgcct gtagtcccag ctacgcagga ggctgaggca gaagaatcat atgaactgg 154860
gaaacagagg ttgcagtgag ctgagatcac gccattacac tccagcctgg gcaacaagag 154920
caaaactaca tctcaaaaaa aatgtttttt aattagccgg gtgtggtggt ccatgtctgt 154980
agttccagct acttgggagg ctgaggcagg aggattgctt gagcccagca gttcaaggct 155040
gcagtgagct atgatcccgc cactgcactc cagcctgggc aacagcaaga ccccatctct 155100
taaataaaca cataagtaaa taaatgatca tttttatttt attattaaat acacaagata 155160
aatgaaaaac aggcaaatct ttcttacaaa agaattccat ttaaagtatg taaacttcac 155220
tccccactgc cccaggaggt ggagactaat ctcccctact ttgagagtgg gctggattta 155280
gtgactcatt tccgaagaat agagtaggta aaggggaaaa tagaagtttt atagcggagg 155340
aacagataga taccacttta accaaatgat gaagattagt atcccccagg gatgtggata 155400
ttatgtaacc cttgatttta tgcctatata gcgttcttcc caaaaactcc taatcccagt 155460
tttttggggt tttgctctgt cttctaagct ggagtgcgat gatgcaatca tagctcactg 155520
cagctcaaac tcctggtctc aagcgatcct cccacctcaa cctcctgaat agctagggct 155580
gtaagcacat accatcatgc ccagctaatt gtattttttt ggtagagaca tgttctcaca 155640
cattgcccac gctgtcctcg agctactggc ctcagtgat cctcccaccc cagcctccag 155700
agtcactggg attataggca tgagccactg tgaccagccc agaattttt tttaaggagt 155760
tgtgatgtcg tttaagagat gtgattcttc ataacacatc aacaacaagt cccagcgatg 155820
ggttggataa gtcttgggat ttcatggag tattaagctt aaaagacttt gcatgatatc 155880
tgtgaactat atgtgatttc tgttggtaat gggggtcact gattctgcgg tttgccacct 155940
ccaatcatca tggaagaaaa tgttccactt ccagtgaaag taagaggaag taagggggta 156000
attattttct atctaaattc acgaactcct tgaattctgt ccacagaccc ctaagtgttt 156060
cctcccccaag gtgaaactga gagaatcttg ccagtgcctt ccgcagtcac ctgtggctaga 156120
aaacccctca gaagaggtga tagtttagca ggtaactgga gttctcacca tccgtgtctg 156180
gctcagcccc catcacaacc agttacccag cccaaaatgt cagtagtact gaggttgaga 156240
ggctctgctc taggaggcca ggcctctcag aggaaggagg attggggtac tggctgggcc 156300
tcaagatgaa cctaccccct aagagctttg ggatggcgtg agtttctgtc catacccaag 156360
gactacaaat gcaggttttac tggaaattct gtgccaaaag tgggttccaa ctcacttcta 156420
actgctacaa aacaaacctc catcaacata gccatctct gttcttgacc tggaagctcc 156480
aaggtatcca catggctccc atgcccacta gacgggcctc ttcctggac cttcctgggc 156540
cagagaaggc tctgggtagc cttgtggaat caagatgggt gatcagccac ttcctctgtg 156600
ccaccctgtt ttggctactt ccctaggcat cagcctggga ttccttgatg gtaaaaatat 156660
aaaactctct agcctagggc ctttaatatc cccattttac agatgaagaa actgagtccc 156720
agagctgtgc acagcgattg agagtcagaa ttcagctctg tctcactcag tgtcaacatc 156780
ctcagattct gccatttata gcctcccaca gcaaatagga ttgagggctg cttctctgag 156840
ctcaagggga tagaatgggg aaccccatga gtactgcaac aaaactgttt gctggagaca 156900
agagctggtg gctctgtgtt gttctagtga caggtggcct catttcacag ggaccccctc 156960
accctatgtg ctccccatgtgg ctcagaaaag ccagaaattg ttctccactct cacagggaa 157020
ggtcctgac cccctcttttg ccagctgggc caagcaaat tggggtcact tcatgggta 157080
caggacctac cctctcttgg ttgccccaa ggaggggatg tggaggggct ggggacctgg 157140
caggaccagg gtgtcttgag ttaatttggg gctgccttta gccgagggct tctgtgtgcc 157200
tggcatcagc tttacattgt gtcttgatcc gtaaaacagc cctgtgagga aagatatttt 157260
taaccccatc ttccagatga ggaaacggag gcccacaggg tgacgtgacc tgccaaggtc 157320
```

```
ccctagccaa gagtgacaaa gccagggttc acacacagct ctggacacaa ttcatcaccc    157380
ttcatccgtc tctctctgac tctttctttt tccctctctc tctttgtctc tcttttttt    157440
tttttttttt tttgagacag cgtctcactc tgtcacccag gctagagtgc agtggcgcaa    157500
tctcggctca ctacaacctc catctcctgg gttcaagcga ttcttgtgcc tcaacctccc    157560
aagtagctgg gattacaggt gcgtgccacc acacccagct aattttgggg ggttttgttt    157620
tgttttgaga tggagtcttg ctctgtcgcc aggctggagt acagtggcgt gatctcggct    157680
cactgcagcc tctgactccc aggttcaagt gattccctg cctcagcctc ctgagtagct    157740
gggactacag gcatgcacca acacgcccag ctaattttt gtattttagt aaagacgggg    157800
tttcaccatg ttggccagga tggtctcgat ctcctgagct catgattcgc ccgccttggc    157860
ctcccaaagt gccgggatta caggcgtgag ccactgtgcc tgccaattt ttgtatttt    157920
aacagagact gggtttcaac atgttggccg ggctggtctc gagctcctga cctcaagtga    157980
tctgcctgcc ttggcctccc aaagtgctgg tattacaggc atgagccacc atgcccagcc    158040
tttgtctctt ttattcttgt gttctctctc tctcttcctt ctctttctcc acctccttct    158100
ccttctctcc cttctcctca cccttctttg tgcttttctc tgtgagtttc tcttcttctc    158160
tatttctctc ctttggtgaa tgtcaattag aaaagcagaa aaactgcgtt taatttgtga    158220
tcataaatgc atgtccctgg ccaggcgtgg tggctcacgc ctggaatccc agcccttga    158280
gaagctgagg caggaagatt gcttgagacc gggagttcaa aaccagcctg gtcaaaaagc    158340
aagacccat ctttaaaaaa gaaaaataat taattagctg ggcatggtgg tgtgtacctg    158400
tagtcccagc tactcgggag gctgaggaag gaggattgcc tgagcccaag ggtttgaagc    158460
tgcaccagc tgtgattaca cccctgcact ccagcctggg tgacagaacc agaccctgtc    158520
tcaaaaaaaa cctaataatt aaaataaat aaataaataa atgcgtgtcc cctggccagt    158580
ggttgctaat gtttggaatc acctttgacc catgcccttt ttcattcata gatgtttgtc    158640
ttgaccaaaa tcaaagcatt agactttgga ctataaatca ctggttcatt caacaaccat    158700
cattgaatgc ctactgtatg cagacactct tctggacaca gaggagttga cgtgttggtg    158760
gggaaagcca gtgatcagtt gggataaaa gggcagacag cagacattaa atagtttagg    158820
ctttgtgggc cagatggtct ccatcgcaac gactcaatct gctcctgtag cgtgaaagta    158880
acgacagata aagcgcgtaa gtgaatgagc atggctgtgg gccaattaaa cgttaaccta    158940
taaaaacagg tggctggccc gcgggctgta gtttgtggat cactgcctta gagatagtgt    159000
tagagggtgg tgagaggtcc gggatagaat aaaacagtag agagtttgtg cattgtcaag    159060
atgagaggtt gcagttcttc ttatacaccc cgaatggccg ggcaccgtgg ccattatgat    159120
ctataattct aacactttgg gaggctgagg caggaggatc ccttgagccc tagagtttaa    159180
gaccagccta ggcacatagt gagacccat ctctacaaaa aaaaaaattt aaaaattagc    159240
tggacatggt ggagcatgcc tgtaggccca gctacttgag aggctgagat gggaggactg    159300
cttgagcctg ggaggttggg gctgcagtga gccgatcatg ccactgcact ccactcccgga    159360
tgacagagca agaactgtct caaaaaaaaa aaacaaaaaa acaaaaaaaa cagacctgga    159420
ggaacaaatc atatgaatgc attaaagtat cacatgtatc caaaaaatat atacatctat    159480
cagcctggca cggtggctca tgcctgtaat cctagcacat tgggaggcca aggcaggcag    159540
attgcctgag ctcaggagtg caagaccacc ctaggctaca tggtgaaacc ccgtctctac    159600
taaaatacaa aaaattagct gggcatggtg gcaggcgcct gtagtcccag ctacttggga    159660
ggctgaggca caagaattgc ttgaacccag gagacagagg ttacagttag ccgagatcgt    159720
gccactgcac tccagcctgg acaacagagc aagactctgt ctcaaaaaaa aaaaaaaaaa    159780
aaaaaaaaaa aaaatatata tatatatata tatatatata tatatatata tatatatata    159840
tataatcaat taaaaatttt ccttaataaa taaacatttc tctcccttctc tcccttggtg    159900
aatgtcaatt aataaagcaa caaaactatg tttagttagt gatcattaat gtatgtccct    159960
ggctgggtgt gatggctcac acttgtaatc ccagcacttt gggaggctga ggcaggagag    160020
gatagtttga ggccagcaat tgcttgaggc tttttgaaag acatgaagga gatgaaggga    160080
gccatggaga tatctcaggg aacagcagcc gaggtagatg gaacagcccag tgcaaaggtc    160140
ctgaggcagg atgttcctgg catttgtgag gacatgtagc tgcccagatg tccagtgggg    160200
agtgagtgag gatgaaggaa ggagctgatg aaggaagatg ataaaatact tcatggatca    160260
gccaggcatg gtggctcccg cctgtaatcc cagcactttg ggaggccaag gcgggtggat    160320
cacaaggtca agagttccag accagcctgg ccaacatggc gaaaccccgt ctctactaaa    160380
aaatacaaaa aagttagcca ggcgtggtca tgcacgcgtg tactctcagc tacttgggag    160440
actgagactc gagaatcgct tgaacccagg agatggaggt tgcagtgagt tgagatcacc    160500
ccactgcact ccagcctagg tgacagacgc agactctgtc tcaaaaaaaa aaaaaaaaa    160560
aaaaagactt cgtgaacaga cagcctatat aatttatgat ccaaaccagg acagtttga    160620
gagtgaaagg ggaaaaagag cactgaaaaa ataattagca ggcctggcat gatctataac    160680
gggtataaag tgggacacac agcctctctc acggtcactg tcagcttca gctttttcac    160740
actcaaatcc accccccatgt ttatcccata tactggagaa acgggtgttc tcctgagctg    160800
agttttgggg ttttttccctt ttgttttgtt tttttttgt tttttaaca tcctgtatac    160860
ttttctcaa tgaaccatgc tcaaaaaaat tagaggaaaa taaaccataa aacagaaggc    160920
actgaaggat tttgctggga ctcagccatt agtttgtttg atgagtattt atggagcgct    160980
ttctaagcac caggcaccac cagcgatact gggatgaatc agtaacatcc ctcacccttg    161040
aagctctctt gggcccattg ttatttactt aaaatactat gcaagtacgg agaaggggtg    161100
aagtgggaaa aatcagttg gttgtaaagg ccagaatgac cgtctagtc ccacccagtg    161160
catctgcacc ctgtgtgatc caggcacatc atgttgcctc tctcagcttc agttctcca    161220
tccaccaggc acagagatgg cgggaatcga ggaagatgtg gggagtattt catcagccca    161280
aaaagacttg gctaatgcga ccataattct gccttctgcc tctcctttcc cagaaaaata    161340
gcttaatcat ttggatttgg gataaacaca tttcctgtgt ttattattta aatgatccac    161400
caagctggga atggtggctc acccctgtaa tcccaactct ttgggaggct gaggagggcg    161460
gattgcttga gccaggagt tcaagaccag cctggccaac atggcgaaac cccatcttta    161520
ctaaaaaaat acaaaaaaat tagctgagcg tggtggtgcg tgcctgtaat cccagctact    161580
tgggaggccg aggcacaaga atcacttgaa cctgggaggc agaggttgca gtgagcctag    161640
atcgtgccat cacactccag tctgggcgac agagtgagat tctgtcccta aataaataaa    161700
taaataaata aatataaata taaataaat gatccaccaa aggaaccttt    161760
gtattgacta tgcaactaat gcttagtgag cacctactat gtccctggtg ctgatctgga    161820
cactgggatt tagacaggaa aaatctctac cctggaggag ctgatgatca agatgacaat    161880
cttgaaatgc ataagttgac aagatgattc agacagtgga acgtgctggg aagagaatga    161940
gatgtctggc tgagctgcag gaaggggcaa gtcctttga ttgagaggtc caagaaggct    162000
tctctgatgg gggcacaatg gatctaaggt tgagtgataa gaagaaattg gccaagccaa    162060
```

```
gacctaaagg cagagttgct ccaggcatag gttcagagaa tggaaataat tggctgattg   162120
tgatcttgaa cttgaccttt cttttcttct gctaactttg ggtttggttt gttcttgctt   162180
ttctggctcc ttgaggtacg tgttgggttc ttaatttgta atttttttt tttttttttg    162240
cttttttgag acagagtctc actgtggtgc ccaggctgga gtacagcagc atgatcttga   162300
ctcactgcaa cctctgcctc ctaggctcaa gtgaacctcc cacttcagca tccccagtag   162360
ctgggactac tggtgcacag caccacaccc agctaatttt tttatttta tttttttagag    162420
atggggtctc actgtgttgc ccaggctggt ctcaaacccc tagctcaagc gatcctcctg   162480
ccttagcccc ccaaagtgct gggatgagag gcgtgagcca ccacatctgg cctctgtttt   162540
ttgtgatgta ggtatttgat gctataaact tccctcttag ttgcttcttg gccctttagc   162600
taaggtcaag tgtaaacttc cctcagcact gcttctgctg catctcacag gtgttggtgt   162660
gttgtgtctc tattttcatt catttccaaa atttttaag tctccatctt aatttttgca     162720
ttgacccaat ggttgttcag gagcatgttg cgtaatatcc atatatttgc atcatttctg   162780
aaattcttct tggtattgat ttctagtttt atcccacggt agtctgagaa gatgcttgac   162840
agaattccag tattttaaaa tttgttgaga gttgttttgt ggcctaacat gtggtctgtc   162900
ttggagaatg tccatgtgct gatgagaaga atgtatgttc tccatcagac atgcaagaga   162960
cagacacttt ctcacctgcc tcatgggatc cataaaagag tcaatcagaa gttggcatt    163020
aagaaagacc agaaggaggc tgggtgcagt ggctcatgcc tgtaatccca gcactttggg   163080
aggctgaagt gggtggatca cctgaggtca ggagttcaag accagcctga ccaacaaggt   163140
gaaatcttgt ctctattta aaaaatacaa aaattagcta ggtgtggtgg cgggcacctg    163200
taatcccagc tactctggag gctgaggcag agaatcactt ggacccagga ggtggaggtt   163260
gcagtgagct gagatcacac cattgcactc cagcctgggc aacagagcaa gacccccatct   163320
caaaaaaaa aagaaagaaa aaaaagaaag aaagaccaga aagaggtgaa ggagcaagct   163380
acagagatat caaactgtat caatctggct gggcgtggtg gctcatgcct gaaatcccag   163440
cactttggga ggctgaagca ggaggatcac ttgagcccag gagttcgaga ccagcctggg   163500
caacagagac ccctctcta caaatataa aaatttaatt aaaaagatgt attggtcagg     163560
gcagccaagt tatgctgcag taacaaacat ccccaaagcc tccatgactt ttgacaacag   163620
atgtatttcc tgctcatgct acatgtccag tgcaggttgg cagtggggaa gaaggggct    163680
ctgttcagtg cagtcacttg agacctagct aatcacctag aacattgcca cttgctattc   163740
cagaaggaaa aaaggaatgc tagaaggtcc cacactgaaa gttcaatgct ctggctccaa   163800
aatgacagct atttccactc actcctcatt ggccagcact tagcatgtgg tcctcagcca   163860
accccaaagg gactcaggaa ggaccatccc accatattgc tggaaatatt tgatggcagc   163920
attaatgggg aacagtgttc caggcagtgg aagtctttga gcccttggaa gaaagacaag   163980
gcgatctcta gagcacatcc ttcccaatat taatgaattt aacaaatgag caagccatcc   164040
tccccactc tccttcccga attcagactt gtgcatatcc ctcccttaac ttgaactgcc    164100
aaagaagaga tgagaaccag gagaagagat ctgtgacccc atctttgctg atgaactacc   164160
acagaacagc catggcatct ccagtccttg tgcttgtaaa atgtacttt cattttgctc     164220
ctgaacgaaa tccacccacc cccacccca aaccagggaa agctcatctc ctaatccaaa    164280
actgcaccca gccttccacc accttcttcc ctgggaattg ttgattccag agtatggaat   164340
tgaataattg gatgagtttg gaagagaaaa agtgtctcta aaatcaggca gcagaagccc   164400
actcccagga gaggatggtg cagatgagag ttcaggaggg agcttggctt ggggttgacg   164460
atctgagcta tgcagggaac ttggacacac ctctcaatca gtcattcaac agacaccact   164520
tattgagcac cgactgtgtg ccagatgttg tcctaggggg ctgggaatac aggaatacag   164580
cagggacaa aaaggacaaa gcccctcct ctttgtcgaat ggacattcca gccaggaaga    164640
cgagagaaca agagaaataa gtaaagtata taggcggtga aatgcaaatg ggaaaaaaga   164700
aacaatgggg accagaaatg aggggtgcaa ttgtaaaggg ccatcagggg aggcctccct   164760
cagaaggtgg catttgagta aaaaacctga aggaggtgag gggaaaccat gtagcaatct   164820
caggaaagag cattccaggc agggagggac agcctgtcga gggccgagg taggactgtg   164880
cttggcgtgg ttgagaaact gcaaggaagc caggtggctg gaaccgaatg agcgagggaa   164940
aaggggagga gataaaagca aggagatggg agggttggag gccccctctg ccattcagta   165000
actgagtaac ttcatttatt tcctgtagct tgaaccacaa agaaccacaa atagagtagc   165060
tgaaaacaac agaaatttat ttattctctc gcagttcagg aggcaggag tccacagacc   165120
atcaaggtca gctgggccac agaccatcaa gatgtcagct gggccatggt gcctcctgag   165180
acttggtctg aaatcccttc ttgcctccct cctagcttct ggtggtttgc caacagtgct   165240
tggtggtcct tgtcttgtag acgtatcacc ctgatcccgc cttcatctcc atttcacatg   165300
gccttctccc tctgtgcaag gttgtctctg tgcccaggtt tctccttttc ttattattta   165360
cttatttgtt tgtttgtttc tttattttag acacagggtc ttgctctgtc tcccaggctg   165420
gagtgcagtg gtgcgatcat agctcactac agcctcaaac tcctggcctc aagcaatcct   165480
cctacctcag cctcctgagt agctgggact gcagatgtga gccactgtgc tctgcccaga   165540
tgtcctcttt ttataaggaa acccgtcatt taggatgagg ttccaccta atgacctgat    165600
cttaacttga ttccatctgc aaagacccta tttccaattc ataggtacca gggattagga   165660
cttcttcaat gcatctttt ggagagaccc actgcaaccc acaacagaac tgtgggcatg    165720
taacttgacc tctcggccag gcgtgatggc tcacacctgt aatcccagca ctttgggagg   165780
ccgaggtgag tggatcgcct gaggtcggga gttcgagacc agcctggcca acatggtcaa   165840
accccgcctc tactaaaaat agaaaaatta gctgggcatg gtagcaagca cctgtaatcc   165900
caactacttg ggagggtgag gcaggagaat tgcttgaacc caggatgtag aggttgcagt   165960
gagccaagat agtgccattg cactccagcc tgggtgacag agtgagactc catctcaaaa   166020
aaaaaaaaaa aaaaaaataga cctctctgtg cctcagcttt ctcacccggg aggatgggga   166080
taattatata cccactcctg ggggttcatga gaggattaaa tgagctcaaa cagtccaagc   166140
ctccacgtgt gtctgttgtg gtgctgggta gcatgtcctg ttgccagagg ttcccaagct   166200
tgtcgaggac ccaggcaagg gcagattcgg gtcttgttgg cagcacctga gatggacggg   166260
ctgccttggt atgaaggc ctcggctgtt tttcccttc agtcctgtcc ctctccccca       166320
tcctccaccc tgtccctgtc atctgagcct gctcctcgtg atggctcaga gtctccctac   166380
tggcggccgg tgcagagttt cgttccctgg gctatattta gccctgagaa atgggaacga   166440
gaaccctcag ccgccaaagt gatggagaga ggagcacaaa gccagtgctg ccgttcccgg   166500
agcaatgttc cgctgactcg gttctttctt ccagaaccttt ccagaagcaa agcattggca   166560
tttctgagct cgttaaaaca aggatgtggg ctggtggctg gcacattcat tgtccccaga   166620
acctgtctgt gtccatgatt aaagctgact tgttagttt tatttagt gctttttttt      166680
tttttaatc catggcaaaa cacacatgac ataaaattta ccatcctaat attttttta     166740
actttgtaac attttttaat tgacaagtaa ttgtacttat tcatggggta catagtgacg   166800
```

-continued

```
tttcaatgca tataatgcgt agtgctcaga tcagggtaat tagcatatcc atcttctcag  166860
acctttattg tttctttctg ttaggaacat tcaagctcct ccttctagct atttgaaacc  166920
attaatatat tgttgtcatc ctaaccattt ttaaggatac agtttcgtga aattaagtat  166980
aatacattca cattgttgtg caactgtcac caccatccat ctcccaaact tttccatctt  167040
ccaaatgtaa ctctgtcccc actaaacgcg aactccctgt tccccctccc ccagcccttg  167100
gcacccacca tgctactttc tgttttttata aatctgacga ctctagggac ctcctataaa  167160
tggaatcata caggattttc cctttttatga ctggtttatt tcacatagca taatgccctc  167220
aaggttcacc catgttgcag cacgtatcag cattttcttt cttttttaagg taaagttgac  167280
tattaaaaaa aaacttctgc cgggctcagt ggctcacgcc tgtaattaca gcactttggg  167340
aggccaaggc aggcagatca ggaggtgagg agttcaagac cagcctgacc aacatggtga  167400
aaccccatct ctactaaaaa tacaaaaatt agccaggcat ggtggcgggc gcctgtaatc  167460
ccaactactc aggaggctga ggcaagagaa ttgcttgaac ccgggaggca gaggttgcag  167520
tgagctgaga tcatgccact gcactccagc ctcggcaaca gagtaagact ccgtctcaaa  167580
aaaaaacaac tttttaagaa ttgaagtaga ataaacatac agaaaaatcc aggattata  167640
agtgaagagc ttgattaatt gtcacaaact aaacacatcc atgtaaccag cacacaaatg  167700
aggaaacaga aacttctcag ccccagaagc cccctcata tcctgttcct agtcactacc  167760
tccccgcaag ggtaccccta ccaggacttt gagcatcatt caccagttta gcctgttttg  167820
tattttgcat aaatgaagtc tggcttcttt tgcttgacgt taactttta agatctcatg  167880
tgacctgtgg cattgttcat tgcatgtatc ctctctctcc tattgataac agtgtggatt  167940
gtttgcaatt tggagctatg atgaatacca ttgctatgaa tgttcttgtg tgtgctttct  168000
gttgtgtaat tattcagaat tactatttcg gaattactat ctaattgtag tgatcttgga  168060
tcagtaacta tccaagaatt actgggtgtt ggcaaaggta catacagtta tacactgcac  168120
aatggcattt tggtcaacaa cagatcaaat atgtaacagt ggtcccataa tggaccgaat  168180
acataacagt gattatcata cagtattttt actatagctt ttctgttttt agattctttt  168240
ttttttgaga cgaagtctcg ctctgttgcc caggctggag tgcagtggtg tgatctccgc  168300
tcactgcaag ctccgcctc tgggttcacg ccattctcct gcctcagcct cccaggtagc  168360
tacaggcgcc cgtcaccagg cccgctaat tttttttgta tttttagtag agacgggggt  168420
tcaccatgtt agccaggatg gcctcgatct cctgacctca tgatctgccc gcctcggcct  168480
cccaaagtgc tgggattgca ggcgtgagcc accgcacccg gctgttttt agatattttt  168540
agatacacta tagagttaca attgcctaca gtattccata gaataacatg ctgtatgggt  168600
ttgtagccta ggagcaatag gcgagaccat gcagcctagg tgtgtagtag gctataccat  168660
ctaggtttgt gtaagtacac tccatgatgt ttgcacaaca aaatgaccta gtgcacatt  168720
tttcagaatg tatgcccatt gttaagcatg acttaattt agcatagaaa ctctcaacca  168780
atttttcaag tagttgtacc atgtgttatg ggttttattg tctcacccca aaattcatat  168840
gttgaagtcc taaccccccag tacctcagaa tgtgacctta tttggaaata gattcattgc  168900
acatgtaaag gttttgccat tggcaaaact gccgttattt ttgccaccaac catagcagtt  168960
aagatgagat cattagggtg ggtcctaatc taatacgatg gtgtccatat aaaaagggga  169020
gattttggca cagagacagg cacactcaca ggaagaatgc catgtttaaa caaaggcaga  169080
gctcaggatg atgcctctac aagccaagaa tcagcaaaga ttgccagcaa accgccagaa  169140
gctaggagag aggcataaaa cagattctgt ctcacagctc tcagaaggaa ccagcccttc  169200
tgacaccttg agcttggatt tttggcctct ataactgtaa gacaatcaaat ctttgttgtt  169260
taagccacct aggttgtggt tccttgttac agcagccaca ggagatgaat acagcatggt  169320
gccctcccat tggcagatta tgagggttcc agttgctcca cagcttcaca gacacctggt  169380
agtaatgacc tcatcttaac ttcttttctca ttttagcctt tcttccaggc agcagcagtg  169440
tcatacatgc ttttaaaggt gggctttaa agccacactt gagagccctg cattctgcag  169500
gtgtcacagg gtgatcaact attcaaaggc tacccctgcc ctgacagctg gaggcaaggc  169560
ttcccagcac agaggttaag cccatggact ctgggggccag gtggttgtg caaatcccat  169620
gtccactagt gaataactct gtgatcttgg gctgatgatt ttgtctttct aagcctcagt  169680
ttcctcaata gtaacatggg cattataaca tagaggcatc atgaggatta aatgactaag  169740
tgagctaaca tacataatgt gcttaggaag gtgccagcac accataaata ctctgtaagt  169800
gctggctttt atcattcttt tctctctctc tctctctctc tctctctctc  169860
tctctccctc tctctctctg tctctctttc tctctccacc ccccaacctc ctctccttga  169920
ttttcttccc ctcatcttac ttccttcttg ctatagtgtt ctatttttctg tttcagagag  169980
tattctattt gtggactttt ttcctcttga aaattgagct gaaacttctg agaatttttt  170040
gtgattggca ttaaggctgc agggaatgga gcagggagac acttgaggaa agggctcatg  170100
gaccatctgt ctggcttggt gatttcacca ggccatcaga ctctgtggtc atgcatctcc  170160
tctaagggga gtctatgact gtgttgggag aagagaagga accagggatt aattaatcca  170220
tttcaatagg ttttgtgttt tgtttggttt acttttttcct tctccttctg gactgtggtc  170280
tgggaagtcc tcttgtgttt cttactccat tcccaggtca atatatgttat gtgaggagaa  170340
cataattaag agagagcttt acccttttgga tgttttcttc agaaaacgtt cctccatttc  170400
cccctctggg atgccagagc cccagaactc cacaagccaa gaacatttaa gacagagcca  170460
caagagaacc gagcttcccc ttccctcacc tgtcaggttc tatctgagtc ccagtcaact  170520
ctcacctgct ttccctcctc acaccctaca gagcaacgat gcctcaggga acacttggaa  170580
ctggttgtac ttcatccccc tcatcatcat cggctccttt tttatgctga accttgtgct  170640
gggtgtgctg tcagggtaag tttctgctac tccccacccc atcccactca ctcctctttg  170700
ctaacttctt tccaagtaga ggccattgaa gctttgtttt cattcactag acagagaaaa  170760
ggcttcttcc cttgtttggg ttaccagact gttattagca agccatgcac aggtgcagag  170820
gttgtgtact gctaggggta cccagtgaga gggttcatat gggctttact ttcttttact  170880
tttttttaaa aaccaatagt ttgggtttac ttctccccca ttttccaaat ataaaatcat  170940
agcatatgct ctaacggtgt attttcctga cccatattgt cctctatccc caagatttt  171000
ttggcttaat cataaatggg cttcattttt cttaccataa gaagtctggg cacttgtatg  171060
gtggctctat ggcaccatca gcaacccag attcttccag ctttccattc tgacatcttt  171120
accagaggct tccaatctcg tggatacctc atggtcttaa gatggctgcc tcacgccctc  171180
cggatggcca cttcatgttc caaacaggaa aaggaagagg agaggttgga acttgtgggg  171240
cctatggcag agaagccaac ctgctgcaga aatcttcat tcatggctta ttggtctaac  171300
ttaaaagagg gctgaaataa ttattagcca aaagtatgaa gagaatgaga atgaggtatg  171360
cagccagtgg tggttggcat ggcatggttt tatccttttcg gttttttct tttttattgt  171420
ttttttttga gacggtgtct agcttttatta cccagactgg agtgtagggg gcgatcatag  171480
ctcactgtaa cctagaactc ctaggcacaa gcgatcctcc tgcctcagcc tcctgagtag  171540
```

```
ctaaggcaac aagtgtatgc caccatgccc agctacattt tttattttc atagagatgg   171600
ggcccactgt gttgtccagg ctggtctcaa attcctggcc ttaaatgata ctcccatctc   171660
agcctcacaa agtgctggga ttacagacat gagccactgt gcctggcctt tttctttacc   171720
taggcacagt tgtcgggaaa tgtgtgaagc tggcagaagc acccatcact ataatatccc   171780
agtcttttcc cagaagtcct gactcctcct gttgaaaact cctgacctcc agggacttct   171840
gaatccccaa acacacacac acacacaaac acacacacac acacacacac acacacacaa   171900
acacacacac aaacgtttcc taacattttc aaaacagcca tactctggct tttctatgct   171960
tctccaggga gtttgccaaa gaaagggaac gggtggagaa ccggcgggct tttctgaagc   172020
tgaggcggca acaacagatt gaacgtgagc tcaatgggta catggagtgg atctcaaaag   172080
caggtgaggc cctttcatcc tggggcccag ggatggagat cccaggccac ggagtacaaa   172140
gagagtcatg cagtttggag aaggctaagc tgggagggtt atgatgggag gagaaagaga   172200
acctgaattg gtagtcccaa attttatcaa caagaatcca gagtctgata tgaagaagtc   172260
taagatgaag ccaggatctg acatcacgta acttgaattc tgaaatcaga cgctggttta   172320
catcccggcc ctgccacttt ttacccatgc accacacate cctgtacctc cgtttcctca   172380
gctgttacat ggaggcgatg gtagtgccta agtcatagta ctattggagt atttagtaaa   172440
ataatctcag ctgagtcact tggggagaga agtgcctgat acacggtagg cacatattta   172500
tttgttcagc catttaacaa acatttaggg agcacctgct gtgtgccagg cactgatcta   172560
agcactgagg atatgggagt aaacaataca caccaaatcc ctgccctcag agctctgata   172620
ttctaatgag agagataaag caaacaaata catgtcatgt tgggaactcc caaattcaga   172680
gaaggaagat aaaacagact aggaagataa aacagagtag gaagttggcc gggcgcggtg   172740
gctcacgcct gtaatcccag cactttggga ggctaaggcg ggcagatttc ctgaggtcag   172800
gcattcgaga ccagcctggc caacatggtg aaaccctgtc tctactaaaa atacaaaaat   172860
tagccaggca tggtggcgca cgcctgtaat cccagctact cgggaggctg aggcaggaga   172920
attgcttgaa cccaggaggc agaggttaca gtgagctgag gtcgcaccac tgcactccag   172980
cctgggcaac agagtgagac tctgtgtcag agaaaaaaaa aagagtagga agttagaggc   173040
agggtggtca gggaaggctt ctctaaggaa gtaccctctg agcagaagga cctgaaggac   173100
gtgaagaagg aagctgtggg gatgtcaagg gaaggggcat tccaggcaga gacagcaagt   173160
gcaaaggccc tgagctagga acgtatttga gacacagcaa ggaagccagt gcagctgaaa   173220
cagagtgaga ggtggggaca gctggaggag aggaagacag gaaggtgatg gagatcagat   173280
caagcaggga cttataggct gtggtgtgga cattggtttt tattttgcgc gaggtgggga   173340
gaatgttggc tattgctact gttgcggagg tggggcttga agtcacaaac cacccagcag   173400
catgtttttt ggtcggttga gctgtcacca tcagtcagca gagaatgggg gtggccgggc   173460
agaccctcct tcctggtcca agggagaact catcctccaa atgcaggagc ttaactctgt   173520
gctcttcctc ttcagaagag gtgatcctcg ccgaggatga aactgacggg gagcagaggc   173580
atccctttga tggtaactgc tctaaaccca cctcaggggt gggtcccagg ggagaaggga   173640
gaagctgtgg tggggagtcg ggggagagca ggtgactggt tctaaggatc ttgcagaggg   173700
tagacgttcc tcttggagga attttaggac ttccatgcag agtttcccta ttctggcctc   173760
cactttttg ttttaaccat ggacctggtt tttttctgctt tgtgccttgg tttttctcat   173820
ctgcaaaatg ggtatgatat aaacaatacc ctagctcacg agattgtttc tcagaatgat   173880
attcgttatg gcaaatagaa cacctgggat agtgcctggc atgggtcag cacgtttctg   173940
tttgctaaat aagtaataat tccaccaata atccagttta ctgtgaacgg ctgctgtctc   174000
ccatgttaga aacttaacga gacagaacca tgacttctt tcttttcttt ttttttaat   174060
tgagacagag tctcgctctg tcacccaggc tggagtgcag tcacacgatc tcacctcact   174120
gcaacctctg gctcccaggt tcaagcaatt ctctgcctca gcctcatgag aagctgagat   174180
tacaagcatg agccaccatg cctggctaat ttttatattg ttgatagaga tggggtttcg   174240
ccatgttggc cgggctggtc ttgaactcct tgcctcaaat gatctgcaca ccttggcctc   174300
ccaaaatgct gggagtgtag atgtcaattc atggtcccct ggaaacctga atatgaaagg   174360
agggaccatt aaaaaggtgt ccaaaagccc aacctcccca gcatagctgg gagtcagggg   174420
acagactgta agagtcactg tgtatccaac ctgaggcttc atgaaagtaa agtttcctag   174480
aatttagaga taggggttgga tgcggtctgt ctgtggctca catctgtaat cccaacactt   174540
tgggaggcca agacaggagg aacacttgag cctgggagtt caagaccagc ctgggcacaa   174600
taatgaggtt ccgtctctac aaaaaaataaa cttagccaga tgtggggca cacgcaccta   174660
tggtcccagc tactcaggag gctgaggtgg gaggatcact tgagcccaag aggtcgaggt   174720
tgcagtgggc accactccac tccagcctgg gtgacagagt gagaccctgt ttcaaaagaa   174780
aaaaaaagaa tttagagata ggccagaata atatgtctgc aatataataa taacagcaat   174840
aagaaaaata atagtactcc ctgaaaaatg caacttcttg cttgagattt atcttctcat   174900
actttagaaa actggttaga caggggctgg gcgtggtggc tcatgcctgt aatcccagca   174960
cttgggagg ccaaggcggg tggatcactt gaggccagga gttcaagacc ggcctggcca   175020
tcatgcgaa accccatctc tactaaaaat acaaaaatta gctaggtgtc atggcacacg   175080
cctgtaatcc cagctactca ggaggctaaa ctacgagaat tgcttgaacc tgggagacgg   175140
aagttgcggt gagccgagat cacaccactg cactccagcc taggcgacag agcaagactc   175200
tgtctcaaaa aaaagaaaga aagctggtta gacagggtga tgacttttga ttaaaaatct   175260
gagagatttg agggaaataa aagaactggc actgcgtccc agaaggttat aaaatgaatt   175320
ttattatctt agttggggag gggagattac ctaactcccc taatgagtt aggtaatcta   175380
actcattag ggtacctaaa tctttttatt ggaagtctac acctgaactt gtctgctgtg   175440
gagccctgg ggtgtatagc ttgaatatgg gggcagaatc ccaaaattgc agcctgccta   175500
gcgagtatgc tacaggtcaa ggggtggact gttttcataa gaaagtgagg tttcttagaa   175560
tttaaaaata gaggctgagt ggggcggctc acgcctgtaa tcctagcact tttggaggcc   175620
aaggcaggca atcacttga ggtcaagagt ttgaccagcc tggccaacat ggcaaaaccc   175680
catctctact aataatacaa aaattagcca ggcgtggtgg tgcatgcctg tagtctcagc   175740
tactcaggag gctgagggag gagaatcgct tgaactcagg aggcagaggt tgcagtaagc   175800
caagatcaca ccactctctg ggtgacagag caagattctg tctcaaaata aataaacaaa   175860
taaataaata aaccagaagg aaaatagtgg ctgagggccc agcctggag tcggactgaa   175920
cccgacttga ttcttgtctt taccccttta agcaaagtga tagtgccacc ttgaacctca   175980
gtttacacat ctgaaaaatg ggtatactat tagttcccgt gagaacagtt gccgtgagag   176040
ttaaatccaa ggcacactg tgtccatatg gtctgtgttg caaaaggggt aacgtctttt   176100
tctcttgcca tgtttccatt gttggagctc tgcggagaac caccataaag aaaagcaaga   176160
cagatttgct caacccgaa gaggctgagg atcagctggc tgatatagcc tctgtgggtg   176220
agtcccttcc tctgccacct atcagttgtt catcacctat cgcccaagag acatggtggg   176280
```

```
gtgggggcag agggcttgca aaccgtgctg cctggatttg ggtctcagct ccacccttc   176340
ccacctgtgc gtgtgtcctg ggcagattac atcattatgg gaataacatc cgtgcctagc  176400
ttctcattat tttgtgggaa ttcaactaaa tgatccccat gaagcatggc aaaccagcac  176460
ctggcaggga cgaagctccc agtcaagttg gtgaatgttt gtgactcatt cgggaagtat  176520
tcatgaggga cctgcttata ttaggtgctt ggttgcaaac aagacaaggc agtcacgagg  176580
ctgagctggg aggatcactt gagcctggga agtggaggct gcaataagcc attattgtgt  176640
tactgcactc cagcctgggc acagaaaaaa aaaaaaagac acaaactgag ccaggcacag  176700
tggctcacgc ctgtaatccc aacactttgg gaagctgaga tgagcggatc acctgatgtc  176760
gggagttcga gaccagcctg gccaacatgg tgaaaccctg gctctactaa aaatacgaaa  176820
aaaattagcc tgtagttcca gctactctgg aggctgaggc gggagcatca cttgaacctg  176880
ggaagcagag gttgcagtga gctgagatct catcactgcc ctccagcctg gcaacagag   176940
caagatcctg tctcaaaaaa aaaaaaaaaa aaaagacaca aaccaaatcc ctacctacat  177000
ggagctcaca gtccagtgca ggaaatagaa attaaacaga gaattacaca aataaacctg  177060
taatgtaat ggcacttcag ggagaggctc tgggcttagc ttgctctaga aggatgggga   177120
gcagtcaggg aaggctacct ggaggaagtg acggttaagc tgggaactga aggatgggta  177180
ggagatcact gtggtggtga tagcagaagg aacagtgtga gaggcagggc tcagacctt   177240
gccaccacaa gggccagagt tcgagggagg agggaacatt tattctttcc cttctcactc  177300
ctctgtccta ttgattcatt ggctgtgatg atgttgattt tgaccttcta aagtgagaat  177360
gtattgttat tgttgttgtt gttctttaat gggttttgt ttttaatgga aggaagagca   177420
tccaggcaga ggaaataaga ctggaataag attgagggga gaaggaattt aggctgcttg  177480
ggaaactgtg tggccgcagt ttagaggaag aaaggatggc aagagaaaga ggaagggagg  177540
aagagaagga gggagagaag tgaaggaagg agggaagtta gtacatccat gtgtttctga  177600
tccatagttt ctgatccact atttcgtatt cccctttat cgctcgcccc tagtttataa    177660
ccttattgct gagtttaggc ataatttcca ttgcgatcac atatctcgta gggtggatac   177720
actatggttt gtttagccat agctctatta tagggtgttt gagttgtttc caataatttc  177780
tcttacgaag aacactgctg tgcactttta cgtacaatga ctcccccac cctttgggcg   177840
tatttccttg gggataatta taggatcaaa gatattaaca gcttttcaac tcattattca  177900
aagagccatt ctgagtttca aaaacatgga acccatttat aaacctgcca agtatgcata  177960
tgttcatgga ttccccaccc aggccatcga atattaccaa tttaatttcc tttcccagtt  178020
aagtgggttt gtaatgaaac cttaaagctt gttttcattt gcattttaa tttccagcca   178080
aaacacgctt ttctttgtaa tggagaactc attctgcttc cactcgtgtg tgcatctgtt  178140
taatttcctg taagcaaatg tcaagaattg gagcgctcag taggtgtctt gagtatttga  178200
tcaattatgt ctgtctcacg tgttacgtta cctccattgt ttaaaatctg ttttatgacg  178260
aggtacagtg gttcacgcct gtaatcccac tgctttggga ggccagtgca ggaggatctc  178320
ctaagatcag ccgttcaaga ccagcctggg caacataaca aggtccatc tctgaaaaac   178380
aaaatgttga aaaacttagc caggcattat ggcacacacc tatagtccca tctatttagg  178440
aagctaaggc aggaggattt cttgaaccca ggaattcaag gttgcagtga gctatgattg  178500
tgccactgca ctgcaacgtg ggcaacagag tgagaacctg tctcttaaaa aaataaaata  178560
acatacattc ttaaaaatct actttgctgg ccgggcgcgg tggctcacgc ctgtaatccc  178620
agcactttgg gaggctgagg cgggtagatc gcttaaggtc aggagtagga gaccagcctg  178680
gccaacatgg tgaaaccgtg tctgtactaa aaattcaaca attagctggg tgtggtggcg  178740
tgagcctgta atcccagcta ctcaggaggc tgaggcacaa aatcacttga acccgggagg  178800
cggaggctgc agtgagctga gatggcgcca ttgccctcca gcctgggcat caagagtgaa  178860
actccatcaa aaaaataaaa aatctgcata tacatatata tgtatatata tttttaattt  178920
ttttaatttt tttttttttt tctgagatgg agtcttgctc tagcacccag gctggagagc  178980
aatggtgcca tctcggctca ctgcagcctc cgcctctgtt aacaaggcag gtgacattgc  179040
agctttctaa acagacccaa aacccaggcc agtggcttgt tctttcatag ccacgtttgc  179100
tacaggcaaa tccaccaaaa cccacctcat cagcctgatt actcaaaaag acaaagaaag  179160
gagccccaa tctagccagt ggttttctag accaccccaa aagagatctc tggaattcca   179220
ggattctggc aaggaatcac atttagcttt atttatttat gtaaagaatg caacaataca  179280
ggctgggtgt ggtggctcac gcctgtaatc ccaacattt aggaagctga ggtgggagga   179340
tcgtttgagg tcaggagttt cagaccagcc taggcaacat agtgagaccc tgtctctatc  179400
aaatattagc tgggcattgt ggcacacgcc agtagtccca gctactcgtg aggctgaggt  179460
ggatcacctg agcccaggag gtcaaggctg cggtgagcca cagcatgccc ctgcactcca  179520
gcctgcgtga cagagacttc atctcaaaaa aaaaaacaaa aaaaagtaat aatacagtaa  179580
tgcatatttc aaagtaaggt gggagctatg tggtatttgc gttcacgttc acattatacc  179640
acagtatgca cagtcctttt tttttttttt ttgagacagt gtcttgctct gatgttcagg  179700
ctggagtgca gtggtgcagg catagctcac tgcagcctca aaccctggga ctcaagtgat  179760
cctcccacct cagcctccca agtagctggg actataggtg tacactgcta cactcagcta  179820
agttttttat attttttact agagatggga tctcaatatg ttgcctaggc tggtctcaaa   179880
ctcctggcct caaacaatcc tcctacctcc acctcccaaa gcagtgggat tacaggcgtg  179940
agccaccaca cctggcccac atgcagtctt atataattgg tgattctact gcgctgttga  180000
atcagttgat aaacgcacta taaagcaggt tcattcctaa ttgatgaact tactgctgaa  180060
ataaggaact tgaatcattt acatgaaaag ttgctgagga ttgctgattg gatatcaatt  180120
ttttttttctt ttttttcttt tttttgaga tggagtctta ctctgtcgcc caggtgggag   180180
tgcagtggtg cgatctcggc tcactgcaac ctccaccttc caggttcaag cgattctccc  180240
acctcagcct ccaagtagct gggactacag gtgcacacca ccgcgcctg ccaattttg   180300
tactgttagt agagatgggg tttcaccatg ttggccaggc tggtcctgaa a ctcctgacct  180360
caagtgatct gcccacctca gcctcccgaa gtgctgggat tacaggtgtt agccaccgcg  180420
cctgacagga tatcaaattt catttagact gcaggaatac gttcaagaga tctattttgt  180480
acagcctggc gactgtatta ataacaatgt attatatact tgaaaattgc tcagagagta   180540
ggttttaagc attctcaccg tgagaaaagt gataagcata tgtaataatg catatgttaa  180600
ctagctcaac tgagccactc catagtgtat acatatggtc aaaatatcat gttatgcact  180660
ataaatagat aaaataata tctgtcaatt taaaataaat gaataataac tttaaaaaga  180720
aaaataacag tatggctggg cacggtggct cacacctgta atcccagcac tttgggatgc  180780
caagacaggc ttgaggccag gagtttgaga ccagcctggc caacatgcg aaactttgtc   180840
tctaataaat atacaaaaat cggctgggca tggaggcggg cgcctgtaat cccaactact  180900
tgggaggcag aggcatcact taacctggga gatgaaggtt gcagtgagcc aagatctgca  180960
ctccagcctg ggtgatagag tgagccttta tttatttctg taaagaatgc aataaatcag  181020
```

```
gcctggtgcg gtggctcatg cctataatcc caatgttttg gaaggccaag gtgagaggat   181080
catttgaggc tacaggcgca tgccacagtg cccagctaat acttgataga gacacggtct   181140
cgctatgttg cccaggctgg tctcaaaacc ctggcttcaa atgagcctcc caccttggcc   181200
tcccagagtg ttgtgattac aggtgtgaga cactgtacct ggcctgtatt aaaaaaaaaa   181260
aaaagaagaa gaagaagaag aggaggaaag aagaagaagg aagaagaaga aagaagaaga   181320
ggaggaggag gaggaatggg aaggggaagg ggaagaagaa gaggaggaag gggaagggga   181380
agaaggagag gaggaggaag gggaagggga agaggaagaa gaagaggaag aagaagacga   181440
agaagaagca caatgataaa taagtaaaat gtggagcata tgaaaacaaa acaaaaaaaa   181500
gttgatccat tatgaatgga agctgccatt gtaactctgc tttttaggaa aaaccagacc   181560
ccatttagat gattttattt gtttttaaag gcaggttctt gctctgtcac tcaggctgga   181620
gtgcagtgat atgatcatag ctctctgcag cctggagctc ctgggctcag gcgatcctcc   181680
cagcttagcc tcccaagtag ctgggactac aggcaccacc acacccagct aatttgttgt   181740
tgttgttgat gttgttgttg agatggggtc tggctatgtt gccaggctg gtctcaaact    181800
cctggcctca agtgatcctc ctgccctggc ttcccaaagt tctgggatta caggcatgat   181860
tttttattaa tttatttgca gctgacaaat ggtaattgtg tatgtttatg gagtgcagtg   181920
tgatgtttta atctatgtat acatcataga atgattcagt catgctaatt aacacatcca   181980
tcgcctcacc acctcaccgt tttttgtgtg tgggaaggc attaaaaatc tcttagcaat    182040
tttgaaatat gcaacacatt actatttatt aataatgcaa tataaataca caataagta    182100
ttaatgcatc actaaatgcg atgcaatgca atgcaatgca atagatcact aaaacttact   182160
cctcagtct aactgcaact tataccctt gatcaacatc ttctccttct caatccctcc     182220
tcctcccctg cagcctccag gaaccacctt cctgctcttt ctatgagatc aatttttttt   182280
agttttaagc tcccacatgt gagatcatac tgtaattgtc tttctgtgcc agcttattt    182340
actcagtata atgtcctcca gttctgtccc tgttgtcaca cattacagaa tttctttctt   182400
ttagggctgt atagtattct atttgtatac ataccacatt tctttatcc attcatccat    182460
tgtgggacac ttagtttgct tccatatttt ggctattgtg aataatgctg aagtgaacgt   182520
gggagtgcag atgttctgaa aagacttaaa tgtcagacct gaaatggtaa agatgctcca   182580
agaaaacata aggagaaagc tccatggcat tggtctcggg aatgattttt tggacaggac   182640
ctcaaaagca caggcaacag aagccaaaat ggacaaatgg gatcgtatca aactaaaaaa   182700
tttgtgcaca gcaaaggaag cgttcagcag aggaaagaga caacctaagg aatgtgaaaa   182760
aacgtttgca aacaatacat ctgataagga gctaatatcc aaaatatata aggaactcaa   182820
acaactcaac agcaagaaaa caacccaatt aaaaatgggc aaagacagct actcgggagg   182880
ctaagatgtg acgatccctt gagcccggga ggaggaggtt gcagtgagct gacattgcat   182940
cactgcactc caccctgggc gacagaagga gaccgagacc ctgtctcaaa ataaaaaata   183000
aaaatgtgca aaggatctga acatacatat cccaaaagaa aagacataca agtggccaac   183060
aggtatatga ataaaatgct gaacatcact catcatcagg gaaatgcaaa tcaaaaccac   183120
cattagctat cacctcacac ctgttagagt agctattatc ttttttgtttg tttgtttgtt   183180
ttttgttttt tgttttgttt ttgagaggga gtctcactct gtcacccaag ctggagcgca   183240
gtgttgtgat ctcagctcac tgcaacctct gcctcctggg ttcaagggat tctcctgcct   183300
cagcctcccg agtaactgaa attacaggca cacgccacca tgcccagcta acttttgtat   183360
ttagttttcac tatgttggtc aggctggtct tgaattcctg acctcaaatg atctgccctc   183420
cttggcctcc caaagtgctg ggattacagg tgtgagacac tgtgcccagc ctagagtagc   183480
tattatcaaa aagacaaatg aggtttgttg aagttctaac ccctggtacc tgcaaatgtg   183540
gccttacatg aaaatagggt ctttgcaggt ggtaatcaag ttaagatgag atcaaactta   183600
attagggtgg gtcctaaatc caatgactgc tgtctttata agaggagaag caggctgacc   183660
aacatggtga aaccccatct ctactaaaaa tacaaaaatt agctgggtgc agtagtgcac   183720
acctgtagtc ccagctactc aggaggctga ggcaggagaa ttgcttaaac ccaggaggtg   183780
gaggttgcag tgagccagacg tcatgccact gcactccagc ctgggtgaca gagtgagact   183840
ccatcttaca agaaaaaaaa aaagacaaa tcataacaag tgctggcaag gatgtgggga    183900
aacggggatc catttacatc atttttaataa cacaggctct atatgggtgg tattgagttc   183960
ccagagttgc cattacaaaa tgtcacaaac ccagtggctt aaaacaacag aaatttcttc   184020
tctcacagtt ctagaggcca gaagtccaaa ctgaaatcaa ggtgtcagca gagccaccac   184080
gttccctcag aaggttttag gggagaatct gttccatggt attttcttag tttctggtgc   184140
tgccagcgat acttggtgtt cctcagttca tagatgcata attccagtct ctgcctctgt   184200
tgtcatatgc tcttctttct gtgtttctgt atgcgatttc tttttttttt tttttttct    184260
gagacaagtc tcactccatc acccaggctg gagtgcaatg gcacgatcac agctcactgc   184320
aaccccaacc tcacaggctc atgccgtcct cccaccttcag cctcccgagt agctgggatt   184380
acaggcgtgt gccaccatgc ccggctaatt tttgtatttt tagtagatac ggggtttcac   184440
catgttggcc aggctggtct cgaactcctg accttacgat ctgcccatct cggcctccca   184500
aagtgttggg attacgggca cgagcccacc gcacctggcc ctaattactt tatttttttg   184560
taaattttt tttgtaaatt tcatgtagcc tgagcataca gtgtttataa tatatacagg    184620
agtgtacaat aatatcctag gccttcacat tcactcacca ctcaactcac tccctcacca   184680
agagcaactt ccagtcctgc aagctccatt catgccaagt accctatgca gctgaaccac   184740
cttttctctt ttatactgtg tttttactgt acctttcta tgtttagata tgttcagaca    184800
cacaaatact atgatgttac agttgcctac agtattaagt acagtaacat gctgggcagg   184860
tttgtagccg aggagctaca aaccacgtag cctgggtgtg gagtaggcta caacatctag   184920
gtttatgtaa gttcactta agatgctcac acaaggacaa aattgcctaa caatgcatt     184980
ctcagaacac gtctccctca ttaagccaca catggctgta ttacaattta catataattt   185040
taagcgtata taaattgcca gaaatcacca gatgaatcct tggcggtgac atacccttc    185100
ccccaccata gaacattgca gactggcccg gacgcccagt atctcatgcc tgtaatgcca   185160
gcactttggg aggctgcagc gggcagatca cttgaggtta ggagttcgag accagcctga   185220
ccaacatggc aaaacaccat ctttactaaa aatacaaaaa ttattcggac gtggtagtgg   185280
gcacctgtag ttccagctac ttgggaggct gaggcaggag agtcacttga acttgggagg   185340
cagaggttgc aatgagccaa gatcgtgcca ctgcactcca gccgggtgac agaggcagac   185400
ctctatctca aaaaaaaaag aaaaaaaaaa aaaaggaaa aacatttc agactggtac      185460
cagttacacc ggctcttgat cccttgaatg tggctgaccc tgaactagga tgtacttcat   185520
aataacacgt ccggctggga atacttagta caaaagaaag agtataaaat atcttttgaa   185580
tccaccttga tattgattcc atgttgaaat ggtaatatttt tggatgtatt gggttgaata  185640
aaacatctca tgaaagtgat ttttaaaaat ctagaaattg tctgcaatta taattccaga   185700
ccacagagaa aaacgagaga caggaatgta tagaaaaagg gaacgtggga caaagtgagt   185760
```

```
atgaaattca actaacagaa gtgacagtgc ctagcatggg gtccagcact tagtaggtgt   185820
tcaattaata ttcatttccc tctcccttac cagtgaaggg tatgcctgtc gtggggaatg   185880
tgtcttcagg ctgagtgatc aggaaggact ttctcaatgg ctggcacgtg aacctagtca   185940
tgatttcagc tcttgaggtt gtactagaag atttatatcc aataatcgta aggtaccact   186000
tagcatcacg ctaagatgta ttaattcatt tatgcctttg gatggccctt tgaggtagga   186060
agtgtggttg tctccagttt accaaggtgg cttgcccaag gtcatctgct ggttggtgat   186120
taagccaggt tttcagtgtg gctccagcag gagtgggggc tggggacctt ctacctgctg   186180
tggtttctct ctctctctct ctctctctct ctctctctct ctcgatctgt ggaacatccc   186240
ccctgtcccc caaggtccca agggtcttat ttcttttggc caagcccttt ggagacctgt   186300
agatctggac acatctttga gagtttcagg aactagggcc agaaatgctg ggcagggtca   186360
tgaggagctg ccactggggt tgagaaggtg atggacatga ggggaagggt ctttgcagaa   186420
aggagaggcg tccctgtaag caggtcacag ccactgggcc tggccaactg cagccgagtg   186480
gaatgtgccc ctgccccatg accatatgcc ccaggtgtgc aatgtggcgg cccagagcac   186540
acactctgaa ccatcttgac acatcttcac tggttactag acccccctca gcctgtttcc   186600
ttggctgtaa aatggggatg acgctggtcc ctacttccta gggctctgag caggagtaag   186660
tagcttgtcg tataaaacat gttccctgca gtgcctggtg cctgctaaat gttccataaa   186720
cgtcagctgt tattttcatt caggggaagc tgaaatccat attttcatgg aaaatctccc   186780
agtttttaaa tgtggaccaa taatttcagc tttcacaaac ccagtatgag tcggtatggc   186840
ccctagggtg ccaactcaaa atctctgttg agaattttgc tgataggaag tggcctcctt   186900
ggaggtgttt gctgtgtcct gtgtctggca agtggggtgg ttttgataaa cgtgctggat   186960
ggatgtatgg gtgaatggat aaatggagga atgaatggag aaacaaatga gcaaatgaat   187020
aatgaatgga tggatgaatg gatgagcgaa tggatggatg caaatgaatg   187080
atgtacacac aaaggaatgg ataaatgatg aatgtgctaa tgaatttaag aatgatgaaa   187140
gaatgaatga ataaatgaac aaatggatgg atgaaagaat gaatgaatgt actaatgaat   187200
gaatcaatca atgaagaacc atttaaaaat gaatgcaact gagggtttat aagaaaaggt   187260
atcttaagcc tgggcatggt aattcatgct ggaatcccaa tgcttaggga cgctgaggcg   187320
ggaggatcgc ttgaacccag gagttcaaga ccagcctggg caacacaggg agacctcatt   187380
gctaccaaaa acaaaattgt tttaattaag cgggcatggt ggtacgtgcc tgtagtcata   187440
gctacttggg aggctgaggt gggaggatcg cttgaaccca ggagttcaag gctgcagtga   187500
gctaggatca agccactgca ttccagcctg ggcaacaaaa caagatcctg tctcaaaaaa   187560
aaaaaaaaaa gatgtatttt agaaggtaaa ttcaatctgt ccaaaactga gctctgacct   187620
tcccctaaac ctgtgcccat tcagtggatg agagctccat cccttaaggg gttcaccaat   187680
tcatccattc ctttgtatgt acatcattca ttcaccttgg ctcatccctc tctcttacat   187740
ccacaccgtt ccatcagcaa atgttgaatc tgtcttaaat gattcatccc aaatcctcat   187800
cgcttaacta ccacccaact ccagccccca tccatcatca tcatcacttg cctggatggg   187860
ttcagtcacc tccagcctgg tctcccagct cccgtcctca cctctcactg tctactctcc   187920
cactcggcag ccagagggtg cctgtgaaca cccaaatcag gttccatccc tcctctactc   187980
agaaccctcc acggctcccc cctcactcag ggtaaaagcc aaagtcctcc ttgtggtcca   188040
ccaggccatg catgatctgc ctgtcacctc cctgccttca ccaccttcct cttttcccct   188100
caaccactcc actccagcca cactgacttc cttgtgctct tccccaaaaa tgtcgggcag   188160
acacattcat gcttcaggac cttaaatttg ctgtttcctc tacctaagat actaaagtga   188220
caagtcaaca cactcacctt gaccatgcaa tttaatgttg cagcctaccc tgtggactct   188280
ccaaggctc ccagtccctc tgtgatgctt tacttttct cttaaaaaaa aaattgttat   188340
ttaaagaac ttgtctcgct gtgttgccca ggctggtgtc aaactcctgg cctcatacag   188400
tcctcccatt ccagcttccc aaagtactgg gattagaggc atgtgccact gcacccatcc   188460
caactttttt tttcccatag cacttttcat tttccatccc actgttaatt tacttattac   188520
gtccactgtc tgtctcctcc ccttagaggg tcagaccccg gaagtccagg ctctgttgcc   188580
taatgtatcc tgagcccctg aacagagcc tggcacaaaa taggtactca ataaatgcat   188640
aagagcaaaa ctatatgtag gcagaggaca cacccagctt attcctcagt gatcacttct   188700
aaagttaaat gtccatggaa aacagtctca tccacatctc tttctggagg ccttccaagc   188760
gtgctccatg cagctctgtt gcctgcccct gcatcaggga atggaggctc tgcttatcc   188820
tgccctgtgg tgtgactccc agaggcatca gatgtggctg ggagtgggag acatggaaaa   188880
ttggctcctg caacagagaa ctatcagcct tccatcaat tggttacttc taattctgtt   188940
attttttcagg ggcactgtct tctcataagc tccatctatg caaaactaag cccatgggtc   189000
atgatggttc cctcaggcca gaggcttgct ggagagacta atggatccct tggctaaaat   189060
ctgtgcttgg gctgcacatt ggttaatttc ttctgaagga acagcctgag cctgacattg   189120
tccatctttt ccctggcagg ttctcccttc gcccgagcca gcattaaaag tgccaagctg   189180
gagaactcga ccttttttca caaaaggag aggaggatgc gtttctacat ccgccgcatg   189240
gtcaaaactc aggccttcta ctggactgta ctcagtttgg tagctctcaa cacgctgtgt   189300
gttgctattg ttcactacaa ccagcccgag tggctctccg acttcctttg tgagtatcac   189360
ccagccccac ccctgccaac tccctgatcc ctccctcaca ccctttttcc acttctcttt   189420
ctctggtagt atgtgtatct tctttggtcc tcattgaatc tgccctttcc tttagccatt   189480
tctataactg tcactgggc caatgttact gttgctatga caatgaaacc catctcccttt   189540
agacctgaga gctggaaagct ggaattcaga ccaacaaatg ctcctgtgat tccttttctaa   189600
gagagaggga cagaggggtg ctggtcaagg ggatgttgga agagagacag agaaagacgg   189660
agctcataag atagacagat agaaacagaa acatacatgt attaataatt tttatgtaca   189720
tctctggaaa tgttcataac ttatggttaa gagaggatgc cttagaaata aggagtggct   189780
tatatgttgc cctcattttc tctacttatt tctgactcta cttctctctt ctttcaaacc   189840
ttctgcttct ttcctgttag gttggtgcaa aattaattgc gtttttttgcc tttttttttt   189900
tttttttaa ccacagttac ttttgcacca acctaatact tcctccccctg ccctttttgg   189960
cttccttatt cattcataga acatcccctc cagtatctgc gagagcgttt tgctccctca   190020
aggtacaagg cccactaagg ctttgccctc tgggcctatt cccagattct atgtgagtta   190080
gcatgagata gtatcaaaat tgagggccaa gtgagggtgg ggaaagcag caaagatggg   190140
agagatgct gagcaggatt taaaagtaa agagctcgag gaatcaacaa gagcagcgac   190200
tggggccagg catggtggct cacacctgta atcccagcat tttgggaggc tgaggtgggt   190260
ggatcacttg aggccaggag ttcaagacca gcctggccaa tatggtgaaa ccctgtctt   190320
acaaaaaata caaaaattag ccagatgtga tggtgcacac ctgtaatccc agctactcag   190380
gaggctgagg cactagaact gcttgaatcc aggaggcaga ggttgcagtg agccaagatc   190440
atgccactgc actccagcct gagcaacaga gagagtgtct gtctcaaaaa ataaagtaaa   190500
```

```
ataaaataaa ataaaataaa gagtagtgat tgggcagtga gggggcagg tggatgccct    190560
ggctttggct cacaggcccc aagtaaggac ttctcaaaac gtcttttgcc tactggctgt    190620
ctaatttatt cactgacctt ctgacctggt tcagaattga cttaggacag caagaagaga    190680
cagtctagtc tttgacctag aaaggcccgt gagcctagtc caggccattg tcttcttata    190740
accctccttg ttcccagtca cgttggctga ccccccagga caccccctcg gaaccagttc    190800
tccttcccag ggccctgacc tagtttcaaa cttagtaatt gttttagtc cctctggagt    190860
ctcttataaa tgaggactct acttcgtgtt ttaacttcct ctaatactct atttttaatc    190920
tcctatattc tctctactaa tcatcttgta cagtctgtcc tggttcagga caagggact    190980
gagacttcct gcctgggtcc tcagtgtcta taaaggtcct ttactcattc ccactttccc    191040
tttgagaaaa ctgagacaca gagaggttaa gtagattgcc caggatcaca cattagcttg    191100
gcatgatggc gggcgcctgt aatcccagct acttgggagg ctgaggcagg agaatcgctt    191160
gaacctggga ggcagaggtt gcagtgagcc cagatcatgc cactgcactc tagcctgggc    191220
aacagagcta gacgccatct caaaaaaaaa aaaaaaaaaa aaaagataca cattaatttc    191280
agagatgtca aaatataaac aaaaatgtat atcttggcat cagtgaagtg tagttgtttc    191340
tctggatctc agactccaca tctatgtggt agaaaccgga tttgatggtc ctgaaagttc    191400
ttccagatgc aacaatgcta aggataagta attctttcaa gtcttgtgca tcacctgcta    191460
tcatgttttc atggtaactg aggaacaaga tctcagaaac tcttcagtcc tcccagagtt    191520
acttctggtg ggtctaggaa tgtgtcagat gttacaaaca gacttcctct gctgatattt    191580
tggtcctagg aaccctagag ttcccctcag cactaagat ctccttagcg tcctataaat    191640
aaggagaaat tttggtgata aatactgtga aggactttga cggtcagttc aaaacacctc    191700
ttaaaagcat gacatagcaa cacccttgg caaatatctt agttcatttg tactgctata    191760
acaaattacc cgagactggg taatttgata agaacagaaa tttattttct cacagttctg    191820
gaggctggga agcccaagat caaggcattg gcaggtttcc ctgtctggcg aaagctactc    191880
tctgcttcca agattgcacc ttgaacactg tatcctctgg aagggaggaa cactgggtcc    191940
ttacatggca gaaggtggag gagcaagagg acaaacttc ctctgtcaac ctcttttata    192000
agggcaccta atcccattca tgagagctct accgtaatga cttaatcacc tcctgaaggc    192060
cccacctctt aatactgtta cattggcaat taagtttcaa cgtgaatttt ggaggggaca    192120
caaacattta aaccatcaca accaccaaac acaattagct ttgtggcctt aattagctat    192180
atgaaattca tggaagttag tttcagtcct ctgtctcttt cctttctgta tgctttctgc    192240
tcctcagaaa ccctcctcat ctctccttc tatccattaa gtacccacgc ccttcctaac    192300
tcctcatctt cctaccctac caagaaagcc ctctcagaaa aggatctgat gtcagccatt    192360
tatttgctgg agcaaatgca tatccatgtt ttaccccctcc ctgaggcatt tgcaatttta    192420
tgcttgctca tcaaagaaca aaaggctttg tcttactcaa gactttttag gtcactcaca    192480
acacaggatt tctaggggac ataagacaag ttttctgagt taggagaaaa gccatacctt    192540
aggtgggttg cctgtgtcgc tccaactaag tacttaactt caggattaca aataggatat    192600
cattatgatt tctatttcct tttatccttt ggagctcagt cacgtagaag tagattaaat    192660
ataattgtta gatcacagca ccctggcatt atggggccgt tatggtccat tgttattatg    192720
tgaattattc agttaattag ttttatttttt aaatgtgata aacacccagg aacccaccag    192780
tcaacacaaa agtccttggc aataatctat atccgatcct tctcatcgaa ccagggcaaa    192840
aactacaaga tggagaccca ctgatatttt tctcattcct tttaaaatcg gcctaaggtt    192900
ggttagcttg ttggttggag ggtagggcat aattgttgct tttttttttt tttttttttt    192960
ttagacaagg tcttgctctg tcacccaggc tacagtaggg tggcccaatc ttggctcact    193020
gcaacctcca ctcccaggt ttaagtgatt ctcatgcctc agcctcccaa gtagctgggt    193080
ttacaggcat gtgtcaccac actggctaat ttttgtattt ttagtagagg cggggttttgc    193140
catgttagcc aggctggtct caaactcctg acctcagttg atctgaccgc ctaggcctcc    193200
caaagtgctg ggattacaga cgtgagccac catgcccagc cagctcttcc tttttaacag    193260
aggggaaact gaggcccatg ggaaggacac cttggacagg gcgtggccac agtgggtcat    193320
gtatataatc ccagcacttt ggggaggctgt gctgggagga tcacttgagg ccaggagttc    193380
aagaccagcc agggcaacat agtgagaccc ccatctccac ataaaaattt taaaagaaa    193440
aaagataagt cagaagttgg gtgtggtgac acatgcctgt agttctagca tgttggaggc    193500
caaatcaggg aaactgtttg aggccaggag tttgaaacca gcctaacagc atagcaagac    193560
ctcatctcta caaaaaataa aaagtttaaa aatgataata aaggaaagt cagagccacc    193620
tggaacccct accctcagca agcctaacct cctctctgtt tcctccttct cccttctaga    193680
ctatgcagaa ttcattttct taggactctt tatgtccgaa atgtttataa aaatgtacgg    193740
gcttgggacg cggccttact tccactcttc cttcaactgc tttgactgtg gggtaagtgc    193800
tcttgtttct aagagttcat ttctccagct cttgcctgaa atgacagata cctggacaca    193860
ttaaagggag aaaggtaaag tcaccctga atatgagaga ctcagatgga tgcagaagga    193920
atgagaaaac aatcccaaac actggcaagg atacagtgta cccagaaccc tcaaccaccg    193980
ccagtgggag gaaaacgtat agaccccctt tggaaagcta agtggggac ataagcaag    194040
ttttccaagt tgggagaaaa gccatgcctt aggtgggttg cctgtgtcgc tccaactaag    194100
tacccaactt caggattaca aacaggacat caatatgatt tctatttctt cttttcctttt   194160
gtagctcagt catgtggagg tagatgaagt ataattgtta gattacaaca ccctggcatt    194220
atggagccat tatggtcctt tgttattttg tgaattactc agttaattaa ttttattttt    194280
aaatgtgatt aacaccagt aacccactag tccacacaaa agtccttaagtcc tggagaataa    194340
tctacgtcca atccttctca tcgaaccagg gcaaaaacta caagatggag atatgaccca    194400
gcattccatt gctaggaatt catcctagaa aatctcaccc agataccag agacacagg    194460
ccagaatgtc cctgcagctg gaagtgaaat taaggttgtt cgcaaataag tggagaatgc    194520
ctggcccagg gcagccctaa tcattacca tagtcctgtt ggtctcagaa aggcttaata    194580
atttatttat ttttttttat tttttgtttt tattttttgt tttgagatg gagtctcgtt    194640
ctgtcaccca ggctggagtg cggtggcgcc atctcggctc actgcaagct ccgcctccca    194700
ggttcactcc attctcctgc ctcagcctcc cgagtagctg gactacaggt gcccgccat    194760
catacctggc taatttttg tattttagt agagatgggg tttcaccgtg ttagccagga    194820
tggtcttgat ctcctgacct cgtgatccac ccgccttggc ctcccaaagt gctggatta    194880
ccgtgagc ccaccacacc cagccagctt aataatttat aataactgaa tgttgtactg    194940
ttttctgcca ttatagaaaa ttatgttgtt ggagaaaaca aaatacatac aaacaagcaa    195000
accttcccta cataaatgac ccaagtagtt aagaataaaa accaatttct ttccattaaa    195060
aagaaaagaa agccgggtgt gatgcctcat gcctatagcc tcagctattc aggaggctga    195120
ggcagcagaa ttgcttgagc ccaggagttg aaaaccagcc caggcaacat agcaagaccc    195180
tgtctctaca aaaattaata ataattagcc aggtgtggtg gtgcacacct gtagcccag    195240
```

```
ctactcagaa ggctaaggtg ggaggattgc ttgagcccag cagtttgagg ctgcagtgag   195300
ctatgatcac accactgccc tccagcctgg acaagagagt gagacccat  ctctaagaaa   195360
taaaagtagg ccaggcacag tggctcacac ctataatccc agcactttga gaggcggagg   195420
caggtggatc acctgaagtc aggagttcaa gaccagcctg gccaacatgg cgaaaccccg   195480
tctatactaa aaaaatacaa aaattagcca ggcgtcgtgg cacatgcctg taatcccagc   195540
tacttgggag gctgaggaag gagaatcact tgaactgggg aggcagaggt tgcagtaagc   195600
tgagattgca ccactgcact ccagcctggg tgacagaatg agactccgtc tcaaaaaaaa   195660
aaaaagaaaa atttttaaaat gtcctgagca accttgtttg taatagttcc aagtctcaat   195720
atccgtgtat cccttttgctg tagaacagat aaatattttg tggcatatct atataatgaa   195780
atactctgtg acaatcaaag tccaccaaca gcagccacat gcccaacaac aggaatgaat   195840
ctcacccatg taacatggca cagaaggagg caggagctag caacgtaagt ccatacagtt   195900
catgcaaagt tcaagtggac aaaattaaac tctctctctc tctctacata tatatatata   195960
tatatatata tttttttttt tttttttttt tttttttttt tttttgaga cagagtctca   196020
ctctattgcc caggctggag tgcagtggcg caatcttggc tcactacaac ctccacctcc   196080
cgggttcaag ccattctccc gcctcagcct cccaagtagc tgggattaga ggcatgcacc   196140
accaccccg  gctaattttg tatttttgt  agagaccggg attcagcaat ttgcccaggc   196200
tggtctcgaa atcctgatct caggtgatcc acctgccctg gcctcccaaa gtgctgggat   196260
tacaagcgtg agccaccacg ccccgcctta aactgtattt tttaaggatg atacttgaat   196320
acgttaaaaa ggcgaggacc ttgaaaaaca aacgctcggt aaaagaaacc aaacacaaaa   196380
ggtcaagtat tgcataattc catttgtatg aaatgtccag agcaggcaaa tccatagaga   196440
cagaaagtag attagtggtt gctagggtct gggtgaggga gagtggggag taactgctca   196500
tggggacagg gcctccttgg ggtgatga  aaatgttttg gaacttgata gaggtgatag   196560
ttgcagaata ttgtgcatgt acctaaaggc actgaattgt gtaattcaaa gtgtgaattt   196620
tatgttatgt gaatttcacc tcagtttttt ttaaggtaag aaaatggtta ttacaaaatt   196680
caggatggta gttatatcac agtgtctctg gaaacttcca gggtatccac atgtcccttt   196740
ttattttatt ttattttta  ttttatttga gatagggtct tgctctgttg cccaggctag   196800
agtgcagtgg caggatcatg accctctcct gtctcaaatt cctaggctca agctatcctc   196860
cctcctcagc ctcctaagta gctgggacta taggcacatg ccaccatgct tgactaattt   196920
tttttttttt tgtaaagtca gggtttccct gtgttaccca ggctggtctt gaactcctgg   196980
gctcaagtga tctgcccacc tcggcctccc aaagttccaa aattacaggc atgagccact   197040
gccctagcct tctcctaatt gttgacatag gtagtagttg catgacattc actttgtaat   197100
tatgtgtttc aggaattctc aggcctgtgg gagctcttaa taaataaaaa agaggccagg   197160
tgtggtggct cacgcctgta atcccagcac tttgggaggc cgaggcaggc ggatcacgag   197220
gtcaggagtt cgagaccagc ctggccaaca cagtgaaacc ccgtctctac taaaaataca   197280
aaaaattagc cgggcgtggt ggcgggtgcc tgtaatccca gttacttggg aggctgaggc   197340
aggagaatcg cttgaacctg ggaggcggag gttgcagtaa gctgagatcg cgccactgca   197400
caccagcctg ggtgataaga gcaagactcc atctcaaaat aaatgaataa ataaaaataa   197460
ataaaataaat aagaggccgg gtgcagtggc tcaatgcttt ggaaagtgga ggccaacagt   197520
tggagagacc aaagcaggag gatgcttca gcccagaagt ttgaggccag cctgggcaat   197580
actagcgaga cactatctct ataaaaatgt tttaaaatta gccagatgtg gtggggcaca   197640
cctgtaatcc cagctactca agaggctgag gtgggaggat cacttaagcc caggaggaca   197700
gtgctgcagt gagctatgat tgcgccactg cactccagcc tgggtgacac agtgagaccc   197760
ggtctctata gataaatgaa tggataatg  aggggtcaa ggatcctcac ccggcttcca   197820
tttggagggga ggagtttggt tgagttcttg caaggttggt acctaggaaa tgcttgccag   197880
ttctggagcc cagacactgt ccctggacat gagaccaggt tctctgccct aggttatcat   197940
tgggagcatc ttcgaggtca tctgggctgt cataaaacct ggcacatcct ttggaatcag   198000
cgtgttacga gccctcaggt tattcgtat  tttcaaagtc acaaagtaag tcttttgggt   198060
tcctggacat ttgtacaggg ggtggggatg ggggacatgg tgggggccgcc tccagaaagt   198120
tgggaaagtg agcctcgtgt ttcgagggct gactccgggg ccctgcctcc cccgcctggc   198180
ctgagtcctc gcctggcctc tgtcggcagg tactgggcat ctctcagaaa cctggtcgtc   198240
tctctcctca atccatgaa  gtccatcatc agcctgttgt ttctccttt  cctgttcatt   198300
gtcgtcttcg ccctttttggg aatgcaactc ttcggcggcc agtaagtcct tcacaggaat   198360
tccaactcct ggttccctgg ggtcaggctc agggaacaca cagtcccctc caccgtgcag   198420
gctgccttcc tcgtagccca gacacccatt gcggtcaccc aaatgggcag ggccctgggt   198480
accactcagg gtttcctggg gacagagatg atggagacgt tcgtttcctt ggagatgaca   198540
tactgagcca caccctcaga gcaccccggg tggggccaac gtgaaatgtc tgtgtcctcc   198600
ctgcaggttt aaatttcgatg aagggactcc tccaccaac  ttcgatactt ttccagcagc   198660
aataatgacg gtgtttcagg tacagcctcc acctggcccc acgggccaac acctctcagt   198720
gtcacagatg aaagtgcctg ctccacatcc aaggggcttc cctgaactcc tccttctcta   198780
cctggccttt tcacaccact ttgaaacaca gattttatgg ttatcattat tcaattatgt   198840
tgaggccaac agatcaggag atgaatgtca ttggaaagat agtttgtggc tgggcacggt   198900
ggctcacacc cataatccca gcactttggc caggtacggt ggctcacacc tgtaatccca   198960
acgctttggg aagcccaggt gggcggatca cttgagatca ggaattcgag accagcctgg   199020
ccaacatggt gaaaccccat ctctactaaa aatacaaaaa ttagccgggc gtggtagcac   199080
atgcctgtaa tcccagctac tcgggagatg aggcacaaga attgcttgaa cctgggaggc   199140
agaggttgca gtgagccaag atcgcgccac tgcactccag cctgggcaac agagtgagac   199200
tccatctcaa aaagaaaaa  gaaaaaaaaa accactttgg gaggtcaaga tgggaggact   199260
acttgaggcc aggagtttga gacagtctg  ggcaacatgg tgagactccg tctctgcaaa   199320
aaaataataa taattag    ctgggcatgg tgatacatac ctcctagcta ctagggcagg   199380
tgaagtggaa ggattgcttg agcccaggag gttgaggctg cagtaagcta caatcacacc   199440
actatactcc agcctgggcg agagagcaaa gccctgtctc aaaaacgaaa agaaagtttg   199500
ttatactcac agatcctcag agaaggagca caccatgcag gaccaagcag agaagcaaca   199560
gggtcaagca ggaagagaag gaaaatgtgg gcaagaggct tgattgtggt ttccatggga   199620
cggaatgggt ggagcagagt aaacagctcg agactggcta gtttgatca  tttcagtggg   199680
ctctggggca gaggagctgt tcctacttgt ctaggacctg gccttgggt  gattagggca   199740
ggtggatagt gctgggaaga taaaggaggt ggttgggata tggctggtt  gggatattgt   199800
ttggtttgct tttaaaaagc ctgctcaggg ctaaattgtt tactacctct agggactggc   199860
tagtgctgga ccgggcagtc cctccagagt cagcaagacc ccagatgcat cagaataaag   199920
aaaataaaat gcgtggccag gccaatgagg tggttcatgc ctgtaatctc agcactttgg   199980
```

```
gagaccaagg cgggaggatt gcttgagccc aggagttcaa ggctgccgtg agctccagcc      200040
tgcaccacag agcaaggccc tgtctcttaa aaaaaaggca gagaaaaaaa atggctaata      200100
cacccatcaa atctgaagat accttggtct catattccag ggtgatcaac ccaaagcaac      200160
ttctgcaccc atgtgggcgc attccctgag gcttgggact ggcccagccg ggaccttcag      200220
agcatctttg gtggattctt tctctttgag ggactgagga tgtatagaaa atgtgacttc      200280
actctctcct tctcctgggg aggtagtttc taaatgagac cccaagacag ggagttgaag      200340
aggaaacctt ccatgaaggg aagttctgag cccccacata agcgattttt ttttttttttt     200400
tgagatggag tctcgctctg ttgcccaggc tggagtgcga cggcacgttc ttggctcact      200460
acaacctctg cctcctgggt tcaagcgatt ctcctgcctc agcctcccga gtagctgaga      200520
ctacaggtgc atactaccat gcctggctaa ttttttgtatt tttagtagag acagggtttc     200580
actatgttgg ccaggctggt ctcgaactcc tggcctcgtg atctgcctgc ctcggcctcc      200640
caaagtgctg ggattacagg catgagccac cacacctggc ccataagcga ttattaatag      200700
cactgatcgc tagtcatgta tctttagctc agaggttctc acccaaggac aagtctgtcc      200760
tccaaggaca tgtagcaatg tctgcaagca ttgttggttg tcacagctag gggagagggtg     200820
ctactggcat ctggtgggtg gagactagga atgctgctca atatcctaca atgcacagga      200880
cagccccaaa tagaataatc tggccccaaa tatcagcagt gctgaggctt agaaaccctg      200940
ttttagcaga ttcatgtttt tggagttctt taacatttac tttatcctca tggggatatg      201000
gatagaagga aggaagttgg atcttttta aaggagcatg taggtgctgt ttgaatatcc       201060
ccttggttct ttcagtatgc atcagcacaa cttgcgtctg tcaacaccta atcctttgcc      201120
ttggtctttc tctggtcccc tgctctgccc caaggaact gcagtccagc agtactgtga       201180
atttttgtg ccacacctta aaaggagcag ccgttggtgg ataaatacc cagctccctc        201240
accctcaggt gggatgaccc ctagagctcc ccagcaagac ggcccccgg ttacctacag       201300
tggaaactcg cttgatcaca tactgtttac gttccaccct cttttccctt ttctcacttc      201360
tcctctcccc tactggtgct tcctgagatc acctcccaga caaccactt gcacccgaac       201420
ccttgttcca gggtctgcct caggcagggg gaccccaaac gtgtccttgt gctacatttg      201480
tgctatccac gtagtagctt gtttaatcat caccatgacc aatgaggaa cacaggtaaa       201540
tattaaaatc ctgtcttagt ctgctcaggc agccataaca aaataccaca cactgggtgg      201600
cttatacagg aaacatttat tctctctag ttctggaggc cgggaagtcc aagatcaaag       201660
tgttagcagg gttagttagt tcctggtgag ggccctcttc ctagcttgca gatagccacc      201720
ttcttgctgt gtcctcatat gtcaaagaga gagagagaga gttgtgatgt ttcttcctgt      201780
tcttttttt ttttttttt tgagacaaaa atctcaaaaa aaatctatt ttttttttag         201840
gcaaatcaca ttttttgtc acccagcctg gagtgcagtg gcacaatcat agctcactgc       201900
agcctcaaac tcctaggttc aaacgatcct cccacctcag cccccttgagt agctgggact     201960
acagatgggc accagctaat tttttaaat tttttgtaaa gatggggtct tgctatattg       202020
cccaggctaa tcttgaactc ctgggctcaa gtgatcctcc caccttggcc tcccaaagtg      202080
ctgggattac aggcatgagc catggcatgc ggtctcttcc tgttcttata agggcactaa      202140
taccatcatg aagtcccca tgacctcatc taacccctagt tacctcttaa aggcccatc      202200
tccaaatacc atcccatcat aggttagggc ttcaactcat gaatttggag gcgggcacaa     202260
tttagtccat aacaaatccc cttaatcaca tcaagtaaga cagagttaca ggagggctg      202320
tgactcctcc agggtcccat tttcctagaa gccaggctaa gagccccacg acgcaggaac     202380
ggcccctttt actcgcaaac aaagagaaaa gccaaggaga agcaacacg gagtctggct      202440
ctgcaaaccg ggcaggattg ttaaagacct cctgggctcg gggatgggggt gggcggattc    202500
cggctccaca gctgcatctc caaggggccc gtggctgaga ggggggttgg ctgtgtgttt     202560
cttcctcccc tttcagatcc tgacgggcga agactggaac gaggtcatgt acgacgggat     202620
caagtctcag gggggcgtgc agggcggcat ggtgttctcc atctatttca ttgtactgac     202680
gctctttggg aactgtatcc ttcatggaga gagagaaggg gacaggcctg gacctctggc    202740
agaggagagg ttgcagggc tcaagggagg gtactgagga acccagatac ccaggggccca     202800
agtggtgtcc caccagtggt tgcttttcct gactcagaca tttgcagaca ccctcctgaa     202860
tgtgttcttg gccatcgctg tggacaatct ggccaacgcc caggagctca ccaaggtgga     202920
ggcggtggga gaatgttcct ctgcaaagt taccacctgc ccatggcaga tcaggacggg     202980
ggtggggtgg ggggtgggg tgggggtggg ggcatgggaa caggttaga acttttgccg      203040
gggatgcacc atgcaaagag aaggcgcctc tcccccact cccagaaaca gactgtccct     203100
catcaagcaa attctacagc caagagggtg ggaaggggga aggcagtgag gtcgctgcag    203160
gaaacggatg gcaaactcaa ccaaaaggcc gtttacaggg agtaagcagg gtttccaagg    203220
aatggttgtag cccccaggct agtggatggg agaggggatg ctgttatggg gacccagtca   203280
gagctgggc caaggaaaaa gggctgccac cagcccgggg accttagaga acccagaacc     203340
atggcaaggc acagatggag tggccaataa atgtccccac cttctctctt cctctggctt   203400
cccgctggag cctcccctta gccaaacgca gcatgttaag agctagcctc cgtccagcct    203460
aagcctctcc ccaaggaccc tattaagtta agattacatg taacaggtac agggtcttca    203520
tctcagccct ggggtctccc tcagcattgc agccccacct ccagtgcctc gaggtattca    203580
ggacatgttt gtgaaattga accaaaccaa gcagacgttg ccaacgctcc atctgccggc    203640
cctggcagga gggagagaga gtttcccggc cccagctccc agtggaggga agcggaagtc    203700
tctgccatcc caagcacacg gccacaagcc tggccactgt ggagctggct ggcatggctg    203760
agccgagggc tgatccagcc atgagctcat ccaagttcca aagtccatc cttagggagt     203820
ggtgcaggaa ggtagcagaa ggggagggag aaaggccagt tcgtttatct cctgggaggt    203880
gtggacattc ctctccagat ccacattctt tctttcattg atcctacaag catttcttgg    203940
tcatttaata cgtgttttta atcctattca gtccctcatgg aaaccttagg agccaagttc   204000
tctgagcccc attttacaga ttcatcatt cagtaagcac ttaatgagca cctactgtgt     204060
gaccaaggcc ctggtctagg acttagggat taagcagtga acaaaaaaag gcaaaatcc     204120
ctgcctccgt ggagcaggga ttcaagaggg gagacagaca agaaacaaga taaatttgta    204180
aacatacgta gcttgtcagt tggtgataaa cacaacagag aaaaattcag tagggaaagt    204240
cagggagagt tggaatttta gatgagatgt gtgtcgcaca gagaggttga gacttgcc      204300
caaggccaca cagcagtaag ttgtggagct gggatttgaa cccaggccgt ctgggtctgc    204360
agcttgtgct cttaactgct gtgtaccagt tgcttgaagt tttatgctcac              204420
ttgggaacct gtgggaaatg cagattccag ggcccagcac tggttctata gattatttgg    204480
ggagcctgag gatctgcatt ttaggtgttt ctgaggcaga tggtcagag acctagctct     204540
gaaaaatgct gggaatggtg ccaggagggg tggggtggc cctatgagag cagggtggcc     204600
agccagatcc catctccatg ttgtctctga cagtgtcctg atctgaccat ttccaaggtg    204660
gtaaggttgc tccccgttcc agtgattcgg agcacagcgg gagagctgcc tgcaatggca    204720
```

```
tgactttct  tatgggcggg  ttcatttctg  gccatttctt  tctcgttgcc  ttttctttgc  204780
tttttctttg  ttggcttttc  tgttttacga  atgaggccct  gcatgaaggc  tgaagaagga  204840
tttaaagtcc  aaaaacgtct  ttttctgtat  gtatttttaa  aacctcttcc  cccattctcc  204900
tcctctctga  acctaaccac  cagtgagcag  cagcaccctg  ggcagttggc  tgtagcccaa  204960
gtgccctgct  ctcctctccc  caccgccttc  ctgtcatggg  ggctgggaat  ataaattcct  205020
ctcctcattc  tccttctggg  ggctgttgac  agtgcatggc  aggggccatc  ggatgccagg  205080
ctcttctgtg  tgtgagggta  gttggtgttt  tttgaaagtt  ggttcagaga  gttcacatgg  205140
ctcagaaagc  ctagtgagag  gaaaatcttt  gcactgcttt  ccagctcatt  aagacaggat  205200
gcaggggcca  ggcatggtgg  cacatgcctg  gaatcccagc  actttgggag  gccgaaatgg  205260
gaggatcatt  tgaggccaga  agttcaagac  cagcctgggc  aacatgagtga  gaccctgtct  205320
ctacaaaaaa  aaaaaaaaaa  ttaaatgtat  acaggcatag  tggcatgcac  ctgtagtccc  205380
agttgcttgg  gaggctgagg  tgggaggatt  gcttgagccc  aggagttcaa  ggttacagtg  205440
agctatgatt  gtgccactgc  actccaggct  gggcaaccaa  gggagactct  gtctctgaaa  205500
acaaacaaaa  gaaaaaaaaa  taggctgcag  gaaagtcttc  attgtaggaa  gagaagggac  205560
atttttattt  tttgttatct  ggctgtgtgt  taaaataggc  ttcataatga  gttagatgtc  205620
aaacttatac  acagagggga  tagcaataca  cttaaccaat  agcaggtacc  cattccaatt  205680
ggggagcctt  ggttctgatt  ggtcgaaata  tttcaaatgt  tgcccctggt  cagcaacagg  205740
gtcagaagtg  agtccccaag  gcctagttca  tgttttgtga  acaaagattc  cacgtgcctt  205800
ttaggacgag  caagaggaag  aagaagcagc  gaaccagaaa  cttgccctac  agaaagccaa  205860
ggaggtggca  gaagtgagtc  ctctgtccgc  ggccaacatg  tctatagctg  tgtaagtgcc  205920
cctaatccct  gggatgctac  cctggctcct  gaacgtccac  actatcccag  gcacagattt  205980
gggaagcagt  ggggtggtc  cttgacagaa  ctgagcttta  ggaagagaca  cttcttgtcc  206040
ttccacccac  tttcactcaa  taaatatttg  gttagcagct  gttatgtacc  cagcactgtt  206100
ctaacttctg  gggatacagc  attaacaagg  aggaaaaaaa  aaatcccacc  tgtgtgtagc  206160
cattctagca  agggaaggag  tcaataaatt  agataaataa  gtaaattata  tattgtgtta  206220
gaaggcgatg  gaactacaga  gaaagtaggg  gagggaaata  gcaaatgctg  ggagtgaaga  206280
gagttgtgat  tttaaacgaa  gttgtcaggg  aaggcatcac  ctagaatagg  ggtccccagt  206340
cccgggggctg  tggactggta  ccaggccgag  gcctattagg  aacggggctg  cacagcagga  206400
ggtgaacagt  gagcaagcaa  gcattaccgc  ctgagctcca  cctgccgtca  gatcagcagg  206460
cagcattaga  ttctcatagg  aacacaaaca  ctattgtgaa  cggtgcatct  gagggatcta  206520
ggttgcgtgc  tccttttaag  aatcgaatgc  ctgatgatct  caggtgaaac  agtttcatcc  206580
caaaccacc  ccccacacct  aggtctgtgg  aaaaactgtc  ttccacaaaa  ctggcccctg  206640
gtgccaaaaa  ggttggggac  tgctcaccta  gaaggttaca  tggcctgaag  gaggtgaggg  206700
aggagccact  gggggggcctg  gggaagggca  tcccaggcag  agggaacagc  ataggcaatg  206760
gccctgaggc  aggaacatgc  ctgatgtgaa  ggaggcctgt  gtgactagaa  tcgaatagta  206820
agtgtgagga  ggtgaaggca  aggaggtgac  aagcagatta  cacagggcct  tctgggtcag  206880
gggggaggac  ttgggctttt  gcccctagcc  aggtgggagc  catggagggt  tcttgagcag  206940
aggaggctgg  gacctgactc  agatgctcac  agactcctag  cattcagtgg  ggagtagagg  207000
gtggagagca  ggagtgggag  gctgagatgt  gggttggttc  gcctgggtca  tccatccaag  207060
ctacagtgcc  tagcaatgct  ctaagtcctg  tgaccatgcc  actgcaggaa  agagcaacag  207120
aagaatcaaa  agccagccaa  gtccgtgtgg  gagcagcgga  ccagtgagat  gcgaaagcag  207180
aacttgctgg  ccagccggga  ggcctgtat  aacgaaatgg  acccggacga  gcgctggaag  207240
gctgcctaca  cgcggcacct  gcggccagac  atgaagacgc  acttgaccg  gccgctggtg  207300
gtggaccccgc  aggagaaccg  caacaacaac  accaacaaga  gcccggcggc  cgagcccacc  207360
gtggaccagc  gcctcggcca  gcagcgcgcc  gaggacttcc  tcaggaaaca  ggcccgctac  207420
cacgatcggg  cccgggaccc  cagcggctcg  gcgggcctgg  acgcacggag  gccctgggcg  207480
ggaagccagg  aggccgagct  gagccgggag  ggaccctacg  gccgcgagtc  ggaccaccac  207540
gcccgggagg  gcagcctgga  gcaacccggg  ttctgggagg  gcgaggccga  gcgaggcaag  207600
gccgggacc  cccaccggag  gcacgtgcac  cggcagggg  gcagcaggga  gagccgcagc  207660
gggtccccgc  gcacgggcgc  ggacggggag  catcgacgtc  atcgcgcgca  ccgcaggccc  207720
ggggaggagg  gtccggagga  caaggcgagga  cggagggcgc  ggcaccgcga  gggcagccgg  207780
ccggcccggg  gcggcgaggg  cgagggcgag  ggccccgacg  ggggcgagcg  caggagaagg  207840
caccggcatg  gcgctccagc  cacgtacgag  gggacgcgc  ggagggagga  caaggagcgg  207900
aggcatcgga  ggaggaagta  agtggaggtg  acctcgaatc  cgcagaatga  cggtaacatt  207960
aataatgaca  acagccaaag  tagcacgtgc  tgtgtatttg  tttataaaaa  tatattataa  208020
aatgctgtat  ttggccaggc  gcagtggctc  acgcctgtaa  tcccagcact  ttgggaggcc  208080
gaggcggatg  gatcacgagg  tcaggagttc  aagaccagcc  tggccaagat  ggtgaaaccc  208140
cacctctaat  aaaaatacaa  aaattagccg  ggcacggtgg  caggcgcctg  tagcccagc  208200
tactcaggag  gctgaggcag  gagaatcgcc  tgaaaacagg  gggcggaggt  tgcaatgagc  208260
cgagatcaca  ccaccgcact  ccagcctggg  cgacagagtg  agactctgtc  tcaaaaaaaa  208320
aaaaaaagtg  ctgtatttgg  ccaggagcag  tggctcatgc  ctgtaatccc  agcactttga  208380
gaggccgagg  cgggcggatc  acttgaggtc  aggagttgga  gaacaggctg  gccaacatag  208440
tgaaacccccg  tctctactaa  aaatacaaaa  attagtggtg  gtgcccacct  gtattcccac  208500
tactcaggag  gctgaggcgg  gagaatcagt  tgaacctggg  aggtggaggt  aggttgcagt  208560
gagctgagat  cgtgccatca  cactccagcc  tgggcaacag  agcaagactc  tgtctcaaaa  208620
aaaaaaaat  gctgtatgtt  tttgttttt  tgacacaggg  tctcgcctgt  tgcccaggct  208680
ggagtgcagt  ggcagtcata  gctcagtgca  gcctctacct  cccgggctca  agccatccgc  208740
ctcagcctca  caagtagctg  ggaccacaga  catgtgccac  atgcctggct  aattttgta  208800
agacagtgt  tttgtagaga  caggttttca  ctgtgtttcc  tcagttggtc  tcaaactcct  208860
gaactcaagc  attccgcctg  ccttagcctc  cctaaagtgc  tgggactaca  gggttgagcc  208920
accacactca  gcctaatttt  tttacctta  gtagaaatga  ggcctggctc  tgttgcccag  208980
gctggtccc  aactcctggc  ctcaagcaat  catcccacct  cagtctccca  aagtgttcgg  209040
attagaggct  tcacagatgg  ggaaactgag  agattgagtg  agctcctcaa  ggtcattcct  209100
ctaaccagtg  tccttgaacc  caggctctct  ggcaccagag  cctttgagca  tttcagggaa  209160
actattaaga  gaagcccac  tgtcgtccag  aattatatag  tcttctgtgt  tcttgctgtg  209220
tgactttgc  aaagtgactt  catatctctg  ggcctcacac  aatggaaata  gtgggatcta  209280
attgggtcat  tgccaggatt  gaatgaggta  atgtatgcaa  agggcctgga  agagcagctg  209340
acacataata  agtgctcggt  aaatttagag  cattttggc  cattttcagc  caactctatt  209400
tacctaatgc  tattctttgg  aagtttgaaa  agccactctg  ttgggaggcc  aaggtgggag  209460
```

```
gatcacttga taccaggagt tggagaccag tctgggcaat agaggcagac cccatctcta  209520
taaaatataa aaaattaaac agatgtggtg gcatgcacct gcagtcccaa ctacttggga  209580
ggctgaggca ggagggtcac tggagcccag gatgtctagg ctatgatgag ctatgattgc  209640
accactgcac ttcagcctgg gcgacagagc aaggctttgt ctcaaaaaat aaaataaaaa  209700
ataaagaaaa agaaaaggca cttttgggcc ttagaattga agggagagca gagtttcaaa  209760
gctttggatg cagcgggatg tggtggctca tgcctgtagt cccagcactt tgggaggcca  209820
aggtgggagg atccacttga gccccggagt tcaagaccag cctgcgcaac atagtgagac  209880
ctcacctttt aaaaataaat aaaaatgtta gaaagctttt gaggcatctt ccaggccagc  209940
aacttatcca ttcagaacca gcatcctctt tttcataacg acattttgta atactttcta  210000
gcagatgcta tagtgattct gcatataggg actcaacaac ttacccatta aaatagacat  210060
cgtagacatt gtcctattac aaattaacct gctcttagtc ctcttttata ttaccatcag  210120
ggcataaatt tgatttttt aatgatgggt ttaagtgatc ctgttgtatg acatatgagg  210180
taggccagca cttctcaaaa tctaatgtgt atgtgaatcc ccagggatct tgttaaaaca  210240
caaattgtaa ttccgtaggg ctaaggactc agtggagcct ggagattctgc atttgcaacg  210300
agctcccaga tgaggctgat actactggtc cagggaccac atttttgagta atgagactct  210360
ggaggacata gtgaagtaat tctgatatgt acaccataca caaaatcacc atgaagtgac  210420
aggcacaaat gatggctaac tctgggttgt gtggacaatt caaaccacat gagggggagtt  210480
gccagcagtg tcaagatgtt ccacaatgtt gaacacctct tggcaaagtt ccatatacaa  210540
aagagtctag tctttcttcc atttatttaa tagttgcatt gcaggaaaat gcatgtgtata  210600
ttaaaaacat acaaaaaata tgttgtgttc ttatgtaaaa gagttaggtt taaactaaaa  210660
gcacaggatc aggtgcagtg gctcccacct gtaatcccag tgcattggga ggctgaggaa  210720
ggagaatcgc ttgaggccag gagttcgaga ccaacctggg cgacataagg agacctcgat  210780
ctctacaaaa gaagttttttt aattagccag gtgtggcggc aggtgcctgt agttctagct  210840
acttggaagg ctgaagcagg aggattgctt gagcccagga gttcaagatt acagtgagct  210900
atgattatgc cattgcattc caacctgggc aacagaacaa gtccttgtct caaaaaaaaa  210960
aaaaagaaag aaagaaagaa aaaacccaaa caaacaagca aactaaaagc acaggtaatt  211020
acaagcaaga tttttcacct ctttgaggga cattagaaag tcatgaagag gaaaagataa  211080
gtctttccca tatgggactg tcatgtacat ggtagggtat ttagtataac tgcctaccat  211140
tctctaagtg cctgcagtgc ccctcaatca ttatgttatt aggtttccac gtagttctac  211200
aacagttttc tgaaaaccat tgttctaggt cattcttcg cttcaatctt ctcctatggg  211260
tttatgcatt cattcagtta gtatttacta agtgcctact atattctaag ctcatgctgt  211320
gagttcagtc acacaactgc aagtgaagtg gtctgagaca ttctgagaaa tacgaccaag  211380
aaactgctcc cagggtctca gggcaggttt ccagaggagc aatctgagaa gggagtagag  211440
tgtttcagtc taacaacagc atgtgcaaag gccctggggt ggaccagaag gaggccagtt  211500
tgcaggacat gactagtgac gagaaagtga caaagaaatt gaaggtgcat tgatgagact  211560
ctggggctgt cagtcactca ggggaatgag agatcaaaac gggagtttag gtggaataaa  211620
gtgtttacca cagcactctc tgtatagtaa agaccaatga agagcaggt acaggccagt  211680
gtgatggttc acgcctgtaa tcccagcact ttgggaggca gagacaggtg gatcacctga  211740
ggtcaggggt tcagaaccag cttggccaac atggcaaaac cctgtctcta ctaaaaatac  211800
aaaaaattag ccaggcgtgg tggtggacgc ctataatccc agctactcag gaggctgagg  211860
cacaagaatt gtcctgcgag gcagaggtta cagtgagctg agatcacacc actgcactcc  211920
agcctgggca acagaacaag actctgtctc aaaaaaaaaa aaaaaaaaaa aaagccaggt  211980
acagtggtat gcacctgtaa tcccagctac tcaggaggct gaggcaaagg attgcttgag  212040
cccaggagtt cgagaccagc ctgagcattt agagaatggg aggccagtat actaaatacc  212100
ctaccatgta caagacagtc tcatatggaa aagaattatc cttttcctctt catgactttc  212160
tagtgctcct cacacaggtg aaaaatcttg cttataatta tctgtgcctt tagttttgttg  212220
gtttatttag ggttttttgtt gttttttttt tttttttggg gcaggtgtt gctctgttgc  212280
ccaggttgga ttgcagtagc attgctcatt ttagagatga gcaagacctc atgtctaaaa  212340
aaaaaagaaa gaccaatgat tattaattac tcttgctatt attactaata ttactgttat  212400
tatcagcctt attaacagat ctactgttat tgaaggaggc agagtgacag ggacaaaatg  212460
tctctcccta acaatatgcc aggaagagtt tttgaaagac aacagtaaac attggaaact  212520
acaagagcag caaagcctgg ttgtgaaagg caaggacttt ggggcaggca gtcacattcc  212580
tgccctatca cttccaggct gtgtgacttt cagaatttca ctcctctctg ggcctccatt  212640
tcctcatcta taaaatgaag ataagaatag tagctacctc cttctctggg tataagattt  212700
aactgagccg ggcgcggtgg ctcatgcctg taatcccagc actttgggag gccgaggtga  212760
gcggatcaca aggtcatgag ttcaagacca tcctggctaa tatggtgaaa cccccatctct  212820
actaaaaata ccaaaaaaaa aaaaaattag ccgggcgtag gtggtgcacg cctgtagtcc  212880
cagctactcg ggaggctgag gtaggagaat ggtgtaaaac ccgggaggcg gagcttgcag  212940
tgagccgaga tcgcaccact gcactccagc cggggagaca gagcgagact ccatctcaaa  213000
aaaaaaaaaa aaaaaaaaaa agatttaact gagttagtac gtgtaaaatg ctttgagtgg  213060
ttcctggctt ataccaagag ctcaataaat gttagcaatt ttttgtagca ttttggggtc  213120
tcactatgtt gcccaggctg gtgtcaaact cctggcctca agaaattctc ccactttggc  213180
ctcccaaagt gctggattta cagacatgag acaccatgcc tggccatgtt agctattatt  213240
aatatgaata ttattaagta ctcaatgaat gctattttta gcagtaatag taagcacctca  213300
ggaagtgtca gctaatactg ttagtaatac tctcatcaat aaacataaaa agcaataagg  213360
acccagcttg cccaaatccc acagatggtt cctgctccct ctcttcttca gaggaagaaa  213420
ctatctcccc actttcaccc ccatagcctc agctggccag accccattc tgaaccaggg  213480
gagtactgct aattccatta ttaatagaca catcaaacaa tctggccggg agacatta  213540
ttcatttgac tgataaagag gttctaaggc tcttttggaaa taaagttca tgaagattca  213600
tgcactttaa gagaaaaaaa ttcaagatca gtcattcatc tgctttaaaa aaagtggcaa  213660
agataaaact ttatttgaga atataaaata ataaaaagac attttcgttc tctgttgtga  213720
caaagccagt ggcttcgga ggtctgcctt gtacattttt cctcttcttc agtcattcct  213780
tgaggctttt tgcaaacgta ccctgtgtttt ttcattctcc agcatattga taattttttt  213840
ttttgagac atggtctcgc tttgtcatcc aggcccggag tacagtggt acaatcatgg  213900
ctcactgcag ccttgacttc ctgagctcag gtgattctcc cacctcagcc tcccgagcag  213960
ctgggactac aggtgtgcat gaccatgcct agctaatctt tgtattttt tgtagacaca  214020
gggttttgcc acattgccaa ggctggtctc caactcctgg gttcaagcga tcctcccacc  214080
tcagcctccc aaagtgctgg gattacagga gcgagctacc ttgccaggcc gatcatattt  214140
ttttcctttt tattcacttt gtcttctcct cattcctacc ttcatctgtc tttcagtggc  214200
```

```
tcactccagt gaaaagtgga ctgacgcaca ttctatttca tataattcaa tggctgctgg  214260
ccccagatcc cccataccag gtggccgagc ccagtggccc tgcagggtgg acaaaatgag  214320
ggtggaactt tcccagactg tcagtaaaaa tctatggagg acagagcttc tgcctctccc  214380
ttgcaaccag gcagtgcctt ctcccaggcc tatctgcttg caaagggaac ttttgccaag  214440
acctgctcca ctctagaatt cttatctctg ctgttcgcat cctaattcca cctgcatctg  214500
tcaccatgac aacctgctcc ccaaaaggaa caggaagaga gatgctggac ttttgagctc  214560
cacagtttat cctgcatggg ggtagggagt ggttaattac ttagcactct aattcttacg  214620
gtaccccaa tgggcccaag ttggttttt taaaaaaaaa cagtcttgct ctgttaccca  214680
ggctggagtg cagtggcaca atcatagctc actgtagcct caaactcctg gactcaaatg  214740
atcttcccac ctcagcctcc caagtaactg gaacaacagt ctcgtgcaac tacgcccagc  214800
taattttttt ttttttttt ttttttaga gatgggtct cactatgttc cccagactga  214860
tctcaaactc ctgggctcaa gcgatcttcc ttcctcagcc tcccaaagtg ctaggattac  214920
aggcgtaagc cactgtacca agctgcccca ttaaagcttt gaacaccaga gagcccagct  214980
cagctgtttt ccagctgggt aactctgggt aactttgcct ctctgaacct cagtctcctc  215040
ctgtgtgaaa tggggctgat cactataccc atctcggatg gtggtagttg cagggattaa  215100
atgagttaat acgtgaggtc cttaggacag ggggtgggga cacgagataa gcaatataca  215160
ggaactgctg ttattatcac ccccacataa tccgatctca gggtctgagt gtgccccagg  215220
caaggtgtcc acagccctct gcagaaggat gcccaagtga tcagctggca caagaacgcc  215280
acgcacagca ggtgttatgc aactggccac ctattccagg cagaggatgc cagatccca  215340
gggagaaggg ggtaggggtg cagcttcaaa gttttctgcc cctttgagt tctccttgga  215400
gacactttg aaatgaaacc tcccggaaat tgatattagg cctctgcagg ctgagcttgt  215460
taaaatttcc caacaaacag agccaacaga cgctctacaa ggaagcaaaa acaagacaaa  215520
acacattggc agacccttt ccatctgctc ttggtagatg gtattcctct aagaaaatgc  215580
cgccacgagt ttctccatgg cttcttgagc tggtggccaa aggatttagg ttctctttga  215640
aattataact taactgggcc tgcttatgg cagggatatc actctctgaa atgtgtatat  215700
atatgtgtat gtatatatat acacatatat acacatatac ataccacaggg ccaggcgtgg  215760
tggctcacac ctgtaatccc agcactttgg gcggccaagg caggtggatc tcttgagccc  215820
caggagttca ataccagcct gaacaacata gtgagaccct gtctctacaa aaattaataa  215880
aaataaccag gcatggcagt gtgtgcctgc aatcccagct acccagggtg ggaagatcgc  215940
ttgagcccag gagttaaaag ttgcagtgag ctatggtcat accactgcac ttcagcctgg  216000
gcaacagagc aagaccctgt ctcttaaaaa tatattatta ttattataca cacacagaca  216060
cacacagaca cacacacaca ttacagatga tgagaaaata ctctcagcca ggttttcatg  216120
atacacaact tctcaaaaag catcacaagc aggttagaat tagggatttc tttgtggact  216180
gtccaagatg ttgaggaaat attggtttag aatttaccatc atttaggcca gaaatggtag  216240
ctcacgcctg taatcctaac actttgggag gccaaggcca atggatctct tgaagccagg  216300
agttttagcc tggccaacat ggcaaaatcc tgtctctact aaaactacag aaaaaaaaa  216360
aaaaattagc cgggtgtggt ggcacaggcc tgtagtccca gctactctgg aggctgaggc  216420
aggagaatca cttgaacctg ggaggcagag gttgcagtga gccgagatcg tgcattacac  216480
ttcagcctgg gtgacagagc aagactccat tcaaaaaat aagtagata agataaatat  216540
atataatata tatgttatat atataatata gaaactacag aacaagtgat ctttgtatgt  216600
ttccagaata taacagcggg acaggcatag gatagacgtt cccattgcaa aagggagaaa  216660
ttggaaggga taaagaggtc accagtccta agcaagtgct aaatccagca agacaaatcc  216720
cattagtttt caaggcctga gaataatcct cggtgactct cagctcatta acatacttag  216780
ttctcagagc cagactcaat gaggttacgg cccgcatgtt atgggtcagg aactgaggct  216840
aagtaactca ctggagatta tgtggtaaag aaggtccagg atcattgctt cagtctccag  216900
gatatgggga aggttctact cctgttatcc caaattttaa aatgtgggaa ctaaggctca  216960
gagaggttaa gcaaatcaca caggggttgca cagctagtga tgttgctgag atttccctgt  217020
gtgtagtggc tcatgcctat aatcccagca ttttgggagg ctgaggcaag agggtcgctt  217080
gatcccagga gtttgagacc agcctgggca atatagtgag acctcatctc tacaaaagag  217140
aaaattaaaa agttagccag gcgtggtggc aggcacctga agtcccagct actgggaagg  217200
ctgaggtggg aggattgcct gagcctggga ggtggcgatt acagtgagct gagatcgcgc  217260
cactgcacta caacctgggc gacagagtga gaccctgtct caaaaaaaaa aaaaaaaaa  217320
gacattgccg agattcaaac ccaggtcagc ctgtcttctg aaatgtccct ctatgaccca  217380
ctcacaaaac tgagaaggca gaaagttgct tggacctgtc tatttcccct gtgcagtctc  217440
agagaaacag tggaactgcc tcggtttctc cttccgggaa gtattcatag aagcatccca  217500
cttaccactt ttggtctgaa aataaattag cttgtctctc ttccacttac taaaaacacc  217560
gtgggttttt gcaagttaaa atgcaaaaat aaaatgagga gaatggtgct ggtagtttag  217620
ccagtgggaa gccctctggg gaaagccagc ctttttattta ttacttatt attattttat  217680
tctttctaga tagatttatg ggaaaccagg gctgtgttgt cagggggtct gtagtccaaa  217740
aggcatcaga tgggctacta agtgagtctt tgtccacctg tagatggcaa gaggcagggc  217800
ccaggtgtcc atggcttgga gaggcagggg ttgatgggag gtttgaggct gtgggatctc  217860
tcctggggcc tcagtatcct catctggata atggggacat tctggccagg cacggtggct  217920
ctatatatcc agcacttagg gaggcctata atcccagcac tttgggaggc tgaggtgggt  217980
ggatcactgt aggccacgag ttcaagcagc ctgggcaaca ctgtctctac  218040
tgaaaataga aaaactagct gggtattgtg gtgcacactg gtaatcccag ctattcggga  218100
ggctgaggca cgaggatcac ttgaatccac gaggcagagg ttgcagtgag ccaagatcct  218160
gccactgcac tccagcctgg gcaacagagt gaggctctgt tcagttaaaa aaaaaaaga  218220
aaaagaaaa agaaagaaag aaaaaagaaa tggggtatt catttatcat ttgacagtaa  218280
gtttacccag cattgactgt gtgagaggcc ctgtactagg cagtgaaaac tcagctaaga  218340
ataagaaagt taaaaacaag ctgggcattg tggtttacgc ctgtaatccc aacattttag  218400
gaggccgagg aggaagaatc acttgaggcc aggagtttga gaccaccctg ggcaacatag  218460
tgagacgcca gtctctacaa aaaattgtaa aattagccag acatggtggc gtgagcctgt  218520
agcctcagct acctggaggc tgagatggga ggatcactgg agcccagaag ttcaaggctg  218580
cagtaagcta tgatcctgcc actgctctcc agcctgtgca acagagtaag accctgtctg  218640
aaaaaaaaa aaaaaagag gccaggtgca gtggctcaca cctgtaatct cagcactttg  218700
ggaggctgag gtgggtggat cacttgaggt caggaattcg agaccagcct ggccaaaatg  218760
gtgaaacccc atctctactg aaatacaaaa aattagccgg tcgtagtggt gggcacctgt  218820
aatcccagct actcaggagg ctgaggcaag aaatcgctt gaacctggga gccagaggtt  218880
gcagtgagcc gagatcacgc cactgtacga cagagcaaga aaaagaaag aaagaaagaa  218940
```

```
aagaaataag atgatgggga gttgtggaaa cctgtccatg ggcacgtgaa ggtcttgacc    219000
tctgaccaag aagtgaacag gctcctctca attccaggca ctgcagggat ctgggacatg    219060
acttctccat gaccaaactg tacccttttcc ttttctttttt tgtttttttg gtgacagggt   219120
ctcactctgt cacccagact ggagtgcagt ggggcgatca cggctcactg cagcctcaac    219180
ctcccaggct caagcaatcc tcccacttcg gcctcccaag tagctagaac tacaggcaca    219240
cagcgccacg cccgtcaatt tacacatttt ttgtagaaat agggtctcac tatgttgccc    219300
aagctggtct tgaactcctg gccttaagca atcctcctgc ctccgcttcc caaagtgctg    219360
ggattacagg cgtgagccac tgcgcccagc ccaaattgta ctcttgaaag atggaatctt    219420
agctaggatc ctgaactgtt gccttttatc ctaaatcagt tgttggtttct ttttcattca   219480
cttgccttcc tcagagagaa ccagggctcc ggggtccctg tgtcgggccc caacctgtca    219540
accacccggc caatccagca ggacctgggc cgccaagacc cacccctggc agaggatatt    219600
gacaacatga agaacaacaa gctggccacc gcggagtcgg ccgctcccca cggcagcctt    219660
ggccacgccg gcctgcccca gagcccagcc aagatgggaa acagcaccga ccccggcccc    219720
atgctggcca tccctgccat ggccaccaac cccagaaccg ccgccacgcc ccggacgccc    219780
aacaacccgg ggaacccatc caatcccggc cccccccaaga cccccgagaa tagccttatc    219840
gtcaccaacc ccagcggcac ccagaccaat tcagctaaga ctgccaggaa acccgaccac    219900
accacagtgg acatccccccc agcctgccca cccccccctca accacaccgt cgtacaaggt   219960
gagaccctct gctctcacat cactgggcag gggacctggc gtccctggag ccagaggctc    220020
tgctgagtga ccctggactg tgaccccatc tctctggcct cagtctcctc ccctggaaaa    220080
tgggcatagg cgtagtttcc taccccacag ggctgtggag ggtcagtgaa gataatttgt   220140
gcacagtgcc tggcacgggg ttgtgttcag tcggttagc aatatcttct acgtccttcc    220200
ttcccaaggg gagccaggaa gccacccccat ttgaggagca ataggtcct ctgatggaag   220260
cttgagggg tcagatgatt gattctctcg gcccagcact gtccaaaaga aatgtaacac    220320
aggccacatg caaatgtcag tttaaactct ctagtcgcca cattaaaaaa ggggccagat    220380
gtactggctc atgcctgtaa tcccagtact tcaggaggcc gaggtagagt gagccaagat    220440
ggcacctctg tactgcagcc tgggtgacaa agcgagactg tctcaaaaaa aaaaaaaaaa    220500
aaaaaaaatg gtgaactgct gggtggatta tgtcttaagt tcatctagtg tcagttctat    220560
gtgagagatt ttcatgagtt tgctggataa aggcttcca tggtcctgag acctaagatc     220620
ctaaggtctt gtcactgtgc ccattttata gatgtaggga ctgaggctca gagaggctca    220680
gcctgcccgt gggcacataa gcaggctggg tgcagaatg gaagctccag aggctgatgg    220740
ctcctccccc tgagtcaaga gaggggtgct aatgggggca tgccatgcag tttatgggag    220800
gtctcagtat ttctatctgt tcagtgggtc tcttggcact ctcccctacct gcctgcaagt   220860
gagggtgtga aggtccaacg aggatagggg caggtctgtg ttaatatccc atgagggccc    220920
caccgcactc aaggctatag agtggttgag agcaggctct cgggggccag gccgcctggg    220980
ttccaaatgc cagctctgcc acttcctgct gtgtgactt agacaagtca ctttacttct    221040
ctgtgcctca atttcctcat ctgtaaacag gagatcagaa tatatcaacc tcagggctat    221100
acaagggttc agtgatgtca taagatgcct ggtatataca gcaggcactt tagaaatgtc    221160
agccgcttct tgcctgccct gggagtacac aggagttccc agagacttgt gggaaattgt    221220
ggaggggagcc ctgtgttggt tcttgtccca acagtgaaaa aaaacgccaa cccagaccca   221280
ctgccaaaaa aagaggaaga gaagaaggag gaggaggaag acgaccgtgg ggaagacggc    221340
cctaagccaa tgcctcccta tagctccatg ttcatcctgt ccacgaccaa cccgtgagta    221400
tggccccccag caagggcagg gggggcctgg ggctcccacc agggtggcgg aagtcaggcc   221460
agatagaggg caatgagtga gtgttgacca ccatgactgc agggatacct ttgaacaagt    221520
tgaaaatgga tgctccttcc gtaagtcagg taagatgatt tgtcacaata tactttgttg    221580
gaagagaccc ctgtcctgcc atccactaga aaatcattgt tatttatgac aataaataaa    221640
caaatttgtc ataaataaac aaataaattt gtccctaaaca acaaataaat ttgtcataaa   221700
taaacaaatc ttcactgtga tgtaagaggc acccccttag aaatggctgc cttgtgcagt    221760
acacagcctg aacaactgca cgtggcagca ctaggacctg aactctgttt ctaacctaga    221820
ctctgtaagg gtttagattc tgggcggata tgtctgagt tccatggcct tctgtcttgg    221880
gcatctttga aatggataga ctatttaggg gagaaattta tccatgaat gtcgtagtgg    221940
ctcggaggtt gttttagaat tgaatgtctc ccagggtatt ttcttgaaag cctgaccgct    222000
caaaatgctt cttgacaatg aaggatcatg tcagataaga tgggggagaa gctgcttttct   222060
ataatctgcc tcttggcaac tcaccctggg tagtaataaa taaaagtacc tttaaagtac    222120
ttttttattt agttgactta tcgattttac taaggaaaca cttatgtggt atctactcag    222180
tgccaggcac tgttctgagt gccttaaaat ttttttttaat ttctctgagg ttgttactat    222240
gcttagctcc atttgacaga tgaaaaaact gaggtccaga gacgtgaatt cacctgccca    222300
aggtcacaca gcaagccagt gggagagctg gagtttgagc ccagacactg gctctagcct    222360
ccttgttctt aaccactcag ctctgctgcc attcacacaa ccttatgaac tatttattat    222420
tggctccact tattaagagg ttaactggca catcccattg gcacattcaa ggctctgata    222480
aggcctgcaa ttcataattt caataactaa ctttttggag ccccatcatg gagccaggca    222540
taaattaagt cttgggtctc atgatttttgt gaagtaagca ctagtattac ggctatttta    222600
cagatgaggg caccaaggca cagaggggac aagtaacttg cccaaggtca cacagctaat    222660
ttttaaaaag aaagaaagaa atctacttaa cccatagatt cacaatattg tttggccctg    222720
ggacatttaa tatcgaaaag cctttttatc tcctacagaa ttaaggaccg tattcttca    222780
acctagcttg gggatcaaga tacttcaaga gggtcgtttg ggagtgatag gaactttgct    222840
aaacagggca tgtgaatgtc ttctctcacc gaggtcccct ctgccttctt ggggttccag    222900
gacccagaga gggcccccac ctggaggagt ttaatagttt gttgtgtagg aggccttggg    222960
ggttggagat ctcagtagtg gtaggtaaca tgagattatg gaagaaaagg gtttgtgagc    223020
ctgtggctg agtggacctc tgcacgccca tctgtctcca acagccttcg ccgcctgtga    223080
cattacatcc tgaacctgcg ctactttgag atgtgcatcc tcatggtcat tgccatgagc    223140
agcatcgccc tggccgccga ggaccctgtg cagcccaacg cacctcggaa caacgtgagt    223200
cccacagagc acacccctcc ctagcctggc tgctctgcct caggccactt tctcctgcat    223260
ccaaaatgct cataggtagg gtgggatgtt gggtcaccc ctaggcatag cccttatggc     223320
tgcggttga gaggggaagc tctgattcct tgggagtgct cttgggagca agacattcct    223380
tgaggcagtt tctctgtgag cctggtgggg tggaggtggc ccagagtgac tggggctgaa    223440
aattgctgga ttctctcaatg gaggcgtgag actagcagga tatggatgtt gcacattctc    223500
tacatggaat agggggttta ctgggcagg gcggtgctc agaggtggtc ccctccgcag      223560
tagacatttc ccttttgtaca cgaagctttg aaagaaacaa ctatttggct cagaaacaca    223620
gcctaagctt ttggttttta tgaaagcaag ccccctttgcg gatggtgggt ctgttgacaa    223680
```

```
cccctgttaa ttgagcactt gctgtgtccc aggaagaaac tcagcatgca gtatctcatt   223740
taatcctcac aatgcgcccc cccaaccccc cgcccaggca tccccatttg acagatggga   223800
aaactgaggc tcagggaat gagagagtgg taagtggcct gtccagggtc acacagcaga   223860
attccaactc tgcatccccc aaagctccca ctgcttcccc caactgtctg catttactaa   223920
tcacctactg tatgctacgg atgggtgtgc atagccccct tgagtcctga caagcaggaa   223980
tgagtgcatg cttgtggttg agatggggaa accgaggcac caacaggcaa gggcgtgcct   224040
cagtcatggg ctgcgggcag aggcttgacc ccagggcctg gtagagggtg gactggtggc   224100
tcctgttttc ctccccagct ccctccccca acccttccct cccaacccag agccaaaaaa   224160
gtgtgttttc tgctggtcca aggctctgct gccctggcta agtaggttag gacccaggca   224220
aagctggcga gccccatccc tcaagcccgc ccacagctta ccatgcactt tcccttcctt   224280
cccaggcctg gcaggccccc ctggggacct gatgggggag atggaaggaa ataattagaa   224340
cgcagctcct ggaggaagct agagccagtg ctcagcctcc tcacagtccg cttagttgct   224400
tcccgcagcc tggtttcccc cagggggcctc caggagccag gcgtggggag gaggtgtccc   224460
tggaggggtc cacaaacccc ctgctgacgc gaggatgctg aagaaggcgt tgccttcggc   224520
agggagggca caggcatgga tgatccaggg ggcacgggaca ctcccagggc tgaagggaat   224580
ctaggcagtg ctcagaccag gccccaggga ctgtttgcaa agagcgttca gctcccggc   224640
ccctcccctc gtccatctcg cagtcgaaac ttctctacaa gaacactgtg gccccataac   224700
gttcacacca cgtaaccacc atccagggca agaaatagaa caaaaacgcc ccacgcggca   224760
tgtgcctcct cgatccccca cccccaccgc cttctttccc tctagagctg ctggggacac   224820
tgtctggaga catttttggt tgtcacgaca ggaggggga ggtgctcctg gcatctggtg   224880
ggtggaggcc agggatgttg ctcagcaccc gccgatgccc aggacagccc ccactctaga   224940
ggatgatcca gacccaaatg tccacagagc ccagcttgag aaaccctgcc ttaccggtaa   225000
ccacgacccc agcttctgga atgagcgttt ttggcttctc tcttttttccc acctgcacag   225060
gcttttttttt tttttttttt taagagacaa tgtctctctc tgtcgcccag gttggggtgc   225120
agtaacgtga tcatgcgctca ctgcagcctc aacgtcccgg gctcaagtga tcctcccacc   225180
tcagccagca aggtagctag gaccacaggc atgcaccacc acacccagct aattttttaaa   225240
tgcttgtaga aacgggcctc gctatgttgc caggctggtc tcgaactctt gacctcaagc   225300
aatcctccct cctcagattc ccagagctct ggaattacag gcatgtaatt ccaattctta   225360
catgcctgta attggccaac actggccaat tcttaaaaac tgaatttatg tttgctcttc   225420
tgtaacattc aataaatgag aacacttctat gcttcgcatt aaatgagtac atgttgcttt   225480
tgcaggattg atgggcattc tttttttttt tttttttttt gagatggagt cttgctctgt   225540
cacccaggct ggagtgcagt ggtgcaatct tggctcactg caacctccgc ctcccgggtt   225600
taagcgattc tcctgcctca gcctccagag tagctgggac tacaggcagg cgccaccaca   225660
cccggctaat ttttgtattt ttagtagaga cgggggtttca cactatgccgc cagactggtc   225720
tcaaactcct gacctcaagt gatccgcccg ccttggcctc ccaaagtgct gggattacag   225780
gcgtgagcca ccacgcccgg tcaatgagca ttctttatga tgctgttttg agatttactg   225840
tgtggcatgg gatgtgttat ccatcccctg ttgacagatg ttttgggttgt ttctaagtgt   225900
gaatactgtc cccatgccac gccccctcaac atgtttcctg agtcacctgg acagtaattt   225960
ctccaggagg ccagatgcag tggctcacgc ctataatccc agcacttcga gaggccaagg   226020
tgggagcaat gcttgaggcc aggagttcaa gaccagcttg gcaacatag tgagaccccc   226080
acctctacca aaaaaaaaaa aaattttttt tttttaatt aaccgagcgt ggtggtgcac   226140
acctgtggtc ccagccactt gggaggctga ggtgggagga tcacttgggt ctggaaggtc   226200
aaggctgtag tgatccatgt tcataccact gcactccaac ctgggtgaca gagcgagacc   226260
ctgtctcaat aaataagaat tcctccaggg tataaaccaa aagcgaagtt tctagagcat   226320
ataatttgca agtggttggc ctcagtaaat gcagcttgaa tgtttattgg acaataaaca   226380
cagtgaccct tgggaggcc aaggcgggtg gatcacctga ggtcaggagt ttgagaccag   226440
cctggccaac atggtgaaac cccgtctcta ccaaaaatac aaaaattatc tgggcgtggt   226500
aacacacaac tgtaatccca gctactcggg aggctgaagc acaagaatca cttgaaccca   226560
ggaggtggag gttgcagtga gccaagatgg cgtcactgca ctctagcctt ggcgacagag   226620
cgagaccctg tctccaaaat atatataaat aaataaaaat aaacacagtg ggccgggcac   226680
agtgggccgg gctcgcacct gtaatcccag cactttggga ggccaaggtg ggtagatcac   226740
gtgaggtcag gagttcgaga ccagactggc caatatggta aaacctggtc tctactaaaa   226800
atacaaaaat tagccgggcg tggtagcatg cgcctgtaat cccagacact tggaggctga   226860
ggcagaagaa ttgcttgaac ccgggaggca gaggttccag tgagccaaga ttgtgccact   226920
gcactccagc ctgggtgaca gagtgagaca ccatctcaaa aaaaaattaa aaaataaatg   226980
aacgcagtgc cccttgcacc agtagctcat gggaactcct gttcttccac atccttgtca   227040
acacttggta ctgtcgactg tttcatttgg ccgatctgct gggtgtggag tgagatctta   227100
ttggggttgt gcttggcatt tccctgtaat gaatgagatc aagcacttttt ttggattaga   227160
ctgagccaca ggaaataaca ttttcaaata gatgaaaaag atctaagtat taggaatact   227220
tgaacctaat ttattggtct tttgatttcc tcttgcacag cttattaaga gctccagaat   227280
tagattcacc tgaccccccac ggcctgccct ttcccagctc cctctcttcc ttcttttcctt   227340
ccattcattc ctttagtaag tatttgataa gcaactacta tgtgccaggt actgagcgag   227400
ccagggagga ttgacagggt atgagatggt ccctgcactc ccagagccca caaaccacca   227460
ggcctttgac caggctgtgc ccactgcctc gtgcacctga aatactctcc caccaccatc   227520
ccctctgccc acccaggtct ttcaagccaa tcccctgca ccagcccctc cctccaggaa   227580
gtcacctcac cctgacccca ggcactctgg tctctgattc ctcttcaagc accacatata   227640
acaggaatat aagttataac cacacagatc acagagccca gctcctccag gacccagtac   227700
agcccaact gttgatgcat tcattcaaca acatttctt gagcacctac tgtattcctg   227760
accctgtatt ataagctgga gacgccatgt tgacagacaa acatccctgt ccttgtgggg   227820
ctgacatttg ggtgggggag atggacaatg agattatcag taactacaac aaatgttcag   227880
ggagtgataa gtgccgggg gtgtggtggg cagagggaag gagagacttc gtaaagagga   227940
tctcaagcac caggagatgg aatttaaaca gccggtcagg ggagtcctca ctgggaaagt   228000
gttatttgag ctaagtcata aaggaggaga aagacggaat caaatgggat gtgggggaaa   228060
gcattccaga gagacgaaac aggctgtgca aaggcctga gggagaca tcttgggaa   228120
caaaggaag tgagcaaggg agagaatgag aggaagtgga ggcagggagc tgaatggtca   228180
gatcgtgcag gggcttgagg gcctcgggga ggacttgac ttttatccct gaatgaggtg   228240
ggagccacgg aggattgtaa gcaggggaag gatgtgcctg acttctttgg tgttcacagc   228300
gccctctggt ggccatgttc agtaatgctc agcccttgca gcttctgggt ggatctgatt   228360
tttttttttt tttttttttt agacagtctc tgtctcccag gctggagtgc agtggcacga   228420
```

```
tctcggctca ctgcaacctc cgcctcccac gttcaagtga ctgtcacgcc ttggcctccc  228480
aagtagctgg aattacaggc acacgccacc atgcccagct aattttttat attttttagta 228540
gacacggggt tttgccattt ggttaggctg gtctcgaact cctgacctca agtgatctgc  228600
ctgcctcagc ctcccaaagt gctgggatta caggctcgag ccaccgtgcc cagccggtgt  228660
ccacccatg tctagcacca gccagacact gtgccggcac accctcatct tcaggcctgg   228720
gtgacaccag aggtgtgcta tggtgtgtcc tggacagggg ctgggccaga ggacattgct  228780
cgtccaggca gaaacatcag gcctggggag gggcacagga aaaatcaacc taccctggca  228840
ggggcctggc cttgaagcag gaagagatgc cgtggcagga agttggcccc agtgtttaaa  228900
aaaaccacgt agcaactatt tctcgccag gatgcccagg aaagcaaggg tactggggga  228960
ttagatccat caccaagaag gatacagtca gccctgaact tctctggggc cgcttctaat  229020
ccactacagg gcttggggca aattttaaaa ggtaccttc ccgtggggtta gcgaactggc  229080
ctagtacagt gatttttttg ttaggatttg ctgccatctg ctggacaatt tcattcacaa  229140
catacaaatc tgcagtatga aaagagatgg gagggcccct tgtgcagtgc acgccctgcg  229200
caactgtata tagcagctgt gtttcctctt ctgggtagaa actctgctcc ccagtaggcg  229260
atcgttagtt ttaccggggc tctgctgaa caggccagtg atccactgct ctcttgcttt   229320
tatcccttac aggtgctgcg atactttgac tacgttttta caggcgtctt tacctttgag  229380
atggtgatca aggtgagtgc agattataag tgagaacaca cggtaatttt tttttttaag  229440
caagtgcagg gctgggcaca gtggatcatg cctgtaatcc cagcactttg ggaggctgag  229500
gcaggcagat cacttgagat caggaggttg aggccagcct ggccaacatg gtgaaacccc  229560
atctctacta aaaatacaaa aattagccgg gcatggtggc acatgtctgt aatcccagct  229620
actcgggagg ctgaggcagg agaatcactt gaaccctagg ctgcaatgag ccgatgtgga  229680
ggctgcagtg agccgagatc ttgccactgc atttccagcct gggtgacaca gcgagactct  229740
gtcaaaaaaa aaaaaaaaaa aaagagctgg gattccagga gatcctgagc ctccaagaat  229800
gcccccttg agaggatgag tctcccagag gattagaaat gcctggtgtg tttgaagagc   229860
agcaaggaag ctggtgtggc tgggcggagt gagagaacag tggggaaacg aaggacagag  229920
agatgagtgg ggaggtgagg gggcaccttg tgccgggaagt cacagagagg gctcttcggc  229980
tcttactttg agtgaggtga gggcataga gtgttctgag cagaggaggg acttgatcca   230040
ggtgttcaca ggtgccctt ggcatctgtg ggaagccaga ggacctgtga gcaggtgatc   230100
acactggtcc ccatgggcga tgacgggac aggatcaggc tggtgaccaa agaagaggtg   230160
agaagtggac agattcttgg aaggttctgg aaatagagcc agtgagtttt gctgatagag  230220
ccaccaatga gggatttggg acaaagaggc atcaaagagg atcccaaagt ttggatctaa  230280
gagccggcaa gccagagctg gcttccatca ggcaaagggg ggccgcctca tgggcaggg  230340
gctccccact cctccctgga gtcctctggc cactgcccat ccctgcaaga tgaggtggcc  230400
tcattggctt ccctgcctct cccgagagg ctagagagtg ggtggcagca cccagggtg   230460
gggatcaggt gggggttctg agcaccctct cttctccccc acagatgatt gacctggggc  230520
tcgtcctgca tcagggtgcc tacttccgtg acctctggaa tattctcgac ttcatagtgg  230580
tcagtggggc cctggtagcc tttgccttca cgtaagtctc ctcgcaaggg ttcctcttgc  230640
ctcttttccc ccaacccca gcctgggcca cacatcggat tacaggacat gttctcaggg   230700
tctagggatg gggtgttgg gctccgggga cgtgggagat atcagcatgc caccaggaag  230760
agcttgcgatg gcttttttgca tgatgtccat ggaggaagaa ggagaaggga ccccccctcc  230820
tgccaaccttt ctacctcctc acacagcaac gggcctcagc cacatcactg gcccctgctt  230880
gtgcagcttc ctgtagacta gcctcgccgg aacatctcat ccccctacta ctccacaagc  230940
gccgcccaaa ccgctgtctc tttggaaagt ccctaaagag acaatcagga aacgaatgtg  231000
catgagaatt ctgacccct ccctatgcct gaaggccccg tagttgtaga cctggtgact   231060
ccctttgtgt gtcttcact tctcctggca gtcctaggat tctctgccct ctgaaaggcc   231120
atgtgtcatc ctgcagctcc aagatggcgc cccagttgta ggcagccatt tcaggatggc  231180
acccaagctc ttagtagtca tcccaagatg gcatccaagt tctggtgtgc cattccaaga  231240
tggcccctga gttctgagct atcattccaa gatggcctct gaatttgggg tggtcattct  231300
tagatggtcc ctgagttcca aggtgacctt caagttctgg gtagccattc caggatggtc  231360
cccaagctct gggtggctat tccaagatgg ccccaagttc taggcagcca ttgcaagatg  231420
gccccctgagt tccaggtgg cccccaagtt ctgggcaacc attccaaggt ggcatccaga  231480
ttctgggtgg ctattccaag atggcctctg atttctgggc taccatgcta agatggcctc  231540
tggattcttg gtgccattc ttacatggtc cctgagttcc aagtggcct tcaagttctg    231600
ggtagccatt ccaagacggt ccccaagtct tggatggcta ctcgaaggtg accccaagt   231660
tctggggcac catctcaagg tggcaccta gttctgggta accattccaa aatggcaccc   231720
aagttctagg gcaaccattt caaaatggcc cccaagttct gggtgactat ttcaagatgg  231780
tacccaacag gtgagtggcc attagcccttt agggccctga tagcagactt agcagtacat  231840
tcctgaagtt gtagacattt ggagcgggat gaaaaatatc taatcagtct ttaatcaaga  231900
aacaaatctt ggggaccctg gctgtgccca tcatggtgaa tgattccctg acagggttttg  231960
aaaggatctt gacacattca ctcccatcgt gagagaatca gggcttcct cctgtgcctc   232020
tgcctctagg ctccctcctg agccaatctg gaggggccct tgaatggtct ccctcaccaa  232080
acaatgagga cttggtttgt caggaggcc aaaatagtgg cccatttcca gtagaagggc    232140
tgttaagtag gccacactta gattcttctc tgggaacaca atgaggtcaa gttgtgttag  232200
aacaaaaaat ctccagagtt tttgatgcc tcagagctgg agatgtatca tgaaggttgg   232260
gaggctgatt atacttctt ctcttttctct ttcactcctt cctcctcttt ctcctctctt   232320
tttgttcgtt tactcttttc tttttctctt ctcctctccc tccccacatc cttccctctc  232380
ctcaaagctt ttcagtgtct atttgactac tagagcaatg cacggtggct tacacctgca  232440
atcccagcac tttgggaggc tgagacaggc agattgcttg agccaggag gccaagacca   232500
gcctgggtaa catagggaga ccccatctct aaaaaaaaaa aaaacaatt agccaggcat    232560
ggtagtatgc ctgcactagc agctacacgg gaggctgagg tgggagaatt gcttgagccc  232620
aggaggttca aggctgcagt gagccgaaat cgcaccactg cacccagtc tggggaacac   232680
aggaagaact tgtctcaaaa aaataaaaag tttaaaaat taaaatcaa tgaatttgct    232740
atttagaata ttatgcttta tatggttact gaataatttt aatagtgatg agtacaaaaa  232800
aaacaggttt agcaagctgt tctgtaggtt aaaaagtaaa taaataaaaa attaattaaa  232860
caaaatacaa tgcacatcaa attagggggac aaagattgtg acgaataaga caaggagtcc   232920
atgtctttaa aatatgaaaa gcagttacaa atcaataaga aacactactt ctcaatggat   232980
aaatgggcaa aggacataaa cagaaatctg atagaatgct ggcaactagt aaaaatggag  233040
gtaaatcaac ccttggaatt cagagaaatg taaaataaaa acgagataca attcattccc  233100
tatcaagtta gcactgttcc cgccgcaccc ccacacacac acaaaaaatg attttttag   233160
```

```
ctaataaaca gcatatataa gaatgtatta taataggctg ggcacagtgg ctcacgcctg  233220
taaccctagc attttgggag gccaaggag  gggatcacc  tgaggtcagc agttcgagac  233280
cagcctggcc gacatgacaa aaccctgtct ctactaaaaa atacaaaaat tagccaggca  233340
tggtggcgga tgcctgtaat cccagctact caggtgggta aggcaggaga attgcttgga  233400
cccaggagat ggagactgca gtgagccgag atcatgccac tgcactccag cctgggtgag  233460
aaagcaagat tttgtctcaa aaataaaaaa aggaatgtat tataataaaa tatacttttc  233520
tcccctcta  tcacctattt aagcaggtcc ttcaagttgt caggtagaca tcatgctatg  233580
agaaaattta aatcctgaaa agccagaatg ttttaccacc ctcagcctgg aatgaatcct  233640
tctcctatgg aaataaccta cgggtttctc caccccctc  tgccttcag  cccttcct    233700
ccctctcccc tccttttctt tctccctctt tctcttcctc ctttccctc  tcttccctct  233760
ctcttcttcc ctctctctgt ctctttctgt tcgtctttct ccttttaccc cctctcagtt  233820
tctatctttt tattttcctc tttctctctc tctctccctc tctttctctc tcactccctg  233880
cactgttgat gacctatgtc cttgggtgat gtgggcctcc cctggaccgt gtagcttgga  233940
gaaagctgac cctctgtcat cggtctggca acagggactt ggccccccta ccctgcattc  234000
tgatgaggaa tggtattcag acaaaggcag atcccaggac acaggaggac atgctcaggc  234060
agggaccccc gcccctttcc tctgggcaa  ggtctgctca gcagcctcca agattcctag  234120
ggctcaagag gtggcaggta gctcagggca ctagggcagg cagtgggtg  aatatgtcac  234180
tcatatccac ctgtccacac acaatgctta ccttggccac ctgtgcccag gggaatgggt  234240
tttatcctgt gaatcctccc agtgaccacc actgagtgtg gcacagataa atggtaccaa  234300
gcccaagctg ttcaggtctc caatgtcact ttcctctcag acctctgttg tagctgacat  234360
actgtaatgc tgaggagggc cgggcacagt ggctcatgcc tgtaatccta gctctttcgg  234420
aggccaaggc agatggatca cctggggtca ggagttcaag accagcctgg ccaacatggt  234480
gaaaccccag gcaacatggt aaaaccctgt ctctactaaa aatacaaata ttagccaagc  234540
gtgatagcag gcgcctgtaa tctcagctac tcgggaggct gaggcagaag aattgcttga  234600
acctgggaag tggaggttgc agtgagccaa gattgcacca ctgcactcca gcctgggcaa  234660
cagagcaaga ctctgtctca aaaaaaaaaa aaaatgctga ggaggtgact gtcccacctc  234720
catcctccga gttgaccatc acaatttagg gaggggaatg acctacaaag gacccagaag  234780
caagcctttc aattgttgag cttttgccat tatgggccat cgtttacaac atgctgtttc  234840
taggttctct ggaggtaaaa ttagcctcct cttttaaaca aagctaatct gcaaaagcga  234900
accaaaaatt cttttccacc agagatcaat tagcagaatg agctgggtgc agtggctcac  234960
acctgtaatc ccagcacttg ggaggccgaa ggcaggtgga tcacttgagg tcagggtcc   235020
aagaccagca tggccaacat ggtgaaaccc catctctact aaaaatacaa aaactagctg  235080
ggtgtggtgg ggagggcctg tagtcccagc tactcgggag ggtgaggcag gagaattgct  235140
tgaacccagg aggtgaaggt tgcagtgagc caagattgtg ccactgcact ccagcctggg  235200
tgacggagca agactccatc tcaaaaaaaa aaaaaaaaaa aaaaaacagc agaatgattc  235260
ttttggggag ttgactttt  ttttaatttc tgagttttct ttttaaatat caagttatac  235320
aagggcattc aaattggcct acaactcaca ggaatttggc agcctgtttg cagagtcaag  235380
cttttacatt gttctcatga aattggtaca ggcataaagc cacccttcac tcttgaaaat  235440
ccattttgaa tgttgttgtt ttaattctta tgcaagaaaa ggatctggat agggatttca  235500
ggccatcctg tcaaccctgg caggcttgta gatcatgcag gaactgggac gtgtgagatt  235560
ttgccagtag gatcctggca agtgctgggg actctcccag ggttttggaa gagccgacgg  235620
acatgagtcc aacaggagc  atctttatat catggccgaa gggatgagag aggagaccct  235680
caaacctcac gcctaccaca ccctccccac cccactgtca agagtccatc tggtactgct  235740
gttcctcccc cagggcaggg ctgcaggccc agcacagctg gccaggtgcc ttgatcaagc  235800
cattcctgca cacctaagag ccaaactgct agaaaaccag aataggagct actgcttttt  235860
tccctaaaaa gttttggaat cttctccccg ttacaggttt ctggcctctt ttgcctgaga  235920
aggtctctca ccctatgagg acttttgctta ttgtcttttcc ttgttatcgg atagttggca  235980
cattggaagg agcatggatg ctctgaggtt ctcagcctga gcgctgaact ctccaccgcc  236040
cccccacccc ccacccccagg gtcctctgct tatttccttt ctggtctttt aacttgcttt  236100
gtctgtcctc tgtgcatatc ccctcataga caaggctgag agcccacaa  gtattagatt  236160
gaccttattg ttttaagaaa ttgtccctcc aggtctgttt gatttctctc tagatgtgca  236220
agtcctttag cctctctgtg cctcagtttt tccatctag  atgaggaaac tgcggcccag  236280
agggactgtg gagggaagta agtccgacaa gatcactgag gttgggttca gctgtcagat  236340
gctacccatc tcccagccct gaatacgag  gctcacagtg agcagaatga tgctcagcag  236400
cctgccagc  ctgggttctt tgaggcctgg cagggctggg agatccaggg gaagggaata  236460
ggggaaggga gcataaggtt attcccttcc ttgttgaaag gaaccttgcc attctgcct   236520
gttgggtca  aagcaaggat tcttcccca  gtgctgtgat tgtggcctcg tctccgatat   236580
gggagaaaac tatccctgtg gtcccaccaa gggatgtatt gaagctcttc tgaagatgtc  236640
cacccctcct gcacctcacc caaatatctg tgtgtgtgtg tcctgctcaa ttcactgact  236700
gtgtcccttg tatccatgcg tctaccataa acacccccatt tcatgagcca tcacacgtgg  236760
tatcacgctc tgtgcccatg catcagggcg gccaactgac atttctcagc agctggcaga  236820
tcatgatcct gccctcaccg ccaagagtcc atctggcgcg ctgttcttc  ccccaaaggc   236880
aggaccgcaa ctggcagagc gccttgatca agctgctcct gcatacccag gagccaaact  236940
gtcaggaagc caaagatgga gccctcaggc tgctatctct tgatcctcat cttcaaaaca  237000
gcccccaccc ctgaaggcat tattttttctt gtgtatgatg aaatggaaag aagattagag  237060
tgcgagatac ccacacctgg gttgaatct  tagtctgtct tccagctgt  gtgcctgccc   237120
ttgggcaggt cactctttt  ctctaggcct cagcttcctc atctgaaaa  tggtcataat   237180
ggtgctgtct tcccataggc aaatgcagtg atgtccagaa gactcccata ttaaacctaa  237240
agtcagcaga ttaggcaaaa atcactgtca ttgaaaactc cctcaatcat ccgtaaagaa  237300
gctgggtgtg gtgtctctca cctgtagtcc cagctacttg ggaggctgag gtgggagaat  237360
cacttgagcc agggagttca aggctgcggt aagctatgat tgtgctactg cactccagcc  237420
tgggcgacag agcaagacca cgtctctaaa aatataaaat aaagccgggt gcggtggctt  237480
acgcctgtaa tcccagcact ttggaaggct gaggcagcct ggcaacagag tgagaatcca  237540
tcaaaaaaaa aaaaaaaaaa aaaaaagta  gaatctatat gattctacgt atgcaataat  237600
tcctagatac actgaatttg agaacccaa  gtcagactac aggaaaagga gatgaggggg  237660
tgtgaggag  aatccacttg gaatatttgt agacatttaa accattctgt gttttaaaaa   237720
atatcacagc cgggcgcggt ggctcacacc tgtaatccta gcactttggg aggccaaggt  237780
gggcggatca cgaggtcaag agatggagac catcctggct aacacggtga aaccccatct  237840
ctactaaaaa tacaaaaaaa attagctggg cgtggtggtg ggcgcctgta gtcccagcac  237900
```

```
tcgggaggct gaggaaggag aatggcgtga acctgggagg cggagcttgc agtgagccga    237960
gatcttgcca ctgcactcca gcctgggcga cagagcgaga ctccgtttca aaaaaaaaaa    238020
aaaaaatcac taacttccag aggggtcgtg gatgggaaaat tccatagagt ccgcttggcg   238080
acagggtttc cgccattctg atggcggtca agtctttcta acctggatct ccagtcattg    238140
ttgaaggcgc ctaatgagcc ccaagcctga ttccaatgaa tcacgagagg accagctgct    238200
aggtgctgat agcttccccc aggcccgcat ttgctcagag ggcttcagag ttgcttctaa    238260
ttccatccca agtcagaact ctttgctgac ccctccttc ataaagagca aagccaaggc     238320
catagctttt gttaatcaaa catcagaatt ccacagacct gagttggttg gttgtttgtt    238380
ttaagagaca gagtcttgcc caggatgcag tggctcacac ttgtaatccc agcgctctgg    238440
gaggcctagg caggaggatc acttgagccc aggagtttga gaccagcctg agcaacataa    238500
tgagaccccc gtctctacaa aaaatggaaa aatttgcctg tatttccagc tacttgggag    238560
gctaaggtgg gagaatcacc tgagccctgg aggttgaggc tacagtgagc caagatcccg    238620
ctactgcact gcagcctggg caacagaggg agaccctgcc tcaaaaaaaa aggagagaag    238680
gagagagaca gggtctccct atgttgtcca ggctggtctc gaacttctgg cctcaagcaa    238740
tcttcccaac tcgtcctccc aaggtgctgg gattatagct gtgagccacg gcacccagtc    238800
tgggcctgtt ttgcagatga ggataacgag aggcagagtc aggattcaaa cccaggtccc    238860
ctcaacttca aagctcacaa ccttttagac attctaaaac cttgcagctc cacaacgcct    238920
ggagaagagg ggtttctccg gctcttggca gtgacttttcc gtggtgaatt caccttttggt  238980
aactgacagc tttgcagctg tcctgctacc tggaaatttg gctttcttag tgctttcttg    239040
ggcagtgcca ggtgcctgcc aagggcgggg gactgaatgg aggtgggggc ggcttccaga    239100
tggaaggatg gacatcggcc agcgccatga gcctgaggct ccccccaactg ctgcccgggc   239160
gggactcggg ggtgctcagg ggtgctgtg tgtacgtgcg tgttctgtgt tcttttttct     239220
gaggccactt acgatctgtc tctccctccg atgccacatc accaggagca gtacacggta    239280
aagtctctct ctatctttct ctctctctct cttctctct ctctctctct catattctgt     239340
ctctcgtgat ctgtccctg gtgcagcctc gttagttctg ggcctgtttc tgtggccttg     239400
tgtccttgct gccgctgtcc tgtcgcttca aatgaccaga actcactccc tgcgaaggag    239460
gcatcccaaa gggtcttgcc aatgcctccg cccatgcccc accagttctt cagagaaca    239520
gaaggggcag aggttcagtt tcaataggca agctgggtgg agcagttatc agaagcaatg    239580
aaagtgggcc agacacggtg gctcacgcct ctaatcccag cattttggga ggccgaggcg    239640
ggtagatcac ttgaggtcag gagtttcaga ccagcctggc caacatggtg aaaccccatc    239700
tctactaaaa atgcaaaaaa ttatctgggc ttggtggtgc acacctgtaa tcccagctac    239760
ataggaagct gaggcaggag aatcacttaa acctgggagg tggaggttgc agtgagctga    239820
gattgcacca ctgcactcca ccctgggtga cagagtgaga ctctgtctca aaaaaatata    239880
taaaataaat tgaacaataa aaaaataaaa tggccatgaa atcgttttca gatgaggaga    239940
tgcagaatgc ccatggagac atgctcccaa ttgtcacttg tttttttctat caacatgtat    240000
gccagttcca tgtgcaacct ggatgtacag ttccttgact ttttttctat caacatgtat    240060
tctaaagttc aatttcaaaa ggaaacttta gccaggtgca gtggtgcatg cctgcagtcc    240120
cagccatttg ggaggctgag actgaaggat cacttgagcc caggagttgg aggctgcggt    240180
gagctatgat cgtgccactg cactccccccc tgagattcca tctctttaat ttaaataaaa    240240
aaaaaggaaa ctatattatc cacttacaac cagcattgct aacctaagat aaatctgcaa    240300
ctgcaaaagt aaatgtaggc cagacatggt ggctcacacc tataatccca gcactttggg    240360
aggccgaggc aggtggatca cttgaggtcg ggagttcgag accagcctga ccaacatgga    240420
gaaaccccgt ctctactaaa aatacaaaat tagccgggcg tgatggcaca tgcctgtaat    240480
cccagctact cgggaggctg aggcaaaaga atttcttgaa cccggagcc agagactgct     240540
gtgagctgag atcacgccat tcactccagc ctgggtaaca agagagaaat gccatctcaa    240600
aaaaaaaaaa aaaagtaaa tctaacagaa accagacaat gttgttgcct tcaagctggg     240660
ctctttgtta aaaggaaaat tactaagtgt tagggaggtg ttaaaggcct attagcatct    240720
acctgaggct tcctttctcg caaaagcaga gcgtctgaaa gatacgtgga aaagaaactt    240780
aaagtataat aaaaaagaaa gaaagaaaaa gaaatgatta tgcccctctg agatccaatt    240840
atttaatctg tgccctgtt ctgcctaaaa ttatctcagt gactgtccaa cgtgtgtctc      240900
acacttgggg gcacagcctt gagatgataa tgatgatgtt agttttaaaa agaaaaaaaa    240960
aggttcagag ttctgaatcc tggagtatat ctctgcctag caggctaaaa tacaattatc    241020
gtctttgttc cctgaaaaat gaaaaaaatg gagtccttta aaaagcaaat ggtgtgaaga    241080
atgatgtttt tgcactggat actgagaccc atcgtgatgg gggtctctgg ggcagctctg    241140
ctcatgacct gggaggtcac tgtagggaga tgttttctag gtgacctccc cacccaaata    241200
ctccaaccgg aggcattcac gtgtcctgag accacacgcc aggcgcaggc taggggctag    241260
gacaagaatc aagattaaag gggaaatggc caggtcgcgt ggctcatgcc tgtaatccca    241320
gcactttggg agtcaaggcc agtggattac ttgaggtcgg gagttcgaga ccagcctggc    241380
caacacggtg aaaccctgtc tctactgaaa atacaaaaat tagccaggtg tggtgactca    241440
tgcctgtagt cccagctatt cgggaggctg aggtgggaga atcacttgaa cccaggaggc    241500
agaggttgca gtaagccaag atcatgccac tgcactccag cctgggcaat agagcaagac    241560
tccatctcaa aaaaaaaaaa aaagattaaa gggaaatga acacagagaa gagtagatta    241620
cactgtaagc ctttgaagag ttttctgtct aaaaccagag accgaagaaa caaacaaaga    241680
ttaactccga aatagcacat aggagctggc aggagcaga ggtaggcagt caggaaatgc     241740
tgtcggaggg agcaacaggt aatttgggct ttgaggaccg ggtagttctg tgactggaga    241800
agtggaggaa gggcatttct agcagcggga acagtatatg cataagcaga cagaggcaaa    241860
agaatgtggc tggggcttga gatatgtagc cataaatggg aatgcaaagg tgaaggtaag    241920
ttggactaga tttttcaagag cattgaatgc catgcccaga agtttgcact tgctcttctg    241980
agaattcacg tgctccagaa gaattctgag caagagaaga agtgacaagg tcattggctt    242040
tagccactgt gtgcataaaa catgaagaa aaggcaggga atgaggagca agttgggaga     242100
cgggtgaggg gggatggcac ccaggaatgg atggcgggat gttaaggaag gtgacccact    242160
ggggatgggg atgggggatag agggcaggca gttgaccatg actctcaggt ttctggtgtg   242220
gacaactgga tgggtcatga gtgccatgaa ccacaagcta ttcatggtcc cactcaatac    242280
cctcctcttg gggggcctga gtcatggttg gccaaggggtg tctgtgcagt cctctctggc   242340
gcattgctaa gctcagttcc aacagaccct ggactgaact tctgtgcagt cctctctggc    242400
aaagatgggc tcagagaccc ttggagcaat gcagcagaga ccatggcagc agccacatca    242460
gcatctgaaa acagcggcac ccggttattt tccctccttc agactcaggg aatatggtgg    242520
gggagggag atttggtata agggccactt taagtatctt ccagaatccc attggaaggg     242580
ggagaaaatc ccatttttttt aagagcccac tgataccacc tttaaaaaga atacacaggg   242640
```

-continued

```
ggccaggcgc agtggctcac acctgtaatc ccaacacttt gggaggccaa ggtgggtgga 242700
tcacctgagg tcaggagttc aagaccagcc tggccaacat ggtgaagccc catctctact 242760
aaaaatacaa aagttagctg ggcatggtgg cacgcacctg tagtcccagc tacttggaga 242820
ggctgaggca agagaatcac ttgaacctgg gaggtggagg ttgcagtgag ccaagatcat 242880
accattgcac tccagcctgg gcaacaagag tgaaactcca tctcaaaaaa aaaaaagaat 242940
acataggggga ccactaaact cctagaccaa gggcttttt gaaaatagct gtgaccaggt 243000
gtagtggctc acacctgtaa tcccagcact ttgagagggt gaggagggca gattgcttga 243060
gctcaggagt ttgaaaccag cctgggcaac atggtgaaac ctcatctcta caaaaagaca 243120
aaacaattag ccaggcgcag tggcgtgtgc ctgtagtccc agctacttgg gaggctgagg 243180
tgggaggatg gctttagccc aggaggcgga ggttgcagtg agccgagatc gtgccactgc 243240
actccagcct tggtgacaga gccagaccct gtctcaaaaa agaaaaaaga aaagctgtgc 243300
agaaatgggg gtggggaatc agccaaccc cttgtgctgg gtctcaggga cacccaatac 243360
agctgctcag gcccagccag atggcaaagg gccctcaacc aacctggga ccagaaccac 243420
aaaaagccac gtacttactg gctcccgagc ccaagcttaa caggtgaaat ggaccactct 243480
tcaccaggaa gggcagggct gtgccaagct caccccagac ttctaggcct gggagggtag 243540
ggtcccatgg agctgtgggc tgcccctac ccaacctgac ctctgcttcc tctcttccct 243600
tcttcccacc taaacattcc tccacagtgg caatagcaaa ggaaaagaca tcaacacgat 243660
taaatccctc cgagtcctcc gggtgctacg acctcttaaa accatcaagc ggctgccaaa 243720
gctcaaggtg agattgggag atggtggggt gcggtggggg ggactgtcag ggttatcatg 243780
tacagctgag caggttgtac actgctcaag gacaacacat taaaggaggt gctgataaca 243840
tcctagccat cgtgtatgga tatttgtatt attacaactt cccagcagat ggcagtaaag 243900
tgagctgacc taaaataatc tgtgtattat ggcagttttt ctttagatga agtgtcttgg 243960
ggttaagatc cttttttccta attcgcatga aggcatcata tggatttaaa agggtataac 244020
cgtgatctgg gaagcaggaa ctagatttct tgttccataa aatttgact tttcatctac 244080
ctattctagg ctctagtatc tcccattcca aaatagcatg aaccagcatt tcccaaaagc 244140
ctgtcattca aaaacatata tatatattaa gggaaataaa atccagtcat tagagcaccc 244200
actttcactc tatgcttcac ctgggggtcc ccagtattat ctcttatgta atatgtttct 244260
ttaaatcaag tcacacccgt aatccctgca ttttgaaaga ccaaggcagg agtgttgctt 244320
gagcccagga gaatgagacc agcctgggca acatagttag actctgtctc tactaaaaat 244380
taaagacaga aaacagatac tgttatgaaa atctaaccaa atatggctgc ctgcctaagg 244440
ctttgtgcat tgacaactgc tcttttcttgg ttaaagaggg aaaatgtcaa tggtaggtgt 244500
taacatggta gcaactaagt aaaaaatttct ccttcactca aaaggattga gagagttgga 244560
aaggaagtaa ctttgttacc ttgttttttct gtgttgggct cctgtatcac ttaaaagcat 244620
ctctggtatc ccatctggga gttttagatc catagaatgc caggattgag tccaactcct 244680
ccaacgctta tttctgaaag ctgggggac cttaccctag tgacttgact tatgaccttg 244740
cctgtaaaat gggaatgatc atggcagtat tttggtatga tgggccactg gaggcagaag 244800
gttgggcagg tccccagccc ctcatgtctc tgtcaactc caccccacag gctgtgtttg 244860
actgtgtggt gaactcactt aaaaacgtct tcaacatcct catcgtctac atgctattca 244920
tgttcatctt cgccgtggtg gctgtgcagc tcttcaaggg gaaattcttc cactgcactg 244980
acgagtccaa agagtttgag aaagattgtc ggtgggtctc cactttccag cacattccca 245040
ttggaaccag caggtgggca ggggggaagt ggctagaggc attggccact tgggctcaga 245100
gactggaaa gtgatgagcc ttgaagtga ctcagttgca accagcttgg atcttgggta 245160
gaaagaaaac cggttttaga atttgatca ccacccagga ccacagaatg agtcataagc 245220
aaattgattg acctttcagc caccgccttt gtcatgtgag ggatattaat acacatccac 245280
agttccttac ttgaaatcgt tacaggcaga tgtgtttcaa agttgagaat atttgagat 245340
tcccatgtgg gacatgacac cctcagctgg gtctaaggca gccctataat caaacacaat 245400
atttctgcca taaaatgtgt aactatttac atcaaatggg gtaaataaca agtataaaga 245460
gcttcatgtc caatcagatc aggtttcatt accaaataag ttaggtaaga ggccaggtgc 245520
agtggctcac acctgtaatt ccaacacttt gggaggctga ggtgggagga tcacttgagg 245580
ccaggagttg gagaccaggt tggcaacat aatgagagcc catcctacaa aataaatttt 245640
aaaagttagc ggggcatggt agcacacacc tgtagtccca gctacccggg aggctgagc 245700
gggaggattg tttaaacaca ggagttcaag gctgcaatgc actatgatgg taccactgca 245760
ctccagcctg cgtgacagag tgagaccctg cctctcaaaa atatatcat ataggccggg 245820
cgcagtggct catgcttata atctcagcac tttaggaggc cgaggcgggc ggatcatgag 245880
gtcaggagat cgagaccatc ctggctaaca cggtgaaac ctgtctctac taaaaatca 245940
aaaaccctagc tgggcatggt ggcagacgcc tgtagtccca gctacttggg aggctgagac 246000
aggagaatgg cgtgaacccg ggaggcggag cttgcagtga gccagattg ggccactgta 246060
ctccagtctg ggcaacagag ccagactcca tctcaaacaa acaaacaaac aaacaacaac 246120
aacaaaata tatatatata tatatgtata tatatatatg tacacgcaca cacacatag 246180
tattatatgt gtgtgtgtat atatatgtat gtgtatatat agtgatattg ttaccagtgt 246240
aaagtggcat tttgcaacac atggtagcct gttgttatct tgatggctat ttattgaaat 246300
taggaggatg ccagatgtct ggataggagt ctggaactaa cccttgtttc ctgccttgaa 246360
aaggagtagc aacctcccctt agcctgatga acctctaaat gtccctatg tctctctgcc 246420
tcctcctaaa ctccctccac cccaccccca gcaagcctga ggctctcc ctgaggacta 246480
gaagttatca cgttggaaga gggtgctgga ccctgggtca gctctcccac caggagtaag 246540
gttgtgccat cacccatgga tttatctcaa agtagatgca cacgtcatcc cctatgaagc 246600
acaggaacac atggtggcag gatggggagt cactgcttcc caagcagtct aggctggtgg 246660
accactcttc cttttccctcc ccctgtctct gataaccaaa gacaagtgca agacagcccc 246720
tcttttcccat ttactaacag tcccactct ctgtggcaga gcaaataccc tcctctacag 246780
gaagaatgag gtgaaggcgc gagaccggga gtggaagaag tatgaattcc attacgacaa 246840
tgtgctgtgg gctctgctga ccctcttcac cgtgtccacg ggagaaggct ggcacagta 246900
agtggcccga ctgaaatct atccaggagg agcctgggg agcaggagga taagggcct 246960
gagagcttag caataagaaa ggtcttggag gccgggcatg gtggctcacg cctgtaatcc 247020
caacacttta ggaggccaag gcagatgtat cacttgaggt cagatcagct 247080
ggccatcatg gcaaaactcc atttctacta aaaatcccaa aaaaaaaaa aaaaaaaaa 247140
aaaaaaaagc tgccaggcat ggtggctcac acctgtggtc ccggctactc aggaggctga 247200
gacacgagaa tcacttgaac ccaggaggca gaggttgcag tgagccgaga ttgcaccact 247260
gcacttcatc ctgagtgaca gagcaagact atggcctccc cgccttcaaa aaaaaaaaa 247320
agtgaggctg aatcatggac ttagtcttta tttaaaatttt tgagccactt gtggtggctc 247380
```

```
atacctgtta tcccagctac tcaggaggct gaggtgggag gatcgcttga gcccaagagt    247440
tcaaggctgc agtgagctgt gattatgcca ttgtactcca gcctagacaa cagaaggaga    247500
cccctatccc tgaaaaaaaa aaagaagaag aaattgatat ttgttcatca tggactttt     247560
gcattaattt tgatttttta aaatattgga gcaaaagatt atcttgatta ctgagatttt    247620
cagtacccc  ttaatttgca cccaaaacaa atgcctccct ccctccacctc gtccaagtaa   247680
tggtctttct ctcagaggtc ttggaaatgc caggctgaca gcttggtaga ttccagcatg    247740
tgccctcagc atcctcacct ccctccctct ctcagcaaat atgccaacct gaacatgccc    247800
tactacccac tctcagacac atccagtact cacacatgtg ggaataatgc taacccacaa    247860
ggcacctttg agcaaagttt ttttaaacac ctttctcaac agacttcatt tccatctgtc    247920
tgaaaatcat cgcaatagac ttaaatgatt ttgttcaaac aaggcactga aggaccacct    247980
gccaaaaaat tgtcatcatg aatacacaaa tctatcatgc ctatcatgtg aaggtatcgc    248040
ttagacacag agcctttgag cagtgtgcaa cctgcactac tgtacagagc tgctgtgcac    248100
ttacccactc tcatatatat ccccattgta cctcctgagc acccagcacc acctgtgctc    248160
aaatacccac tctacatgca tacacccacc tctactccct ccattgccac aacctgtctt    248220
taaatcccaa cttggccact tataagtggg tggtcttcag cacgtccctt taaattgctg    248280
aacctcaagt tcctcatgtg caaagtggag ccagtaataa cctccctggg aggggttgctg   248340
agccggtggg gatgaattgt tgaatattgt ttccagcaca cagcaagccc ttcatgcaca    248400
gcagtagaaa tgactgacat tggccaggcg tggtggctca cacctgtaat ctcaacagtt    248460
tgggagaccg aggcaggtgg atcacctgag gtcaggagtt caagaccagc ctggccaaca    248520
tggtgaaacc ccgtctctac taaaaataca aaaaaattag ccaggcttgg tggcgcatgt    248580
ctgtaatccc agctacttgg gaggctgagg caggagaatc atttgaaccc gggaggcgga    248640
ggttgtagtg acccaagatc acgccgttgc actccagcct gggcaacgag acgaaactc     248700
catctcaaaa aattaaaatt aaaattaaga aataactgac attgttgtca gcctttcaaa    248760
aaacagcgac tacttaaatt tctttttcat ttccctctgt tcctgttctg ccatctcact    248820
tccaccctc  ctccaccttc ctcatcaccc cttgggtccc tgtctctctc cttcctgccc    248880
cttccctctc cctgcccccat tccttgcagg gtcctcaagc attcggtgga cgccaccttt   248940
gagaaccagg gccccagccc cgggtaccgc atggagatgt ccatttttcta cgtcgtctac   249000
tttgtggtgt tcccctttctt cttttgtcaat atctttgtgg ccttgatcat catcaccttc   249060
caggagcaag gggacaagat gatggaggaa tacagcctgg agaaaatgaa ggtgccactt    249120
ccaattccat ctgtccttta aaaactgggg acacacacaa actttaaaac acacacaaca   249180
cccaggaacc cctttctagg ggtacctggg ggagggaaca gaagcattgt cccaaccgaa    249240
tccagtcttc agggcagccc ttcatggagt ttccagagga aacacatcat atagtgtatg    249300
tatcagtcag tttagactag gttatgccgc agtaacaagc aaccccagat ttcattgcca    249360
aatatccaca aagggactta tttttttgctc acactgcatg tcaacatcag ttgtggatct    249420
tgccatcttt attctggttc ccaggctggc agagcagcag agcagcctcc ctctgagatg    249480
ctccagatga aaaagagagt atgtcagact gaggttcagt tcttcaggct tgtgctcaaa    249540
aattacacat gtcacttctg ctcacatttc atcagccaaa gcaagtcaca catccattct    249600
gacatcagtg gagtgggcaa atacaatctc ccctagcgaa gggtggtgaa tatttatgaa    249660
tgaaaagcca agccaggtgt ggtggctcac acctgtaatc ccaacatttt gggaagctga    249720
ggcaggagga tcacttgagc tcaggagttt gagaccagcc tggccaacat agcaagaccc    249780
catctctact acaaatcaaa aaaattagcc aggcaggatg gtgcacacct ttagccccag    249840
taacatggga ggctgaggtg ggaggatgct tgagcttggg agttcgaggc tgcagtgagc    249900
tatcattatg ccactgcact acagcctggg caacagagca agaccctctc tcaaaaaaag    249960
aaaaggaaag aaaatccagt cccctgtcta ccagagagta tagacatgac tctttgcctc    250020
tctggcatca tccaagctaa atagaggacc tagaatatat cctctgctcc cttgacccctt   250080
aagacttaat aaccactatt cctccttctc tctccctcaa agagaaggag aagacgcagc    250140
aaagtattca gtaagaaaga atgggctggg cgcagtggct cacgcctgta atcttaacac    250200
tttaggaggc caaggcagga ggattgcttg agcccggaag ttcaagacca gcctgagcaa    250260
catagtgaga ccccatctct atgattaaaa aaaaaaagtt ttaattagct gggtgtggtg    250320
gtgcacgcct gtagtcccag ctactcagga ggctgaagcg ggaggatcac ttgagtccag    250380
gaggtcaagg ctgcagtgag ctgtgattgc actgcactcc agcctgggtg acaaagcaag    250440
cccgtgtcaa agaaaaaaaa aaaaaagga aggaggagg  gagggaggga aggaaggaaa    250500
tgagagagag aaaagaagga gggagggaag gaagggagata gggaagaagg aatgaagaag    250560
aaagaaaggg agcgaaggaa agaaggaaga agagagaaag gaaggagaa  aggggaaagg    250620
aaggaggaa  tgaagggaag gaaggaaaaa ggaagtgaaa ggggagggagg aggaaggaa    250680
gaaaggaggg agggaaggag ggggaaggg  agggaggggg ggaagggggg agggagagaa    250740
ggagggaggg agggaaggaa ggagggagga aggaaggaag gagggaggga gcgagggagg    250800
gaggaagggg aagaaggatt aggcttcaat ttgatttggc acactcggta gctgtgtcac    250860
ctcaggcaag tggtttaacc tttctaagcc tctattttgg tgatctgcaa agtgaggcca    250920
ttgatagtac ccacttccca tgtttgtatt agccatgcaa taatgggaa  atgtcagtgc    250980
aagtttggc agttggtgac atctcaagca actgtagctg ttgggataag aaagcaatgg     251040
tgagaaggaa gagagagccc aggaatcctg gctggggca  agagaggcag agactcaagc    251100
agaagcactt gagaaccgcg acgagttaga cagagggtgc ccggtgtaca gccaccttcc    251160
tcctgcctct gccgctctca ccactggcct ctctcccgca gaggggcctgc attgatttcg    251220
ccatcagcgc caagccgctg acccgacaca tgccgcagaa caagcagagc ttccagtacc    251280
gcatgtggca gttcgtggtg tctccgcctt tcgagtacac gatcatggcc atgatcgccc    251340
tcaacaccat cgtgcttatg atgaaggtaa gtgcccccaca ccagccccca gcactactta    251400
accccacct  cgttcctgcc tctaccctga taaaatgaaa ccatctgcag tttcccagac    251460
agaccacact ctggatcacc tctgagattt gttcctgct  gttccctcta cctgacacac    251520
tgttcccacc actccccgg  ccagcttctt cttcccagct gtacctgcag acctcttcct    251580
ccagaaagcc ttccctgacc acccaagact gcttgaggtg cccatcttag caggcatcct    251640
atctttatgt cgcctgccac aaaaatctgc gtcaggttgc atgacagtgt cccccaccca    251700
tttatgatga cctcagccct gaattcctag aggccaacaa ggatctggct cagacggaac    251760
aagaagctct ctataaatgt ttgattaatg aaatgagggc gcggggcgcg gtggctcatg    251820
cctgtaatcc cagaactttg ggaggccgag gcgggcggat cacctgaggt cacgagttcg    251880
agaccagcct gaccaacacg gagaaaccgc atctctacta aaaatacaaa attagccagg    251940
cgtggtggtg cgcatctgta atcccagcta ctcgggagg  tgaggcagga gaattgcttg    252000
aacccggag  gcggaggttg ccatgagccg agatagcgca attgcactct agcctgggca    252060
acaagagcaa gactccatct caaaaaaaaa aagaaaagaa aagaaagaa  atgagggaga    252120
```

```
aggggtaggt gaggaccctc aaatccccag ggctaaggag cggcttccaa aaaaaaactc 252180
tgaaaacctt tcaccctgtg ctttggactc caaagcgtgg attcaagccc agctcttcca 252240
tttaattcat ttacctttgt acaagcaacc agtgactttc tggggactca gtttccctgt 252300
caataaaatg ggaatgataa taagagcaca tttgccccct ccagaggagg tgagaggatt 252360
gaatgagaaa gttcatgcaa ggaccttagc tccttctcgg cacttcaaaa acgatcaata 252420
gtggccgggc aaggtggctc acacctgtaa tcccagcact ttgggaggtc gaggcaggcg 252480
gatcacttga ggccaggtgt tcgggaccaa ctggccaaca tggtgaaatc ccgtctctac 252540
taaaaataca aaaattagct gggcgtggtg gcgcatgcct ataataccag ctgcgtgaga 252600
ggctgaggca tgagaatcgc ttgaacccag ggggcggaag ttgcagtgag ctgagatcgc 252660
accactgcac tccagcctgg gtaacagagt gagactccgt ctcaaaaaaa ataaggaagc 252720
cggggacggt ggctcacgcc tgtaatccca gcactttggg aggccgagga gggcgatcac 252780
aaggttagga gatcaagacc atcctggcta acacggtgaa acgctgtctc tactaaaaat 252840
acaaaaagtt agctgggcat ggtggtgggc acctgtagtc ccagctactt gggaggctga 252900
ggcaggggaa tggcatgaac ccaggaggtg gagcttgcag tgagccgaga tcgcgccact 252960
gcactccagc ccgggtgaca gagtgagact cctcaaaaaa aaaaaaaaaa aaaaagtata 253020
attcagccaa gcacaatggc gtatgcctat agtcccgact atcaggaggc taaggtagga 253080
ttgtgagttc aagcccagcc tgggcaaaat aggaagaccc cgtctaccaa aaaaaaaaaa 253140
aaaaggttgg gggaggtttt tgttttttttg gatgtgaaaa gaagagccta gtccggccga 253200
gagcggggct ttcctgaact gtgcctccta ccagtgaggt tgctcagacc ttgcctgggg 253260
ctggagtgtt gcctggagaa cagccatgaa gctgcctccc cacttcccac ttcccacccc 253320
tgctcgctga cccctgctac tcctgcttct ttcccctagt tctatggggc ttctgttgct 253380
tatgaaaatg ccctgcgggt gttcaacatc gtcttcacct ccctcttctc tctgaaatgt 253440
gtgctgaaat tcatggcttt tgggattctg gtaagtacca ccttgggggct acagctatgg 253500
gcttgggaga agcccaaggg ggaacaatgg gtcctggatg atggtctccc aacgtggccc 253560
caagaacccc aacctcaagg gtggcttcag tatcctgcca gtggccacag atcctactta 253620
ggcattcttg tgtttgccaa ggagtcccag ggagacccaa cctgtgagtg ttaccatatg 253680
gctgcttatg tatccagttc ctcaaaatga tgggagtcat catggctggg agtctttagc 253740
atccattttta gagataagaa aactgaaatc aggctgggcg aggtgtctca tggctgtaat 253800
tccagcactt tgggaggcca aggtgggcgg atcacctgag gtcgggagtt cgagaccagc 253860
ctgaccaaca tggagaaact ctgtctctac taaaaataca aaattagccg ggtgtggtgg 253920
cgcatgcctg taatcccagc tactcggag gctgaggcag gagaatcgct tgaacctggg 253980
aggcagaggt tgtggtgagc cgagatcaca tcactgcact ccagcctggg caacaagagt 254040
gaaactctgt ctcaaaaaaa agaaagaaag aagaaaact gaaatcaggc tgagcacagt 254100
ggctcatgcc tgtaatccta gcacttcagg aggccaaggc aggaggatcg cttgaagcta 254160
ggagttctca accagcctgg gcagcaaagc aagcccccgt ccctacaaaa aaaaaaaaaa 254220
tttttttttta attagccagg catggtaact cgtgcctgta gtgccagtta ctcaggaggc 254280
tgaggtggga agatattttg agcccaggag gtggaggttg cagtgagcta tgatcatgcc 254340
actgcacccc agcctgggca acagcaagac tccatctttta aaaacaaaac acagaggtca 254400
ggcacagtga ctcacacctg taatcccagc actttggggag gcagaggcag gcaaatcact 254460
tgagcctagg agttcgagac caccctggcc aacatggcaa aaccccatct ctactaaaac 254520
tacaaaaaat tagcctggcg tgctcgttggg tgcccatgat cccagctact caggaggctg 254580
aggcaggaga atcgcttgaa cccacaaagt ggaggttaca gtgagctgag atcacaccac 254640
tgcactccag cctgagcaac agagcaagtc tcaaaaaaaaat aataataata aaaataaata 254700
tgtctttatt tttcaccagc cactaactaa attttaacat ttccttccat cttaaaggga 254760
gataacaaac ccttagtatt agtattatca acccttaata ttatcaacat gacctgtgtc 254820
acttataaac atcagatatt ttcatactgc attataagag ctgcagatac cttaacattt 254880
aatttgcatt catcattgct ttaaaatgtt gcttgtgatt aaacctacag ctagaatttg 254940
ttactcagtg ttttttttgtt gttgttctgt tttgttttgt ttgagacagt ctcgctgttg 255000
cccaggctgg agtgcagtgg cgcaatctcg gctcactgaa agctccaccc cctgggttca 255060
cgccattctc ctgcctcagc ctcccgagta gctgggacta caggtgcctg ccaccacacc 255120
tggctaattg ttttgtatttt tagtagagat ggggtttcac catgttggcc aggatgtgtct 255180
tgatttcctg acctcatgat ccgcccgcct cggcctccca aagtgctggg attacaggcg 255240
ggagccaccg caccggcct actcagtgtg ttaatggaga agtatattca ttgttagatc 255300
gccatttttta aaacttttt ttttttttg agacacagtc ttgctctgtt gcccaagctg 255360
gagtaccgtg gcacaatctt ggctcactga acctccacc tcctgggttc aagcgattct 255420
cccatctcag ccttctgagt agctgggact acagatgcac accagcatgc caggctaatt 255480
tttatatttt tagtagagac ggggtttcac catgttggcc aggctggtct cgaactcctg 255540
gcatcaagca atctgcctgc ttcagcctcc caaaatgctg ggattacagg catgagacac 255600
tgtgcctagc cttaaaaaat attttgatag ctatttttatt acaaaaggta acccttgaagc 255660
ccttgctatt ttgttatgca tttacaagcc tttatgcata aaataaaata gccagcacta 255720
ttctcacatg gccaaggttc atagcacaca cacaaaagta tagttggctg agtgcggtgg 255780
ctcacacctg taatcccaac actttgggag acagaggtgg gtggatcatg aggtcaagag 255840
atccagacca cccttgccaa catggtgaaa ccccatctct actaaaaagt acaaaaatta 255900
gctgggtgtg gtggcgcatg cctgtagtcc cagctactcg ggaggctgag gcaggagaat 255960
catttgaacc tgggaggcgg aggttgcagt gagccgagat cttgccactg cactccagcc 256020
tgggtgacag agtgagactc catctcaata aataaataaa ttaaattaaa ttaaattaaa 256080
attatttttt aaaaaattgg gggctgagtg tgatggctca cacctgtaat cccggcagtt 256140
tgggagcttg aggagggcag atcccttgag gtcaggagtt caagaccagc ctggacaaca 256200
tggtgaaacc ccgtctctac taaaaataca aaattagcc aggcatggtg gcgtgtgcct 256260
gtaatcccag ctactcgtga ggctgaggcc caagcatcgc ttgaacctgt gaggcggagg 256320
ttgcagtgag ccaagatggc accagtgcac tccagcctgg gtgacagagt gagactttgt 256380
ctcaaaaaaa aaaaaaaatt aaggtgaaga aggcttatac tagtgggctg ggacttgaag 256440
tgaagtgaat tcttgaaggt cccagtgag tggccaaggt gggacttgaa ccaggacatc 256500
ctgttctcttg accaccagct tagtccatcc cttgaagag agtgacctac agtctgggtc 256560
tcagccaggg tctcaggaaa ccaggttccc accttggctc acggaggtgg ttaggggcat 256620
cagctttagc accagagttc agatcttgcc tcgtcctata taagctttgt cacctcccca 256680
tcattaaaag gagccatcct cccccctcac ctcagcagag ccctggtaaa cagcaaatgg 256740
actaacgtga atctagaggg ttgaggatga agcctgcct ggcatgggca ctcaataaat 256800
gctagggccc aggcacggtg gctgacacct gtaatcgcag cactttggga ggctgaggca 256860
```

-continued

```
ggtggatcgc ttgagcccag gagtctgaga ccaacctgga caacatagtg agattctgtc 256920
tctacaaaaa gtacaaaatt agcctggtgt ggtggcgtgc acctgcagtc ccatctactt 256980
aggaggctga ggtgagagga tggattcagc ccaggatgtc agggctgcag tgagtcgtga 257040
ttgagccgct gcaccccacc ctgggtgaca gagcaagacc ctgtatcaaa ataaataaat 257100
aaatgctagg aaagggatcc tactaatgga ccttttttcc ccaaaacagt ggctttcatt 257160
tggtggagat gctacttatt agaagcactt gaggccaggt gtggtggctc atgcctgtag 257220
tcccagcact ttgggacttc tgccaaggca gaagaattgc ttgaacccag gcgtttcaga 257280
ccagcctggg caacatagca agacctcatc tctagaaaac attgaaaaat tagccagcat 257340
agtggcacat gactgttgtc ctaactactt aggcgaaggc aggaggatta cttgagctca 257400
ggagttcaag gctgcagtga gctgcgatca catcactgcc ctccagcctg agcaacaaca 257460
caagacccgg actctaaaaa tcaaaaaaga agcacttagg gaaatttctt aaaattaaat 257520
gataccctga gcaaacccct agatgttctg attcatttgg tttggtgagg tgggagggaa 257580
tcactgaatc tgtaatttat tattatttttt tttttttttga gatggattct cactctgttg 257640
cccaggctgg agtgcagtgg tgcaatcttg gctcactgca acctctgctt cccgggttca 257700
agcaattgtc ctgcctcagc ctcccgacta gttgggatta caggcgccca ccatcacgcc 257760
cggctaattt ttgtattttt agcagagacg gggattcacc acgtcagcca ggttggtctc 257820
caactcctga cctcaggtga tccgcctgcc tcggcctccc aaagtgctgg gattataggc 257880
atgagccacc gtaccctagcc tgcagttatt ttattctgag ttgatcttct gctggtgaag 257940
tgagtcttcc actggggcct ggagctgcat ctccctcacc ctgccaatcc tgcaagagcc 258000
agcactgagc ttcccctctg cttttctcttt ttttttttttt ttttttttttt tgagatggga 258060
tcttactctg ttgcccagcc tgttcttgaa ctcgtggcct caagcagttc tccctccttg 258120
gcctcccaaa gtgctggaat tataggcatg agccaccacg cctggtctcc cctttcagtt 258180
ttaaatgaag ccacaagttc cctgtataac atttgggaga tagagggggag ctctctagcc 258240
taggggttga ggtctgtgac caaacgccta taaagttgtc tttgtttgga ctcccccaga 258300
agcagagcct gagacaagga ttgagtgcaa ggaatttatc tgggatgcag ggcagtaagg 258360
gagagaggaa gtgacacagg gacagaaagg caaccaggaa agagtgtatt attaagcacg 258420
ttcctgctgt gaacaaatgg ggctcagttt cagtggatac ctccaggagg caacagagag 258480
cacataccac agagtcatcc cacctcacag gaagggaatt ggagtatttta tcctccagtg 258540
cccatcagac ataatcacag gccactccca ggggagctat taattcccta acacttgtgc 258600
agccacagag agaccctggg caaagtagtg tacctcagct gtgtagttga gctatgggca 258660
gggcccagc aacacctgcc aaaatgccaa aagtgccagt gggacctgaa ttccttttta 258720
tttatttatt tatttattta tttattttta tttatttatt tttgacggag tctcgctctg 258780
tggcccaggc tggagtgcag tggtgcaatc tctgctcact gcaagctctg cctcccaggt 258840
tcacgccatt ctcctgcctc agcctccgga gtagctggga ctacaggcgc gcaccaccac 258900
gcctgcctga ttttttgtgtg cgtgtatttt tagtagagat ggggattcac catgttatcc 258960
aggatggtct tgatctcctg acctcgtgat ccgcccacat cggcctccca aagtgctggg 259020
attgcaggcg tgagccaccg cgcccggccc ctgaattcc tttttaggc agttgtgaaa 259080
caacaacatc ccatctgttg ggcacctact gtatattcca tgctcagcga cgcacattca 259140
ttgtctgatt gctgtgttac cactgccttc cagagaaggg cgcagaggcc ccaggcactt 259200
cgcctaggag ggaagcacag ctctaaggtc aggctccttc tctgtaaggt agaggggcta 259260
cttcagggtc acactgaccg ccccaacccc tgacctggcc tctgcttctg cgaagatgct 259320
gagaaggccc tgtgttttgt gttttgggtc ccactgaccc cagaggggag ggccatctct 259380
ttgacccaga ctcttggatc caaactgggg tgccacccat caccatgtca gtacccggtt 259440
gaggggagtc agagatagca ggagaccttg tgggacttga ggctgtgact gttctccaaa 259500
caatgtggag tatttccata ttttaacaaa agagaggcca ggcgtggtgg ctcacgcctg 259560
taatcccagc actttgggag gccgaggcgg atggatcaca cgtcaggag atcaagatca 259620
tcctgctaa catggtgaaa ccccgtctct actaaaaaat acaaaaaatt agccaggcgt 259680
ggtggtgggc gcctgtagtc ccagctactc aggagactga agcaggagaa tggtgtgaac 259740
ccgggaggca gagcttgtag tgagccgaga acgtgccact gcactccagc ctgggcgaca 259800
gagtgagact ctgtctcaaa aaaaaaaaac aaacagagag gttatgcttg tgtttcccct 259860
tgagccagca cccagcccag gaatgcagca gtcaggatag atcaagtgaa gctgcagtaa 259920
caaacagccc ccacatctca gtgacttaaa ttgatgggaa gggtttttta cattcagcag 259980
ggaagctgtt tgcctcatag ttacccaggg acccaggctc acagagtagc tgccattcaa 260040
aatgttactg gtcgccaagc ccagggttga gaggctagag agtccaacac tgaccagaaa 260100
gtgaccacac tgcttccaca cacagcacat cactgcacct agacacacat ggccccatct 260160
aaacacaagg ggaccaggaa gtgcgtgtgc ctgaaaggcc ccaaagcccc gtccagtgcc 260220
tgttctgcac cctgttactg tccgcctcca gatcaggaaa tggaggccca gagaggttaa 260280
gccacttgcc catagccaca cagctgtggt agcagagctg ggatttgaac ccagagtctc 260340
cttctcttgc gagtatgctg ccaacctagt ggggacctga acacagactg tgggctctct 260400
gaggcctggg ttcaaatcct ggctttacat ctctgtgctg ctagcctcag gcagatgagt 260460
ggcttggtta cctcctagaa aatgggtata cctgggagtg gtggctcacg cctataatcc 260520
caacactttg gaaggccaaa gtgagcagat cacttgaggt cagaagttcg agaccagcct 260580
gaccaacatg gtgaaaccc gtctctacta aaaatacaaa aattagctgg gtgtggtggc 260640
atgcacctgt ggtcctacct acttgggagg ctgaggcagg agaatcgctt gaaccagga 260700
ggcagaggtt acagtgagcc gagatcgtgc cactgcactc cagcctggat gactgagcga 260760
gactccatct caaaaaaaaa aaaaaaaaag agaaagaaag aaaaagaaaa tgggtgataa 260820
cccttccctc caggatcttc atgaggagct cagtgatgtc atttataaag cccctgggt 260880
ctcgggagcc ctcaaaaatg ctggagagac aggccacagc tctgaagaga agcccagcc 260940
ctgtgagct gaagcagggt ctggaggccc cctctgggga agccaatc atgggaaggc 261000
ccccaggagt tcccagggag ggagactcag cacagatgat gtcgaacagc ctttaccgca 261060
gcccttcgaa caaccataac tgtcccgggc actccgctga tgggcaactg tgcctctaac 261120
atgcacccgg ccagcctagg gggccgggaa ccaagccctc tgttggcatc tctgtcttgt 261180
gggtccccat tctagaatta tttccgcgat gcctggaaca tcttcgactt tgtgactgtt 261240
ctgggcagca tcaccgatat cctcgtgact gagtttgagg taagtctccc tccagctct 261300
ctctgggtga ctctgggctg gacgaggcag gcgcaggggg gcggggagc ggtcccagag 261360
gcagtgtgtc ccggaagcca tagctgcttg agccagcact tggccatgac cagagaggga 261420
gaactggggc cccggggaca agggcagccc ctcaggaggg cattgtgggg agatgggggt 261480
aaccaaagct tggctgtagg gccagcactg agggtgggc tttcctgcat cctggcctag 261540
gaattaataa tgcagatgag tacactgagg gaactgagac actcaaaagc tctgaaagct 261600
```

```
gagccggctc ccaaacacca ccctatgtca ggagcccaga aagaatgggt ttcaagtcaa  261660
ttctgtttga accaaccctc tcctagttag tgggcaggag agagccacag ccctcaggcc  261720
agtgtgggga caccactccc agggccatag aggggtcccc agggtgtctt ccctcctcta  261780
gccccgggcc tgggagactc tcaacatggg agtctctgga cctctctgtg gtggcccac   261840
aggccacatt gcccttctcc tttcttggaa gactcaggtgc cccagaggtc ctgtcctaga  261900
ccctctcctt ggccatctgc caatgagccc aggcttgggg tccctcagga gattgggggg  261960
agggtagaag atccttgcag ggggaagcaa tggtcaaaaa agggtgtcaa agccaagggt  262020
caagggtgat accaatgtca tcttactaac aataaaaata acaatagctc acgagaatcg  262080
cagccttgct gtgtgccagg gaactgtgcc aagtggttta cgtggattgg ctcagggtag  262140
aggtcttggt ctcagctcgt aagagaattc cctcggaggg ttcaactgaa ggcacccaaa  262200
tgcagacctc actggtggag gggaaggggaa gggtacccac aagggtggca aggtgtccag  262260
cgaccaccca ccgtggggag ctgtcacctg cccaggtgct gaagtgggga gggaacctga  262320
gccggaggcc aggagaagcc accaagtggg agctgtcctg tcaatgtgga gagacagaga  262380
ccagggccca agcaggcaga gagcaatagg ggagaaacac cccaacctt ctctccctc    262440
atcccttatc tcctgccaga gcctcccatg gcccaaagta aaccggaagc aagctgaata  262500
tgatgctcag agcaggcagg gaagtcagga gaatagatct gggtgtggtc gggcctgagg  262560
aagagggtgt tgcctcattt cacagatggg aaaactgacc tcagctgggc acggtggctc  262620
atgcctgtaa tcccagcact tgggaggcc gaagccggcg gatcacctga ggccaggagt   262680
tcaagaccag cctggccaac atggtgaaac cccatctcta ctgacaatac aaaaaaatta  262740
gccaggtgtg tggtgcatg cctgtaatcc cagctactcg ggaggctgag gcaggaaaat   262800
tgcttgaacc cggaaggcgg aggttgcagt gagcgacggt cataccattg cactccagcc  262860
tgggtgacaa gagcgaaaac tccatctcaa aaaaaaaaag aaagaaagaa aactgatctt  262920
caatgcctgg ggaagtgaga gacactccca aggtcacaaa gccaggcctg ggtgactcct  262980
gagagtacac tgacagctcc tggggtgtcc cagtcagatc cccctacaga aaaggatctg  263040
tttgcctgct cttccgtcct agaaggccag gaggggctgg ggaactacac aaaagagggg  263100
gccattcttt gatatgtcct acggcacccg cacccaagtg atacacactt atttgccttc  263160
agctccagtg agccagaatt ttccccttcc cctcaccta tccctgaaac cttcctctag    263220
agggttcttg cccacatggg ggctctctcc actggggtgc cccacctgg tcattctccc    263280
ctgtcctgag tttctagaga gggctggagc tccagctggc aatcaaaata tcttgccatc  263340
cggctacata caagacagcc ttgaaccaat gtcccttttgg gtcaaggagt tagaaggatg  263400
gtccagctcc ccagaagggc aggtggggtg gaggaagtta gctgaaacgt tcaatcacca  263460
gtaagagagc tgtagggaca gactccaaca gcctgttctc ctggctggca ggaagatggg  263520
gcatggggtg ttcatgggac atcaggaccc ttgcagtagc caaacagccc ccagccctcc  263580
ctaccagctg tttgatcttg gacaacttgc gctatctctt ctcatgtaga gtggggctaa  263640
ccattgcaac caacctcaga cacttgcaag actcacagtg atgcatgcac tcaaaagaca  263700
ttcattgagc acctactgtg tgcctggtgt gattataagt gctggagaca gaacgagaag  263760
gaggggtgcc aaacaaaaca gaccaagaat acagagtgtc tgctcccata gagctgacat  263820
tctaaggaga gagacgggaa cttttttacaa gtaaaagcat caacaggccg ggcatggtgg  263880
ctcacgcctg taatcccagc acttttgggag accaaggcag gtggatcact tgaggtcagg   263940
agttcgagac cagcctggcc aacatggtga aactctgtcc ctactaaaaa tacaaaaatt  264000
agccgggcac ggtggcaggt gcctgtaatc ccagctactc aggaggctga ggcaagagaa  264060
tcacttgatt ctcaggaggc gagaggttgt agtaagccaa gattgtgcca ctgccctcca  264120
gcctgggcga cagagtgaaa ctctgtctca aaaagaaaag gaagaaaaag aaagaaagaa  264180
acgtgaagtg cttggcacag aacctgccag gaaaccagga gttgaaat ggtggttgtt   264240
aactattact gctgttgtta ttgttattgt gaatgggtgt gtagttttgt tagccagccc  264300
tgagttacag tcaatttgag ggaaagatag ggggtgggtg tttgggtcct tctgggacaa  264360
ttaactccca acctggagta gggaaggagca tgtcctggca ggcaaggagg tctcagttgc  264420
cccttttctgc ctcccaggta agcccactag ttctgaggcc agggcttggc caggctgaga  264480
caggaaatgc cagatgcttg ggcgggcagg tcctgtgggt ttaggggggca gagggcatgc  264540
ggcagtacta accagtgctg tctcagctgc tgccccaag tggctggggt gatgtgggtt    264600
tgccctgtgt gcaatggata atgactgtgt ttcttgtctt gtctctttc atgcctgtcc    264660
ttaaaactgt atattggcgc aacgccgtct gaaaaactca tccaatcaaa atgcactatg  264720
aaattcattt gttcatccat gacatggtct gtgtgttcat acaccaatga cttatctccc  264780
aacccaccgc caccaccacc cccactcccc gcccgggaac cgaaacccat tggtttttg    264840
gcactggtta caaatcaacc taaaaaatgc tgaacacgcc tccccaactg cccccgcccg   264900
cccgctcccc ctcatcttca acatctgcat ctagaatccg gttggtctta cttctttctg  264960
aagtctaaat gccttacatt aactgtgaac gcatctcctc gcgtcggcat tgcatgccac  265020
accctgcctc tccaacgtgg gatgcctgac gctctcctca accctccgct ctcctctgtc  265080
tgtctgtcct cccgccccca gccccctgtgc ctcccacttc ctgtagactc tgtctctctg  265140
tttttatcgg gttctgaatg gggttttct gtttgggtg gtttgcgtct tttgcagaga   265200
aagggatggg ttttcccagc gcagcacctc tctcttgccc catcccgcac acacatcccc  265260
tacactcaga gacaatagag gcaaatccac tcccagccac ctctcaccac tcctgtcccc  265320
cattcagctc catggacccc aggcccagg aaagctgcca actgtctcct cgcccctcca    265380
gctctctcca tcctgctgtc cccaatcctc catctcaagc ccacaagtc tttggccttg   265440
accagcagag acttgactct ccaagtctga taaggagac ctgaaggcca ggcagtgtgc    265500
cggcaaagac tctcaggcag aggaactcag aagtgccaga cttggatctg gtagcttcat  265560
gtggggctgg cccactgagg ccctctcctg gagccttgaa ctgtacgtgc acacgcagtc  265620
acacagtcac tgcacacaga cactgcacac acagtcactg tgcacacact cagtcactgc  265680
gcacacactg tgcacacagt cactgcacac agacgcagtc act gcagtcactg            265740
cacacagtca ctatgcacac acagtcactg cacacagaca ctgcacacac agtcactatc  265800
cacacacaca gtcactgcgc agacactgca cacactgc acacacaa tcactgcgca       265860
cacacagtca ctgcacgcag aaactggaca cacagtcact atgcacacac tgcacacacc  265920
actatgcaca cacactgtgc acagtcacta tgtacacaca ctggcactgc atgtagtcac  265980
tatggacaca cactgtgca cactgtcaca catgcagtcactg                             266040
aaacagtca ctgcacacag tcactatgca cacactgc acacagtc actgcacaca          266100
gagccactat gcatgcacac acagtctgca ttcacacatt gaacacagag tcgctataca   266160
cacacagtca ctgcacacac agtctatgca cccacacact gaacacacag tcactgcatg   266220
tacagacact gcacatagtc atgacctctt ctctttttct cactcattct ccaattctct  266280
ctctctctcg ctcttttttt ttttttttt tagacagagt ctcgctctgt cacccaggct  266340
```

-continued

```
ggcgtgcagt ggcacaatgt cagctaactg caacctctgc ctcccgttt caagcaatta  266400
tgatgcctca gcctcctgag tacctgggat tacaagcatg taccaccacg ccaggccact  266460
tcttgtattt ttagtagaga cagggtttca ccatgttggc caggctggtc tcgaactcct  266520
gacctcaagt gatgcaccg cctcagcctc ccaaagtgtt gggattacag gtgtgagcca  266580
ctacacctgg cctctaatcc tcattcactg ttcctgtctc tgtgtctctc acatacagtc  266640
atgcatgcat gcacgcatgc acacacacac acactgggcc tctctgctac atctacccac  266700
cctgtacccc cactccagta catactgcac acatctctct ccctccccca cttctcagcc  266760
ccttgcacac cccttgttct gttaaatctc aactgcctct gcccctctcc tacccaccaa  266820
tgaggccctt agagggacgc cccaatggca tcttttgccct ggaatcatcc cttccctgct  266880
ggcaatacac atgcattcac ccaccaaaca tttaatgagc ccctatttgg tgccacagat  266940
ggaattatgg gcagaagcag acaccattac tgtcccctct taccacatac agtcaggtgg  267000
gggaggcagg catcggtcaa ataacccctt gactccactt aaaattatac ctgcactgcg  267060
agctgaagga tgagcagcat taacaaggca gagagagatg cacagagcat tccaggccca  267120
ggacagcaca tgcaaaggcc ctgtggtggg acggaacctg tgaggggtca ggatctgcaa  267180
gcgagggaat gtggctgatg caaagacagc cgagaaaggc tggcctggag acagccgaag  267240
aaggcagaag gggacaggac ccggggctgg ggagggcggg gctatattgt ggaatatggg  267300
cttttctccta agcaccagga agggcctggg aggataggaa gcagggagg cgcgactggt  267360
catgtgacta gacaagctcg ctctggttgc agggcaggga acagcttgac aggaggctgg  267420
gctggaggtg ggcaccagga atcgcagcaa gagatgacag tggaggagag agaacagtgg  267480
gagggttgtc ctctgcagga cccagggaaa gatcaggtct gaactgagat gaggtgcctg  267540
ggagcagtcg ggtctggctt aaaactggga gataggctga gcacggtgac tcaagcctct  267600
aatcccagca cttttgggagg ctgaggcagg aagatcagct gaggtcagga gttcgagacc  267660
agcctgacca acatggtgaa accccatctc tcctaaaaaa tacaaaaatt agccaggcgt  267720
ggtggcaggt gcctgtaatc ccagatcctc aggaggccga gacaggagaa tcacttaaac  267780
ctgggaggtg gaggttgcag tgagccgagt cgtgccatt gcactccagc ctgggcaaca  267840
gagtgagact ctcttaaaaa aaaaaatactg ggtgataga gtgagcgagt gcaaggaaag  267900
gaccaggttg ggggaagaga ataggtgtg gcatagcaag tttgaggtgc ctttaggaca  267960
tcccgaaata agtcagatag gcaggtgttg tgggggctgc agcttggagc tgaggtctac  268020
aagtagtagg acttttctgg agcccttagg tgggtggtct ccatatcctt ctgagcactt  268080
gaggaacatc tgagcacagc actggaaaag aaaagaccac aaggacgctg tcctcatgtc  268140
ttccaggggc tgtgtcccac ccccatcaca ttctagccag gaagttcagg ggaggtgttg  268200
aagagaggaa gctgcacctc ccaagccatg gattgaaatg tggaaggcag gaagagggaa  268260
cttgtcagaa gttctggggg cagtggaaag aattggtact gatgcaggaa gagatggagg  268320
gtggatgagg gcagactagt acccttcccc cactgcccca aacccttccc gtctccaccc  268380
ctgcctgcct catgtgtctc ctccccccact tggctccaag aagggaagca tgttttctgc  268440
acgcatctcc ctgccagatc cctggctttt ttgcatggtt gcaagcttcc cctgctctcc  268500
tccaaacccc cctcctgagg ctgcttccag ggtccgcctg ccttcgcatg cctggccgag  268560
tccacatgtt atgatccgcc ccatgaaagg gatggccttgt actctggggt tgaacggag  268620
gggctgggg atacctgagc catcggcccc atccccaggt ggagctgggt ggccaggcag  268680
ggatggggt caggggcagca gggcacagag agtgactctg ttagccaagc tgggtttggg  268740
gcttgttcga ggcactggag acattctcac agcacttgag cccagtgtgg tcagggtagg  268800
atccccccagc ccccttcccc atcctagagg cctaaggacg cactgatgtg tcccagagag  268860
catcctagac attgccatca aacccagagg cctcagaaat tccttgaact ccagtccttg  268920
cctctcagct cccaggccaa agccagcaca agacacagat ctggcagcca gaaagccctc  268980
tggaagccac caagtaggat gcccatgtca cccaaactag gacacttttg aaacaggagg  269040
gaggctgtga ctgtatggtc accctgtgcc atttgggggg tgaaggttag accaagttaa  269100
atcttgctac gtggcctgta gcaaatccta caatccccat agaacaagtc tgattaagcc  269160
ccttcccta gtgtggagag accctctact cctcctgcct tcaccctgct gggtactggc  269220
cagcgaagga gggtttccat gtctgcctga ggctggggtc tcaaactcaa atgcctctgg  269280
gggccaggca gacaccagtc aaccaggaaa gcaagtgcca tttctaaaac gtgaggaccc  269340
tggaaaactg gagatcatgt ggcctgcttc caggaggcaa tcgcagcagg cctggggttg  269400
ccagaaagcc agattggtgg gcaaaatctc ttgatttta aacaatggca ataatttta  269460
attaaaaaca aggacaaatg aaaaaacact gctcgggccc aacaaaacag ttttattagc  269520
tagatttggc ccactcgtga cttcgagagt cccacccccc ccaccaaggt cccttgaagc  269580
cccacaatgg ccacttaact ctagctggtc tcctccctga ctctccaact ctctggcccc  269640
ctggttcttc tagcttgggt gggaggaggc agaggcagtg actagacagg gggttttga  269700
gcagaggcag tggccaccca gggaggtcct ggggcaggg atggcccac ctcccggccc  269760
ccagcacccg ccccttggtg ggcccgggct gatttctgag ctcacccacc catgggagct  269820
gagtgcttcc tgcttcctgc aggcctggtc ccgtgctact ccacccagcc ccagaagctg  269880
agaagccatc cctgagaggg gggaaaaggg cccccaaatgc atcttctccg actcagcggg  269940
cagcgaggac tcaccctgca gccgaacagt cccagctccc tcccgtcctc cccattcccg  270000
ctcgccaagg gggtaagaaa agatgctctt ccgcttctcc caattggctc gagccgctgc  270060
tcctcttggc cgtggggtga ggtcagggcg ggcaggagcg ggtgggcagc tcggcagggc  270120
agggcaggga agggtgcccg gtgactcccg tgacagatga atttctgacc cggagcgtaa  270180
catgccctcg gaaccgcac atgtccacca ggcctgactg tgctggcgac ctccaccccc  270240
acccccgccc tggtgtttgt gcatcgtaca cgtatgatag attccgcaac ttgaccggct  270300
tgtgtccttt cgtctcagtg catttggttg ttgggagaaa caaaaccat ctcgattttt  270360
ttcctgattg gatgattcgg atatatttc ttttttcttgt tcttttgtta tttcttcccc  270420
atccccgttc cttttttcctc cttttctttt ccccattgtg ggtggggctg  270480
gcagggaggg cttatgcttt tgagttgatg cctttttcctc cctcccaccc tctctctccc  270540
aacattattc cttttcgag tttttcctct gcatcattgc attaatagtg cttttctctct  270600
ccctccttat tggggtctg gcttgctttt ttcctgttgg ttggcttcat gtaggggcct  270660
ctgtgagtgg tgacagctct gagccttttg gggtgggtgg atggtcaccc ctcttcctcc  270720
atctcccccag aataacttca tcaacctgag ttctctccgag tgcccggct  270780
catcaaactt ctccgtcagg gttacaccat ccgcattctt ctctgaggcct tgtgcagtc  270840
cttcaaggtg agtcctcgtc cctgctgctg gcccagggct gagaagacag gtgaccctca  270900
tgctctggct gaatgtagaa gtcagattgg aagtgcctct gtgatgtagt cgtgcagaga  270960
atctgttatc tccaaggctg ttgtcaaact tcctgtccct ggtgtgtctt cagagctgta  271020
agggcctcat cctagagccc ccagagatgc ccaccagccc tggaaggact ctggcacgtg  271080
```

```
gcatatggcc acccaaccca gtggggcaga gcactgggac aagggaggaa gacagtgcgg   271140
ctgagggacc cccagcactc ttcttcattg ccttttttcc caccaggccc tgccttatgt   271200
ctgtctgctg atcgccatgc tcttcttcat ctatgccatc attgggatgc aggtgagtgt   271260
cgtgtcccta aggttcccag agcctcccaa ggagggcagc cacccttaga aagggggtggg   271320
tcagaggagc ctggttcaca gaagcagcca tggaggttga gctgggtttc ccagaagcca   271380
ctggaggaat ggcagcccct ggtcgtcacc ctccaattcc acaggtgttt ggtaacattg   271440
gcatcgacgt ggaggacgag gacagtgatg aagatgagtt ccaaatcact gagcacaata   271500
acttccggac cttcttccag gccctcatgc ttctcttccg gtgagaaggg gacctgctct   271560
gataattctg tttccgtggg gtggggtgcc tgccttcatc cttctgttcc catagaggat   271620
gtaccctcct cttccaatgc aagacgtgcc ctcctccttc tcttctggca ggggcggcgcc   271680
ctcacccttc ttttccggta gggggcgtgc ccttctcttc cggtagggga cgtgccggcc   271740
ttctcttccg ataggggggcg tgccctcctc ctcctttttct ggtgtggggg tggcagatg    271800
tgctcttatc cttcttttcc cgtgaggctg gaaatgggtg tcgtgggggg cccaggaatc   271860
ctagcagggc agaagcagag ggccctggga catagtcatc aaggtcattt tccaggcatt   271920
atctctgaat cttcctgacc accctgtgag gaaagggattc ttggcagccc tatccgacaa   271980
ataagaaaac aggcttacag accgtgaggc ttgattcttt ggttcatcat cttggctgca   272040
cacaaaagtt ccttcactcg ttcagtgtag gttttttggg ggggcttttt tttttttttt   272100
tttttttttt ggagatggag tctcgctctg ttccccaggc tggagtacag tggcgcgatc   272160
tcggctcact gcaagctccg cctcccgggt tcacgccatt ctcctgcctc agcctcccga   272220
gtagctggga ctacaggcgc ccgccaccac gcccagataa ttttttttgta tttttagtag   272280
agtcggggtt tcaccatgtt agccaggatg gtctcgatct cctgacctcg tgatccgccc   272340
gcctcggcct cccaaagtgc tgggattaca ggcgtgccca accgtgccca gcccttttt    272400
tttttttttt ttagatggag tctctctctg ttgcccaggc tggagtgcag tggcgccatc   272460
tcggctcact gcaagctcct cttgtggagg tgtattgagc acctcacagca tgccaggcag   272520
ggctgaaaaa cgaggatgca ccaggaaata gagaaaagag acatttttaag cactttggaa   272580
gctaacatcc ccatggggaa gacgaataat caggaaacaa attatagaag atgctggaaa   272640
aagataaaat tcaagaataa aggggaatag ggcaggtgc agtgactcgt gcctgtaatc    272700
ctagcatttt ggggaggccga ggtgggagga tcgctttagc ccaggagttt gagaccagcc   272760
tgggcaacat agtgagaccc cgtctctaca aaaaaattgt ttttaattaa ctgggcatag   272820
tgccacacac ctgtagtccc agctacttgg gaggctgagg caggaggatt gctcgagccc   272880
aggagttcca ggctacagta agctatgatt gtgccactgc actccagcct cggcaacaga   272940
gcgagactct gtctctaaaa agaaaaatat atttttttaa tttttaaaaa aagttacaga   273000
ggtagatagt ggtgatagtt gcataataat gtgagcttac ttaatgctac tgaattgtac   273060
acttcaaaat gttaaattg ataaacttca tgctgtgtgt attttgccac agtaaaaaat    273120
aataatgttt ttaatctaac aacaaaaaaa gaatagaggg ccggcaggtt atgcctctct   273180
gaaagtgtga catttgagag aaattggcaa gggagggagt cagtgggtat atggggaagg   273240
gcaggccaag ccgaggggac tgcctgtgta aagccctga ggcaggagta tggctggcat     273300
gtttgaggac tgtgaggagc ccagcatacc tagaacagag tgatctaggg agaatatagt   273360
atgagatgac tgtcaccttc atggagggga gcttttttt tttttaatc tgagacagag   273420
tttcggtctt gttgcccagg ctggagtgca gtggtgcgat ctcggctcgg cgcaacttct   273480
gcctcccagg ttcaagcagt tctcctgcct cagcctcccg agtagctgag attataggtg   273540
cccgtcacca cgcccagcta attttgtat ttttagtaga cacggggttt tgccatgttg     273600
gtcaggccgt tctcaaactc ctgacctcag gtgatccacc cgcctcagcc acccaaagtg   273660
ctgggattac aggcatgagc cactgcaccc ggcctgaagg gagcttttt tttttttgc     273720
ttttttttga gacagaatct ccctcttttgt cacccaggct ggagtgcagt ggcgcgatct   273780
cagctcactg caacctccgc ctcctgggtt caagcgattt cctgcctca gcctcccaag     273840
tagctgagac tacaggtgag cgccaccaca ccgagccact ttttggtatt tttagtagag   273900
atagggtttc accatgttag ccaggatggt ctcaatctcc tgacctcgtg atccacccac   273960
ctcagcctcc caaagtgctg ggattacagg tgtgagccac cgcgcccagc caagagggaa   274020
gcttttaaag cataacagtg accagcctga gcaatgcagt gaaacccat ctctacaaaa    274080
aaaaatagtt taaaaattag ccaggagtgg tggcgtgtgc ctgtagtccc cagctactca   274140
ggaggccgag gcgggaggat cacctgagcc tgggaagttg aggctgcagt gagcagtgat   274200
tgtgccacta cactccaacc tgggtaacag agcaagaccc tgtcaaaaaa aaaaaagaga   274260
gagagagaga aagaaagga aagaaaaag agagagaagg aaaagaaaag aaaaaaacat     274320
atcagtgtcc tcaaatccca ccctagacca actgaatcca agtctgctgg ggtggggcac   274380
gggcattggt attttttcaa agctctctgt ggacttcagt gcacagccaa gaatgtgaat   274440
tcccttctct cagctcccag taaaaggagg tggtccaccct ggggcttgcc tggcagctc    274500
cagagcccaa gtgctcaacg tgtgtgctcc acctcctggg gaggcgttgg tacccagtca   274560
gggctgggtg tccgagtctc tgatttctcc ctgtcctcag gagtgccacc ggggaagctt   274620
gcacaaacat catgctttcc tgcctcagcg ggaaaccgtg tgataagaac tctggcatcc   274680
tgactcgaga gtgtggcaat gaatttgctt attttttactt tgtttccttc atcttcctct   274740
gctcgtttct ggtgagtctg tggacactgt gagggccgtc tgggctccct aagcctggct   274800
tcctttcagg ggagtgggtt tctgtggaat gtggctgtgt cgaaggcttg ttccctccaa   274860
ggcttcctg aaccagcctg ggatcaggtg accctgagtc tctcaaactc agcactgttg    274920
acatttgggg gtggctgatt ctttggggtg gggccatcat gtgcactgca gtgtatggca   274980
gcatccctgt cctcccccca ccagatgctg gcagcacacg ccaccgttc ctcctgttgt    275040
gacaaccaaa aatgtctccg gacattgcca ggtgccccca ggggtgggg gtggggttgg     275100
gagtggggc cagaattccc ccatttgaga ctcaatgaaa tatttcagct gggcgtagtg    275160
gccgatgcct gtaatcccaa cacttcggga ggctgaggtg ggaggtcac ttgagcccag     275220
gaatacaaga ccagcctgga cagcatggtg tgaaacccat ctcttaaaa aaaaaaaaa    275280
aaattgaatt agctgcacac gtggtgctgt gcacctgcag tcccagctac tcaggaggct   275340
gaggtgggag gatcacttga gccttggagg tcgaggctgc agtgagccat gatcaccaca   275400
ctgcacccca gccagggcga cagaatgaga tcctgtctca aaaacaaaca aaacaaaaca   275460
aaaaaaaaaa aaacattgcg agggaagaaa tacctcactt tggccttgtt gggggcagat   275520
gtgggaggat ttgggggtcac agtggttctc ttggtgttgg tccctgtttc agaagcctcc   275580
cctccctctc actgactctg tttcttcca tcattcttgg tctttgtctc tctctctctt    275640
tttttttttt ctttgaaatg gagtctcact ctgttgccca ggctaaagtg cagtggcgag   275700
acctcagctc actgcagcct ccacctccca ggttcaaccg attcttcagc ttcaacctcc   275760
caagtagctg ggattacagg tgcacatgcc accacaccca gctaattttt gtattttag    275820
```

```
tagagacagt gtttcaccat gttgaccagg ctggtctcaa actcctgacc tcaagtgatc  275880
tgtccacctc ggcctcccaa agtgctggga ttacaggcgt gatccaccgt gcccggccag  275940
tctttgtctc tttgtatctc tctctctcca tctctctctg tttctctctt cctcttcccc  276000
atctctccac ttgatctctc tctcactgga cctccttgtg tgagtgagca tcacctctcc  276060
attcccagt ctctttctgt ctctgtctca tttccttcc ccatcttctc tctatccctc  276120
tctccatctg ggcctctgtg tacatgtctt tgggtctgtc tgtccgtctg tctgtctgta  276180
tccttctcac tcactcattc attccctcgg tctctgcccc cattctctct tggtccccgg  276240
ggtccccaca gatgctgaat ctctttgtcg ccgtcatcat ggacaacttt gagtacctca  276300
cccgagactc ctccatcctg ggcccccacc acctggataa gtacgtgcgt gtctgggccg  276360
agtatgaccc cgcagcttgg taagaagtca ccccgaatcc tccagccaca atactcacct  276420
ctccctggaa ctggaacacg ggctaggtca ggcccccagac tctggagcac tgaactcctg  276480
gggtcctagc aggggtctca caggttcagt caggagagaa gatataagaa tcatcaccct  276540
tgcataccccc agattaaaca cgtagggtgc caaccctgcc caaaccctgg actttctggg  276600
aaatgagggga gggcgtcaac catgagatgt cctgaagagc cctctcctcc tacgagtctc  276660
tcctgtctct cactgtgaag tctccagatg tgaggatgc attagccagg ctccaggag  276720
aaaccaaca gcatcccagc ctcagttctc ttgagagtgt ggggaggagg gctggcctac  276780
ccttggcaga caggattggc agcaacatca gagtagcaga actcagctcc cactgggacc  276840
cgtgaacctg ggagtgagag gacatacagg ccaggggagg acgcagagcc tcaggggccc  276900
atgcatctt gtggccacaa agggagtggg cgctcccatc tgggtagaca ccagagggt  276960
ccctctccac tgacgggcaa tggtttcaga gggtgggttc caccttgtgc acgtgtattg  277020
agtgcccacc caacaccaag ccttgaagga cactcagagg ctttatctga atacctggaa  277080
cccaccagcc actaactgag gatttagttc aggctggtct tggggcctga agaagcatta  277140
ctggggggcc ctcagcagcc taagcccat cttcctctgg cctcagcacc agagaggagg  277200
ccgtcacgag gaaggtgggc aggaggtggt cttggctatt cccatagcct caaacaagta  277260
ctccatgaga ccgagaggct ggggagagcc gtgggtctgg ggctgggctt tggctggttc  277320
ctaactcttc ctctttgat tttaggtcac agcaattgga tgctgtcccc aaggcctcta  277380
ttccacaagc ccccccccac ccctgtagcc catgtagact gtggaggagg cagatgcaga  277440
gagagcccca ggggagtgc cctgcagtcc cgaactcgac tgacatccta cacccctggg  277500
tctcccagt gtctgggaat gtactgggga ccttcacttg tccccagtct ctcccactcc  277560
ttcaagccag ggacacccca gcctcgggca tcatgaccatc gctgtgtgcc cagggagccc  277620
gtgtgaaccc attgcctgca ctaaccccct ttcttctcct ttcagcggtc ggattcatta  277680
taaggatatg tacagtttat tacgagtaat atctcccct ctcggcttag gcaagaaatg  277740
tcctcatagg gttgcttgca aggtttgact tccactaaaa cctgctagca tccatggaat  277800
gagtgtggct tggggttctt caatatatat atttcatata tatatatata tatatctctc  277860
tctctctcta aaaaaacaga gccatctctc tttcttgcat taaactagaa aactctctta  277920
gccaacagaa tgcagtcatg tagactcgat aaagcatgga acatatttcc tccttccctt  277980
cagccttcag ccatctttgc ttgctcttag ctgaagctgc ccatcctggg gtctccacgg  278040
caccccaaat cagatacatc ccctggggga ttgtaacttt gcatttctcc cccaaccatc  278100
acctccactc tctccccctc caccccctcac ctccaaaagc ccctagccct cctccccctcc  278160
ctggcactgg cccctgctcc ccacctaggc cccctcagag accagcctca gccaaaccag  278220
agaacgtgac ccaactgtag aaataacagt gatggccggg cgcagtggct catgcctgta  278280
atcccagcac tttgggaggc caaagcagga ggatcgcttg agcccaggag tttgagacca  278340
gcctgggcaa catagcaaga accccttct ctataaaaaa ttagccaggc attgtggcgc  278400
atgcctgtag tcccagctac ttgggaggct gaggcagaag gattgcttga gcccaggagg  278460
tggaggctgc agtgagctat gatcacacca ctgcactcca acccaggcga cagagagaga  278520
ccctgtctct ttaaaaaaaa aaaaaaaaa aaaaaaggc aatgaacaaa agcatggctc  278580
tacgtcttcc aaagtgagaa ttctccctcc cctccgcatc cctccagaac tgtagctcag  278640
agcccacgct gaatctgact tttctctttt ctctctctct ccctgctccc gagcagtgaa  278700
gtaatcttt tttactgacc ttttcttcca ttttttttcc tcctcttttc cattgatttg  278760
aaatatctat tttatcattc tctgcatctt tctctctcta ttttttcggc tcgtgtggat  278820
ttcttttttc ttcttctgt ttctcccac ctctcttcct ttggttctct gttcccattc  278880
ccgttttgtt tttttgtttt tgttttgtt tttttcattt tcggtgctgc caggggccgc  278940
atgccttacc tggacatgta tcagatgctg agacacatgt ctccgcccct gggtctgggg  279000
aagaagtgtc cggccagagt ggcttacaag gtagactacc cttgccgacc accgacgtcc  279060
aggcactggg ttttttttc ttcttcttct ttttttttt tagtgctgac cagaaacacc  279120
cggccgactc tctttttcca acgtttctct tctttttgt ttttgattct tttttttctt  279180
ttctcgagtc aactgatcat gaccatccct tgattctaag cagcacactg tgtccgtcct  279240
ttctgatgag tgtcttcgtg ttttgagact ccattatggc cgacatgccg ggggaggggg  279300
gaggggagcg cccaggtccc cttgcacctg gtctcccagg taccaaattg gaaacaaaca  279360
cgcttcttca gggagtcaaa acccatgctt cccacttctg cccaccagaa gcggccccca  279420
tgcccaggct ggggcaggcg ccttgcagag aggggcttta gccccgaaa gcaggcgagg  279480
tcccgggtcc ccgccctgc cacgcacacc tgaagctgat ctctgaccta gggcttggg  279540
gattcgagac cttccaagga gcaccaagaa cctctcttcc cctcccttcc ttccctgga  279600
gttcgtcctc cagccccgt ccctaatccc ccaagacac ccaacatgc ctctccattg  279660
ttccagagtg ggcaggcggc cgcagctgga cccctggacg gtggcacact gatgcaggcc  279720
atgcacgctg ccttggcggg gctggggcg gcaggcacc atggccgacg ggggtggtg  279780
catgctggct gagagagcga gcgtcctgcc gccaagcggc tggcccggc cacccctcca  279840
gatcctgtc ctggaatctc ccttggtgcc caaggacaga tgctctgttc cctccattca  279900
tccacaagaa gttcagggat gaccttaaa gattctccca acccaaaaag tattacccca  279960
tcatcctatt ctcccatcca ccttgatctt ccctgcgtcc ctatccatca atgctatttg  280020
tacctgcccc gtgttgccac ctcattcctt tccttcctct gtgcacccct cctcacctaa  280080
cctatatgtc tcccctcctt tcaatcaaa gccggggaca aggttgtccc accagcatct  280140
cagacaatga gcctctcctg gcacctgtcg ctctgtgccc ctccctgccg ccccccccc  280200
cccccggt tttcctcaag tcgcttctct cagtctcttg ttagatgaat gtgtgcgcat  280260
gtgcaagaga gggagggcga gcccttcctc tcctggtctt tgtgcaggac caccatgggg  280320
ccataagaca actttgtgca aatttgaaaa aggcacccttt tccacagaac atgcctgttg  280380
gaaaattgtt gcaatctacc aatgtggtga gaacaagaca cttttttttct atcacctggg  280440
aagctgttat atttaatata caaatcgggg gctgggcgtg gtggctcatg cctgtaatcc  280500
tagtgctttg ggaggctgag acgggaggat cacttgagcc cagttcgaga ctagcctggg  280560
```

```
caacatagcg agaccccatc tctacaaaaa gaaaaaatat tttaattaat aaataagtac 280620
ataaatctat catttccaag atgggagccc tttgtgcggt gtacaacctg cacaactgtg 280680
cacagtggcc cagtctatgt gtgtttctct atttcccacc tccttcccca ccctaccccc 280740
agtgtcccct ccagtgtcct gctctggatt taccatacccc ctcccatct tcaactctgt 280800
gtttcctgcc cacttgtgtc tgaatcccca cccaagttgc cctcacccc cttctctgtg 280860
ccacttcagc ctgggctggt gcacaccagc ccagcatcct ctcccatgcc accaagcatg 280920
gtggacagag cccctgcctg ggacatgggg aatcttttct tccctgggct ggaagggagt 280980
gcccctcacc ccttcccccct gccattgcac agagagccaa gatctggaca tgcccctgag 281040
atacacttcc cacggagcta tgaatgagtc tcgagattcc gtctgcatgc gccctgtct 281100
gtgctgttct gtgtcacagc ctcgctgcat gcctgcgagg ggcctgcccc gtcagtgggg 281160
ggctgcctgc ctgctgcttc tcagaggaat gatgtggtct gtgccatct gctctgtcct 281220
ggtctgggcc aagccaggga ttgggtgtgg ggagccagtg gcacccccca ccagcggctg 281280
tggtcctggc cccctcagcc ttggctgttg catgcactgc tcaaatccag cttgtgtctc 281340
ttttctttgg ggtcagactg aaacggggcc atccagaaga actctgggtg agggcggggg 281400
tggggcaagg gttgaggcaa accctggaaa tgccagctgc caggtcaagc aggtggggga 281460
aaaaaggaga gggcagggga ccagaagtac aagagagcc tttgtgccct ccctgcgggc 281520
caccaagaga aactgagtac tgggacaggt aacctaagta agagacacct cagccgccac 281580
agctttcaga gttcttcctg ggactccctg ggtagggcg gcgcgggctc acgggagacc 281640
caggaggat gcctgggaat gactgcgctt gccttgggtt ttctgtagcg gcttctgcgg 281700
atggacctgc ccgtcgcaga tgacaacacc gtccacttca attccaccct catggctctg 281760
atccgcacag ccctggacat caagattgcc aagggtaagg aagggacagg ggcgggcaca 281820
gacaggcgtg acagggtgga accgggatc tccctccta cccaaaacta gaggatctgc 281880
tgtcaccacc cggatcttca ttcactcttc cattcattcg ttccacaggg tttttttggg 281940
tttgggggttt tggtgttttt tttttttttt ttttgagaca gagtcttgct ctgttgccca 282000
ggcagcagtg cggtgacatg atcgcaagtc actgcagcct tgacctccca ggctcaagtg 282060
atccttccac ctcagcctcc ccagtagctg ggactacagg cacacaccac catactcggc 282120
taatttttt tttttttggtg tgacaatttc cctctgtcac ccaggctgaa gtgcagtggt 282180
gtgatcttgg ctcattgcta cctccgcctc ccggggttcaa gcgattctcc tgcctcagcc 282240
tcccaagtag ctgggattat aggtacccac cagcacaccc ggctaatttt ttatattttg 282300
ggtagagatg gggtttcacc atgttggcca ggctggtctc gaactcctga cctctggtct 282360
caaactcctg acctcaagtg atccacctgc ctcgacctct caaagtgctg gattacaggc 282420
gtgagccacc atgcccaacc taatttttta tattttttat agagatgggg tttcatcagg 282480
ttgcccaggc tggtctcaaa ctcctgggct caagcagtcc tcccaccttg gtctcccaaa 282540
atgctggtat tacaggcatg agccaccaca cccggcccat ttgcagata tttagtgcac 282600
tccttcaatg tgccagagac ccgtccaagc agggagggac ccagcagctt acactttaga 282660
tggatgggga ggccgccact gaggaggtaa ggcagtgtct catggatccc tgggggggaag 282720
gtgctccagg cagaaggact ggcaaaggcc ctgacagagg ggtgaacaca ggacacccgg 282780
ggcattgagc tgactcacct tctgagtgag ggcacgccag gcaggttcag agcagaggag 282840
gaacctgacc caactcacat ttgaacaggt tccctccggc cactgagggg atgggagacc 282900
gaaaggaggc cagtgtgggg gctgctgata tcatctgggt ggagacaggg cggcagctta 282960
gatctagggg taggctcgac gtggtggctc acgcctgtaa tctcagcact ttgggaggcc 283020
aaggtggggtg gattacttga ggtcaggatg accagcctgg ccaatgtggt gaaacccccg 283080
tctctactaa aaatacaaaa tttagccaga cgtggtggtg ggtactgtag tcccagctac 283140
tagggaggat gaggcagaag aatcgcttga acctgggagg cggaggttgc agtgagccga 283200
gatcacgcca ctgcactaca gcctgggtga cagagcaaga ctctgtctca aaaattaaat 283260
taaattaaat taactggaca tggtggcata tgcctgtggt cccagctact caggaggcag 283320
agatgagagt attgcttgaa gccaggagtt tgaggctgca gtgagtcatg atcgcaccac 283380
tgcactccag cctgggcgac agaacgagat cctagctcaa aacaacagaa agaaaaagaa 283440
aaaaacattt tttttaaagc tgagaagggg ctgggcgcga tggcttacgc ctgtaatccc 283500
agcactttgg gaggccaagg tgggtggatc acgaggtcag gagttcaaga ccagcctggc 283560
caacatggtg aaaccccatc tctaccaaaa atacaaaaag tagccgggtg tcatggtgtg 283620
cgcctgtaac cccagctact ccggaggctg aggcaggaga atcacttgaa cctgggagac 283680
agaggttgca gtgagccaag atcgcgccac tgaactccag cctggatgac agagcaagac 283740
gctgtctcaa aaaaaaaaaa agctgaggcc gggcacgctg gctcacgcct gtaatagcag 283800
cactttggga ggccgaggcg ggcagatcat gaggtcagga aatcgagacc atcctgggta 283860
acacggtgaa accccttctc tactaaaaat acaaaaaatt agctgggtgt ggtggcacgc 283920
acctgtagtc cctgctactc agaaggctga ggcaggagaa ttgcttgaac ccgagaggca 283980
gaggttgcag cgagccgagc ttgtgccact gcactccagc ctgggtgaca gagtgagact 284040
tcatctgaaa aaaaaaaaaa aaaaaagccg agaaggctgg acatggtggc tcacacctgt 284100
aatctcagca ttttgttgag gccaggcaca gtggttcacg cctgtaatcc cagcacgtgg 284160
ggaggccgag gtgggtggat catttgaggt caggagttcg agatcagcct ggccaacgtg 284220
gcaaaaccct gtctctacta aaaatacaaa aattagccgg gtgtcgtggc gtgtgcctgt 284280
aatcccagca ctttgggagg ctgaagcggg tggatcactt gaggtcagga gttcaagacc 284340
agcctggtca acatggcaaa accctgtctc tactaaaaat acaaaaatta gccaggtgtg 284400
gtggcgggta cctgtaatcc cagttactag ggaggctgag gcagaagaat cacttgaacc 284460
cgggaggcag agattgcagt gagccgagat cacatcactg cactttagcc tgggcgacag 284520
agcaagactc catctcaaaa ataaaaataa aataaaaaa taccgagaaa ttcccccaaa 284580
gacctagctc agggctcact ctccatcatt agggggaaag aagaagaga ggcagggag 284640
gcgggcagag accaggcag tgtgggctcc tggaggcagc ttctatgttt aaaagggcgg 284700
cttcaggagg aaggggacca accgtgtcag gcactgccca gagaccaagg atgacaagga 284760
tcacaagtga ctggtcatca tggtcacttt gaccagtgca gctttggcgg aggggtcagg 284820
ggtcccctgt ctggagtgca tttcggaggc ccgaagggg atgtgatgtg atttggcagc 284880
tgattaagga cagcagggca gagagacagg cgcacaattg ccagaagaaa cggggacctg 284940
aggcgc ctgtaatccc agcactttgg gaggctgagg aaggtggatc acttgaggcc 285000
aggaatttga gaccagcctg gccaacatgg cgaaacccca tctccactaa aaatacaaaa 285060
attagccagg catggtggtg cacacctata atcccaacaa cttgggaagc tgagcacaag 285120
aattacttga acctggggagg cagaggttgc agtgagccga atcaaaacca ttgcactcca 285180
gcctgggga cacagcaaga ctctgtctca aaaaaaaaaa aaaaagaaa gaagaaaga 285240
aaagaaaaaa caaatgggac cagaaaaaag gagtgggtgg gagaggagca ggtggatagt 285300
```

```
cccacacatg ggaaggtgct gagcccagct gaaaccacta gtaagtcagg aggagggaag    285360
actgagcctc gagacatatg tgccttccag ggtcttgagg gaaagaaggg aggaagagcc    285420
aaggccacgt ggcaagactc aaggaggaag tggcagggaa ggtgggggac tggaggggtg    285480
gaggacagat attgttaatg ccaggaacaa agtgaaggta aagagagcac aaggaagttg    285540
ggagcagtgg ctcacacctg taatcccagc actttgggag gccaaggcag gaggatcact    285600
tgaggccagg agttcaagat cagcctggcc aacacagaga gaccccatct ctacagaaaa    285660
tttaaaatt agccaggtgt ggtgatgtgc acctgtagtc ccaactactt gggaggctgg    285720
agtgggagga tcactgggga ctgggatgtc aaggctgcag tgagctatat gatgaccaca    285780
gacatagcag cttaagacac acctatttgt cagctcacag tcctgtaggt cagaagtcca    285840
aaaagctgga ctgggctgtc tgctgagggt ctcacgaggc tgaaatcaag gtgtcagcca    285900
agctgggctc ctctctggag gatctggggg agaatctact tccaggttca ttcaggtgtt    285960
ggcagaattg aagtccttgt ggctgtagga ctgaggtctt gttttatcac tggctttta    286020
gcttttgct cctggaagtg catgtaatcc tccatgtgct ctcattctct ctgacttccc    286080
catctgccac ccagcagaga caatactgtg cttttcaagg gctcacctga ttggggcagg    286140
cctaccctga tcatctctgt attttgaggt cagctgactt gatatttttt ttttttcttg    286200
agacagaatt tcactcttgt tgccaaggct ggagtataat agtgtgatct cagttcactg    286260
caatctccgc ctcccaggtt caagcaattc tcctgcctca gcctcctgag tagctgagat    286320
tacaggtgcc caccaccacg cccagctaaa tttttttgta ttttagtag agatgggtt    286380
tcacaaggtt ggccaggctg gttttgaact cctgacctca ggtgatccac ccgcctcagc    286440
ctcccaaagt gctgggatta caggagtgag ccaccatgcc cagcattttc tttctttttt    286500
tttttttttt tgaaacggag tcttgttctg tcacccaggc tggagtgcag tggcgcaatc    286560
tcggctcact gcaacctcca tctccgggt tcaagtgatt ctgcctcagc ctcccaagta    286620
ggtgggacta cagatgcgtg ccaccacgcc cggataattt tttgtatttt tagtagaaac    286680
ggggttcac catgatagca ggatggtctc gatctcccaa cctcgtgatc tgcccacctc    286740
ggcctcccaa agtgctggga ttacaggcgt gagccaccgc accgggcctc cggtattta    286800
attatatctg caaagtccct tcatagcctg ggcaatgtgc cctagattag tgtttgaata    286860
aacagaatct tggcagaagg gcagcttttg aattctgcct accacagttc cttcgtttgt    286920
acaacgggtc taacaacacc cccactcttt gtatgtaatg ccatcgtaac tcagcttctg    286980
tggcactctg agaatctgtg ttcaggggtc ccaaaaccac ccacaggttc agtgattccc    287040
tggaagaact cagaactgag aaaagttttt atactcacag tttattacag tgaaagaata    287100
tagattaaaa tctgcaaagg gccgggcacg gtggctcacg cctgtaatcc cagcactttg    287160
ggagggcgag gtaggcagat cacttgaggt cacgagttca agaccagcct gaccaacatg    287220
gtgaaaccct gtctctacta aaaatacaaa aattagccag gcgtggtggc tggcgccagt    287280
aatcccagct acttggaagg ctaaggtagg agaatcactt gagcccagga ggcagaggtt    287340
gcagtgagcc gagatcccgc cacttcactc caggctggac agagtgagac tctattagaa    287400
aaaaaaaaaa aaaaaaaatc tgcaagggc ctggcatggt ggcttacgcc tgtaatcctg    287460
gcactttggg agggcaaggc gggcagatca cttgaggtca caagtttgag accagcctgg    287520
ccaacatggc gaaaccccgt ctctaccaaa aatacaaaaa ttaggcatgg tgccagaccc    287580
ctgtaatccc aactactcag gaggctgagg caggagaatc gcttgaaccc gggaggcaga    287640
ggttgcagtg agctgagact gtgccattgc actccagcct gtgtgacaag atcaaaactc    287700
tgtccaaaaa gaaaattagc caggtgtggt ggcatacacc tgtagtccca gctactccag    287760
aggctgaggc acaagaatcc tttcaaccca ggagatagag ctacattaag ccaagatcac    287820
gccactgcac tccagcctgg gcaacagagc aagactctgt ctcaaacaaa caaacaaatt    287880
ccaaaaacat aaaatgcgca aggaagggc atctggggaa gggtccagga gacaccaggt    287940
gcgagcttcc agttgtctgc ctccagtgga gttgcacaga caacgcttaa ttctccctgc    288000
agtgtgtgac aacacgcacc gtgtactgcc aaccagggaa gctcacctga gccttggtgc    288060
cccaggggttt ttattgaggg tttgtcatat aggcagggct gacgtagtta ctcagtctcc    288120
agtccctcca gaggtcaaac tgataccacg tggcccaaga ccccaacgat aaatcgcatt    288180
gttagaatga actgtatgga aaattatcca ggcgtggcgg cgggcggctg taatcccagc    288240
tactggggaa gctgaggcag gagaatcact tgaaactagg aggccgaggt tgcagtgagc    288300
caagatcgca ccattgcact ccagcctggg caatagaaca aaaacaccat ctcaaaataa    288360
ataaataaat agaatgaact gtattggccg ggtacagtga ctcatgccta taatcccagc    288420
actttgggag gctgaggctg gaggatcgtt tgaggccagg agttcgagac cagcctaggc    288480
aacatagtga gacccctatct ctttttttta aaaaaaaaa aaaaaaaaaa aaagaatgaa    288540
ctatacagtg tggcccaagg cccccctgcta aataaagaca ctcttcaggc aggacattc    288600
aaaggcttag agatcacctc ccaggagcaa gtcaatgggc cagtcctttc atcggaatgt    288660
gcagggtttg gacaacacta gcctactgag ctagtcctta ctgcttagca ccccagcttc    288720
tatgacacct actggattcc cttcctgagg gtttcaaaga ctcctggaga tgtctctgaa    288780
tttggctgtc acagttgtta cttgtacccc agatgccact cagttccctg aagacaatga    288840
tccccagat ttctcagcca ggagcccctc cacctcttgt cctcagtggg tgccaggcct    288900
catcctggag ttccacagct gagccaggct ctcggggtta cggaaggtca agagggtgtg    288960
gggacaacaa tggaagagtg ataacagtgg cagccctttg agcagatgcg ggtctcagga    289020
gaacataacg cgctttcttt tcatagttca gctcactttc taagcacact gagcttcctt    289080
tccagcaggc taaggggctg caaagggggt acagattaac ctcattcttc agattcctaa    289140
aaatggtgtc accattcatt gctggagact gggagaaagg gggcaagtcc atctcattcc    289200
ctctgtctct gtctctctct ctctcttccc tgtccatctg tttctctctc ccacccaccc    289260
ctctgttctc tctgcccaga agaatctcta ttttggtttt ggttttgttt gttttgtatt    289320
gttttgagac ggagtctcgt tctgtcgccc aggctggagt gcagtggcgc agtctcaact    289380
caccactgca gcctccacct cccaggttca agcgattctc atgcctcagc ctcccagtag    289440
gttgggatta caggcgcacg ccaccacgcc cagctaattt ttgcattttt actagagact    289500
ggtttcacca tgttgaccag gctggaccct atcctctttc aagcccccca ccccaggcat    289560
tgagggcaga gccaactacc tgcctgaacc aattagcata ttaaacgtaa acccagttag    289620
catatccaaa tagcagccca cagtgacatt ctgactgtca gaatgtggat tgcttgagcc    289680
caggagctca aggcttcggt gaacaaagat tgtgccacga cctgggcaac agagtaagtc    289740
cctgtcgatc gatagataga tgatagatag atagatagat agatagatag atagatagat    289800
agatagatag ataaattttt aaaaaaaata taggccagg cacagtggct catgcctgta    289860
atcccagcac tttgggaggc cgaggcaggc agatcacctg aggtcaggag ttcgagacca    289920
gcctggccaa catggtgaaa ccctgtctct acaaaaatat aaaaatagcc aggcagatgt    289980
ctgtaatccc agctactcag gaggctgagg taggagaatc gcttgaactc tgaaggtgga    290040
```

```
ggttgcagtg agccgagatc atgccattgc actccagcct gagtgacaga gcgagactcc   290100
atctcaaaaa taataacaat aataaaaata ataatatatg ctctggcccc aaagtggcac   290160
attacatggt gcacacccca ttagcaagga ctcatcacat ggccctgcca accacaggag   290220
gaaccccccc atgtactcag gtaggagggc caggaaacac cgtcagagag ctttaatgac   290280
tcacccatg actggggtga gggacgaggg actggctgca ggccaaggc atgtccgtgg    290340
cagtggagac ttgggaaagg ggaaaagacc tcctctgagc cacgcacagt ggctttcatc   290400
tgtaattcca gcactttggg aggctgaggt gggaggatct tgagcccagg aggtcgagac   290460
tgcagtgagc tatgtttgtg ccacggcact ctagcctggg cgacagagca aaaccctgtc   290520
tcaaaaatca aaataaaaacc aaaaccaaaa cttcctctgt tgggatgct ccagggcgtc    290580
ccagccttga acagatgggg cactgcagta ataatcctat ggcagacact gtcccaaggc   290640
tgcacgcacg ttactttgat catcaaacaa ccaggtgata gccaggcatg gtggtgcgtg   290700
cctgtagtcc cagctactca ggaagctgaa gcgggagaat ctcttgaacc tgggaggcgg   290760
aggtaacagt gagtcgagat cacatgactg cacttcagcc tgggaacaga gagagactct   290820
gtcaaaaaaa aaaaaaaaac aggccagacg cggtggctca cgcatgtaat cgccagcact   290880
ttgggaggct gaggagggtg gatcacctga ggtcaggagt ttgagaccag cctggccaac   290940
atggtgaaac cccgtctcta ctaaaaatac aaaattagtt gggcgtggtg gtgcacacct   291000
gtaatcccag ctactcggga ggctgaggca ggagaatcgc ttgaacccag gaggcagagg   291060
ttgcagtgag ctgagattgc accattgcac tccagcctgg gcaacaagag tgaaactcca   291120
tctcaaaaaa aaaacaaaaa aaaaacaacc agccaggcgc ggtggcttac gcctgtaatc   291180
ccagcacttt ggaggccga ggcgtgtgga tcacccgagg ttaggagttc gagaccagct     291240
tgaccaacat ggtgaaactc cgtctctact aaaaatacaa aaattagcc aggcatggtg    291300
gtgcatgtct gtaatcccag ctactcggga agctgagaca ggagaattga ttgaacccag   291360
gagtcggagg ttgcagtgag ccaagctcgt gccactgcac tccagcctgg gcaacagagc   291420
aagactctgt ctaaaaaaaa aaaaaaaaca cacacacaca cacacaacaa ccaggtgagg   291480
caagtactct tgctatcatc tccatttcac agatggaaa actgagttac taagtggtag    291540
agtaacctaa gtcatgcagc cgataactga gagacaagat tgggacccag gtcgcccagc   291600
tgttctccat gccgggctgt ctcctgcaca gctgctccat ggtcctggcc ccaccgaaaa   291660
ccagagccca caaggtcatt ccagcagcac tgcccagggc ctcctctggg ccaggccgtt   291720
ggggaactga agaccccatg gggaccagaa agattgggt ctcgttctcg ggagcctatg     291780
gctttgcagc tgacccagag tccagctgac acccaggcag gcagtcaggg tctgtctaca   291840
cccccattgc aggaggagcc gacaaacagc agatgacgc tgagctgcgg aaggagatga    291900
tggcgatttg gccaatctg tcccagaaga cgctagacct gctggtcaca cctcacaagt     291960
gtaagagctg agcccagccc tgggatccaa tccaccagga cagatggagg gggagggaaa   292020
ggggaggcct ggggagagtg ttggcctggg ctggtgtgtg cagggaccca ggacaagggc   292080
cccaaagagg cctgcccttg gtgagctcac cgtgtgtgtg ccccagcca cggacctcac    292140
cgtggggaag atctacgcag ccatgatgat catggagtac taccggcaga gcaaggccaa   292200
gaagctgcag gccatgcgcg aggagcaggt gcgctgttcg ccgctctggg gacatctggg    292260
ctgggacag tggcttgcat gtcaccacg gaaccaactg gaatatgagg gtggctgagc      292320
cccaggcag gtccctgaaa agtaggggct gtgcacagca gctcacacct ccaatctcag    292380
tgctttgaga ggccagggca gagggatcgt ttgagaccag gatgagacca ccctgggcaa   292440
cacagtgaga ctccatctct acaaaataaa acattagcca ggcatggtgg tgcacacctg    292500
tagtcccagc tatttaggag gccaagatgg gaggatcact tgaggccagg agtgggagac   292560
cagtctgggc aacatagaaa gacccatatc tctacaaaaa aaaaataaaa ttagctgcat   292620
gtggcgccat gcacctgtgg tcccagctac ttgggaggct gaggcaggag aatcacttga   292680
acctggggagg tggaggttgc agcaagccaa gatcaagcca ctgcactcca gcccgggtga   292740
taagagcagg actctatctc aaaaaaaaaa aaaaaaaaaa aaaaaaagt tcttgccaag    292800
gacacatcat gtgattcat tcttcattca gctgctccac caacactat tgagtattac     292860
tgtgtgcagg gcgctgttct cagtcctcgg ggatgcaccc atggggaaaa taggccagaa   292920
tccctgccct cagggagcag acattccaag tggggaaatg ccaatggtag caaatgactg    292980
aatcgtgcaa catccagcaa agagaaagaa agtgtcgtgg gggaaagtgg agaagaatcc   293040
agaagatagg agtatccagg gggaggggg atgcggtggg aaatggttga ttggggaggcc   293100
tccctgagaa agtgacatgt gagcaaaggc ttgaaggaaa aggggagagg gagtgagcta   293160
agcaatacct ggaagggtgt tccaggcaga ggaaacagcc agtgcaaagg ctctgaggct   293220
ggaccgtgcc tgggttgttt gggtaacagc aaagaggcca gtgtggtgga aaagagcagg   293280
gaggagacaa gggcaaggag gtgacagggc agatccttca gggccatgga agctgcagga   293340
aggactctgg cttttccccc aagcaagtgg gagccatgga gggttctaag caaaggaggg   293400
ataggacctg actcaagtgc tcatgggcgc cctctggtgg ctcttgtgga acagtggggt    293460
tgaaggtagg agcgggagac ctgggagaag gtgcctgcag tgagagatga ggacgtggga   293520
ccaggctggg gctatgactt gggtggagga gtgaagtg gtccagttct gcgtggaatt      293580
ggaagggtct agatggatga gacctgagag agtgtgtgtg tgtgtgtgtg tgtatactgg    293640
ggatgtcgca atgccttctg ggtaccaccg tcccaccacc ccaccttgt ccacacactg     293700
ctctctgccc cattcccag gaccggacac ccctcatgtt ccagcgcatg gagccccgt      293760
ccccaacgca ggaagggga cctggccaga acgccctccc ctccacccag ctggaccag     293820
gaggagccct gtgagtgtca ccctgccag ggaggtggga tgtgggggtg ccgtggtcco     293880
cacgttctgg aagctgccca agcgcccact gctaccccgg cctctgtccc ccatgcagga   293940
tggctcacga agcggcctc aaggagagcc cgtcctgggt gacccagcgt gcccaggaga    294000
tgttccagaa gacgggcaca tggagtccgg aacaaggccc cctaccgac atgcccaaca    294060
gccagcctaa ctctcaggtg cctctgtccc ccaactcccc aatggctccc agggccgggg   294120
tggttcaggt ggaagggatc tgggcccccc acacacacac acctgcagct ccctccctct   294180
gcagacacca gggatctgga ggtcaggccc cagagctcat ctggctttgc catctgctcc   294240
gcagtccgtg gagatgcgag agatgggcag agatggctac tccagacgcg agcactacct   294300
ccccatggaa ggccagggcc gggctgcctc catgccccgc ctccctgcag agaaccaggt   294360
gagggctttc accactgccc tggggctgga cccctcactc tgcactgggt agggccaggc   294420
cccccacaaa gcagcccagt gcatcccctc cctgccgcac tcaggcctgg gtaggagctg   294480
cttcagtctc tgaagcagtc tgcaggcccc acccaccacc tggtcacacc tggagccct     294540
gcagaccctc ctccctcaca gaggacagag aggaaagtgc tccccctggg gcagagggca    294600
gtggccactg caaaatggtc tctggctgcc ctggttggag gctgcagaca ggggaggttg   294660
tggaagattt gtgggtgcag cagggttcaa cagggccagc tgagacctgc cacgaagatc   294720
accctctcac aaacacacac acatgctc aacatacatg cacacacatg tgcagctgtg    294780
```

-continued

```
cgcctactca gatgcttgca tacacacacg tgtgtgcacg tgggcatata cacactgcac   294840
atgtactcac acatgcacac atgtacgtgc acacgtgtct gcatatggga acttggcagg   294900
tcctaggata cagtagcaga gtctggggtg ggtctggggg cagctgggct cgtattttct   294960
gtctggtctc tgtgggagtc attgggggc acaggggtgt gtgcttgatg tgtgtctgtg    295020
tgtggccgct tcacccagct gccaggccca cctgcaggtg atcccgttgc cttggactca   295080
tgggacagag ggcccagagg catagctggc tgcccacccg gcctgaacag cgggggccca   295140
tgcacgcagc ccgcctctgg aggagaacag ggcatggctg tgagagcctg gcccgggtgc   295200
gtggcatgtg tggctgtggc gagctttccg tgtgccgtgt gtggcgtctg cacggggcag   295260
gaggctgtgc tgtgcctggc tggaccaggg tcacctgagg gcctggcctc tggctgctgg   295320
gaacgtgggt tggggagcac ccagcgtgca tgctgctgct ccctcaggac cgagctgctg   295380
ggccccagga gagggttggg acaagcccag ctgacggcca ccacatggaa gctttgagca   295440
tcggccggag ccaggggttg gggtgtgcat cgcatgaggc agagcccagg gccaggggct   295500
cgaggctgcg ccgtcctgtc tttcggtccc atgcctctgc catttgtctg tctgcatctc   295560
ctgtctgtct cctctgtacc catgggaata gaggacgccc agcccccggg gcctgggaca   295620
cccacccgcc aggactttaa ctttttcttt cctccctgcc ttctccctcc gatttctctt   295680
gatgccagtg ccactcccct ccttggcttc ttctccatgc accacctcct cactctccct   295740
cttgcctttt atatttattt tcttctttct gtttttttctg tgtgcaccat cccatggggc  295800
tgtgacagag gagaagggc cggccacgtg ggaataacct cagtgtatgt accgcgcctg    295860
cccagcgccc agcagggctc cggcccctc ttcctcccca ccccccctcc agggagtccc    295920
gtcatctctc accgtccccg gaccccaccc tttctttggc aatcgcaccc tctcccctcc   295980
atggagccca atccttgtgt gtggtgtcct gtgtgtgccc ctcacccata gccctggtg    296040
ggcggggcca tccccatcct cacccctacc ccctttttctt caggggcccc cacgccggag  296100
gacactggct ctccaagagc ctggcccact ctgcacctct ttctgggggg cttcttctcc   296160
tgacaccacc accaaccct ggtcctgcag ctcctacctg gagcagggcc accagcgctc    296220
agctgggctg gaccctggga ggcgggcgtc tgccccatct ccctccttcc ctcctctgcc   296280
tgctgcagaa aaacctgtgt gtcagggctt gacccaggga tgaagcacca gggaaaagag   296340
tgggccccca gagcctccag tgcctgggta tcccccaccc ccacccagag ctccctagct   296400
tgggcctcac cagaaggact cagacttgtg ggggcagcga gcacagcccc gttagccggg   296460
aggacccaaa gctgccatgc cgggcacctg gtcctgagcc cataggtcag ccagccacag   296520
tcggaggctt ctcaccctcc caggagagca agctggggca gggatgagtg cggcagtcca   296580
gggctcccag gttttgcaccc tggatgtgga gagggcttcc ctctggccag cctgagcctg   296640
cccaactgtg gctgggcccc caggactgga gagtgaggat cagatctttc tggtcagaac    296700
ccaggatggg ctcaaaagga gcagtcctgt ctctgaggga cagaggaatc ctcaggctcc   296760
accctcagag gcctggccac acccagagcc ctgattgatc aggggggagcc aaggcccat   296820
ggcatcccct ggccctgcc ccaggatggt cacaccgcag tcaccgaagg ccaccaccag    296880
gctgccacaa tggggcagga aggaccggga ccacttggtg ctagctgctg accccagccc   296940
accggcctgt cccctccccc agaccatctc agacaccagc cccatgaagc gttcagcctc   297000
cgtgctgggc cccaaggccc gacgcctgga cgattactcg ctggagcggg tcccgcccga   297060
ggagaaccag gggcaccacc agcggcgccg cgaccgacac caccgcgcct ctgagcgctc   297120
cctgggccgc tacaccgatg tggacacagg tgggcagccc tgtggtgctc agggacaagc   297180
agaacagagg agaggagagg ggaggagaag gcagggcgga ggagacacta aggaagaaga   297240
aagggagagg cctccatgga gagggacag aggggggccag gcagcagctg caggaacctg   297300
ggtactaccc cctccccccca acccactgac ctgcctcggt tcaggggatc tctagggccc   297360
ccacaccttc caggtggcct cctgtgtgtg catctgcccc acctctccct cacgaccacc   297420
tgtgtgtctg tctgaccctc acccggccca ggcttgggga cagacctgag catgaccacc   297480
caatccgggg acctgccgtc gaaggagcgg gaccaggagc ggggccggcc caaggatcgg   297540
aagcatcgac agcaccacca ccaccaccac caccaccacc atccccgcac ccccgacaag   297600
gaccgctatg cccaggaacg gccggaccac ggccggcac gggctcggga ccagcgctgg    297660
tcccgctcgc ccagcgaggg ccgagagcac atggcgcacc ggcaggtggg tgcggctgca   297720
agtgaccccca ggctgggctc ggccggagg cggggaggag agaaggggat accccatcca   297780
acagccactc taggcaaagg tcccccggatc ccggctgtga ccacctccca tcctgcccca   297840
aagccaccgg ggtgcccggc ggccggagcg gacacggatc cccaccacac cagctgccta   297900
tgctgtcccc ccagcccct tgcccacccg ccgcccctc cccgccgccc gcagctgctt    297960
gctcctcggt tgtggatcat atttgagttc tgggccgtgc cgcccgacct ttcacttttcc   298020
tttaacccgg cttctgtttt tgtttcaatt atgatttctg tcctctgac gcctgtgagt    298080
aattttgaa acttctgcta ttttaaccc cgaaacttac aaaactccat ttctcatttc    298140
tcttttcact ttgttgtgtt ggttttcgac tcctcccctc cctgtctcac tcccctcct    298200
cccctccctc ctccctgtgg ctgttgcttt tttccattca atgtcctgtg tccccctct    298260
cctcctcctc ctccctccct cctccctctc ctcccggccc ctctccccct             298320
gctcccctct cttcctccca atccgtgtc tcctttgatt ttgttgtatc tttttttttg    298380
atttcctttg tttcaattttt cgtgtagggc agtagttccg taagtggaag cccagccccc   298440
tcaacatctg gtaccagcac tccgcggcgg ggccgccgcc agctccccca gaccccctcc   298500
acccccggc cacacgtgtc ctattcccct gtgatccgta aggccggcgg ctcggggccc    298560
ccgcagcagc agcagcagca gcagcagcag cagcagcag cagcagccgc caggccggca    298620
cgggcggcca ccagcggccc tcgaggtac ccaggcccca cggccgagcc tctggccgga    298680
gatcggccgc ccacgggggg ccacagcagc ggccgctcgc ccaggatgga gaggcgggtc   298740
ccaggccgg cccggagcga gtcccccagg gcctgtcgac acggcgggc ccggtggccg    298800
gcatctggcc cgcacgtgtc cgaggggccc ccgggtcccc ggcaccatgg ctactaccgg   298860
ggctccgact acgacgaggc cgatgcccg ggcaggggcg ggcgaggc catgaccgg      298920
ggggcctacg acgcgccacc cccgtacgact cacgcgtcct cggcgcccac cgggcgctcg   298980
cccaggactc ccgggcctc gggccggcc tgcgcctcgc cttctcggca cggccggcga    299040
ctcccccaacg gctactaccc ggcgcacgga ctggccaggc cccgcgggcc gggctccagg    299100
aagggcctgc acgaacccta cagcgagagt gacgatgatt ggtgctaagc ccgggcgagg    299160
tggcgccggg ccgggcccca acgcacccca cacacaccga gccgcggcag               299220
aggccgcgg ggcccagcac agagggccccg ggagagggcca agccggggaga ccccagactc   299280
tggagaggcc agggctgggc cacaaggggt ttccgcagag accctcggcc aaaagagacc    299340
ctcctggca gccacggcgc ccccccaacca gccccgatcc ccccacccac gacagggggct   299400
ctcgggtggg aggcagggag cagacaaacc acacagccaa gggatttgaa ttaactcagc   299460
catttttgga gaacttttggg gaacatgaaa aaaaaaaaaa aaaaaaaaaa aaaaaacatt   299520
```

-continued

```
tttaaaagaa aaaacgggga gaaaaaaata gcttctattg atgagtttta tcatctcaat 299580
tgaatctttc ctttccctga tgaagacagc tggtggccga gtgcggcaaa gaagccagaa 299640
ggaaccagaa tcccagtgcc ctacacccac caccagacac actcacaccc acacacgttc 299700
tcagacacac acaagagtgc ttgccggtta taccaaaccc tactattact gcctgcgaaa 299760
atcaatttaa aaaaataata ataacaataa acaattttaa aaaggacaaa aaaattaatg 299820
attgagaaaa gaggcatttt tttctgacat ttggtcctgc ttgaaacaac aaaagaagaa 299880
gaaaaaccca ccatcaccac cgattccttt gcttcttttt tccttttttc ctaccttgtt 299940
tgaaaaccgt gggcttggga ctgtgaatta ttgcatgaca ttcaaaaaga aaaaaaaaat 300000
aaaaaaaagt tgaatcaaa                                               300019

SEQ ID NO: 44          moltype = DNA  length = 1000
FEATURE                Location/Qualifiers
source                 1..1000
                       mol_type = other DNA
                       organism = synthetic construct
SEQUENCE: 44
atttcattta tcaggtgttc agtgaatgct tactatgtaa cagcacagtt atcagcactg 60
gggaaataga tgagtaagat aagatttgca cttttcattag cttacatgcc ataaagaggg 120
aaataaagag aacaccagat gatgataagt ttatgctgag aattaaaatg aagtgatgaa 180
ataatgggaa tgtcaggtgg ctacttttgg tgggatggtc aggaaaggca tctctgggga 240
gataaatttt aagctcagac ctgagtgaaa agaatgagcc agccatgaaa acattatgtt 300
aactcacatg gtagtttgaa atgctttatc tgatcaaagt tacttatttt tggtgacttt 360
caacaatatt aagggtctat aaaccaacac tcatttgcat aagaataact accagtgaat 420
cttttttgtat gataggtttt ttgtttgttg tttttttgag acagagtctc gctctgtcgc 480
ccaggctgga gtgcagtggc gcgatcttgg ctcactgcaa cctctacctc cccggttcaa 540
gtgattctcc tgcctcagcc tcccaaagta gctgggatta caggtgcctg ccaccacgcc 600
tggctaattt ttgtattttt agtagagatg gggtttcacc gtgttgtcca ggctcgtgtc 660
aaacttctga cctcaagcca tccacccgcc tcggcctccc aaagtgctgg gattacaggt 720
gtgagccacc actcctggcc atgataggtt attttgtgat gaaatacct acctcttaat 780
ttgtctgata aatttaaatt ttatgtctag atttcctaag atcagcactt ccatatttta 840
aagtaatctg tatcagacta actgctcttg cattctttta ataccagtga ctactttgat 900
tcgtgaaaca atgtattttc cttatgaata gttttctca tggtgtattt attcttttaa 960
gttttgtttt taaatatac ttcactttg aatgtttcag                        1000

SEQ ID NO: 45          moltype = DNA  length = 214
FEATURE                Location/Qualifiers
source                 1..214
                       mol_type = other DNA
                       organism = synthetic construct
SEQUENCE: 45
acagcagcaa aagcagcaac agcagcagca gcagcagcag caggggggacc tatcaggaca 60
gagttcacat ccatgtgaaa ggccagccac cagttcagga gcacttggga gtgatctagg 120
tgatgctatg agtgaagaag acatgcttca ggcagctgtg accatgtctt tagaaactgt 180
cagaaatgat ttgaaaacag aaggaaaaaa ataa                              214

SEQ ID NO: 46          moltype = DNA  length = 135
FEATURE                Location/Qualifiers
source                 1..135
                       mol_type = other DNA
                       organism = synthetic construct
SEQUENCE: 46
aacttgttta ttgcagctta taatggttac aaataaagca atagcatcac aaatttcaca 60
aataaagcat ttttttcact gcattctagt tgtggtttgt ccaaactcat caatgtatct 120
tatcatgtct ggatc                                                   135

SEQ ID NO: 47          moltype = DNA  length = 208
FEATURE                Location/Qualifiers
source                 1..208
                       mol_type = other DNA
                       organism = synthetic construct
SEQUENCE: 47
tccccagcat gcctgctatt ctcttcccaa tcctcccct tgctgtcctg ccccacccca 60
cccccagaa tagaatgaca cctactcaga caatgcgatg caatttcctc attttattag 120
gaaaggacag tgggagtggc accttccagg gtcaaggaag gcacggggga ggggcaaaca 180
acagatggct ggcaactaga aggcacag                                     208

SEQ ID NO: 48          moltype = DNA  length = 214
FEATURE                Location/Qualifiers
source                 1..214
                       mol_type = other DNA
                       organism = synthetic construct
SEQUENCE: 48
ctacttcttg ccctcggtct tcaggtcgtt gcgcacggtc tccaggctca tggtcacggc 60
ggcctgcagc atgtcctcct cgctcatggc gtcgcccagg ggtcgcccca gggcgccgct 120
gctggtggcg gggcgctcgc aggggtggct gctctggccg ctcaggtcgc cctgctgctg 180
ctgctgctgc tgctgctgct gcttctgctg ctgt                              214

SEQ ID NO: 49          moltype = DNA  length = 110
FEATURE                Location/Qualifiers
```

```
source                  1..110
                        mol_type = other DNA
                        organism = synthetic construct
SEQUENCE: 49
ctgtaaatga atgagaaaac cggtttagaa agtgcacagc tgtcagggaa gtcaacactt     60
cagtgagcat gtgaccatgt ggagtcagct tcctgtttcg tgctgcaatc                110

SEQ ID NO: 50           moltype = DNA  length = 374
FEATURE                 Location/Qualifiers
source                  1..374
                        mol_type = other DNA
                        organism = synthetic construct
SEQUENCE: 50
gtaaggcctg ctcaccattc atcatgttcg ctaccttcac actttatctg acatacgagc     60
tccatgtgat ttttgcttta cattattctt cattccctct ttaatcatat taagaatctt    120
aagtaaattt gtaatctact aaatttccct ggattaagga gcagttacca aaagaaaaaa    180
aaaaaaaaaa gctagatgtg gtggctcaca tctgtaatcc cagcactttg ggaaaccaag    240
gcaggagagg attgctagaa catttaatga atactttaac ataataattt aaacttcaca    300
gtaatttgta cagtctccaa aaattcctta gacatcatgg atatttttct ttttttgaga    360
tggagtcttg ctct                                                       374

SEQ ID NO: 51           moltype = DNA  length = 136
FEATURE                 Location/Qualifiers
source                  1..136
                        mol_type = other DNA
                        organism = synthetic construct
                        note = Target site
SEQUENCE: 51
tttaagctca gacctgagtg aaaagaattt gagacagagt ctcgctctgt cgcctttcct     60
aagatcagca cttccatatt tggtgacttt caacaatatt aagggtctat aaaccaacac    120
tcatttgcat aagaat                                                     136
```